(12) United States Patent
Bosanac et al.

(10) Patent No.: US 8,618,300 B2
(45) Date of Patent: Dec. 31, 2013

(54) INDOLIZINE INHIBITORS OF LEUKOTRIENE PRODUCTION

(75) Inventors: Todd Bosanac, New Milford, CT (US); Stephane De Lombaert, Madison, CT (US); Ho Yin Lo, Bethel, CT (US); Peter Allen Nemoto, Southbury, CT (US); Alan Olague, Danbury, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 49 days.

(21) Appl. No.: 13/061,996

(22) PCT Filed: Aug. 25, 2009

(86) PCT No.: PCT/US2009/054837
§ 371 (c)(1),
(2), (4) Date: May 20, 2011

(87) PCT Pub. No.: WO2010/027762
PCT Pub. Date: Mar. 11, 2010

(65) Prior Publication Data
US 2011/0275627 A1    Nov. 10, 2011

Related U.S. Application Data

(60) Provisional application No. 61/094,154, filed on Sep. 4, 2008, provisional application No. 61/222,612, filed on Jul. 2, 2009.

(51) Int. Cl.
C07D 221/02    (2006.01)
(52) U.S. Cl.
USPC .......................................................... 546/112
(58) Field of Classification Search
USPC .................................................... 546/112
See application file for complete search history.

(56) References Cited

U.S. PATENT DOCUMENTS

| | | | |
|---|---|---|---|
| 6,911,444 B2 | 6/2005 | Lacrampe et al. | |
| 7,319,108 B2 | 1/2008 | Schwink et al. | |
| 7,553,845 B2 * | 6/2009 | Alcouffe et al. | 514/299 |
| 8,012,992 B2 * | 9/2011 | Yuan | 514/300 |
| 2006/0160799 A1 * | 7/2006 | Alekshun et al. | 514/233.5 |
| 2010/0035915 A1 | 2/2010 | Mederski et al. | |

FOREIGN PATENT DOCUMENTS

| | | |
|---|---|---|
| WO | 2005123674 A1 | 12/2005 |
| WO | 2006044602 A2 | 4/2006 |
| WO | 2006136859 A1 | 12/2006 |
| WO | 2007031747 A1 | 3/2007 |
| WO | 2007047207 A2 | 4/2007 |
| WO | 2007056021 A2 | 5/2007 |
| WO | 2007120574 A2 | 10/2007 |
| WO | 2008030369 A1 | 3/2008 |
| WO | 2008071288 A1 | 6/2008 |
| WO | 2008097930 A1 | 8/2008 |
| WO | 2008128335 A1 | 10/2008 |
| WO | 2008156721 A1 | 12/2008 |
| WO | 2009048547 A1 | 4/2009 |
| WO | 2011143466 A1 | 11/2011 |

OTHER PUBLICATIONS

Tsuge et al. STN Accession No. 1986:224845, Abstract of Journal of Organic Chemistry (1986), 51(10), 1853-5.*
Tewari et al. STN Accession No. 1985:541813, Abstract of Journal of Chemical and Engineering Data (1985),30(4), 505-7.*
Kakei et al STN Accession No. 1989:439186, Abstract of JP 63238077.*
Iuhas et al. Revue Roumaine de Chimie (2002), vol. Date 2003,47(3-4), 333-338.*
Okada et al. STN Accession No. 2007:642324, Abstract of JP 2007147700.*
Dorwald F. A. Side Reactions in Organic Synthesis, 2005, Wiley: VCH, Weinheim p. IX of Preface p. 1-15.*
Venkatesh et al., Role of the Development Scientist in Compound Lead Selection and Optimization J. Pharm. Sci. 89, 145-54 (2000).*
Khoroshilov et al. STN Abstract of Visnik Kharkivs'kogo Natsional'nogo Universitetu im.V. N. Karazina (2007), 770, 210-217.*
Khairulin et al. STN Abstract of Farmatsevtichnii Zhurnal (Kiev, Ukraine) (2006), (5), 58-61.*
Yavari et al. STN Abstract of Synlett (2006), (15), 2501-2503.*
Chen et al. STN Abstract of Synlett (2004), (7), 1231-1234.*
El-Salam, STN Abstract of Monatshefte fuer Chemie (2000), 131(9), 959-965.*
Zhang et al. STN Abstract of Journal of Fluorine Chemistry (1998), 87(1), 57-64.*
Wei et al. STN Abstract of Synthetic Communications (1992), 22(14), 2103-9.*
International Search Report and Written Opinon of corresponding PCT Application PCT/US2009/054837 dated Feb. 3, 2010.
Teklu S. et al; "Indolizine 1-sulfonates as potent inhibitors of 15-lipoxygenase from soybeans" Bioorganic & Medicinal Chemistry, Elsevier Science, Oxford, GB vol. 13, No. 9, pp. 3127-3139; May 2, 2005.

* cited by examiner

Primary Examiner — Nizal Chandrakumar
(74) Attorney, Agent, or Firm — Michael P. Morris; David L. Kershner; Usha R. Patel

(57) ABSTRACT

The present invention relates to compounds of formula (I):

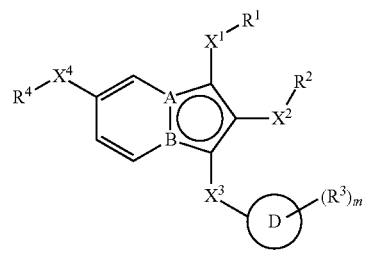

and pharmaceutically acceptable salt thereof, wherein $X^1$ to $X^4$, $R^1$ to $R^4$, A, B, D and m are as defined herein. The invention also relates to pharmaceutical compositions comprising these compounds, methods of using these compounds in the treatment of various diseases and disorders, processes for preparing these compounds and intermediates useful in these processes.

13 Claims, No Drawings

INDOLIZINE INHIBITORS OF LEUKOTRIENE PRODUCTION

FIELD OF THE INVENTION

This invention relates to indolizines that are useful as inhibitors of five lipoxygenase activating protein (FLAP) and are thus useful for treating a variety of diseases and disorders that are mediated or sustained through the activity of leukotrienes including asthma, allergy and cardiovascular diseases including atherosclerosis, myocardial infarction and stroke. This invention also relates to pharmaceutical compositions comprising these compounds, methods of using these compounds in the treatment of various diseases and disorders, processes for preparing these compounds and intermediates useful in these processes.

BACKGROUND OF THE INVENTION

Leukotrienes (LTs) and the biosynthetic pathway from arachidonic acid leading to their production have been the targets of drug discovery efforts for over twenty years. LTs are produced by several cell types including neutrophils, mast cells, eosinophils, basophils monocytes and macrophages. The LTs result from oxidation of arachidonic acid by 5-lipoxygenase (5-LO) and subsequent metabolism to $LTA_4$, $LTB_4$, and the cysteinyl LTs-$LTC_4$, $LTD_4$ and $LTE_4$ (B. Samuelsson, Science, 1983, 220, 568-575). The cysteinyl LTs have potent smooth muscle constricting and bronchoconstricting effects as well as stimulating mucous secretion, and vascular leakage. $LTB_4$ is a potent chemotactic agent for leukocytes, and stimulates adhesion, aggregation and enzyme release.

Much of the early drug discovery effort in the LT area was directed towards the treatment of allergy, asthma and other inflammatory conditions. Research efforts have been directed towards numerous targets in the pathway including antagonists of $LTB_4$ and the cysteinyl leukotrienes $LTC_4$, $LTD_4$ and $LTE_4$, as well as inhibitors of 5-lipoxygenase (5-LO), $LTA_4$ hydrolase and inhibitors of 5-lipoxygenase activating protein (FLAP) (R. W. Friesen and D. Riendeau, Leukotriene Biosynthesis Inhibitors, Ann. Rep. Med. Chem., 2005, 40, 199-214). FLAP is an 18 kD membrane protein required for cellular activity of 5-LO (D. K. Miller et al., Nature, 1990, 343, 278-281; R. A. F. Dixon et al., Nature, 1990, 343, 282-284). Years of effort in the above areas have yielded a few marketed products for the treatment of asthma including a 5-LO inhibitor, zileuton, and LT antagonists, montelukast, pranlukast and zafirlukast.

More recent work has implicated LTs in cardiovascular disease, including myocardial infarction, stroke and atherosclerosis. FLAP and 5-LO were among the components of the 5-LO and LT cascade found in atherosclerotic lesions, suggesting their involvement in atherogenesis. (R. Spanbroek et al., Proc. Natl. Acad. Sci. U.S.A., 2003, 100, 1238-1243). Pharmacological inhibition of FLAP has been reported to decrease atherosclerotic lesion size in animal models. In one study, oral dosing of the FLAP inhibitor MK-886 to apoE/LDL-R double knockout mice fed a high-fat diet from 2 months of age to 6 months led to a 56% decrease in plaque coverage in the aorta and a 43% decrease in the aortic root (J. Jawien et al., Eur. J. Clin. Invest., 2006, 36, 141-146). This plaque effect was coupled with a decrease in plaque-macrophage content and a concomitant increase in collagen and smooth muscle content which suggests a conversion to a more stable plaque phenotype. In another study, it was reported that administration of MK-886 via infusion to $ApoE^{-/-} \times CD4$ dnT$\beta$RII mice (apoE KO mice expressing a dominant-negative TGF-beta receptor which effectively removes all TGF-beta from the system) resulted in about a 40% decrease in plaque area in the aortic root (M. Back et al., Circ. Res., 2007, 100, 946-949). The mice were only treated for four weeks after plaque growth was already somewhat mature (12 weeks) thus raising the possibility of therapeutically treating atherosclerosis via this mechanism. In a study examining human atherosclerotic lesions, it was found that the expression of FLAP, 5-LO and $LTA_4$ hydrolase was significantly increased compared to healthy controls (H. Qiu et al., Proc. Natl. Acad. Sci. U.S.A., 103, 21, 8161-8166). These and similar studies suggest that inhibition of the LT pathway, for example by inhibition of FLAP, would be useful for the treatment of atherosclerosis.

In addition to the work cited above, many other studies have been directed towards understanding the biological actions of LTs and their role of LTs in disease. These studies have implicated LTs as having a possible role in numerous diseases or conditions (for a review, see M. Peters-Golden and W. R. Henderson, Jr., M.D., N. Engl. J. Med., 2007, 357, 1841-1854). In addition to the specific diseases cited above, LTs have been implicated as having a possible role in numerous allergic, pulmonary, fibrotic, inflammatory and cardiovascular diseases, as well as cancer. Inhibition of FLAP is also reported to be useful for treating renal diseases such as diabetes-induced proteinuria (see for example J. M. Valdivieso et al., Journal of Nephrology, 2003, 16, 85-94 and A Montero et al., Journal of Nephrology, 2003, 16, 682-690).

A number of FLAP inhibitors have been reported in the scientific literature (see for example J. F. Evans et al., Trends in Pharmacological Sciences, 2008, 72-78) and in U.S. patents. Some have been evaluated in clinical trials for asthma, including MK-886, MK-591 and BAY X1005, also known as DG-031. DG-031 has also been in clinical trials to evaluate its effect on biomarkers for myocardial infarction risk and showed a dose-dependent suppression of biomarkers for the disease (H. Hakonarson et al., JAMA, 2005, 293, 2245-2256). MK-591 was shown in a clinical trial to be useful for reducing proteinuria in human glomerulonephritis (see for example A. Guash et al., Kidney International, 1999, 56, 291-267).

However, to date, no FLAP inhibitor has been approved as a marketed drug.

BRIEF SUMMARY OF THE INVENTION

The present invention provides novel compounds which inhibit 5-lipoxygenase activating protein (FLAP) and are thus useful for treating a variety of diseases and disorders that are mediated or sustained through the activity of leukotrienes including allergic, pulmonary, fibrotic, inflammatory and cardiovascular diseases and cancer. This invention also relates to pharmaceutical compositions comprising these compounds, methods of using these compounds in the treatment of various diseases and disorders, processes for preparing these compounds and intermediates useful in these processes.

DETAILED DESCRIPTION OF THE INVENTION

In its broadest embodiment, the present invention relates compounds of formula (I):

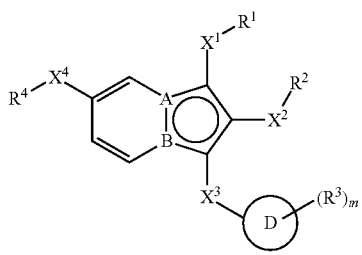

(I)

or pharmaceutically acceptable salts thereof, wherein:
A is N and B is C, or A is C and B is N;
ring D is $C_{3-10}$ cycloalkyl, 5 to 11-membered heterocyclyl, $C_{6-10}$ aryl, or 5 to 11-membered heteroaryl;
$X^1$ is —C(O)— or —S(O)$_j$—;
$X^2$ is absent or is —(CH$_2$)$_n$—, wherein one or more hydrogen atoms of said —(CH$_2$)$_n$— can be replaced by hydroxyl, halogen, $C_{1-6}$ alkyl, $C_{1-6}$ alkoxy, or $C_{1-6}$ alkoxy $C_{1-6}$ alkyl, and wherein when both hydrogen atoms on the same carbon are replaced by $C_{1-6}$alkyl, said $C_{1-6}$ alkyl groups may be bonded together to form a spiro $C_{3-13}$cycloalkyl group;
$X^3$ is —C(R$^9$)$_2$—, —C(O)—, or —C(O)—N(R$^{10}$)—;
$X^4$ is —(CH$_2$)$_p$ or —(CH$_2$)$_p$—O—(CH$_2$)$_q$—, wherein one or more hydrogen atoms of said —(CH$_2$)$_p$—O—(CH$_2$)$_q$— can be replaced by $C_{1-6}$ alkyl;
$R^1$ is $C_{1-6}$ alkyl, $C_{1-6}$ alkoxy, $C_{1-6}$ alkoxy $C_{1-6}$ alkyl, $C_{2-6}$ alkenyl, $C_{2-6}$ alkynyl, $C_{3-6}$ cycloalkyl, 4 to 8-membered heterocyclyl, phenyl, 5 to 6-membered heteroaryl, or N(R$^8$)$_2$—, wherein each $C_{1-6}$ alkyl, $C_{1-6}$ alkoxy, $C_{1-6}$ alkoxy $C_{1-6}$ alkyl, $C_{2-6}$ alkenyl, $C_{2-6}$ alkynyl, $C_{3-6}$ cycloalkyl, 4 to 8-membered heterocyclyl, phenyl, and 5 to 6-membered heteroaryl of said $R^1$ substituent where possible is optionally substituted with one to four hydroxyl, halogen, or $C_{1-6}$ alkyl;
$R^2$ is $C_{1-6}$ alkyl, $C_{2-6}$ alkenyl, $C_{2-6}$ alkynyl, $C_{3-10}$ cycloalkyl, 5 to 11-membered heterocyclyl, $C_{6-10}$ aryl, 5 to 11-membered heteroaryl, R$^9$—C(O)—, R$^9$—O—C(O)—, N(R$^8$)$_2$—, N(R$^8$)$_2$—C(O)—, R$^9$—C(O)—N(R$^8$)—, (N(R$^8$)$_2$)(R$^8$N═)C—N(R$^8$)—C(O)—, R$^9$—S(O)$_j$—, N(R$^8$)$_2$—S(O)$_j$—, R$^9$—S(O)$_j$—N(R$^8$)—, R$^9$—S(O)$_j$—N(R$^8$)—C(O)—, N(R$^8$)$_2$—S(O)$_j$—N(R$^8$)—C(O)—, or N(R$^8$)$_2$—C(O)—N(R$^8$)—S(O)$_j$—, wherein each $C_{1-6}$ alkyl, $C_{2-6}$ alkenyl, $C_{2-6}$ alkynyl, $C_{3-10}$ cycloalkyl, 5 to 11-membered heterocyclyl, $C_{6-10}$ aryl, and 5 to 11-membered heteroaryl of said $R^2$ substituent where possible is optionally substituted with one to four $R^5$ groups;
each $R^3$ when present is independently hydroxyl, halogen, cyano, $C_{1-6}$ alkyl, $C_{1-6}$ alkoxy, $C_{1-6}$ alkoxy $C_{1-6}$ alkyl, $C_{3-10}$ cycloalkyl, 5 to 11-membered heterocyclyl, $C_{6-10}$ aryl, 5 to 11-membered heteroaryl, R$^9$—C(O)—, R$^9$—O—C(O)—, N(R$^8$)$_2$—, N(R$^8$)$_2$—C(O)—, R$^9$—C(O)—N(R$^8$)—, (N(R$^8$)$_2$)(R$^8$N═)C—N(R$^8$)—C(O)—, R$^9$—S(O)$_j$—, N(R$^8$)$_2$—S(O)$_j$—, R$^9$—S(O)$_j$—N(R$^8$)—, R$^9$—S(O)$_j$—N(R$^8$)—C(O)—, N(R$^8$)$_2$—S(O)$_j$—N(R$^8$)—C(O)—, or N(R$^8$)$_2$—C(O)—N(R$^8$)—S(O)$_j$—, wherein each $C_{1-6}$ alkyl, $C_{1-6}$ alkoxy, $C_{1-6}$ alkoxy $C_{1-6}$ alkyl, $C_{3-10}$ cycloalkyl, 5 to 11-membered heterocyclyl, $C_{6-10}$ aryl, and 5 to 11-membered heteroaryl of said $R^3$ substituent where possible is optionally substituted with one to four $R^6$ groups;
$R^4$ is hydrogen, $C_{1-6}$ alkyl, $C_{3-10}$ cycloalkyl, 5 to 11-membered heterocyclyl, $C_{6-10}$ aryl, or 5 to 11-membered heteroaryl, wherein each $C_{1-6}$ alkyl, $C_{3-10}$ cycloalkyl, 5 to 11-membered heterocyclyl, $C_{6-10}$ aryl, and 5 to 11-membered heteroaryl of said $R^4$ where possible is optionally substituted with one to four $R^7$ groups;
$R^5$, $R^6$, and $R^7$ are each independently halogen hydroxyl, carboxy, $C_{1-6}$ alkyl, $C_{1-6}$ alkoxy, $C_{1-6}$ alkoxy $C_{1-6}$ alkyl, R$^9$—C(O)—, R$^9$—O—C(O)—, N(R$^8$)$_2$—, N(R$^8$)$_2$—C(O)—, R$^9$—C(O)—N(R$^8$)—, R$^9$—S(O)$_j$—, R$^9$—S(O)$_j$—N(R$^8$)—, or N(R$^8$)$_2$—S(O)$_j$—;
each $R^8$ is independently hydrogen, $C_{1-6}$ alkyl, $C_{3-10}$ cycloalkyl, 5 to 11-membered heterocyclyl, $C_{6-10}$ aryl, or 5 to 11-membered heteroaryl, wherein two $R^8$ groups when attached to the same nitrogen atom can join to form a 4 to 8-membered heterocyclyl;
each $R^9$ is independently hydrogen, $C_{1-6}$ alkyl, $C_{3-10}$ cycloalkyl, 5 to 11-membered heterocyclyl, $C_{6-10}$ aryl, or 5 to 11-membered heteroaryl;
$R^{10}$ is hydrogen, $C_{1-6}$ alkyl, carboxy $C_{1-6}$ alkyl, or $C_{1-6}$ alkoxy $C_{1-6}$ alkyl;
j is 0, 1 or 2;
m is 0, 1, 2 or 3;
n is an integer from 1 to 6; and
p and q are each independently 0, 1 or 2.

In another embodiment, the present invention relates to a compound as described in the broadest embodiment above, or a pharmaceutically acceptable salt thereof, wherein A is N and B is C.

In another embodiment, the present invention relates to a compound as described in the broadest embodiment above, or a pharmaceutically acceptable salt thereof, wherein A is C and B is N.

In another embodiment, the present invention relates to a compound as described in the broadest embodiment above, or a pharmaceutically acceptable salt thereof, wherein $X^1$ is —C(O)—.

In another embodiment, the present invention relates to a compound as described in the broadest embodiment above, or a pharmaceutically acceptable salt thereof, wherein $X^2$ is —(CH$_2$)$_2$—, wherein one or more hydrogen atoms of said —(CH$_2$)$_2$— can be replaced by hydroxyl, halogen, or $C_{1-6}$ alkyl, and wherein when both hydrogen atoms on the same carbon are replaced by $C_{1-6}$alkyl, said $C_{1-6}$alkyl groups may be bonded together to form a spiro $C_{3-13}$cycloalkyl group.

In another embodiment, the present invention relates to a compound as described in the broadest embodiment above, or a pharmaceutically acceptable salt thereof, wherein $X^3$ is —C(O)—.

In another embodiment, the present invention relates to a compound as described in the broadest embodiment above, or a pharmaceutically acceptable salt thereof, wherein $X^3$ is —C(O)—N(R$^{10}$)—.

In another embodiment, the present invention relates to a compound as described in the broadest embodiment above, or a pharmaceutically acceptable salt thereof, wherein $X^4$ is —CH$_2$—O—, wherein one or more hydrogen atoms of said —CH$_2$—O— can be replaced by $C_{1-6}$alkyl.

In another embodiment, the present invention relates to a compound as described in the embodiment immediately above, or a pharmaceutically acceptable salt thereof, wherein one or more hydrogen atoms of said —CH$_2$—O— can be replaced by methyl.

In another embodiment, the present invention relates to a compound as described in the broadest embodiment above, or a pharmaceutically acceptable salt thereof, wherein:
$X^1$ is —C(O)—;
$X^2$ is —(CH$_2$)$_2$—, wherein one or more hydrogen atoms of said —(CH$_2$)$_2$— can be replaced by $C_{1-6}$ alkyl, $C_{1-6}$ alkoxy, or $C_{1-6}$ alkoxy $C_{1-6}$ alkyl, and wherein when both hydrogen atoms on the same carbon are replaced by $C_{1-6}$alkyl, said $C_{1-6}$alkyl groups may be bonded together to form a spiro $C_{3-13}$cycloalkyl group;

$X^3$ is —C(O)—; and $X^4$ is —CH$_2$—O—, wherein one or more hydrogen atoms of said —CH$_2$—O— can be replaced by $C_{1-6}$ alkyl.

In another embodiment, the present invention relates to a compound as described in the embodiment immediately above, or a pharmaceutically acceptable salt thereof, wherein one or more hydrogen atoms of said —CH$_2$—O— of said $X^4$ can be replaced by methyl.

In another embodiment, the present invention relates to a compound of formula (I) as described in the embodiment immediately above, or a pharmaceutically acceptable salt thereof, wherein ring D is phenyl or 5 to 6-membered heteroaryl.

In another embodiment there is provided a compound of formula (I) as described in the broadest embodiment above, or a pharmaceutically acceptable salt thereof, and wherein:

A is C and B is N, or A is N and B is C;
ring D is phenyl or pyridyl;
$X^1$ is —C(O)—;
$X^2$ is —CH$_2$C(C$_{1-2}$alkyl)$_2$- or

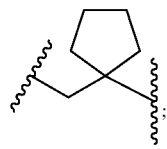 [SMILES: *CC1(*)CCCC1]

$X^3$ is —C(O)— or —C(O)N(R$_{10}$)—;
$X^4$ is —CH$_2$O—;
$R^1$ is $C_{1-6}$ alkyl or $C_{3-6}$cycloalkyl;
$R^2$ is R$_9$OC(O)—, NH(R$^8$)—C(O)— or R$^9$—S(O)$_2$—NH—C(O)—;

each $R^3$ when present is independently hydroxyl, halogen, cyano, $C_{1-6}$ alkyl, $C_{1-6}$ alkoxy, $C_{3-6}$cycloalkyl, phenyl, heteroaryl selected from pyridine, pyrimidine and pyrazine, heterocyclyl selected from morpholine, thiomorpholine, pyrrolidine and piperidine, R$^9$—C(O)—, R$^9$—O—C(O)—, N(R$^8$)$_2$—, N(R$^8$)$_2$—C(O)—, R$^9$—C(O)—N(R$^8$)—, R$^9$—S(O)$_j$—, N(R$^8$)$_2$—S(O)$_2$—, R$^9$—S(O)$_2$—N(R$^8$)—, R$^9$—S(O)$_2$—N(R$^8$)—C(O)—, N(R$^8$)$_2$—S(O)$_2$—N(R$^8$)—C(O)—, or N(R$^8$)$_2$—C(O)—N(R$^8$)—S(O)$_2$—, wherein each $C_{1-6}$ alkyl, $C_{1-6}$ alkoxy, $C_{3-6}$ cycloalkyl, phenyl heteroaryl and heterocyclyl of said R$^3$ substituent where possible is optionally substituted with one to four R$^6$ groups;

$R^4$ is phenyl or heteroaryl, selected from pyridine, pyrimidine, pyrazine, quinoline, isoquinoline, benzothiazole, benzoxazole, thiazole, oxazole and 1,2,4-oxadiazole wherein each phenyl or heteroaryl of said R$^4$ where possible is optionally substituted with one to four R$^7$ groups;

$R^5$, $R^6$, and $R^7$ are each independently halogen hydroxyl, carboxy, $C_{1-6}$ alkyl, $C_{1-6}$ alkoxy, $C_{1-6}$ alkoxy $C_{1-6}$ alkyl, R$^9$—C(O)—, R$^9$—O—C(O)—, N(R$^8$)$_2$—, N(R$^8$)$_2$—C(O)—, R$^9$—C(O)—N(R$^8$)—, R$^9$—S(O)$_j$—, R$^9$—S(O)$_2$—N(R$^8$)—, or N(R$^8$)$_2$—S(O)$_2$—;

each $R^8$ is independently hydrogen, $C_{1-6}$ alkyl, $C_{3-10}$ cycloalkyl or pyridyl;

each $R^9$ is independently hydrogen, $C_{1-6}$ alkyl, $C_{3-6}$ cycloalkyl;

$R^{10}$ is hydrogen, $C_{1-6}$ alkyl or carboxy $C_{1-6}$ alkyl; and j is 0, 1 or 2.

In another embodiment there is provided a compound as described immediately above, or a pharmaceutically acceptable salt thereof, wherein A is C and B is N.

In another embodiment there is provided a compound of formula (I) as described in the broadest embodiment above, or a pharmaceutically acceptable salt thereof, wherein:

A is C and B is N;
ring D is phenyl or pyridyl;
$X^1$ is —C(O)—;
$X^2$ is —CH$_2$C(C$_{1-3}$alkyl)$_2$-;
$X^3$ is —C(O)—;
$X^4$ is —CH$_2$O—;
$R^1$ is —C(CH$_3$)$_3$;
$R^2$ is CO$_2$H;

each $R^3$ when present is independently hydroxyl, halogen, cyano, $C_{1-6}$ alkyl, $C_{1-6}$ alkoxy, $C_{3-6}$ cycloalkyl, phenyl, heteroaryl selected from pyridine, pyrimidine and pyrazine, heterocyclyl selected from morpholine, thiomorpholine, pyrrolidine and piperidine, R$^9$—C(O)—, R$^9$—O—C(O)—, N(R$^8$)$_2$—, N(R$^8$)$_2$—C(O)—, R$^9$—C(O)—N(R$^8$)—, R$^9$—S(O)$_2$—, N(R$^8$)$_2$—S(O)$_2$—, or R$^9$—S(O)$_2$—N(R$^8$)—, wherein each $C_{1-6}$ alkyl, $C_{1-6}$ alkoxy, $C_{3-6}$ cycloalkyl, phenyl heteroaryl and heterocyclyl of said R$^3$ substituent where possible is optionally substituted with one to four R$^6$ groups;

$R^4$ is phenyl or heteroaryl, selected from pyridine, pyrimidine, pyrazine, quinoline, isoquinoline, benzothiazole, benzoxazole, thiazole, oxazole and 1,2,4-oxadiazole, wherein each phenyl or heteroaryl of said R$^4$ where possible is optionally substituted with one to four R$^7$ groups;

$R^5$, $R^6$, and $R^7$ are each independently halogen hydroxyl, carboxy, $C_{1-6}$ alkyl, $C_{1-6}$ alkoxy, $C_{1-6}$ alkoxy $C_{1-6}$ alkyl, R$^9$—C(O)—, R$^9$—O—C(O)—, N(R$^8$)$_2$—, N(R$^8$)$_2$—C(O)—, R$^9$—C(O)—N(R$^8$)—, R$^9$—S(O)$_j$—, R$^9$—S(O)$_2$—N(R$^8$)—, or N(R$^8$)$_2$—S(O)$_2$—;

each $R^8$ is independently hydrogen, $C_{1-6}$ alkyl, $C_{3-10}$ cycloalkyl or pyridyl;

each $R^9$ is independently hydrogen, $C_{1-6}$ alkyl, $C_{3-6}$ cycloalkyl; and $R^{10}$ is hydrogen, $C_{1-6}$ alkyl or carboxy $C_{1-6}$ alkyl.

In a preferred embodiment, the invention relates to a compound as described in the embodiment immediately above, or a pharmaceutically acceptable salt thereof, wherein A is C and B is N.

In another embodiment, the present invention relates to a compound as described in the broadest embodiment above, or a pharmaceutically acceptable salt thereof, wherein R$^1$ is $C_{1-6}$ alkyl, $C_{3-6}$ cycloalkyl, or 4 to 8-membered heterocyclyl, wherein each $C_{1-6}$ alkyl, $C_{3-6}$ cycloalkyl, and 4 to 8-membered heterocyclyl of said R$^1$ substituent where possible is optionally substituted with one to four hydroxyl, or $C_{1-6}$ alkyl.

In another embodiment, the present invention relates to a compound as described in the embodiment immediately above, or a pharmaceutically acceptable salt thereof, wherein R$^1$ is $C_{1-6}$ alkyl or $C_{3-6}$ cycloalkyl, wherein each $C_{1-6}$ alkyl and $C_{3-6}$ cycloalkyl of said R$^1$ substituent where possible is optionally substituted with one to four hydroxyl or $C_{1-6}$ alkyl.

In a preferred embodiment, the present invention relates to a compound as described the embodiment immediately above, or a pharmaceutically acceptable salt thereof, wherein $X^1$ is —C(O)— and R$^1$ is 2-methylpropyl, 2,2-dimethylpropyl, 2-hydroxy-2-methylpropanyl, cyclopropyl, 2,2,3,3-tetramethylcyclopropyl, cyclobutyl, cyclopentyl, cyclohexyl, or phenyl.

In another embodiment, the present invention relates to a compound as described in the broadest embodiment above, or a pharmaceutically acceptable salt thereof, wherein R$^2$ is $C_{1-6}$ alkyl, $C_{3-10}$ cycloalkyl, 5 to 11-membered heterocyclyl, $C_{6-10}$ aryl, 5 to 11-membered heteroaryl, $R^9$—O—C(O)—, $N(R^8)_2$—, $N(R^8)_2$—C(O)—, or $N(R^8)_2$—S(O)$_j$—, wherein each $C_{1-6}$ alkyl, $C_{3-10}$ cycloalkyl, 5 to 11-membered heterocyclyl, $C_{6-10}$ aryl, and 5 to 11-membered heteroaryl of said $R^2$ substituent where possible is optionally substituted with one to four $R^5$ groups.

In another embodiment, the present invention relates to a compound as described in the embodiment immediately above, or a pharmaceutically acceptable salt thereof, wherein $R^2$ is $C_{1-6}$ alkyl, phenyl, 5 to 6-membered heteroaryl, $R^9$—O—C(O)—, $N(R^8)_2$—C(O)—, or $N(R^8)_2$—S(O)$_j$—, wherein each $C_{1-6}$ alkyl, phenyl, and 5 to 6-membered heteroaryl of said $R^2$ substituent where possible is optionally substituted with one to four $R^5$ groups.

In a preferred embodiment, the present invention relates to a compound as described in the embodiment immediately above, or a pharmaceutically acceptable salt thereof, wherein $R^2$ is carboxy, methoxycarbonyl, aminocarbonyl, methylaminocarbonyl, dimethylaminocarbonyl, pyridylaminocarbonyl, or methylsulfonylaminocarbonyl.

In another preferred embodiment, the present invention relates to a compound as described in the broadest embodiment above, or a pharmaceutically acceptable salt thereof, wherein $X^2$ and $R^2$ together represents:

(a) methyl or phenyl; or (b) a moiety selected from:

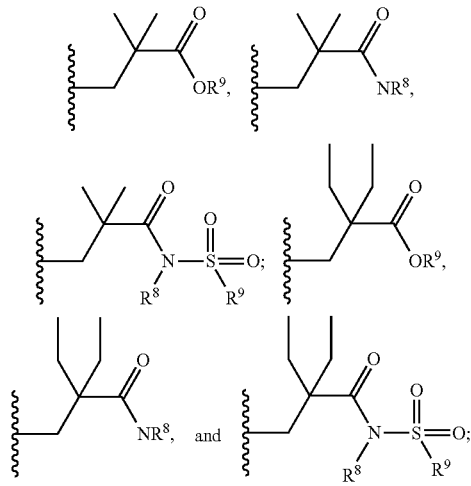

wherein $R^8$ is hydrogen, methyl, or pyridyl; and
$R^9$ is hydrogen or methyl.

In another preferred embodiment, the present invention relates to a compound as described in the embodiment immediately above, or a pharmaceutically acceptable salt thereof, wherein $X^2$ and $R^2$ together represents a moiety selected from

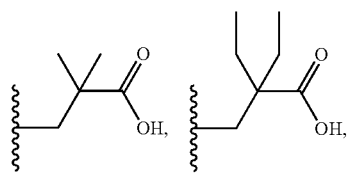

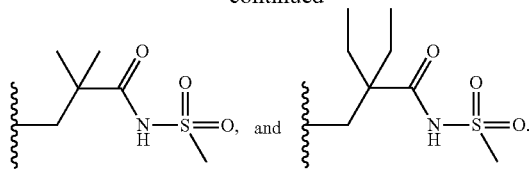

In another embodiment, the present invention relates to a compound as described in the broadest embodiment above, or a pharmaceutically acceptable salt thereof, wherein $X^2$ is —(CH$_2$)$_2$—, wherein one or more hydrogen atoms of said —(CH$_2$)$_2$— can be replaced by $C_{1-6}$ alkoxy.

In another embodiment, the present invention relates to a compound as described in the broadest embodiment above, or a pharmaceutically acceptable salt thereof, wherein $X^2$ is —(CH$_2$)$_2$—, wherein one or more hydrogen atoms of said —(CH$_2$)$_2$— can be replaced by $C_{1-6}$ alkoxy $C_{1-6}$ alkyl.

In another embodiment, the present invention relates to a compound as described in the broadest embodiment above, or a pharmaceutically acceptable salt thereof, wherein ring D is phenyl or 5 to 6-membered heteroaryl.

In another embodiment, the present invention relates to a compound as described in the broadest embodiment above, or a pharmaceutically acceptable salt thereof, wherein $X^3$, ring D, and $R^3$ taken together represent a moiety selected from:

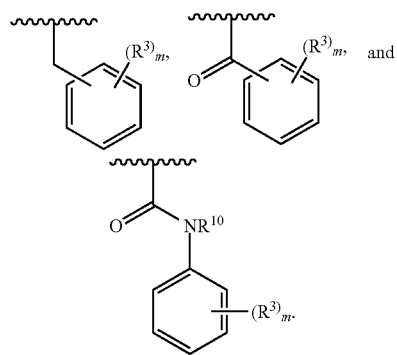

In another embodiment, the present invention relates to a compound as described in the broadest embodiment above, or a pharmaceutically acceptable salt thereof, wherein $X^1$ is —C(O)—; and
each $R^3$ when present is independently hydroxyl, halogen, cyano, carboxy, $C_{1-6}$ alkyl, $C_{1-6}$ alkoxy, $C_{1-6}$ alkoxy $C_{1-6}$ alkyl, $C_{3-10}$ cycloalkyl, 5 to 11-membered heterocyclyl, $C_{6-10}$ aryl, 5 to 11-membered heteroaryl, $R^9$—C(O)—, $R^9$—O—C(O)—, $N(R^8)_2$—, or $N(R^8)_2$—C(O)—,
wherein each $C_{1-6}$ alkyl, $C_{1-6}$ alkoxy, $C_{1-6}$ alkoxy $C_{1-6}$ alkyl, $C_{3-10}$ cycloalkyl, 5 to 11-membered heterocyclyl, $C_{6-10}$ aryl, and 5 to 11-membered heteroaryl of said $R^3$ substituent where possible is optionally substituted with one to four $R^6$ groups.

In another embodiment, the present invention relates to a compound as described in the embodiment immediately above, or a pharmaceutically acceptable salt thereof, wherein each $R^3$ when present is independently halogen, cyano, carboxy, $C_{1-6}$ alkyl, $C_{1-6}$ alkoxy, $C_{3-6}$ cycloalkyl, 4 to 8-membered heterocyclyl, phenyl, 5 to 6-membered heteroaryl, $R^9$—C(O)—, $R^9$—O—C(O)—, $N(R^8)_2$—, or $N(R^8)_2$—C(O)—, wherein each $C_{1-6}$ alkyl, $C_{1-6}$ alkoxy, $C_{3-6}$ cycloalkyl, 4 to 8-membered heterocyclyl, phenyl, and 5 to 6-membered heteroaryl of said R³ substituent where possible is optionally substituted with one to four groups selected from halogen, $C_{1-6}$ alkyl, $C_{1-6}$ acyl, and $C_{1-6}$ alkoxy.

In another embodiment, the present invention relates to a compound as described in the embodiment immediately above, or a pharmaceutically acceptable salt thereof, wherein m is zero or m is one; and R³ is bromo, chloro, fluoro, methyl, methylsulfonyl, methyl (methylsulfonyl)amino, trifluoromethyl, pyrrolidinyl, morpholinyl, phenyl, carboxyphenyl, amidophenyl, pyridyl, 2-methoxypyridyl, 3-methoxypyridyl, 4-methoxypyridyl, pyrimidine, or 2-methoxypyrimidinyl.

In another preferred embodiment, the present invention relates to a compound as described in the embodiment immediately above, or a pharmaceutically acceptable salt thereof, wherein m is zero.

In another embodiment, the present invention relates to a compound as described in the broadest embodiment above, or a pharmaceutically acceptable salt thereof, wherein R⁴ is hydrogen, $C_{1-6}$ alkyl, $C_{6-10}$ aryl, or 5 to 11-membered heteroaryl, wherein each $C_{1-6}$ alkyl, $C_{6-10}$ aryl, and 5 to 11-membered heteroaryl of said R⁴ where possible is optionally substituted with one to four R⁷ groups.

In a preferred embodiment, the present invention relates to a compound as described in the embodiment immediately above, or a pharmaceutically acceptable salt thereof, wherein X⁴ and R⁴ together represent:
(a) hydrogen or 2-propyl, or
(b) a moiety selected from:

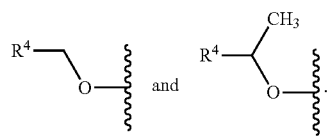

In another preferred embodiment, the present invention relates to a compound as described in the embodiment immediately above, or a pharmaceutically acceptable salt thereof, wherein R⁴ is hydrogen, $C_{1-6}$ alkyl, $C_{6-10}$ aryl, or 5 to 11-membered heteroaryl, wherein each $C_{1-6}$ alkyl, $C_{6-10}$ aryl, and 5 to 11-membered heteroaryl of said R⁴ where possible is optionally substituted with one to four R⁷ groups.

In another preferred embodiment, the present invention relates to a compound as described in the embodiment immediately above, or a pharmaceutically acceptable salt thereof, wherein R⁴ is trifluoromethyl, 1-methyl-1H-pyrazolyl, 1,3-thiazolyl, 2-methyl-1,3-thiazolyl, 4-methyl-1,3-thiazolyl, 2-methoxy-1,3-thiazolyl, 2-bromo-1,3-thiazolyl, 4-bromo-1,3-thiazolyl, 5-methyl-1,2,4-oxadiazolyl, phenyl, pyridyl, 2-fluoropyridyl, 3-chloropyridyl, 2-methylpyridyl, 4-methylpyridyl, 2-methoxypyridyl, 3-methoxypyridyl, 4-methoxypyridyl, 3,4-dimethoxypyridyl, 4-methoxy-3,5-dimethylpyridyl, pyrimidinyl, 2-amino-pyrimidinyl, quinolinyl, or 1,3-benzothiazolyl.

The following are representative compounds of the invention which can be made by the general synthetic schemes, the examples, and known methods in the art.

TABLE I

| Structure | Name | Observed m/e |
|---|---|---|
| 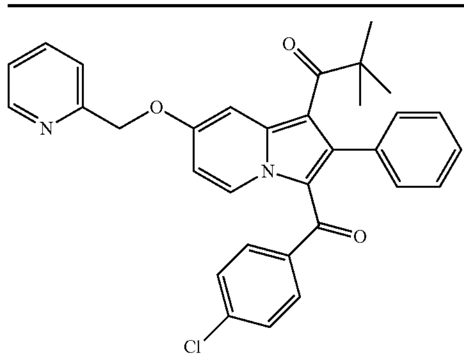 | 1-{3-[(4-Chlorophenyl)carbonyl]-2-phenyl-7-(pyridin-2-ylmethoxy)indolizin-1-yl}-2,2-dimethylpropan-1-one | 523.7 (M + H)+ |
| 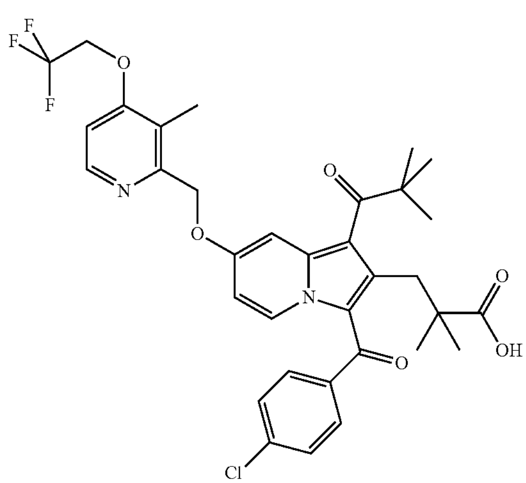 [SMILES: Cc1c(OCC(F)(F)F)ccnc1COc1ccn2c(C(=O)c3ccc(Cl)cc3)c(CC(C)(C)C(=O)O)c(C(=O)C(C)(C)C)c2c1] | 3-(3-[(4-Chlorophenyl)carbonyl]-1-(2,2-dimethylpropanoyl)-7-{[3-methyl-4-(2,2,2-trifluoroethoxy)pyridin-2-yl]methoxy}indolizin-2-yl)-2,2-dimethylpropanoic acid | 659.2 (M)+ |

TABLE I-continued

| Structure | Name | Observed m/e |
|---|---|---|
| 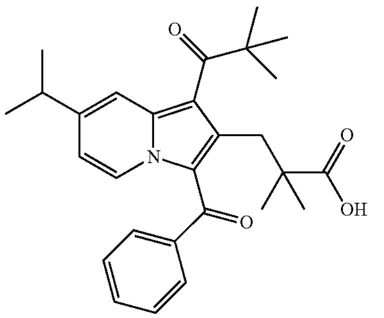 [SMILES: CC(C)c1ccn2c(C(=O)c3ccccc3)c(CC(C)(C)C(=O)O)c(C(=O)C(C)(C)C)c2c1] | 3-[1-(2,2-Dimethylpropanoyl)-3-(phenylcarbonyl)-7-(propan-2-yl)indolizin-2-yl]-2,2-dimethylpropanoic acid | 448.2 (M)+ |
| 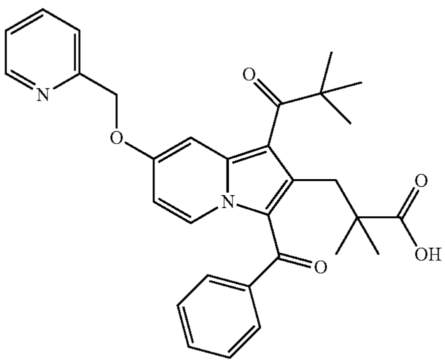 [SMILES: CC(C)(C)C(=O)c1c(CC(C)(C)C(=O)O)c(C(=O)c2ccccc2)n2ccc(OCc3ccccn3)cc12] | 3-[1-(2,2-Dimethylpropanoyl)-3-(phenylcarbonyl)-7-(pyridin-2-ylmethoxy)indolizin-2-yl]-2,2-dimethylpropanoic acid | 513.7 (M + H)+ |
| 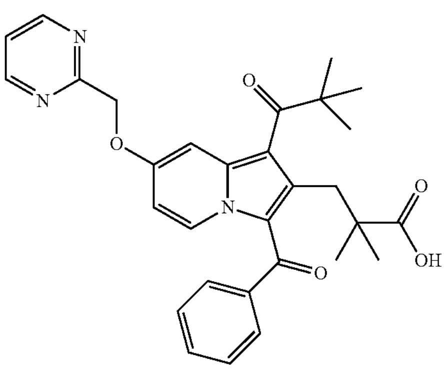 [SMILES: CC(C)(C)C(=O)c1c(CC(C)(C)C(=O)O)c(C(=O)c2ccccc2)n2ccc(OCc3ncccn3)cc12] | 3-[1-(2,2-Dimethylpropanoyl)-3-(phenylcarbonyl)-7-(pyrimidin-2-ylmethoxy)indolizin-2-yl]-2,2-dimethylpropanoic acid | 548.2 (M)+ |
| 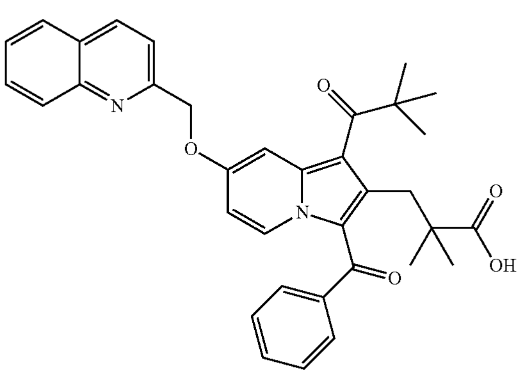 [SMILES: CC(C)(C)C(=O)c1c(CC(C)(C)C(=O)O)c(C(=O)c2ccccc2)n2ccc(OCc3ccc4ccccc4n3)cc12] | 3-[1-(2,2-Dimethylpropanoyl)-3-(phenylcarbonyl)-7-(quinolin-2-ylmethoxy)indolizin-2-yl]-2,2-dimethylpropanoic acid | 563.2 (M + H)+ |

TABLE I-continued

| Structure | Name | Observed m/e |
|---|---|---|
| 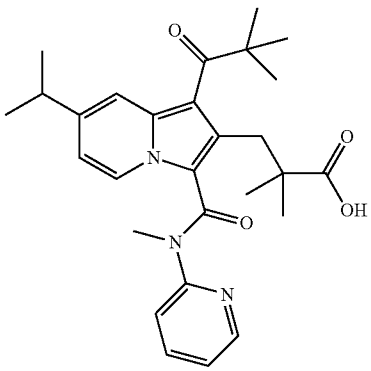 [SMILES: CC(C)c1ccn2c(C(=O)N(C)c3ccccn3)c(CC(C)(C)C(=O)O)c(C(=O)C(C)(C)C)c2c1] | 3-[1-(2,2-Dimethylpropanoyl)-3-[methyl(pyridin-2-yl)carbamoyl]-7-(propan-2-yl)indolizin-2-yl]-2,2-dimethylpropanoic acid | 478.2 (M)+ |
| 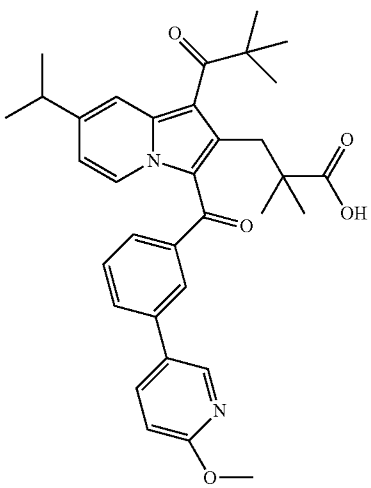 [SMILES: COc1ccc(-c2cccc(C(=O)c3c(CC(C)(C)C(=O)O)c(C(=O)C(C)(C)C)c4cc(C(C)C)ccn34)c2)cn1] | 3-[1-(2,2-Dimethylpropanoyl)-3-{[3-(6-methoxypyridin-3-yl)phenyl]carbonyl}-7-(propan-2-yl)indolizin-2-yl]-2,2-dimethylpropanoic acid | 555.4 (M + H)+ |
| 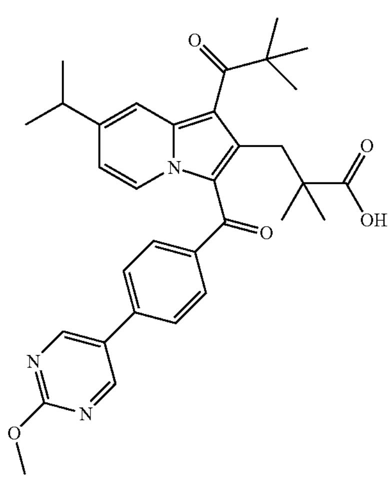 [SMILES: COc1ncc(-c2ccc(C(=O)c3c(CC(C)(C)C(=O)O)c(C(=O)C(C)(C)C)c4cc(C(C)C)ccn34)cc2)cn1] | 3-[1-(2,2-Dimethylpropanoyl)-3-{[4-(2-methoxypyrimidin-5-yl)phenyl]carbonyl}-7-(propan-2-yl)indolizin-2-yl]-2,2-dimethylpropanoic acid | 556.2 (M + H)+ |

TABLE I-continued

| Structure | Name | Observed m/e |
|---|---|---|
| 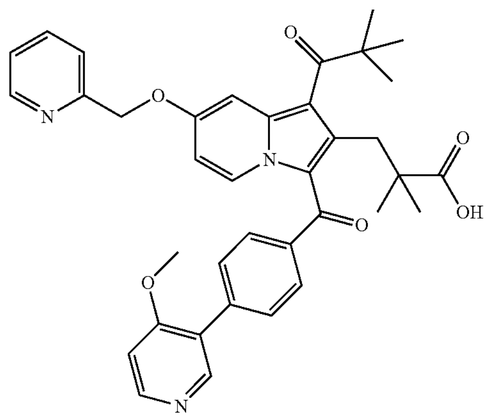 [SMILES: COc1ccncc1-c1ccc(C(=O)c2c(CC(C)(C)C(=O)O)c(C(=O)C(C)(C)C)c3cc(OCc4ccccn4)ccn23)cc1] | 3-[1-(2,2-Dimethylpropanoyl)-3-{[4-(4-methoxypyridin-3-yl)phenyl]carbonyl}-7-(pyridin-2-ylmethoxy)indolizin-2-yl]-2,2-dimethylpropanoic acid | 620.2 (M + H)+ |
| 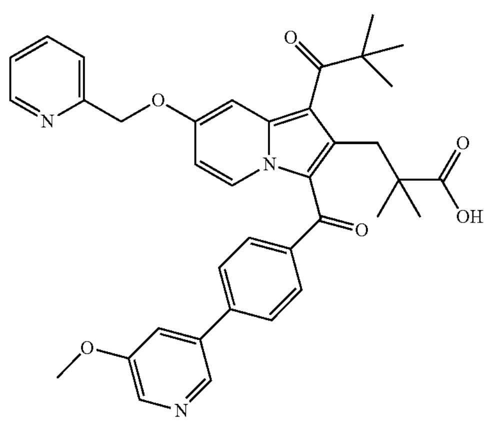 [SMILES: COc1cncc(-c2ccc(C(=O)c3c(CC(C)(C)C(=O)O)c(C(=O)C(C)(C)C)c4cc(OCc5ccccn5)ccn34)cc2)c1] | 3-[1-(2,2-Dimethylpropanoyl)-3-{[4-(5-methoxypyridin-3-yl)phenyl]carbonyl}-7-(pyridin-2-ylmethoxy)indolizin-2-yl]-2,2-dimethylpropanoic acid | 620.2 (M + H)+ |
| 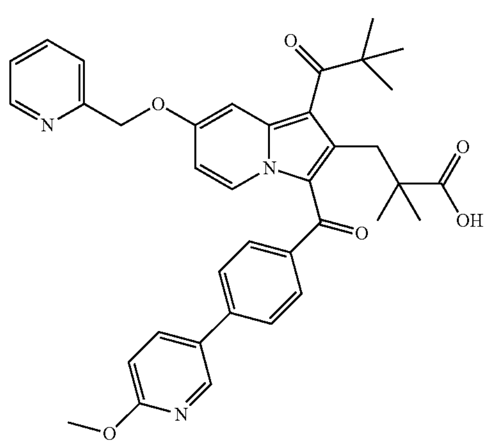 [SMILES: COc1ccc(-c2ccc(C(=O)c3c(CC(C)(C)C(=O)O)c(C(=O)C(C)(C)C)c4cc(OCc5ccccn5)ccn34)cc2)cn1] | 3-[1-(2,2-Dimethylpropanoyl)-3-{[4-(6-methoxypyridin-3-yl)phenyl]carbonyl}-7-(pyridin-2-ylmethoxy)indolizin-2-yl]-2,2-dimethylpropanoic acid | 620.2 (M + H)+ |

TABLE I-continued
| Structure | Name | Observed m/e |
|---|---|---|
| 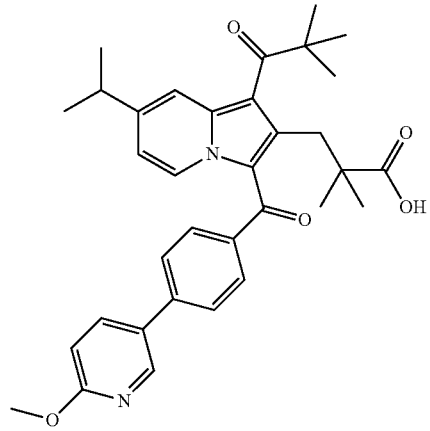 [SMILES: COc1ccc(-c2ccc(C(=O)c3c(CC(C)(C)C(=O)O)c(C(=O)C(C)(C)C)c4cc(C(C)C)ccn34)cc2)cn1] | 3-[1-(2,2-Dimethylpropanoyl)-3-{[4-(6-methoxypyridin-3-yl)phenyl]carbonyl}-7-(propan-2-yl)indolizin-2-yl]-2,2-dimethylpropanoic acid | 555.2 (M + H)+ |
| 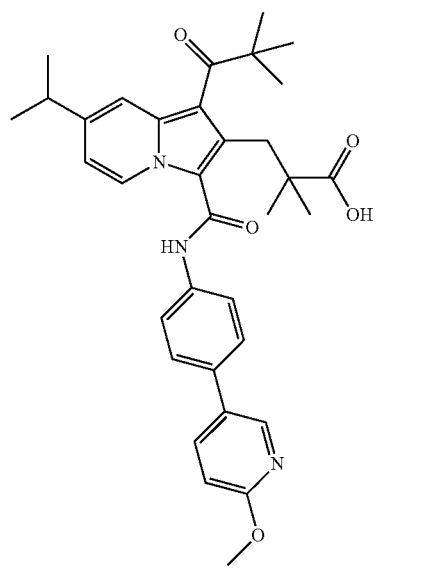 [SMILES: COc1ccc(-c2ccc(NC(=O)c3c(CC(C)(C)C(=O)O)c(C(=O)C(C)(C)C)c4cc(C(C)C)ccn34)cc2)cn1] | 3-[1-(2,2-Dimethylpropanoyl)-3-{[4-(6-methoxypyridin-3-yl)phenyl]carbamoyl}-7-(propan-2-yl)indolizin-2-yl]-2,2-dimethylpropanoic acid | 570.2 (M)+ |
| 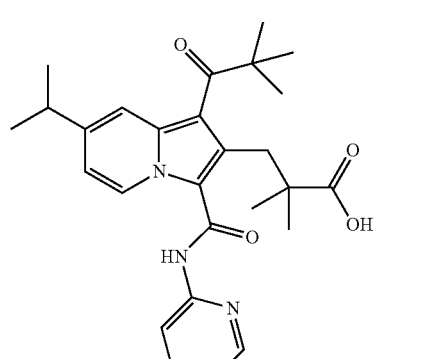 | 3-[1-(2,2-Dimethylpropanoyl)-7-(propan-2-yl)-3-(pyridin-2-ylcarbamoyl)indolizin-2-yl]-2,2-dimethylpropanoic acid | 464.2 (M)+ |

TABLE I-continued

| Structure | Name | Observed m/e |
|---|---|---|
| 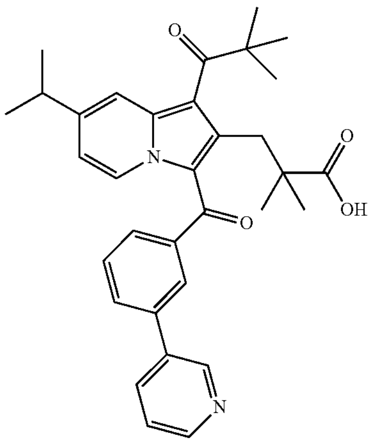 [SMILES: CC(C)c1ccn2c(C(=O)c3cccc(-c4cccnc4)c3)c(CC(C)(C)C(=O)O)c(C(=O)C(C)(C)C)c2c1] | 3-[1-(2,2-Dimethylpropanoyl)-7-(propan-2-yl)-3-{[3-(pyridin-3-yl)phenyl]carbonyl}indolizin-2-yl]-2,2-dimethylpropanoic acid | 525.2 (M + H)+ |
| 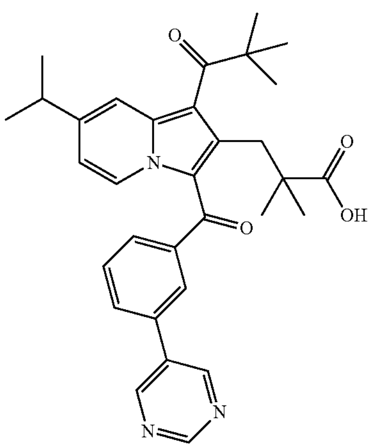 [SMILES: CC(C)c1ccn2c(C(=O)c3cccc(-c4cncnc4)c3)c(CC(C)(C)C(=O)O)c(C(=O)C(C)(C)C)c2c1] | 3-[1-(2,2-Dimethylpropanoyl)-7-(propan-2-yl)-3-{[3-(pyrimidin-5-yl)phenyl]carbonyl}indolizin-2-yl]-2,2-dimethylpropanoic acid | 526.2 (M + H)+ |
| 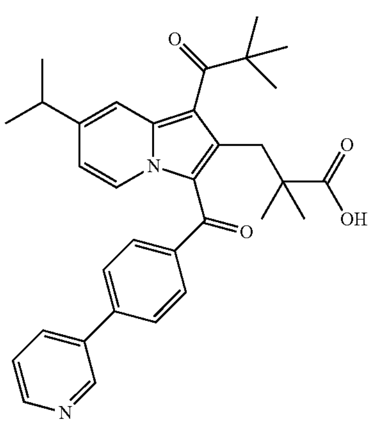 [SMILES: CC(C)c1ccn2c(C(=O)c3ccc(-c4cccnc4)cc3)c(CC(C)(C)C(=O)O)c(C(=O)C(C)(C)C)c2c1] | 3-[1-(2,2-Dimethylpropanoyl)-7-(propan-2-yl)-3-{[4-(pyridin-3-yl)phenyl]carbonyl}indolizin-2-yl]-2,2-dimethylpropanoic acid | 525.2 (M + H)+ |

TABLE I-continued

| Structure | Name | Observed m/e |
|---|---|---|
| 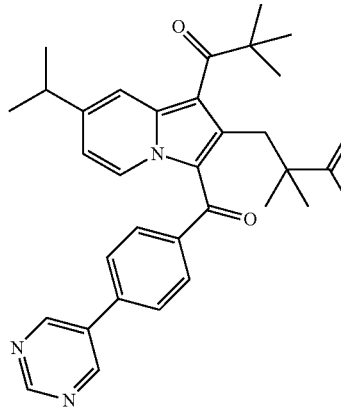 | 3-[1-(2,2-Dimethylpropanoyl)-7-(propan-2-yl)-3-{[4-(pyrimidin-5-yl)phenyl]carbonyl}indolizin-2-yl]-2,2-dimethylpropanoic acid | 526.2 (M + H)+ |
| 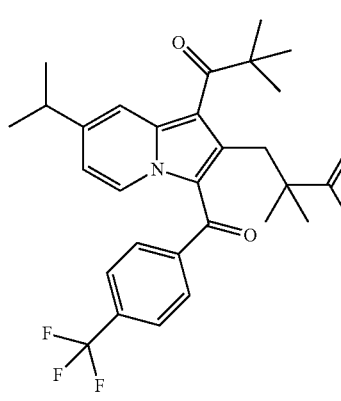 | 3-[1-(2,2-Dimethylpropanoyl)-7-(propan-2-yl)-3-{[4-(trifluoromethyl)phenyl]carbonyl}indolizin-2-yl]-2,2-dimethylpropanoic acid | 514.2 (M)+ |
| 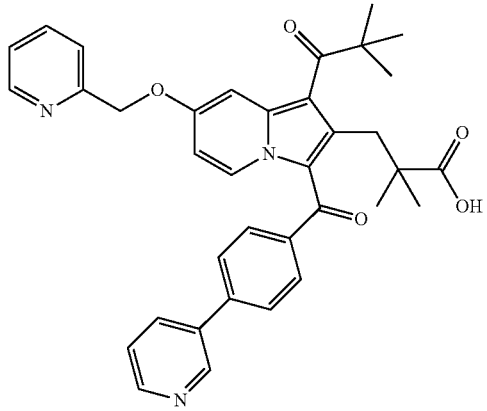 [SMILES: CC(C)(C)C(=O)c1c(CC(C)(C)C(=O)O)c(C(=O)c2ccc(-c3cccnc3)cc2)n2ccc(OCc3ccccn3)cc12] | 3-[1-(2,2-Dimethylpropanoyl)-7-(pyridin-2-ylmethoxy)-3-{[4-(pyridin-3-yl)phenyl]carbonyl}indolizin-2-yl]-2,2-dimethylpropanoic acid | 590.2 (M + H)+ |
| 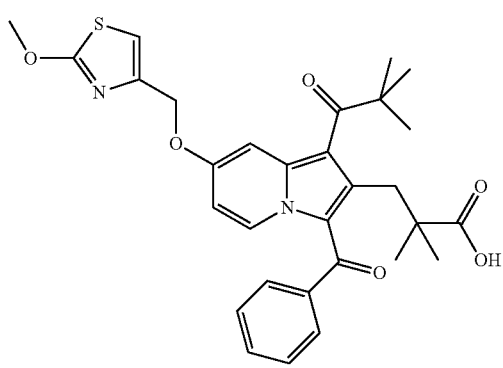 [SMILES: COc1nc(COc2ccn3c(C(=O)c4ccccc4)c(CC(C)(C)C(=O)O)c(C(=O)C(C)(C)C)c3c2)cs1] | 3-[1-(2,2-Dimethylpropanoyl)-7-[(2-methoxy-1,3-thiazol-4-yl)methoxy]-3-(phenylcarbonyl)indolizin-2-yl]-2,2-dimethylpropanoic acid | 549.20 (M)+ |

TABLE I-continued

| Structure | Name | Observed m/e |
|---|---|---|
| 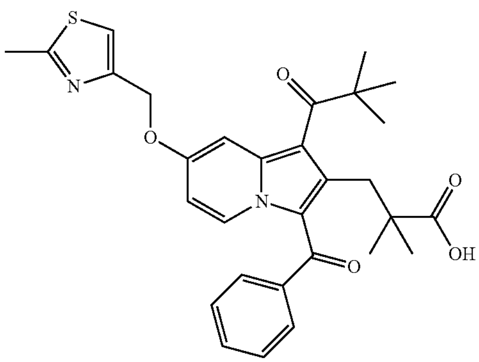 [SMILES: Cc1nc(COc2ccn3c(C(=O)c4ccccc4)c(CC(C)(C)C(=O)O)c(C(=O)C(C)(C)C)c3c2)cs1] | 3-[1-(2,2-Dimethylpropanoyl)-7-[(2-methyl-1,3-thiazol-4-yl)methoxy]-3-(phenylcarbonyl)indolizin-2-yl]-2,2-dimethylpropanoic acid | 533.2 (M + H)+ |
| 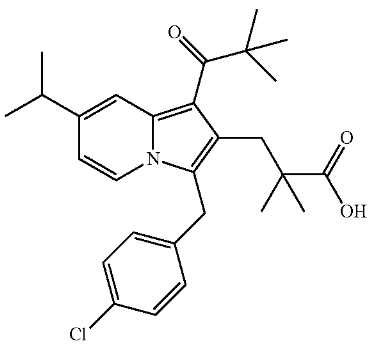 [SMILES: CC(C)c1ccn2c(Cc3ccc(Cl)cc3)c(CC(C)(C)C(=O)O)c(C(=O)C(C)(C)C)c2c1] | 3-[3-(4-Chlorobenzyl)-1-(2,2-dimethylpropanoyl)-7-(propan-2-yl)indolizin-2-yl]-2,2-dimethylpropanoic acid | 468.5 (M)+ |
| 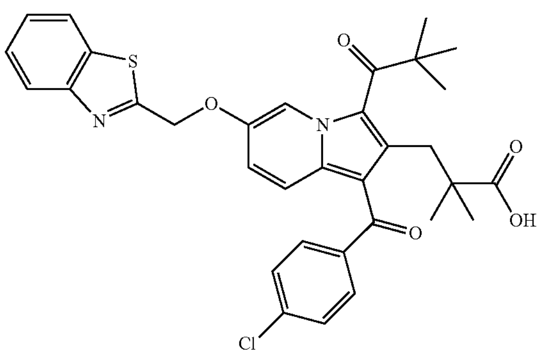 [SMILES: CC(C)(C)C(=O)c1c(CC(C)(C)C(=O)O)c(C(=O)c2ccc(Cl)cc2)c2ccc(OCc3nc4ccccc4s3)cn12] | 3-[6-(1,3-Benzothiazol-2-ylmethoxy)-1-[(4-chlorophenyl)carbonyl]-3-(2,2-dimethylpropanoyl)indolizin-2-yl]-2,2-dimethylpropanoic acid | 603.2 (M)+ |
| 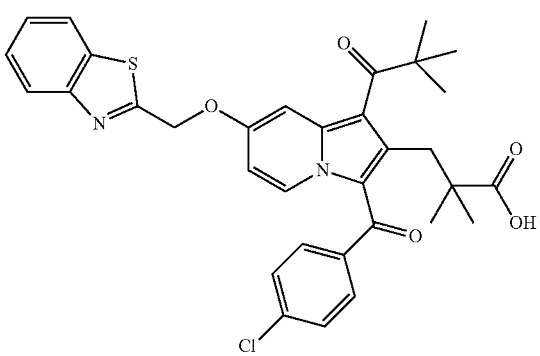 [SMILES: CC(C)(C)C(=O)c1c(CC(C)(C)C(=O)O)c(C(=O)c2ccc(Cl)cc2)n2ccc(OCc3nc4ccccc4s3)cc12] | 3-[7-(1,3-Benzothiazol-2-ylmethoxy)-3-[(4-chlorophenyl)carbonyl]-1-(2,2-dimethylpropanoyl)indolizin-2-yl]-2,2-dimethylpropanoic acid | 603.2 (M)+ |

TABLE I-continued

| Structure | Name | Observed m/e |
|---|---|---|
| 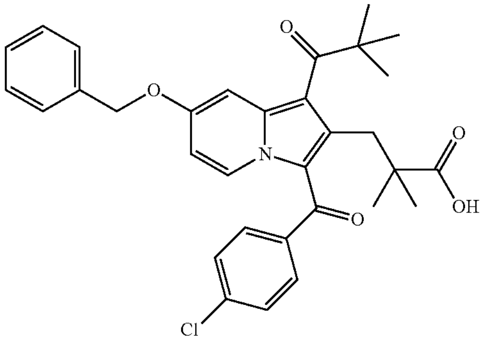 [SMILES: CC(C)(C)C(=O)c1c(CC(C)(C)C(=O)O)c(C(=O)c2ccc(Cl)cc2)n2ccc(OCc3ccccc3)cc12] | 3[7-(Benzyloxy)-3-[(4-chlorophenyl)carbonyl]-1-(2,2-dimethylpropanoyl)indolizin-2-yl]-2,2-dimethylpropanoic acid | 546.2 (M)+ |
| 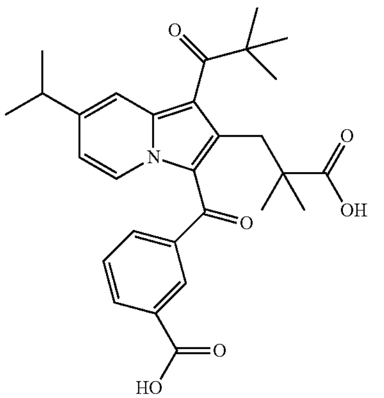 [SMILES: CC(C)c1ccn2c(C(=O)c3cccc(C(=O)O)c3)c(CC(C)(C)C(=O)O)c(C(=O)C(C)(C)C)c2c1] | 3-{[2-(2-Carboxy-2-methylpropyl)-1-(2,2-dimethylpropanoyl)-7-(propan-2-yl)indolizin-3-yl]carbonyl}benzoic acid | 492.2 (M + H)+ |
| 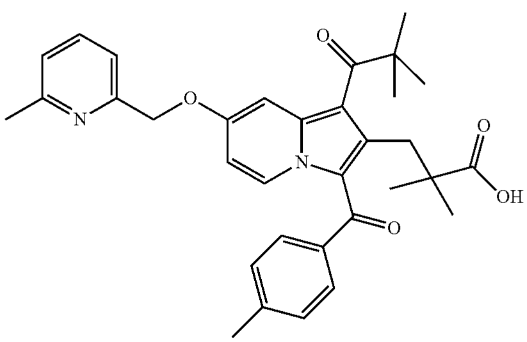 [SMILES: Cc1ccc(C(=O)c2c(CC(C)(C)C(=O)O)c(C(=O)C(C)(C)C)c3cc(OCc4cccc(C)n4)ccn23)cc1] | 3-{1-(2,2-Dimethylpropanoyl)-3-[(4-methylphenyl)carbonyl]-7-[(6-methylpyridin-2-yl)methoxy]indolizin-2-yl}-2,2-dimethylpropanoic acid | 541.2 (M)+ |
| 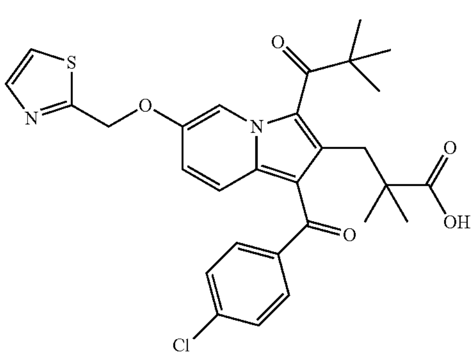 [SMILES: CC(C)(C)C(=O)c1c(CC(C)(C)C(=O)O)c(C(=O)c2ccc(Cl)cc2)c2ccc(OCc3nccs3)cn12] | 3-{1-[(4-Chlorophenyl)carbonyl]-3-(2,2-dimethylpropanoyl)-6-(1,3-thiazol-2-ylmethoxy)indolizin-2-yl}-2,2-dimethylpropanoic acid | 553.2 (M)+ |

TABLE I-continued

| Structure | Name | Observed m/e |
|---|---|---|
| 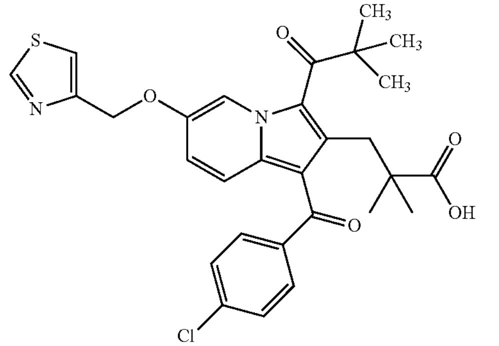 [SMILES: CC(C)(C)C(=O)c1c(CC(C)(C)C(=O)O)c(C(=O)c2ccc(Cl)cc2)c2ccc(OCc3cscn3)cn12] | 3-{1-[(4-Chlorophenyl)carbonyl]-3-(2,2-dimethylpropanoyl)-6-(1,3-thiazol-4-ylmethoxy)indolizin-2-yl}-2,2-dimethylpropanoic acid | 553.2 (M)+ |
| 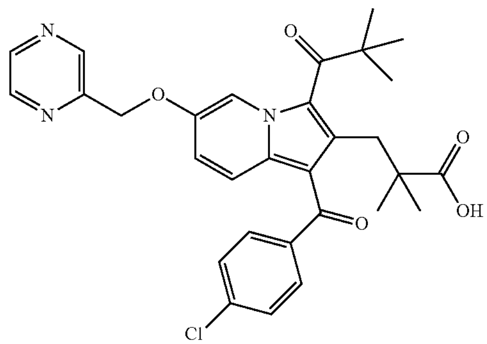 | 3-{1-[(4-Chlorophenyl)carbonyl]-3-(2,2-dimethylpropanoyl)-6-(pyrazin-2-ylmethoxy)indolizin-2-yl}-2,2-dimethylpropanoic acid | 548.2 (M)+ |
| 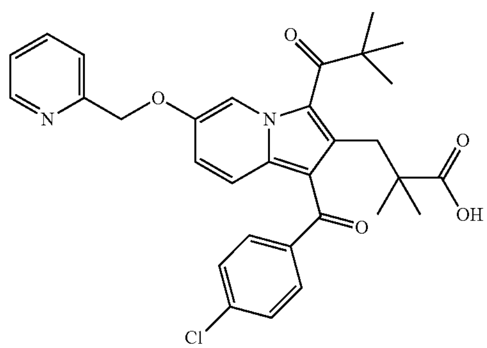 [SMILES: CC(C)(C)C(=O)c1c(CC(C)(C)C(=O)O)c(C(=O)c2ccc(Cl)cc2)c2ccc(OCc3ccccn3)cn12] | 3-{1-[(4-Chlorophenyl)carbonyl]-3-(2,2-dimethylpropanoyl)-6-(pyridin-2-ylmethoxy)indolizin-2-yl}-2,2-dimethylpropanoic acid | 547.2 (M)+ |
| 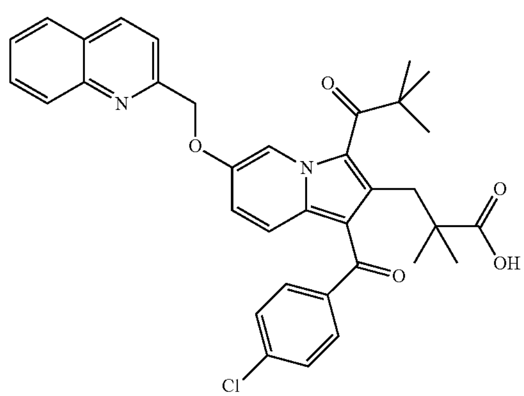 [SMILES: CC(C)(C)C(=O)c1c(CC(C)(C)C(=O)O)c(C(=O)c2ccc(Cl)cc2)c2ccc(OCc3ccc4ccccc4n3)cn12] | 3-{1-[(4-Chlorophenyl)carbonyl]-3-(2,2-dimethylpropanoyl)-6-(quinolin-2-ylmethoxy)indolizin-2-yl}-2,2-dimethylpropanoic acid | 597.2 (M)+ |

TABLE I-continued

| Structure | Name | Observed m/e |
|---|---|---|
| 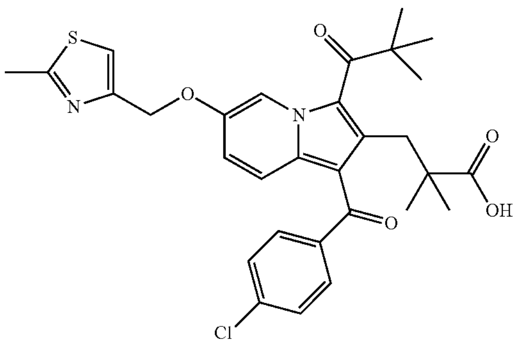 [SMILES: Cc1nc(COc2ccc3c(C(=O)c4ccc(Cl)cc4)c(CC(C)(C)C(=O)O)c(C(=O)C(C)(C)C)n3c2)cs1] | 3-{1-[(4-Chlorophenyl)carbonyl]-3-(2,2-dimethylpropanoyl)-6-[(2-methyl-1,3-thiazol-4-yl)methoxy]indolizin-2-yl}-2,2-dimethylpropanoic acid | 567.2 (M)+ |
| 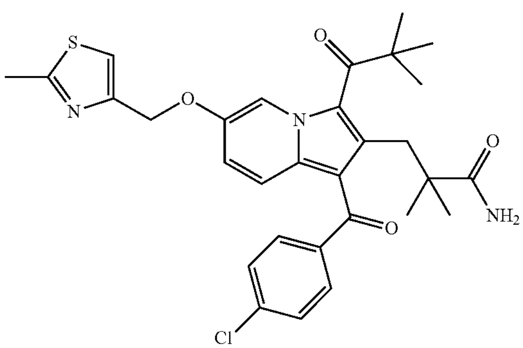 [SMILES: Cc1nc(COc2ccc3c(C(=O)c4ccc(Cl)cc4)c(CC(C)(C)C(N)=O)c(C(=O)C(C)(C)C)n3c2)cs1] | 3-{1-[(4-Chlorophenyl)carbonyl]-3-(2,2-dimethylpropanoyl)-6-[(2-methyl-1,3-thiazol-4-yl)methoxy]indolizin-2-yl}-2,2-dimethylpropanamide | 566.8 (M)+ |
| 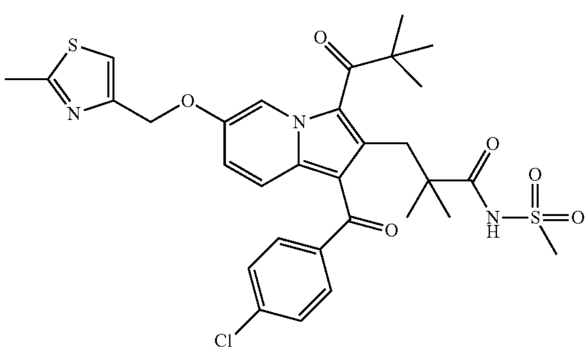 [SMILES: Cc1nc(COc2ccc3c(C(=O)c4ccc(Cl)cc4)c(CC(C)(C)C(=O)NS(C)(=O)=O)c(C(=O)C(C)(C)C)n3c2)cs1] | 3-{1-[(4-Chlorophenyl)carbonyl]-3-(2,2-dimethylpropanoyl)-6-[(2-methyl-1,3-thiazol-4-yl)methoxy]indolizin-2-yl}-2,2-dimethyl-N-(methylsulfonyl)propanamide | 644.5 (M)+ |
| 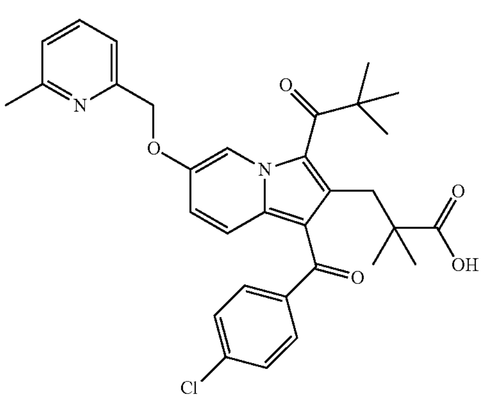 [SMILES: Cc1cccc(COc2ccc3c(C(=O)c4ccc(Cl)cc4)c(CC(C)(C)C(=O)O)c(C(=O)C(C)(C)C)n3c2)n1] | 3-{1-[(4-Chlorophenyl)carbonyl]-3-(2,2-dimethylpropanoyl)-6-[(6-methylpyridin-2-yl)methoxy]indolizin-2-yl}-2,2-dimethylpropanoic acid | 561.2 (M)+ |

TABLE I-continued

| Structure | Name | Observed m/e |
|---|---|---|
| 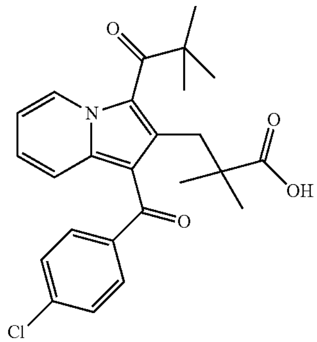 [SMILES: CC(C)(C)C(=O)c1c(CC(C)(C)C(=O)O)c(C(=O)c2ccc(Cl)cc2)c2ccccn12] | 3-{1-[(4-Chlorophenyl)carbonyl]-3-(2,2-dimethylpropanoyl)indolizin-2-yl}-2,2-dimethylpropanoic acid | 440.2 (M)+ |
| 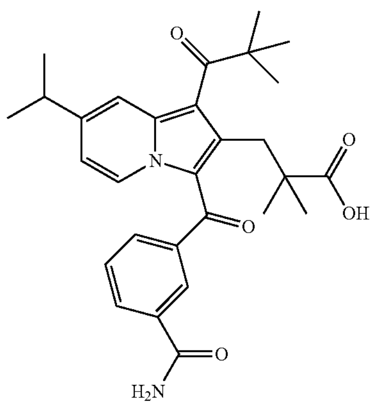 [SMILES: CC(C)c1ccn2c(C(=O)c3cccc(C(N)=O)c3)c(CC(C)(C)C(=O)O)c(C(=O)C(C)(C)C)c2c1] | 3-{3-[(3-Carbamoylphenyl)carbonyl]-1-(2,2-dimethylpropanoyl)-7-(propan-2-yl)indolizin-2-yl}-2,2-dimethylpropanoic acid | 491.2 (M + H)+ |
| 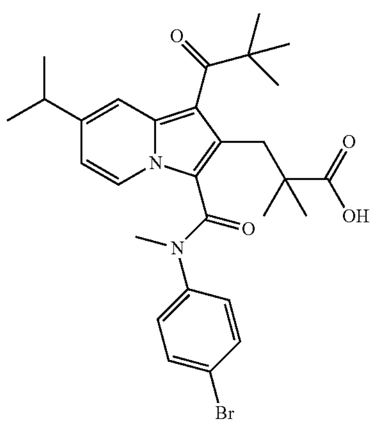 [SMILES: CC(C)c1ccn2c(C(=O)N(C)c3ccc(Br)cc3)c(CC(C)(C)C(=O)O)c(C(=O)C(C)(C)C)c2c1] | 3-{3-[(4-Bromophenyl)(methyl)carbamoyl]-1-(2,2-dimethylpropanoyl)-7-(propan-2-yl)indolizin-2-yl}-2,2-dimethylpropanoic acid | 555.2 (M)+ |
| 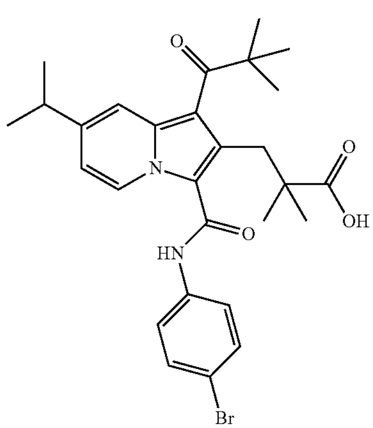 [SMILES: CC(C)c1ccn2c(C(=O)Nc3ccc(Br)cc3)c(CC(C)(C)C(=O)O)c(C(=O)C(C)(C)C)c2c1] | 3-{3-[(4-Bromophenyl)carbamoyl]-1-(2,2-dimethylpropanoyl)-7-(propan-2-yl)indolizin-2-yl}-2,2-dimethylpropanoic acid | 543.20 (M + H)+ |

TABLE I-continued

| Structure | Name | Observed m/e |
|---|---|---|
| 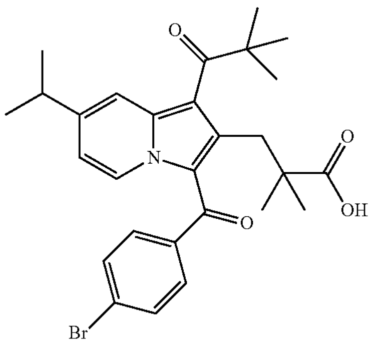 [SMILES: CC(C)c1ccn2c(C(=O)c3ccc(Br)cc3)c(CC(C)(C)C(=O)O)c(C(=O)C(C)(C)C)c2c1] | 3-{3-[(4-Bromophenyl)carbonyl]-1-(2,2-dimethylpropanoyl)-7-(propan-2-yl)indolizin-2-yl}-2,2-dimethylpropanoic acid | 526.2 (M)+ |
| 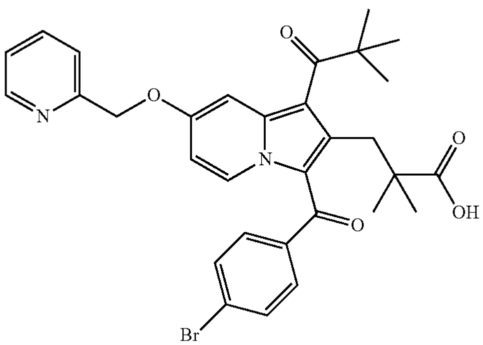 [SMILES: CC(C)(C)C(=O)c1c(CC(C)(C)C(=O)O)c(C(=O)c2ccc(Br)cc2)n2ccc(OCc3ccccn3)cc12] | 3-{3-[(4-Bromophenyl)carbonyl]-1-(2,2-dimethylpropanoyl)-7-(pyridin-2-ylmethoxy)indolizin-2-yl}-2,2-dimethylpropanoic acid | 591.2 (M)+ |
| 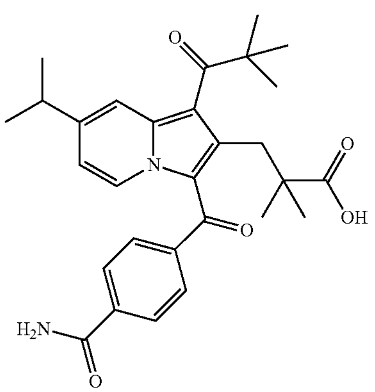 [SMILES: CC(C)c1ccn2c(C(=O)c3ccc(C(N)=O)cc3)c(CC(C)(C)C(=O)O)c(C(=O)C(C)(C)C)c2c1] | 3-{3-[(4-Carbamoylphenyl)carbonyl]-1-(2,2-dimethylpropanoyl)-7-(propan-2-yl)indolizin-2-yl}-2,2-dimethylpropanoic acid | 491.2 (M + H)+ |
| 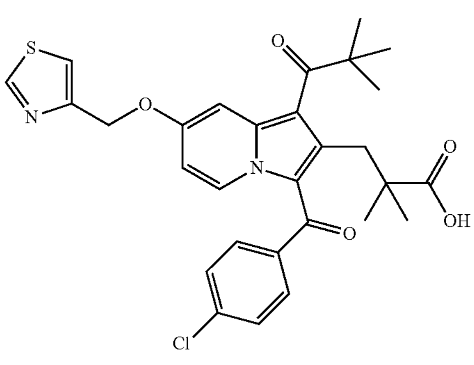 [SMILES: CC(C)(C)C(=O)c1c(CC(C)(C)C(=O)O)c(C(=O)c2ccc(Cl)cc2)n2ccc(OCc3cscn3)cc12] | 3-{3-[(4-Chlorophenyl)carbonyl]-1-(2,2-dimethylpropanoyl)-7-(1,3-thiazol-4-ylmethoxy)indolizin-2-yl}-2,2-dimethylpropanoic acid | 553.2 (M)+ |

TABLE I-continued

| Structure | Name | Observed m/e |
|---|---|---|
| 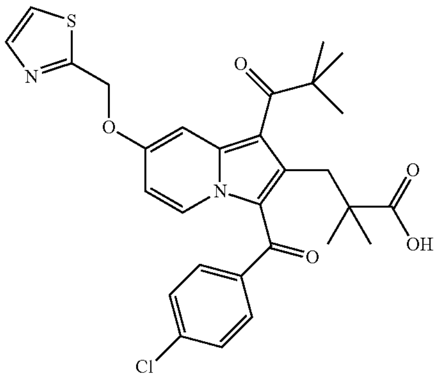 [SMILES: CC(C)(C)C(=O)c1c(CC(C)(C)C(=O)O)c(C(=O)c2ccc(Cl)cc2)n2ccc(OCc3nccs3)cc12] | 3-{3-[(4-Chlorophenyl)carbonyl]-1-(2,2-dimethylpropanoyl)-7-(1,3-thiazol-2-ylmethoxy)indolizin-2-yl}-2,2-dimethylpropanoic acid | 553.2 (M + H)+ |
| 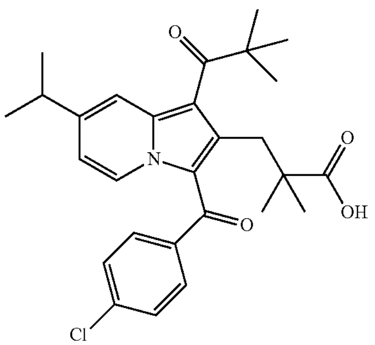 [SMILES: CC(C)c1ccn2c(C(=O)c3ccc(Cl)cc3)c(CC(C)(C)C(=O)O)c(C(=O)C(C)(C)C)c2c1] | 3-{3-[(4-Chlorophenyl)carbonyl]-1-(2,2-dimethylpropanoyl)-7-(propan-2-yl)indolizin-2-yl}-2,2-dimethylpropanoic acid | 482.2 (M)+ |
| 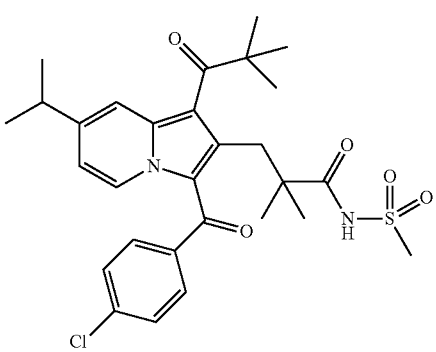 [SMILES: CC(C)c1ccn2c(C(=O)c3ccc(Cl)cc3)c(CC(C)(C)C(=O)NS(C)(=O)=O)c(C(=O)C(C)(C)C)c2c1] | 3-{3-[(4-Chlorophenyl)carbonyl]-1-(2,2-dimethylpropanoyl)-7-(propan-2-yl)indolizin-2-yl}-2,2-dimethyl-N-(methylsulfonyl)propanamide | 559.20 (M)+ |
| 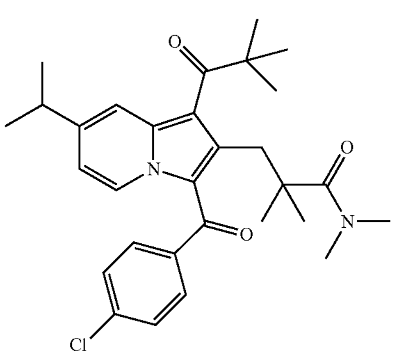 | 3-{3-[(4-Chlorophenyl)carbonyl]-1-(2,2-dimethylpropanoyl)-7-(propan-2-yl)indolizin-2-yl}-N,N,2,2-tetramethylpropanamide | 590.8 (M + H)+ |

TABLE I-continued

| Structure | Name | Observed m/e |
|---|---|---|
| 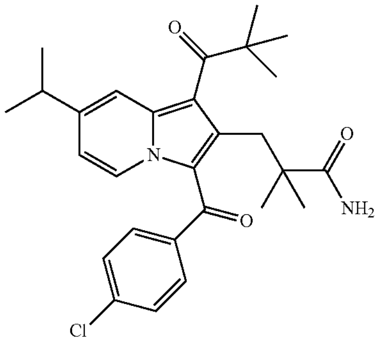 [SMILES: CC(C)c1ccn2c(C(=O)c3ccc(Cl)cc3)c(CC(C)(C)C(N)=O)c(C(=O)C(C)(C)C)c2c1] | 3-{3-[(4-Chlorophenyl)carbonyl]-1-(2,2-dimethylpropanoyl)-7-(propan-2-yl)indolizin-2-yl}-2,2-dimethylpropanamide | 481.2 (M)+ |
| 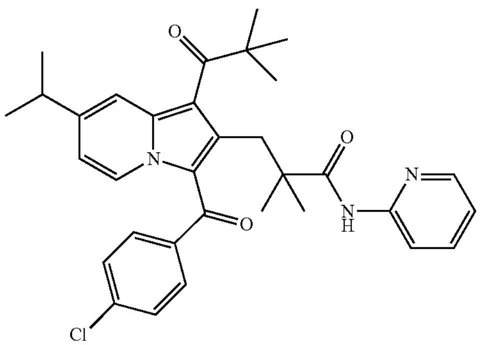 | 3-{3-[(4-Chlorophenyl)carbonyl]-1-(2,2-dimethylpropanoyl)-7-(propan-2-yl)indolizin-2-yl}-2,2-dimethyl-N-(pyridin-2-yl)propanamide | 558.20 (M)+ |
| 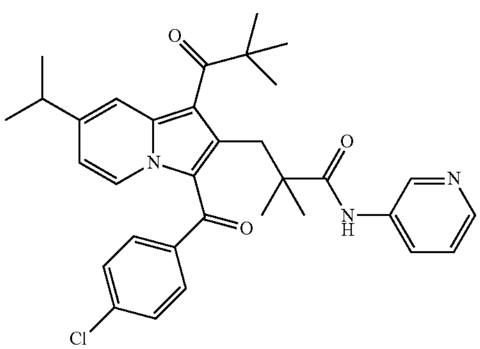 [SMILES: CC(C)c1ccn2c(C(=O)c3ccc(Cl)cc3)c(CC(C)(C)C(=O)Nc3cccnc3)c(C(=O)C(C)(C)C)c2c1] | 3-{3-[(4-Chlorophenyl)carbonyl]-1-(2,2-dimethylpropanoyl)-7-(propan-2-yl)indolizin-2-yl}-2,2-dimethyl-N-(pyridin-3-yl)propanamide | 558.20 (M)+ |
| 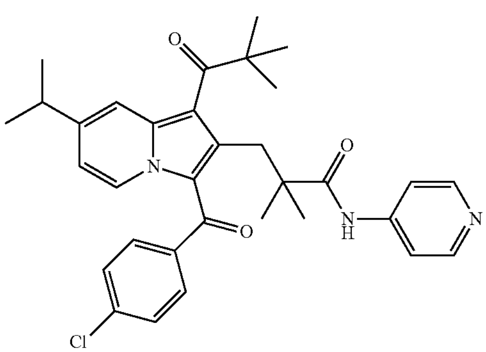 [SMILES: CC(C)c1ccn2c(C(=O)c3ccc(Cl)cc3)c(CC(C)(C)C(=O)Nc3ccncc3)c(C(=O)C(C)(C)C)c2c1] | 3-{3-[(4-Chlorophenyl)carbonyl]-1-(2,2-dimethylpropanoyl)-7-(propan-2-yl)indolizin-2-yl}-2,2-dimethyl-N-(pyridin-4-yl)propanamide | 558.20 (M)+ |

TABLE I-continued

| Structure | Name | Observed m/e |
|---|---|---|
| 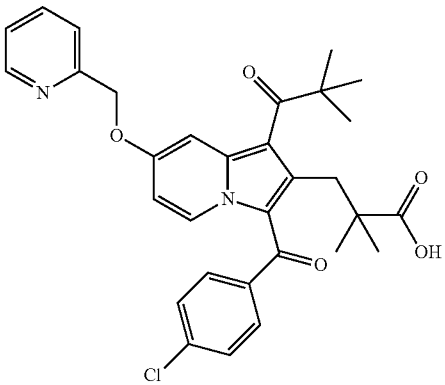 | 3-{3-[(4-Chlorophenyl)carbonyl]-1-(2,2-dimethylpropanoyl)-7-(pyridin-2-ylmethoxy)indolizin-2-yl}-2,2-dimethylpropanoic acid | 547.20 (M)+ |
| 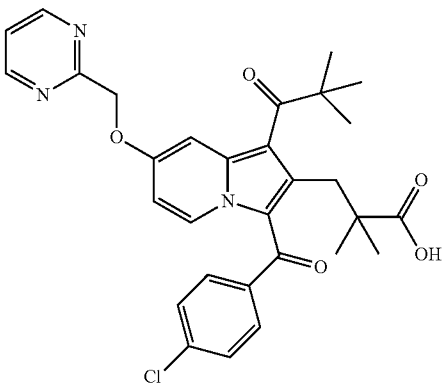 [SMILES: CC(C)(C)C(=O)c1c(CC(C)(C)C(=O)O)c(C(=O)c2ccc(Cl)cc2)n2ccc(OCc3ccccn3)cc12] | 3-{3-[(4-Chlorophenyl)carbonyl]-1-(2,2-dimethylpropanoyl)-7-(pyrimidin-2-ylmethoxy)indolizin-2-yl}-2,2-dimethylpropanoic acid | 548.2 (M)+ |
| 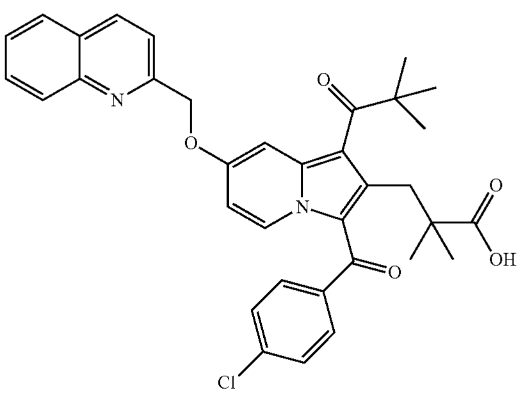 [SMILES: CC(C)(C)C(=O)c1c(CC(C)(C)C(=O)O)c(C(=O)c2ccc(Cl)cc2)n2ccc(OCc3ccc4ccccc4n3)cc12] | 3-{3-[(4-Chlorophenyl)carbonyl]-1-(2,2-dimethylpropanoyl)-7-(quinolin-2-ylmethoxy)indolizin-2-yl}-2,2-dimethylpropanoic acid | 597.2 (M)+ |
| 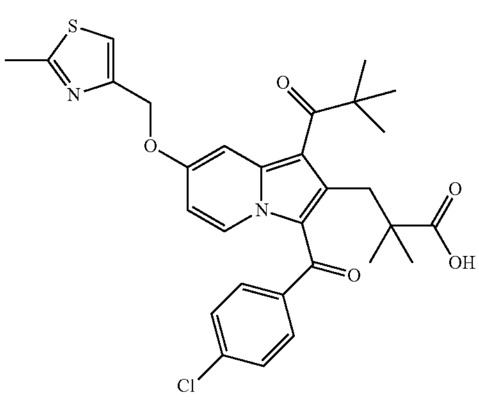 [SMILES: Cc1nc(COc2ccn3c(C(=O)c4ccc(Cl)cc4)c(CC(C)(C)C(=O)O)c(C(=O)C(C)(C)C)c3c2)cs1] | 3-{3-[(4-Chlorophenyl)carbonyl]-1-(2,2-dimethylpropanoyl)-7-[(2-methyl-1,3-thiazol-4-yl)methoxy]indolizin-2-yl}-2,2-dimethylpropanoic acid | 567.2 (M)+ |

TABLE I-continued

| Structure | Name | Observed m/e |
|---|---|---|
| 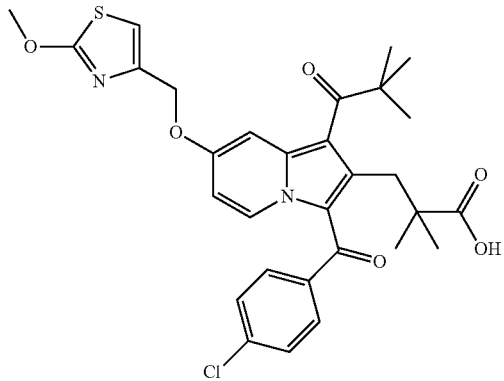 [SMILES: COc1nc(COc2ccn3c(C(=O)c4ccc(Cl)cc4)c(CC(C)(C)C(=O)O)c(C(=O)C(C)(C)C)c3c2)cs1] | 3-{3-[(4-Chlorophenyl)carbonyl]-1-(2,2-dimethylpropanoyl)-7-[(2-methoxy-1,3-thiazol-4-yl)methoxy]indolizin-2-yl}-2,2-dimethylpropanoic acid | 583.20 (M)+ |
| 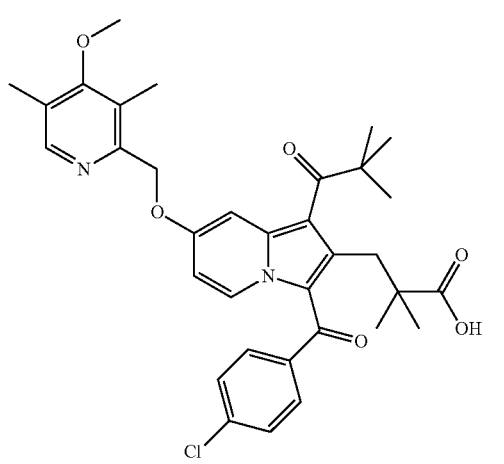 [SMILES: COc1c(C)cnc(COc2ccn3c(C(=O)c4ccc(Cl)cc4)c(CC(C)(C)C(=O)O)c(C(=O)C(C)(C)C)c3c2)c1C] | 3-{3-[(4-Chlorophenyl)carbonyl]-1-(2,2-dimethylpropanoyl)-7-[(4-methoxy-3,5-dimethylpyridin-2-yl)methoxy]indolizin-2-yl}-2,2-dimethylpropanoic acid | 605.2 (M)+ |
| 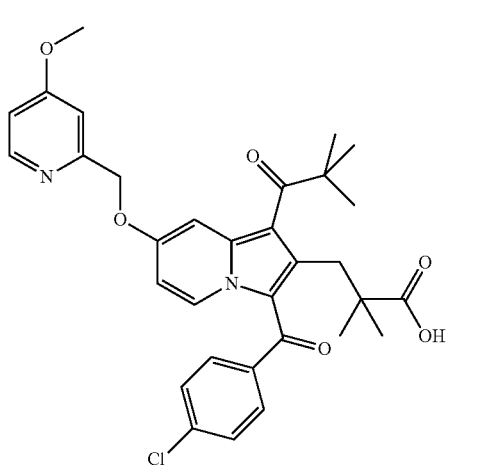 [SMILES: COc1ccnc(COc2ccn3c(C(=O)c4ccc(Cl)cc4)c(CC(C)(C)C(=O)O)c(C(=O)C(C)(C)C)c3c2)c1] | 3-{3-[(4-Chlorophenyl)carbonyl]-1-(2,2-dimethylpropanoyl)-7-[(4-methoxypyridin-2-yl)methoxy]indolizin-2-yl}-2,2-dimethylpropanoic acid | 577.2 (M)+ |

TABLE I-continued

| Structure | Name | Observed m/e |
|---|---|---|
| 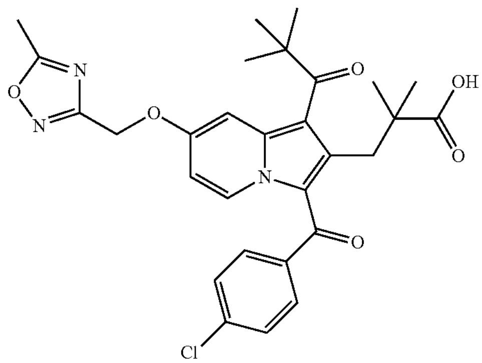 [SMILES: Cc1nc(COc2ccn3c(C(=O)c4ccc(Cl)cc4)c(CC(C)(C)C(=O)O)c(C(=O)C(C)(C)C)c3c2)no1] | 3-{3-[(4-Chlorophenyl)carbonyl]-1-(2,2-dimethylpropanoyl)-7-[(5-methyl-1,2,4-oxadiazol-3-yl)methoxy]indolizin-2-yl}-2,2-dimethylpropanoic acid | 552.2 (M)+ |
| 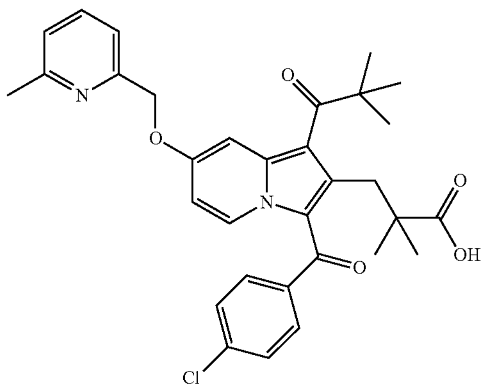 [SMILES: Cc1cccc(COc2ccn3c(C(=O)c4ccc(Cl)cc4)c(CC(C)(C)C(=O)O)c(C(=O)C(C)(C)C)c3c2)n1] | 3-{3-[(4-Chlorophenyl)carbonyl]-1-(2,2-dimethylpropanoyl)-7-[(6-methylpyridin-2-yl)methoxy]indolizin-2-yl}-2,2-dimethylpropanoic acid | 561.2 (M)+ |
| 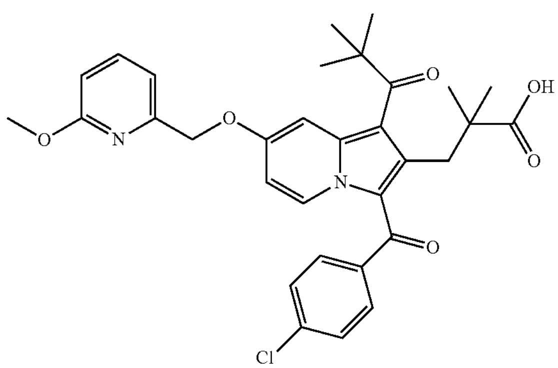 [SMILES: COc1cccc(COc2ccn3c(C(=O)c4ccc(Cl)cc4)c(CC(C)(C)C(=O)O)c(C(=O)C(C)(C)C)c3c2)n1] | 3-{3-[(4-Chlorophenyl)carbonyl]-1-(2,2-dimethylpropanoyl)-7-[(6-methoxypyridin-2-yl)methoxy]indolizin-2-yl}-2,2-dimethylpropanoic acid | 577.2 (M)+ |
| 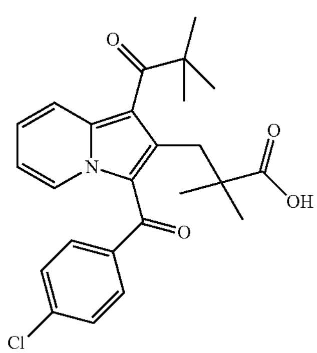 [SMILES: CC(C)(C)C(=O)c1c(CC(C)(C)C(=O)O)c(C(=O)c2ccc(Cl)cc2)n2ccccc12] | 3-{3-[(4-Chlorophenyl)carbonyl]-1-(2,2-dimethylpropanoyl)indolizin-2-yl}-2,2-dimethylpropanoic acid | 440.20 (M)+ |

TABLE I-continued

| Structure | Name | Observed m/e |
|---|---|---|
| 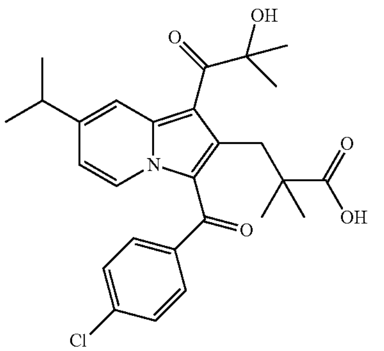 [SMILES: CC(C)c1ccn2c(C(=O)c3ccc(Cl)cc3)c(CC(C)(C)C(=O)O)c(C(=O)C(C)(C)O)c2c1] | 3-{3-[(4-Chlorophenyl)carbonyl]-1-(2-hydroxy-2-methylpropanoyl)-7-(propan-2-yl)indolizin-2-yl}-2,2-dimethylpropanoic acid | 484.20 (M)+ |
| 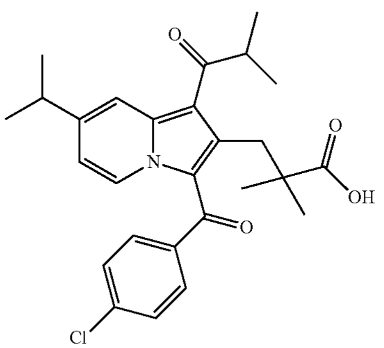 [SMILES: CC(C)C(=O)c1c(CC(C)(C)C(=O)O)c(C(=O)c2ccc(Cl)cc2)n2ccc(C(C)C)cc12] | 3-{3-[(4-Chlorophenyl)carbonyl]-1-(2-methylpropanoyl)-7-(propan-2-yl)indolizin-2-yl}-2,2-dimethylpropanoic acid | 468.2 (M)+ |
| 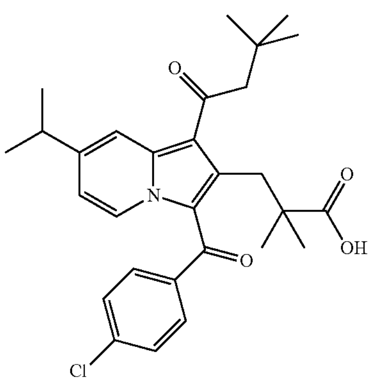 [SMILES: CC(C)c1ccn2c(C(=O)c3ccc(Cl)cc3)c(CC(C)(C)C(=O)O)c(C(=O)CC(C)(C)C)c2c1] | 3-{3-[(4-Chlorophenyl)carbonyl]-1-(3,3-dimethylbutanoyl)-7-(propan-2-yl)indolizin-2-yl}-2,2-dimethylpropanoic acid | 496.2 (M)+ |
| 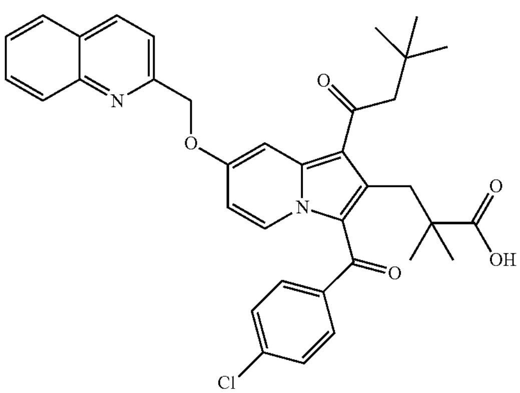 [SMILES: CC(C)(C)CC(=O)c1c(CC(C)(C)C(=O)O)c(C(=O)c2ccc(Cl)cc2)n2ccc(OCc3ccc4ccccc4n3)cc12] | 3-{3-[(4-Chlorophenyl)carbonyl]-1-(3,3-dimethylbutanoyl)-7-(quinolin-2-ylmethoxy)indolizin-2-yl}-2,2-dimethylpropanoic acid | 611.2 (M)+ |

TABLE I-continued

| Structure | Name | Observed m/e |
|---|---|---|
| 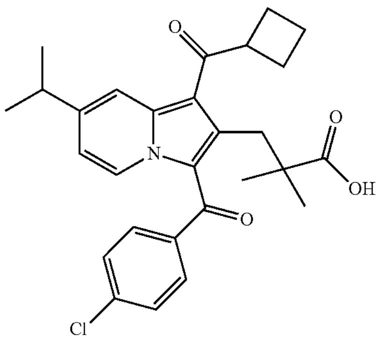 [SMILES: CC(C)c1ccn2c(C(=O)c3ccc(Cl)cc3)c(CC(C)(C)C(=O)O)c(C(=O)C3CCC3)c2c1] | 3-{3-[(4-Chlorophenyl)carbonyl]-1-(cyclobutylcarbonyl)-7-(propan-2-yl)indolizin-2-yl}-2,2-dimethylpropanoic acid | 480.2 (M)+ |
| 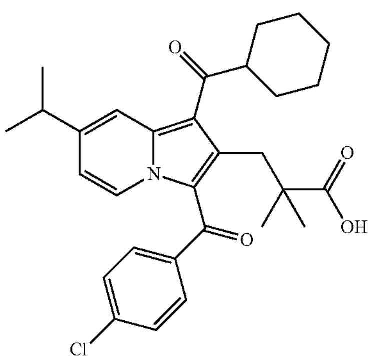 [SMILES: CC(C)c1ccn2c(C(=O)c3ccc(Cl)cc3)c(CC(C)(C)C(=O)O)c(C(=O)C3CCCCC3)c2c1] | 3-{3-[(4-Chlorophenyl)carbonyl]-1-(cyclohexylcarbonyl)-7-(propan-2-yl)indolizin-2-yl}-2,2-dimethylpropanoic acid | 508.2 (M)+ |
| 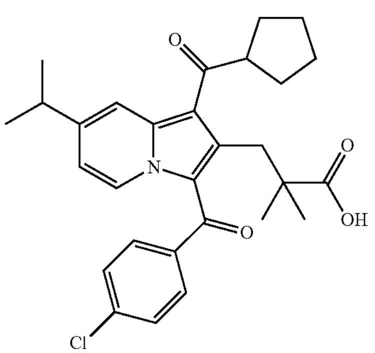 [SMILES: CC(C)c1ccn2c(C(=O)c3ccc(Cl)cc3)c(CC(C)(C)C(=O)O)c(C(=O)C3CCCC3)c2c1] | 3-{3-[(4-Chlorophenyl)carbonyl]-1-(cyclopentylcarbonyl)-7-(propan-2-yl)indolizin-2-yl}-2,2-dimethylpropanoic acid | 494.2 (M)+ |
| 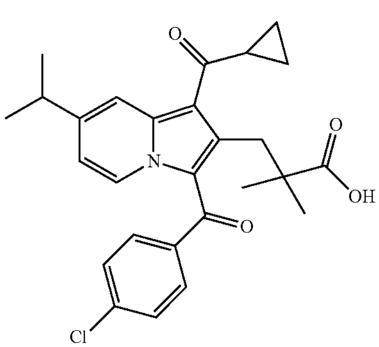 [SMILES: CC(C)c1ccn2c(C(=O)c3ccc(Cl)cc3)c(CC(C)(C)C(=O)O)c(C(=O)C3CC3)c2c1] | 3-{3-[(4-Chlorophenyl)carbonyl]-1-(cyclopropylcarbonyl)-7-(propan-2-yl)indolizin-2-yl}-2,2-dimethylpropanoic acid | 466.2 (M)+ |

TABLE I-continued

| Structure | Name | Observed m/e |
|---|---|---|
| 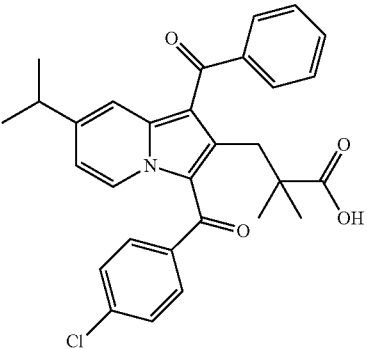 [SMILES: CC(C)c1ccn2c(C(=O)c3ccc(Cl)cc3)c(CC(C)(C)C(=O)O)c(C(=O)c3ccccc3)c2c1] | 3-{3-[(4-Chlorophenyl)carbonyl]-1-(phenylcarbonyl)-7-(propan-2-yl)indolizin-2-yl}-2,2-dimethylpropanoic acid | 502.2 (M)+ |
| 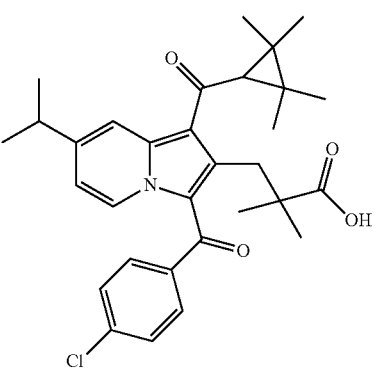 [SMILES: CC(C)c1ccn2c(C(=O)c3ccc(Cl)cc3)c(CC(C)(C)C(=O)O)c(C(=O)C3C(C)(C)C3(C)C)c2c1] | 3-{3-[(4-Chlorophenyl)carbonyl]-7-(propan-2-yl)-1-[(2,2,3,3-tetramethylcyclopropyl)carbonyl]indolizin-2-yl}-2,2-dimethylpropanoic acid | 522.2 (M)+ |
| 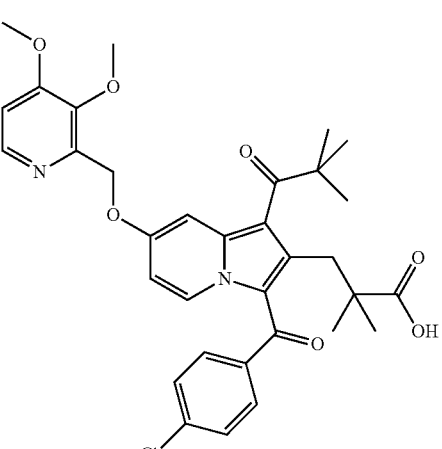 | 3-{3-[(4-Chlorophenyl)carbonyl]-7-[(3,4-dimethoxypyridin-2-yl)methoxy]-1-(2,2-dimethylpropanoyl)indolizin-2-yl}-2,2-dimethylpropanoic acid | 607.2 (M)+ |
| 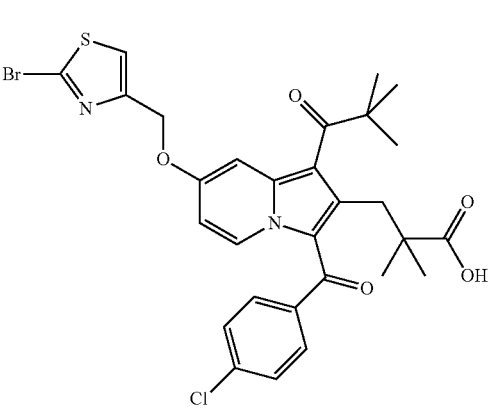 [SMILES: CC(C)(C)C(=O)c1c(CC(C)(C)C(=O)O)c(C(=O)c2ccc(Cl)cc2)n2ccc(OCc3csc(Br)n3)cc12] | 3-{7-[(2-Bromo-1,3-thiazol-4-yl)methoxy]-3-[(4-chlorophenyl)carbonyl]-1-(2,2-dimethylpropanoyl)indolizin-2-yl}-2,2-dimethylpropanoic acid | 633.00 (M)+ |

TABLE I-continued

| Structure | Name | Observed m/e |
|---|---|---|
| 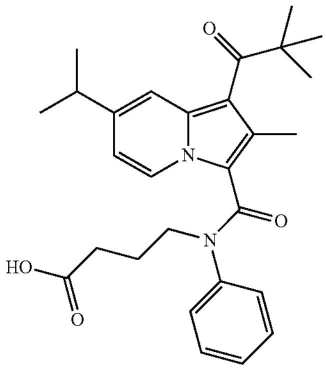 [SMILES: Cc1c(C(=O)C(C)(C)C)c2cc(C(C)C)ccn2c1C(=O)N(CCCC(=O)O)c1ccccc1] | 4-[{[1-(2,2-Dimethylpropanoyl)-2-methyl-7-(propan-2-yl)indolizin-3-yl]carbonyl}(phenyl)amino]butanoic acid | 463.2 (M)+ |
| 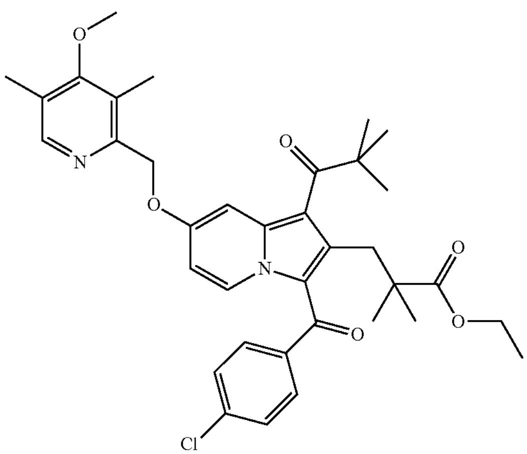 [SMILES: CCOC(=O)C(C)(C)Cc1c(C(=O)C(C)(C)C)c2cc(OCc3ncc(C)c(OC)c3C)ccn2c1C(=O)c1ccc(Cl)cc1] | Ethyl 3-{3-[(4-chlorophenyl)carbonyl]-1-(2,2-dimethylpropanoyl)-7-[(4-methoxy-3,5-dimethylpyridin-2-yl)methoxy]indolizin-2-yl}-2,2-dimethylpropanoate | 633.20 (M)+ |
| 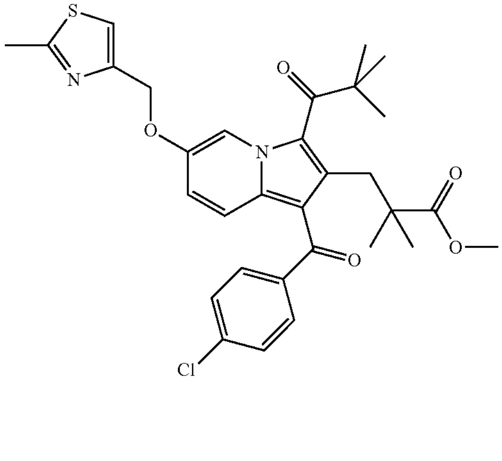 | Methyl 3-{1-[(4-chlorophenyl)carbonyl]-3-(2,2-dimethylpropanoyl)-6-[(2-methyl-1,3-thiazol-4-yl)methoxy]indolizin-2-yl}-2,2-dimethylpropanoate | 581.2 (M)+ |

TABLE I-continued

| Structure | Name | Observed m/e |
|---|---|---|
| 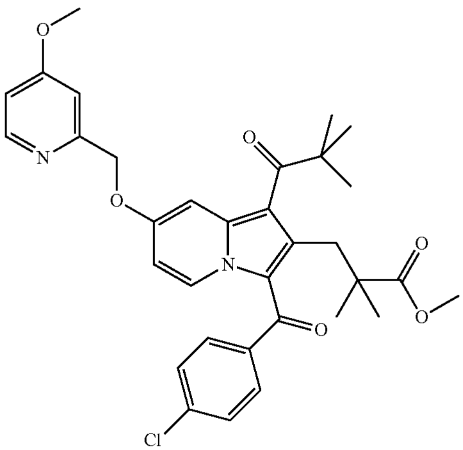 [SMILES: COC(=O)C(C)(C)Cc1c(C(=O)C(C)(C)C)c2cc(OCc3cc(OC)ccn3)ccn2c1C(=O)c1ccc(Cl)cc1] | Methyl 3-{3-[(4-chlorophenyl)carbonyl]-1-(2,2-dimethylpropanoyl)-7-[(4-methoxypyridin-2-yl)methoxy]indolizin-2-yl}-2,2-dimethylpropanoate | 591.2 (M)+ |
| 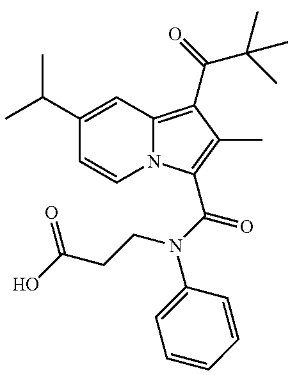 [SMILES: Cc1c(C(=O)C(C)(C)C)c2cc(C(C)C)ccn2c1C(=O)N(CCC(=O)O)c1ccccc1] | N-{[1-(2,2-Dimethylpropanoyl)-2-methyl-7-(propan-2-yl)indolizin-3-yl]carbonyl}-N-phenyl-beta-alanine | 449.20 (M)+ |
| 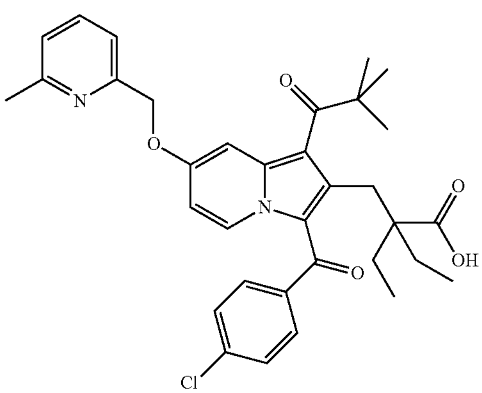 [SMILES: CCC(CC)(Cc1c(C(=O)C(C)(C)C)c2cc(OCc3cccc(C)n3)ccn2c1C(=O)c1ccc(Cl)cc1)C(=O)O] | 2-({3-[(4-Chlorophenyl)carbonyl]-1-(2,2-dimethylpropanoyl)-7-[(6-methylpyridin-2-yl)methoxy]indolizin-2-yl}methyl)-2-ethylbutanoic acid | 589.20 (M)+ |
| 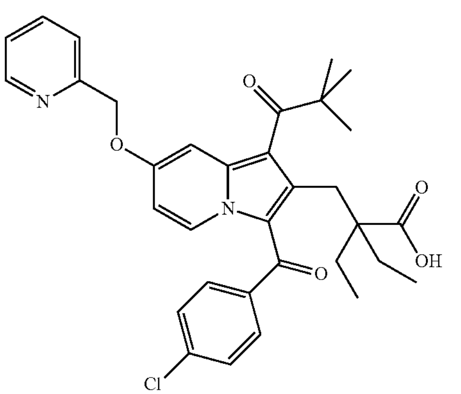 [SMILES: CCC(CC)(Cc1c(C(=O)C(C)(C)C)c2cc(OCc3ccccn3)ccn2c1C(=O)c1ccc(Cl)cc1)C(=O)O] | 2-({3-[(4-Chlorophenyl)carbonyl]-1-(2,2-dimethylpropanoyl)-7-(pyridin-2-ylmethoxy)indolizin-2-yl}methyl)-2-ethylbutanoic acid | 575.20 (M)+ |

TABLE I-continued

| Structure | Name | Observed m/e |
|---|---|---|
| 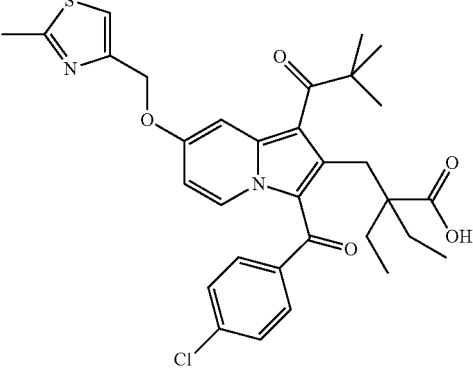 | 2-({3-[(4-Chlorophenyl)carbonyl]-1-(2,2-dimethylpropanoyl)-7-[(2-methyl-1,3-thiazol-4-yl)methoxy]indolizin-2-yl}methyl)-2-ethylbutanoic acid | 595.20 (M)+ |
| 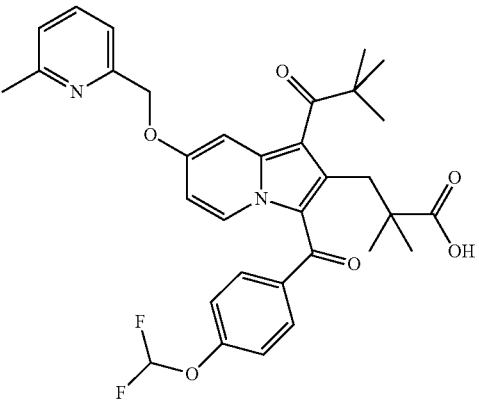 [SMILES: Cc1cccc(COc2ccn3c(C(=O)c4ccc(OC(F)F)cc4)c(CC(C)(C)C(=O)O)c(C(=O)C(C)(C)C)c3c2)n1] | 3-(3-{[4-(Difluoromethoxy)phenyl]carbonyl}-1-(2,2-dimethylpropanoyl)-7-[(6-methylpyridin-2-yl)methoxy]indolizin-2-yl)-2,2-dimethylpropanoic acid | 592.20 (M)+ |
| 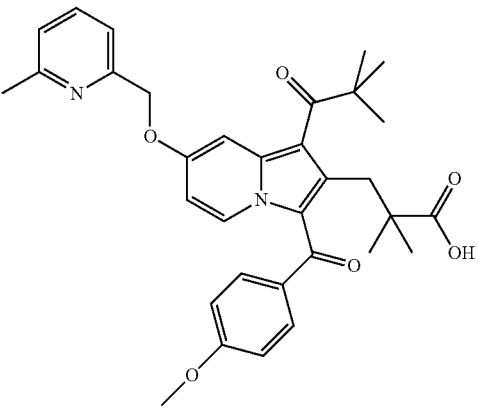 [SMILES: COc1ccc(C(=O)c2c(CC(C)(C)C(=O)O)c(C(=O)C(C)(C)C)c3cc(OCc4cccc(C)n4)ccn23)cc1] | 3-{1-(2,2-Dimethylpropanoyl)-3-[(4-methoxyphenyl)carbonyl]-7-[(6-methylpyridin-2-yl)methoxy]indolizin-2-yl}-2,2-dimethylpropanoic acid | 557.20 (M + H)+ |
| 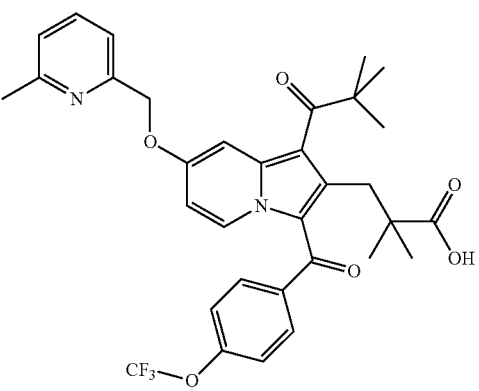 [SMILES: Cc1cccc(COc2ccn3c(C(=O)c4ccc(OC(F)(F)F)cc4)c(CC(C)(C)C(=O)O)c(C(=O)C(C)(C)C)c3c2)n1] | 3-[1-(2,2-Dimethylpropanoyl)-7-[(6-methylpyridin-2-yl)methoxy]-3-{[4-(trifluoromethoxy)phenyl]carbonyl}indolizin-2-yl]-2,2-dimethylpropanoic acid | 611.20 (M + H)+ |

TABLE I-continued

| Structure | Name | Observed m/e |
|---|---|---|
| 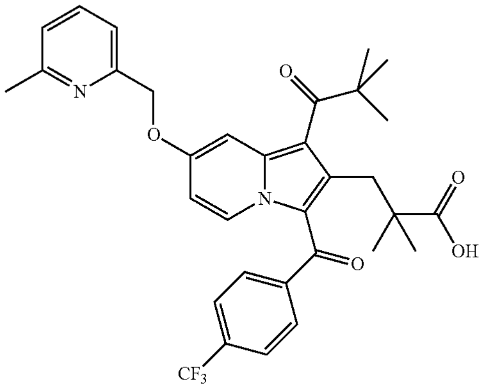 [SMILES: Cc1cccc(COc2ccn3c(C(=O)c4ccc(C(F)(F)F)cc4)c(CC(C)(C)C(=O)O)c(C(=O)C(C)(C)C)c3c2)n1] | 3-[1-(2,2-Dimethylpropanoyl)-7-[(6-methylpyridin-2-yl)methoxy]-3-{[4-(trifluoromethyl)phenyl]carbonyl}indolizin-2-yl]-2,2-dimethylpropanoic acid | 595.20 (M + H)+ |
| 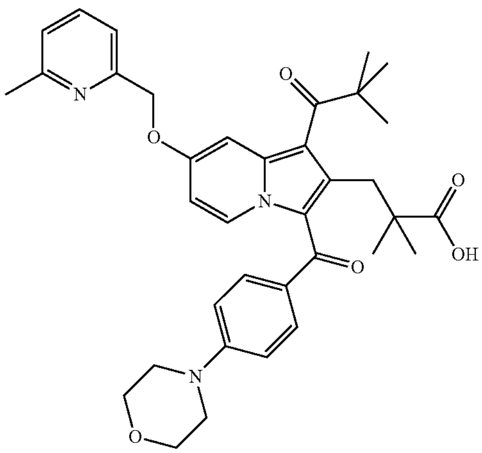 [SMILES: Cc1cccc(COc2ccn3c(C(=O)c4ccc(N5CCOCC5)cc4)c(CC(C)(C)C(=O)O)c(C(=O)C(C)(C)C)c3c2)n1] | 3-[1-(2,2-Dimethylpropanoyl)-7-[(6-methylpyridin-2-yl)methoxy]-3-{[4-(morpholin-4-yl)phenyl]carbonyl}indolizin-2-yl]-2,2-dimethylpropanoic acid | 612.40 (M + H)+ |
| 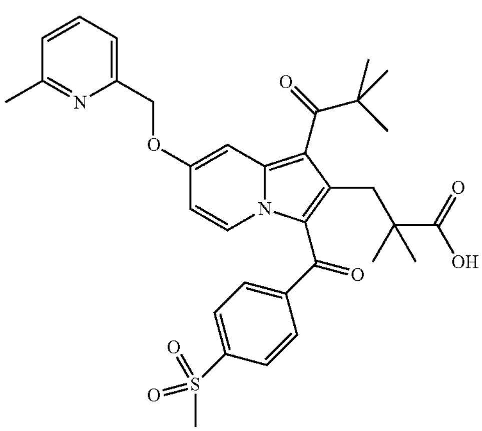 [SMILES: Cc1cccc(COc2ccn3c(C(=O)c4ccc(S(C)(=O)=O)cc4)c(CC(C)(C)C(=O)O)c(C(=O)C(C)(C)C)c3c2)n1] | 3-[1-(2,2-Dimethylpropanoyl)-7-[(6-methylpyridin-2-yl)methoxy]-3-{[4-(methylsulfonyl)phenyl]carbonyl}indolizin-2-yl]-2,2-dimethylpropanoic acid | 605.20 (M + H)+ |

TABLE I-continued

| Structure | Name | Observed m/e |
|---|---|---|
| 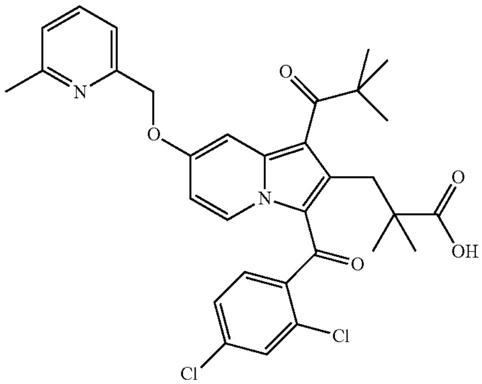 [SMILES: Cc1cccc(COc2ccn3c(C(=O)c4ccc(Cl)cc4Cl)c(CC(C)(C)C(=O)O)c(C(=O)C(C)(C)C)c3c2)n1] | 3-{3-[(2,4-Dichlorophenyl)carbonyl]-1-(2,2-dimethylpropanoyl)-7-[(6-methylpyridin-2-yl)methoxy]indolizin-2-yl}-2,2-dimethylpropanoic acid | 596.20 (M + H)+ |
| 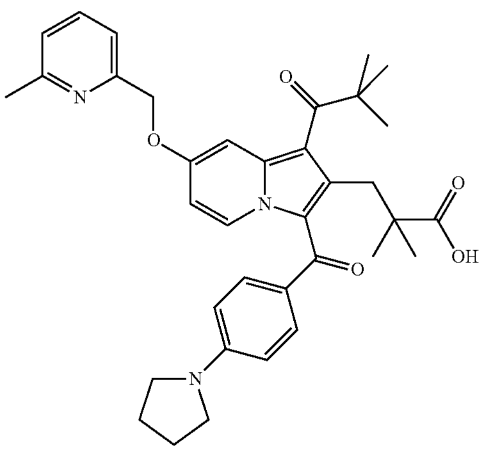 [SMILES: Cc1cccc(COc2ccn3c(C(=O)c4ccc(N5CCCC5)cc4)c(CC(C)(C)C(=O)O)c(C(=O)C(C)(C)C)c3c2)n1] | 3-[1-(2,2-Dimethylpropanoyl)-7-[(6-methylpyridin-2-yl)methoxy]-3-{[4-(pyrrolidin-1-yl)phenyl]carbonyl}indolizin-2-yl]-2,2-dimethylpropanoic acid | 596.62 (M + H)+ |
| 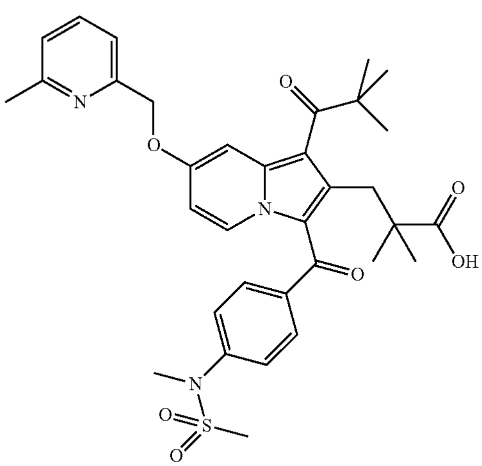 [SMILES: Cc1cccc(COc2ccn3c(C(=O)c4ccc(N(C)S(C)(=O)=O)cc4)c(CC(C)(C)C(=O)O)c(C(=O)C(C)(C)C)c3c2)n1] | 3-{1-(2,2-Dimethylpropanoyl)-3-({4-[methyl(methylsulfonyl)amino]phenyl}carbonyl)-7-[(6-methylpyridin-2-yl)methoxy]indolizin-2-yl}-2,2-dimethylpropanoic acid | 634.20 (M + H)+ |

TABLE I-continued

| Structure | Name | Observed m/e |
|---|---|---|
| 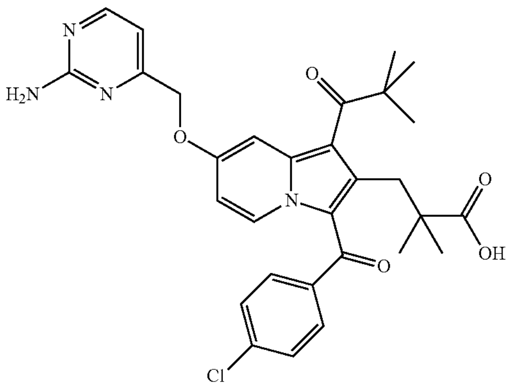 [SMILES: CC(C)(C)C(=O)c1c(CC(C)(C)C(=O)O)c(C(=O)c2ccc(Cl)cc2)n2ccc(OCc3ccnc(N)n3)cc12] | 3-{7-[(2-Aminopyrimidin-4-yl)methoxy]-3-[(4-chlorophenyl)carbonyl]-1-(2,2-dimethylpropanoyl)indolizin-2-yl}-2,2-dimethylpropanoic acid | 563.20 (M + H)+ |
| 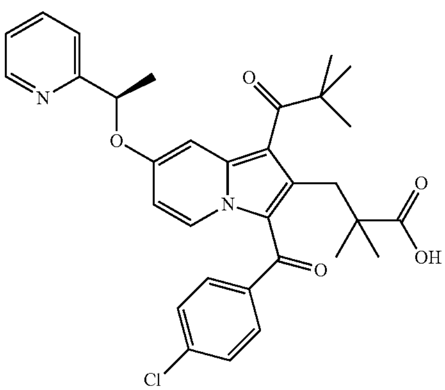 [SMILES: C[C@@H](Oc1ccn2c(C(=O)c3ccc(Cl)cc3)c(CC(C)(C)C(=O)O)c(C(=O)C(C)(C)C)c2c1)c1ccccn1] | 3-{3-[(4-Chlorophenyl)carbonyl]-1-(2,2-dimethylpropanoyl)-7-[(1R)-1-(pyridin-2-yl)ethoxy]indolizin-2-yl}-2,2-dimethylpropanoic acid | 561.84 (M + H)+ |
| 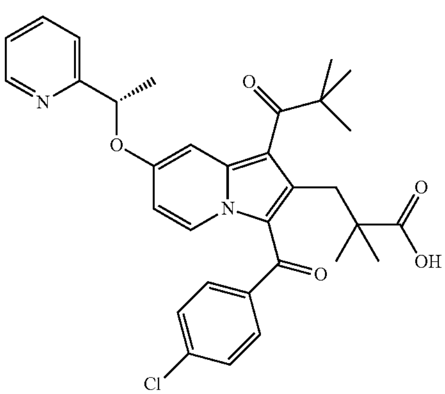 [SMILES: C[C@H](Oc1ccn2c(C(=O)c3ccc(Cl)cc3)c(CC(C)(C)C(=O)O)c(C(=O)C(C)(C)C)c2c1)c1ccccn1] | 3-{3-[(4-Chlorophenyl)carbonyl]-1-(2,2-dimethylpropanoyl)-7-[(1S)-1-(pyridin-2-yl)ethoxy]indolizin-2-yl}-2,2-dimethylpropanoic acid | 561.84 (M + H)+ |
| 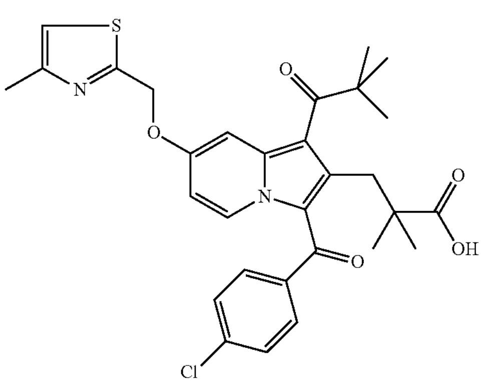 [SMILES: Cc1csc(COc2ccn3c(C(=O)c4ccc(Cl)cc4)c(CC(C)(C)C(=O)O)c(C(=O)C(C)(C)C)c3c2)n1] | 3-{3-[(4-Chlorophenyl)carbonyl]-1-(2,2-dimethylpropanoyl)-7-[(4-methyl-1,3-thiazol-2-yl)methoxy]indolizin-2-yl}-2,2-dimethylpropanoic acid | 567.20 (M)+ |

TABLE I-continued

| Structure | Name | Observed m/e |
|---|---|---|
| 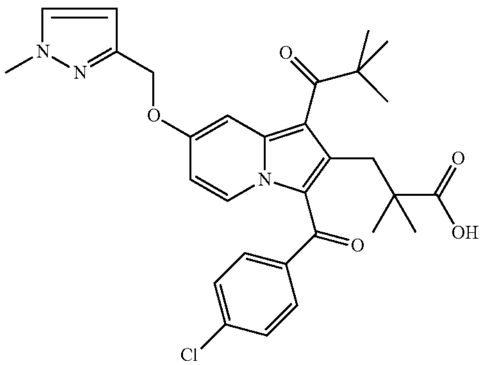 [SMILES: Cn1ccc(COc2ccn3c(C(=O)c4ccc(Cl)cc4)c(CC(C)(C)C(=O)O)c(C(=O)C(C)(C)C)c3c2)n1] | 3-{3-[(4-Chlorophenyl)carbonyl]-1-(2,2-dimethylpropanoyl)-7-[(1-methyl-1H-pyrazol-3-yl)methoxy]indolizin-2-yl}-2,2-dimethylpropanoic acid | 550.85 (M)+ |
| 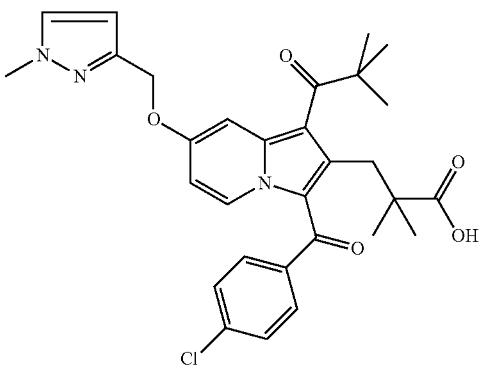 [SMILES: Cn1ccc(COc2ccn3c(C(=O)c4ccc(Cl)cc4)c(CC(C)(C)C(=O)O)c(C(=O)C(C)(C)C)c3c2)n1] | 3-{3-[(4-Chlorophenyl)carbonyl]-1-(2,2-dimethylpropanoyl)-7-[(1,5-dimethyl-1H-pyrazol-3-yl)methoxy]indolizin-2-yl}-2,2-dimethylpropanoic acid | 564.81 (M)+ |
| 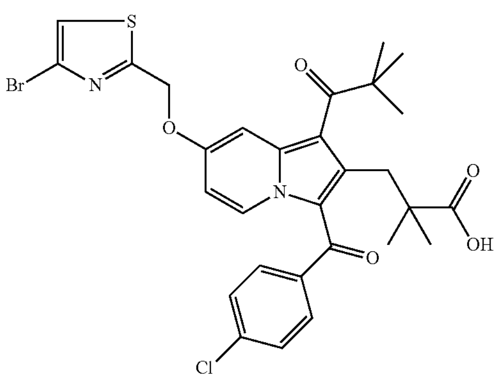 [SMILES: CC(C)(C)C(=O)c1c(CC(C)(C)C(=O)O)c(C(=O)c2ccc(Cl)cc2)n2ccc(OCc3nc(Br)cs3)cc12] | 3-{7-[(4-Bromo-1,3-thiazol-2-yl)methoxy]-3-[(4-chlorophenyl)carbonyl]-1-(2,2-dimethylpropanoyl)indolizin-2-yl}-2,2-dimethylpropanoic acid | 633.00 (M + H)+ |
| 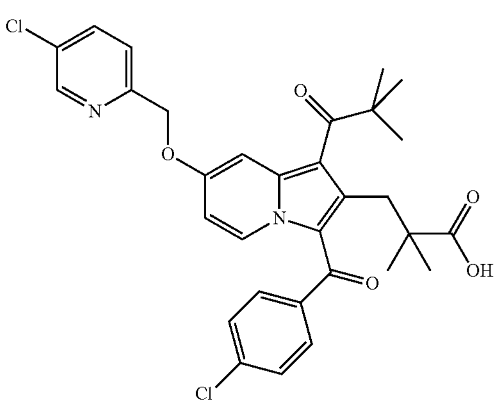 [SMILES: CC(C)(C)C(=O)c1c(CC(C)(C)C(=O)O)c(C(=O)c2ccc(Cl)cc2)n2ccc(OCc3ccc(Cl)cn3)cc12] | 3-{3-[(4-Chlorophenyl)carbonyl]-7-[(5-chloropyridin-2-yl)methoxy]-1-(2,2-dimethylpropanoyl)indolizin-2-yl}-2,2-dimethylpropanoic acid | 581.75 (M)+ |

TABLE I-continued

| Structure | Name | Observed m/e |
|---|---|---|
| 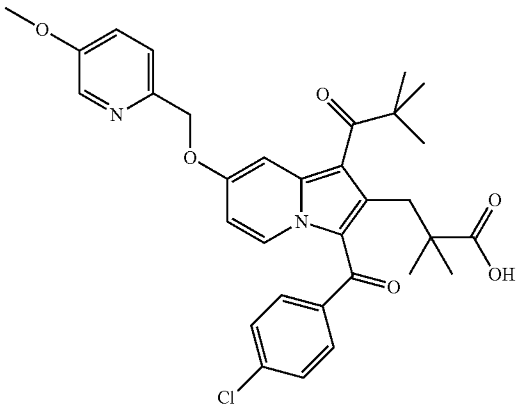 [SMILES: COc1ccc(COc2ccn3c(C(=O)c4ccc(Cl)cc4)c(CC(C)(C)C(=O)O)c(C(=O)C(C)(C)C)c3c2)nc1] | 3-{3-[(4-Chlorophenyl)carbonyl]-1-(2,2-dimethylpropanoyl)-7-[(5-methoxypyridin-2-yl)methoxy]indolizin-2-yl}-2,2-dimethylpropanoic acid | 577.20 (M)+ |
| 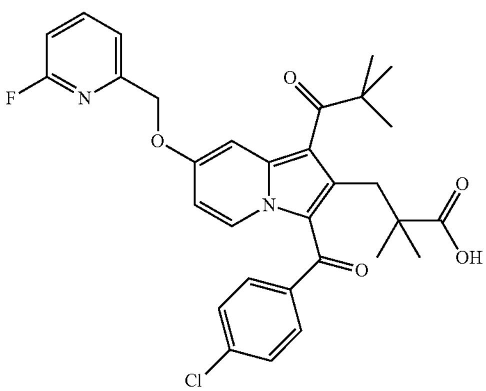 [SMILES: CC(C)(C)C(=O)c1c(CC(C)(C)C(=O)O)c(C(=O)c2ccc(Cl)cc2)n2ccc(OCc3cccc(F)n3)cc12] | 3-{3-[(4-Chlorophenyl)carbonyl]-1-(2,2-dimethylpropanoyl)-7-[(6-fluoropyridin-2-yl)methoxy]indolizin-2-yl}-2,2-dimethylpropanoic acid | 565.20 (M)+ |
| 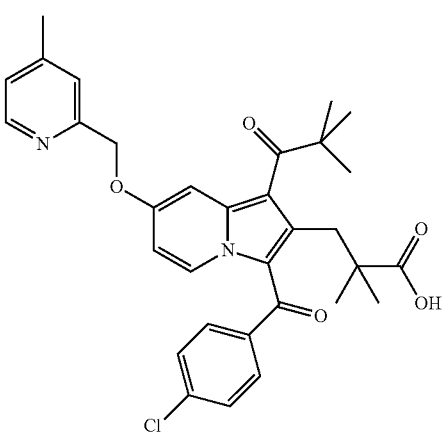 [SMILES: Cc1ccnc(COc2ccn3c(C(=O)c4ccc(Cl)cc4)c(CC(C)(C)C(=O)O)c(C(=O)C(C)(C)C)c3c2)c1] | 3-{3-[(4-Chlorophenyl)carbonyl]-1-(2,2-dimethylpropanoyl)-7-[(4-methylpyridin-2-yl)methoxy]indolizin-2-yl}-2,2-dimethylpropanoic acid | 561.20 (M)+ |

TABLE I-continued

| Structure | Name | Observed m/e |
|---|---|---|
| 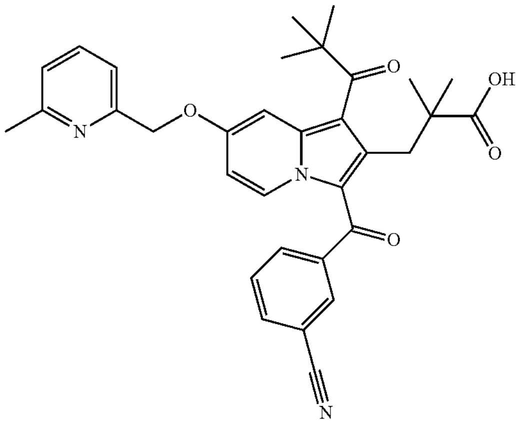 [SMILES: Cc1cccc(COc2ccn3c(C(=O)c4cccc(C#N)c4)c(CC(C)(C)C(=O)O)c(C(=O)C(C)(C)C)c3c2)n1] | 3-{3-[(3-Cyanophenyl)carbonyl]-1-(2,2-dimethylpropanoyl)-7-[(6-methylpyridin-2-yl)methoxy]indolizin-2-yl}-2,2-dimethylpropanoic acid | 552.20 (M + H)+ |
| 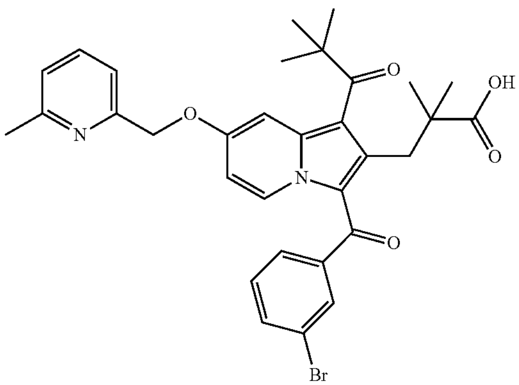 [SMILES: Cc1cccc(COc2ccn3c(C(=O)c4cccc(Br)c4)c(CC(C)(C)C(=O)O)c(C(=O)C(C)(C)C)c3c2)n1] | 3-{3-[(3-Bromophenyl)carbonyl]-1-(2,2-dimethylpropanoyl)-7-[(6-methylpyridin-2-yl)methoxy]indolizin-2-yl}-2,2-dimethylpropanoic acid | 605.20 (M + H)+ |
| 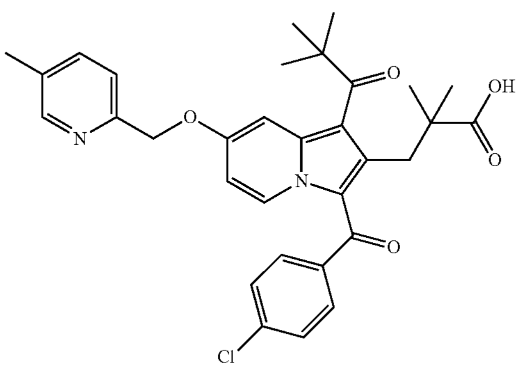 [SMILES: Cc1ccc(COc2ccn3c(C(=O)c4ccc(Cl)cc4)c(CC(C)(C)C(=O)O)c(C(=O)C(C)(C)C)c3c2)nc1] | 3-{3-[(4-Chlorophenyl)carbonyl]-1-(2,2-dimethylpropanoyl)-7-[(5-methylpyridin-2-yl)methoxy]indolizin-2-yl}-2,2-dimethylpropanoic acid | 561.20 (M)+ |
| 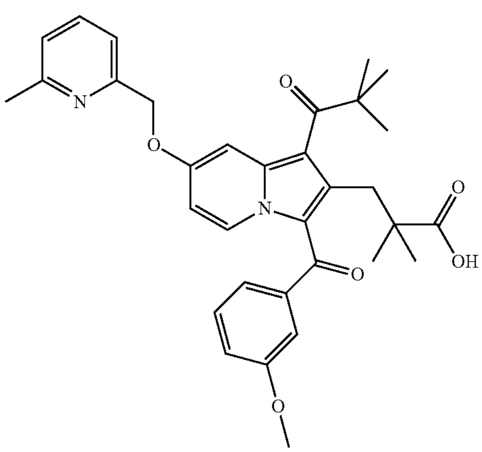 [SMILES: COc1cccc(C(=O)c2c(CC(C)(C)C(=O)O)c(C(=O)C(C)(C)C)c3cc(OCc4cccc(C)n4)ccn23)c1] | 3-{1-(2,2-Dimethylpropanoyl)-3-[(3-methoxyphenyl)carbonyl]-7-[(6-methylpyridin-2-yl)methoxy]indolizin-2-yl}-2,2-dimethylpropanoic acid | 557.20 (M + H)+ |

TABLE I-continued

| Structure | Name | Observed m/e |
|---|---|---|
| 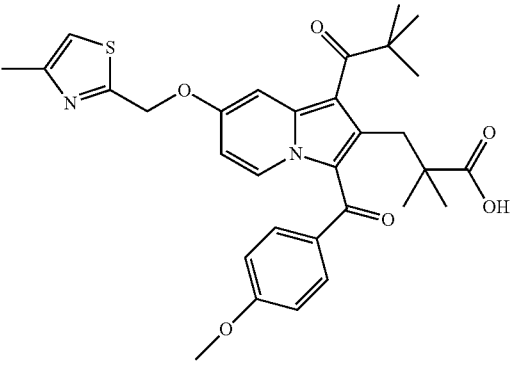 [SMILES: COc1ccc(C(=O)c2c(CC(C)(C)C(=O)O)c(C(=O)C(C)(C)C)c3cc(OCc4nc(C)cs4)ccn23)cc1] | 3-{1-(2,2-Dimethylpropanoyl)-3-[(4-methoxyphenyl)carbonyl]-7-[(4-methyl-1,3-thiazol-2-yl)methoxy]indolizin-2-yl}-2,2-dimethylpropanoic acid | 563.20 (M + H)+ |
| 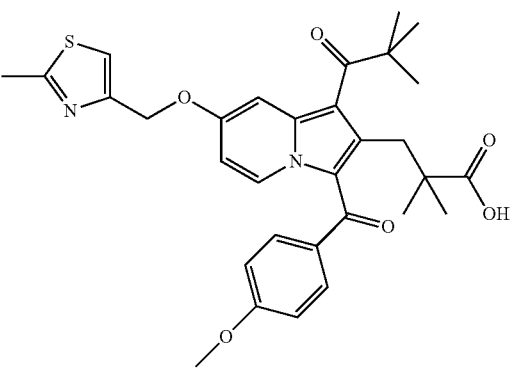 [SMILES: COc1ccc(C(=O)c2c(CC(C)(C)C(=O)O)c(C(=O)C(C)(C)C)c3cc(OCc4csc(C)n4)ccn23)cc1] | 3-{1-(2,2-Dimethylpropanoyl)-3-[(4-methoxyphenyl)carbonyl]-7-[(2-methyl-1,3-thiazol-4-yl)methoxy]indolizin-2-yl}-2,2-dimethylpropanoic acid | 563.20 (M + H)+ |
| 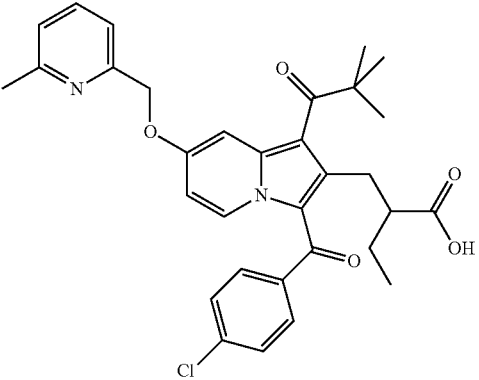 [SMILES: CCC(Cc1c(C(=O)C(C)(C)C)c2cc(OCc3cccc(C)n3)ccn2c1C(=O)c1ccc(Cl)cc1)C(=O)O] | 2-({3-[(4-Chlorophenyl)carbonyl]-1-(2,2-dimethylpropanoyl)-7-[(6-methylpyridin-2-yl)methoxy]indolizin-2-yl}methyl)butanoic acid | 561.77 (M)+ |
| 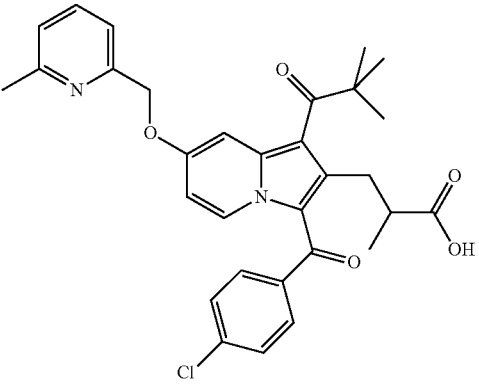 [SMILES: Cc1cccc(COc2ccn3c(C(=O)c4ccc(Cl)cc4)c(CC(C)C(=O)O)c(C(=O)C(C)(C)C)c3c2)n1] | 3-{3-[(4-Chlorophenyl)carbonyl]-1-(2,2-dimethylpropanoyl)-7-[(6-methylpyridin-2-yl)methoxy]indolizin-2-yl}-2-methylpropanoic acid | 547.76 (M)+ |

TABLE I-continued

| Structure | Name | Observed m/e |
|---|---|---|
| 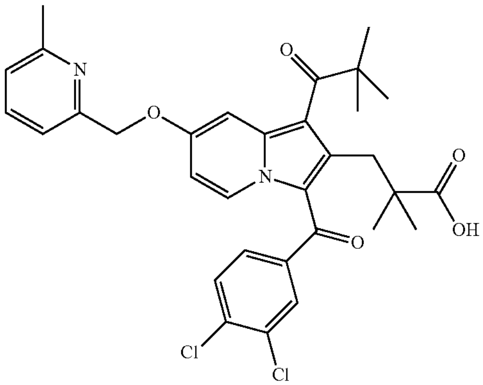 [SMILES: Cc1cccc(COc2ccn3c(C(=O)c4ccc(Cl)c(Cl)c4)c(CC(C)(C)C(=O)O)c(C(=O)C(C)(C)C)c3c2)n1] | 3-{3-[(3,4-Dichlorophenyl)carbonyl]-1-(2,2-dimethylpropanoyl)-7-[(6-methylpyridin-2-yl)methoxy]indolizin-2-yl}-2,2-dimethylpropanoic acid | 595.20 (M)+ |
| 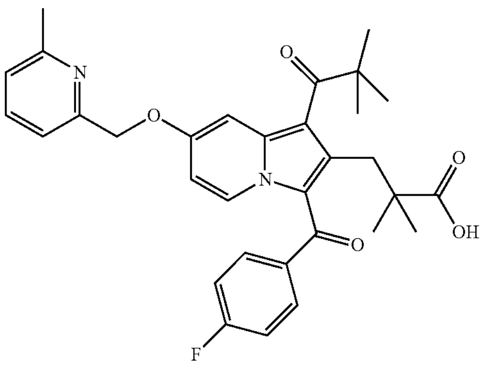 [SMILES: Cc1cccc(COc2ccn3c(C(=O)c4ccc(F)cc4)c(CC(C)(C)C(=O)O)c(C(=O)C(C)(C)C)c3c2)n1] | 3-{1-(2,2-Dimethylpropanoyl)-3-[(4-fluorophenyl)carbonyl]-7-[(6-methylpyridin-2-yl)methoxy]indolizin-2-yl}-2,2-dimethylpropanoic acid | 545.20 (M + H)+ |
| 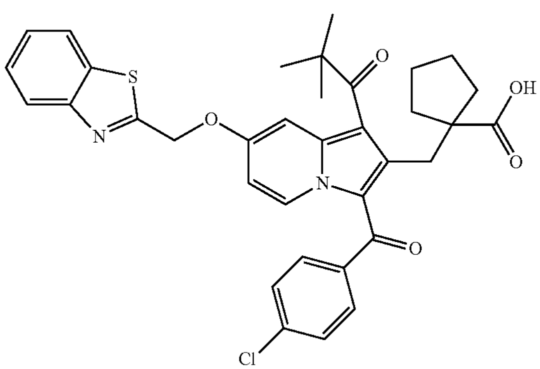 [SMILES: CC(C)(C)C(=O)c1c(CC2(C(=O)O)CCCC2)c(C(=O)c2ccc(Cl)cc2)n2ccc(OCc3nc4ccccc4s3)cc12] | 1-{[7-(1,3-Benzothiazol-2-ylmethoxy)-3-[(4-chlorophenyl)carbonyl]-1-(2,2-dimethylpropanoyl)indolizin-2-yl]methyl}cyclopentanecarboxylic acid | 629.20 (M)+ |
| 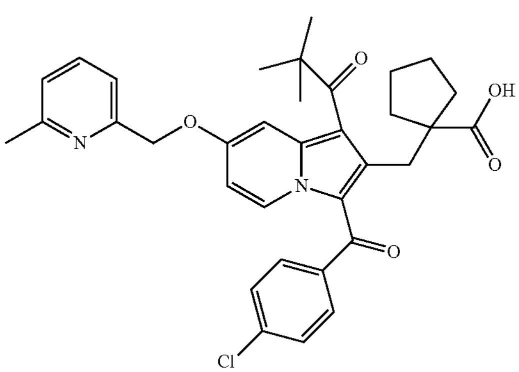 [SMILES: Cc1cccc(COc2ccn3c(C(=O)c4ccc(Cl)cc4)c(CC4(C(=O)O)CCCC4)c(C(=O)C(C)(C)C)c3c2)n1] | 1-({3-[(4-Chlorophenyl)carbonyl]-1-(2,2-dimethylpropanoyl)-7-[(6-methylpyridin-2-yl)methoxy]indolizin-2-yl}methyl)cyclopentanecarboxylic acid | 587.20 (M)+ |

TABLE I-continued

| Structure | Name | Observed m/e |
|---|---|---|
| 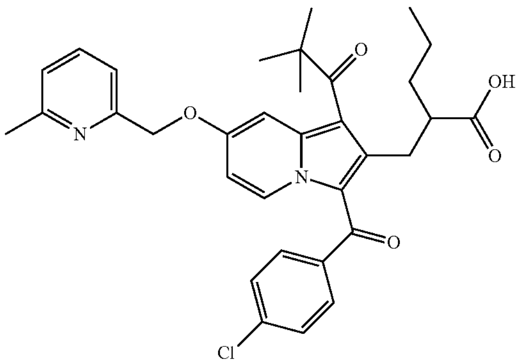 [SMILES: CCCC(Cc1c(C(=O)C(C)(C)C)c2cc(OCc3cccc(C)n3)ccn2c1C(=O)c1ccc(Cl)cc1)C(=O)O] | 2-({3-[(4-Chlorophenyl)carbonyl]-1-(2,2-dimethylpropanoyl)-7-[(6-methylpyridin-2-yl)methoxy]indolizin-2-yl}methyl)pentanoic acid | 575.20 (M)+ |
| 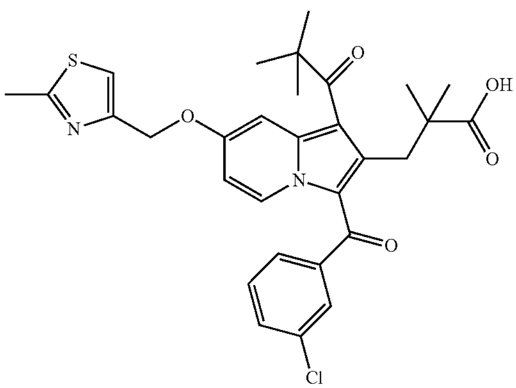 [SMILES: Cc1nc(COc2ccn3c(C(=O)c4cccc(Cl)c4)c(CC(C)(C)C(=O)O)c(C(=O)C(C)(C)C)c3c2)cs1] | 3-{3-[(3-Chlorophenyl)carbonyl]-1-(2,2-dimethylpropanoyl)-7-[(2-methyl-1,3-thiazol-4-yl)methoxy]indolizin-2-yl}-2,2-dimethylpropanoic acid | 567.20 (M)+ |
| 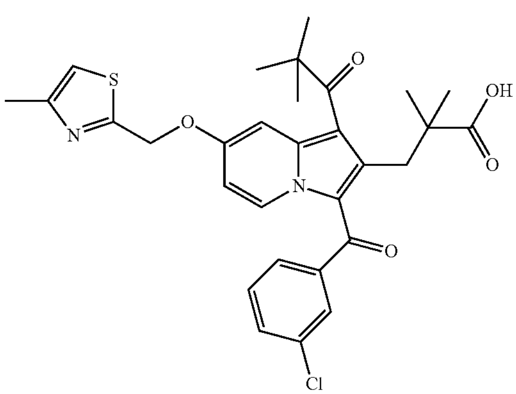 [SMILES: Cc1csc(COc2ccn3c(C(=O)c4cccc(Cl)c4)c(CC(C)(C)C(=O)O)c(C(=O)C(C)(C)C)c3c2)n1] | 3-{3-[(3-Chlorophenyl)carbonyl]-1-(2,2-dimethylpropanoyl)-7-[(4-methyl-1,3-thiazol-2-yl)methoxy]indolizin-2-yl}-2,2-dimethylpropanoic acid | 567.20 (M)+ |
| 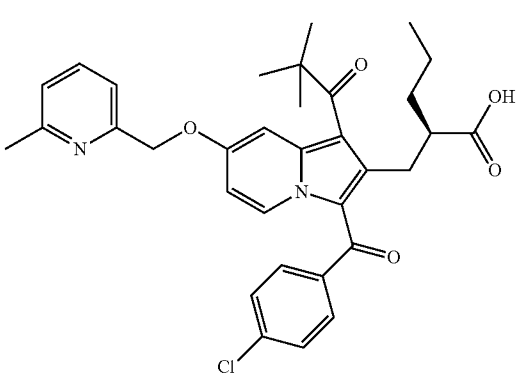 [SMILES: CCC[C@H](Cc1c(C(=O)C(C)(C)C)c2cc(OCc3cccc(C)n3)ccn2c1C(=O)c1ccc(Cl)cc1)C(=O)O] | (2R)-2-({3-[(4-Chlorophenyl)carbonyl]-1-(2,2-dimethylpropanoyl)-7-[(6-methylpyridin-2-yl)methoxy]indolizin-2-yl}methyl)pentanoic acid | 575.20 (M)+ |

TABLE I-continued

| Structure | Name | Observed m/e |
|---|---|---|
| 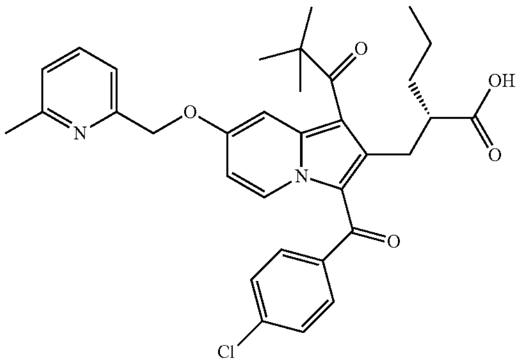 [SMILES: CCC[C@@H](Cc1c(C(=O)C(C)(C)C)c2cc(OCc3cccc(C)n3)ccn2c1C(=O)c1ccc(Cl)cc1)C(=O)O] | (2S)-2-({3-[(4-Chlorophenyl)carbonyl]-1-(2,2-dimethylpropanoyl)-7-[(6-methylpyridin-2-yl)methoxy]indolizin-2-yl}methyl)pentanoic acid | 575.20 (M)+ |
| 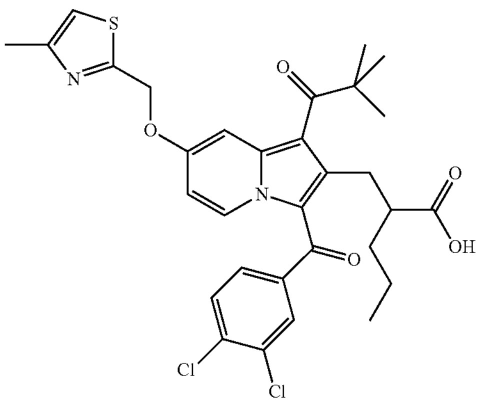 [SMILES: CCCC(Cc1c(C(=O)C(C)(C)C)c2cc(OCc3nc(C)cs3)ccn2c1C(=O)c1ccc(Cl)c(Cl)c1)C(=O)O] | 2-({3-[(3,4-Dichlorophenyl)carbonyl]-1-(2,2-dimethylpropanoyl)-7-[(4-methyl-1,3-thiazol-2-yl)methoxy]indolizin-2-yl}methyl)pentanoic acid | 615.20 (M)+ |
| 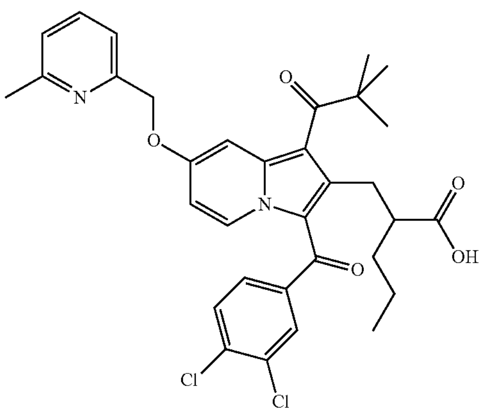 [SMILES: CCCC(Cc1c(C(=O)C(C)(C)C)c2cc(OCc3cccc(C)n3)ccn2c1C(=O)c1ccc(Cl)c(Cl)c1)C(=O)O] | 2-({3-[(3,4-Dichlorophenyl)carbonyl]-1-(2,2-dimethylpropanoyl)-7-[(6-methylpyridin-2-yl)methoxy]indolizin-2-yl}methyl)pentanoic acid | 609.20 (M)+ |
| 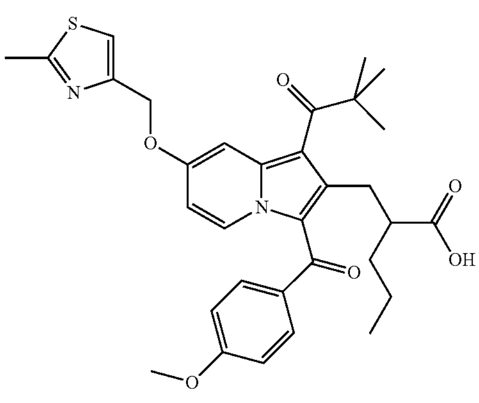 [SMILES: CCCC(Cc1c(C(=O)C(C)(C)C)c2cc(OCc3csc(C)n3)ccn2c1C(=O)c1ccc(OC)cc1)C(=O)O] | 2-({1-(2,2-Dimethylpropanoyl)-3-[(4-methoxyphenyl)carbonyl]-7-[(2-methyl-1,3-thiazol-4-yl)methoxy]indolizin-2-yl}methyl)pentanoic acid | 577.20 (M)+ |

TABLE I-continued

| Structure | Name | Observed m/e |
|---|---|---|
| 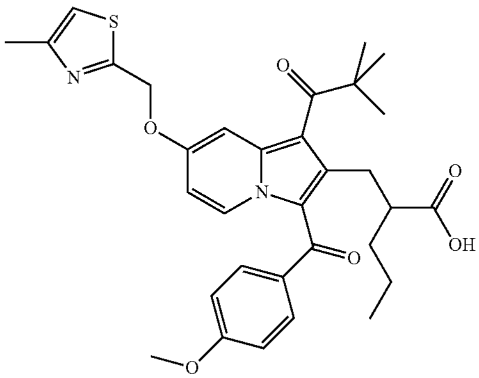 [SMILES: CCCC(Cc1c(C(=O)C(C)(C)C)c2cc(OCc3nc(C)cs3)ccn2c1C(=O)c1ccc(OC)cc1)C(=O)O] | 2-({1-(2,2-Dimethylpropanoyl)-3-[(4-methoxyphenyl)carbonyl]-7-[(4-methyl-1,3-thiazol-2-yl)methoxy]indolizin-2-yl}methyl)pentanoic acid | 577.20 (M)+ |
| 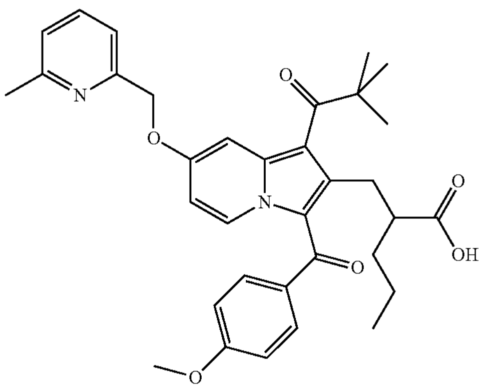 [SMILES: CCCC(Cc1c(C(=O)C(C)(C)C)c2cc(OCc3cccc(C)n3)ccn2c1C(=O)c1ccc(OC)cc1)C(=O)O] | 2-({1-(2,2-Dimethylpropanoyl)-3-[(4-methoxyphenyl)carbonyl]-7-[(6-methylpyridin-2-yl)methoxy]indolizin-2-yl}methyl)pentanoic acid | 571.20 (M)+ |
| 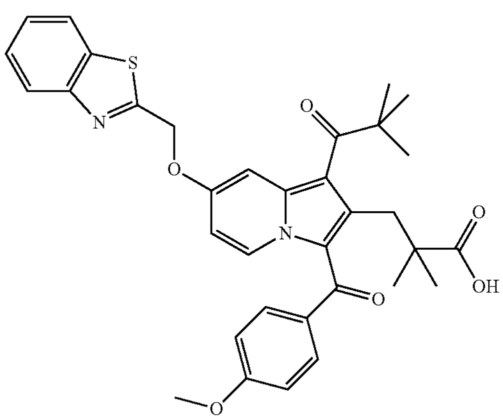 [SMILES: COc1ccc(C(=O)c2c(CC(C)(C)C(=O)O)c(C(=O)C(C)(C)C)c3cc(OCc4nc5ccccc5s4)ccn23)cc1] | 3-{7-(1,3-Benzothiazol-2-ylmethoxy)-1-(2,2-dimethylpropanoyl)-3-[(4-methoxyphenyl)carbonyl]indolizin-2-yl}-2,2-dimethylpropanoic acid | 599.20 (M)+ |
| 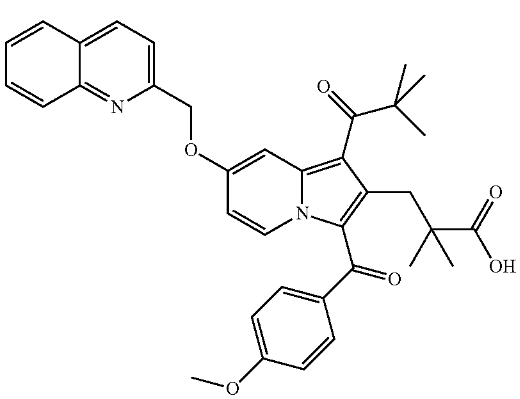 [SMILES: COc1ccc(C(=O)c2c(CC(C)(C)C(=O)O)c(C(=O)C(C)(C)C)c3cc(OCc4ccc5ccccc5n4)ccn23)cc1] | 3-[1-(2,2-Dimethylpropanoyl)-3-[(4-methoxyphenyl)carbonyl]-7-(quinolin-2-ylmethoxy)indolizin-2-yl]-2,2-dimethylpropanoic acid | 593.20 (M)+ |

TABLE I-continued

| Structure | Name | Observed m/e |
|---|---|---|
| 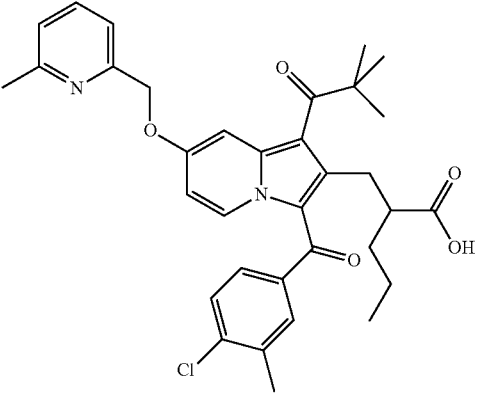 [SMILES: CCCC(Cc1c(C(=O)C(C)(C)C)c2cc(OCc3cccc(C)n3)ccn2c1C(=O)c1ccc(Cl)c(C)c1)C(=O)O] | 2-({3-[(4-Chloro-3-methylphenyl)carbonyl]-1-(2,2-dimethylpropanoyl)-7-[(6-methylpyridin-2-yl)methoxy]indolizin-2-yl}methyl)pentanoic acid | 589.20 (M)+ |
| 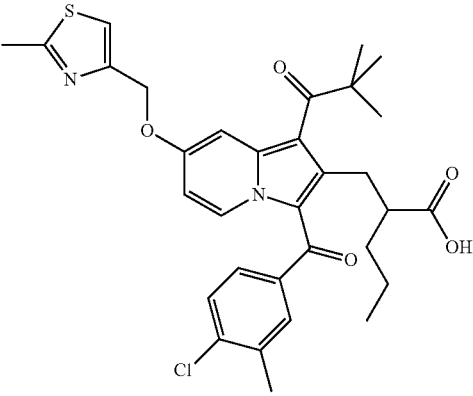 [SMILES: CCCC(Cc1c(C(=O)C(C)(C)C)c2cc(OCc3csc(C)n3)ccn2c1C(=O)c1ccc(Cl)c(C)c1)C(=O)O] | 2-({3-[(4-Chloro-3-methylphenyl)carbonyl]-1-(2,2-dimethylpropanoyl)-7-[(2-methyl-1,3-thiazol-4-yl)methoxy]indolizin-2-yl}methyl)pentanoic acid | 595.20 (M)+ |
| 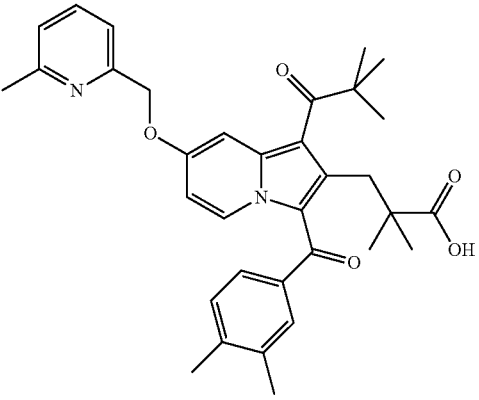 [SMILES: Cc1cccc(COc2ccn3c(C(=O)c4ccc(C)c(C)c4)c(CC(C)(C)C(=O)O)c(C(=O)C(C)(C)C)c3c2)n1] | 3-{3-[(3,4-Dimethylphenyl)carbonyl]-1-(2,2-dimethylpropanoyl)-7-[(6-methylpyridin-2-yl)methoxy]indolizin-2-yl}-2,2-dimethylpropanoic acid | 555.20 (M)+ |
| 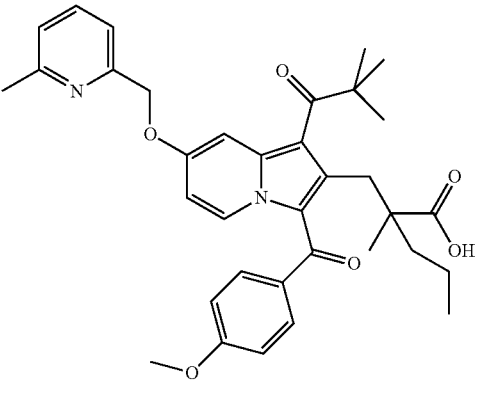 [SMILES: CCCC(C)(Cc1c(C(=O)C(C)(C)C)c2cc(OCc3cccc(C)n3)ccn2c1C(=O)c1ccc(OC)cc1)C(=O)O] | 2-({1-(2,2-Dimethylpropanoyl)-3-[(4-methoxyphenyl)carbonyl]-7-[(6-methylpyridin-2-yl)methoxy]indolizin-2-yl}methyl)-2-methylpentanoic acid | 585.20 (M)+ |

TABLE I-continued

| Structure | Name | Observed m/e |
|---|---|---|
| 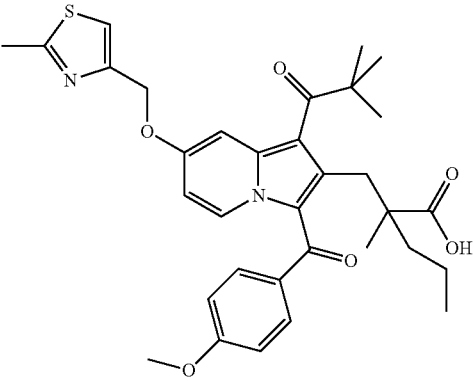 [SMILES: CCCC(C)(Cc1c(C(=O)C(C)(C)C)c2cc(OCc3csc(C)n3)ccn2c1C(=O)c1ccc(OC)cc1)C(=O)O] | 2-({1-(2,2-Dimethylpropanoyl)-3-[(4-methoxyphenyl)carbonyl]-7-[(2-methyl-1,3-thiazol-4-yl)methoxy]indolizin-2-yl}methyl)-2-methylpentanoic acid | 591.20 (M)+ |
| 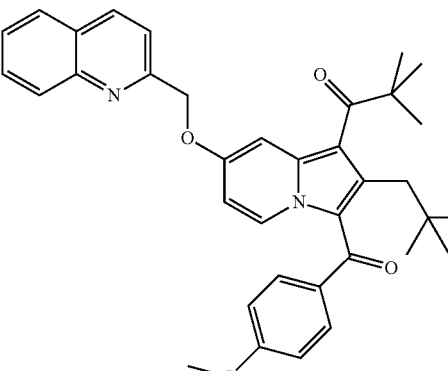 | 2-{[1-(2,2-Dimethylpropanoyl)-3-[(4-methoxyphenyl)carbonyl]-7-(quinolin-2-ylmethoxy)indolizin-2-yl]methyl}-2-methylpentanoic acid | 621.20 (M)+ |
| 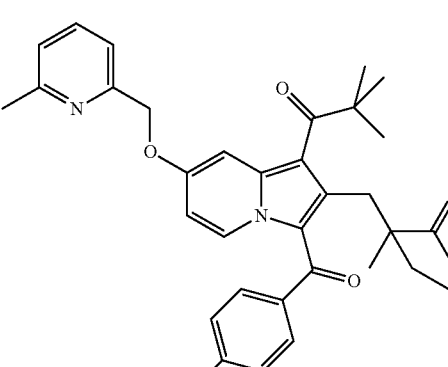 | 2-({1-(2,2-Dimethylpropanoyl)-3-[(4-methoxyphenyl)carbonyl]-7-[(6-methylpyridin-2-yl)methoxy]indolizin-2-yl}methyl)-2-methylbutanoic acid | 569.32 (M − H)− |
| 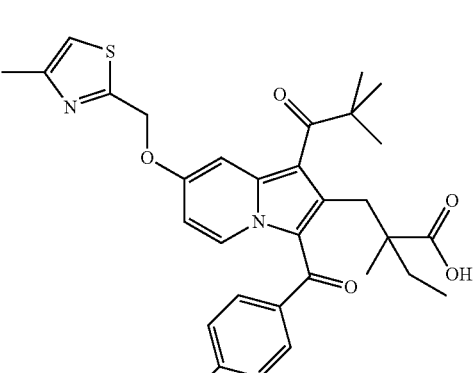 | 2-({1-(2,2-Dimethylpropanoyl)-3-[(4-methoxyphenyl)carbonyl]-7-[(4-methyl-1,3-thiazol-2-yl)methoxy]indolizin-2-yl}methyl)-2-methylbutanoic acid | 575.16 (M − H)− |

TABLE I-continued

| Structure | Name | Observed m/e |
|---|---|---|
| 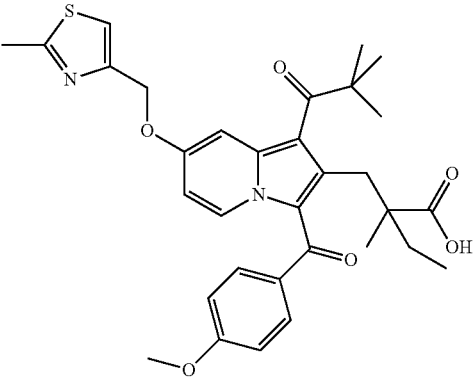 [SMILES: CCC(C)(Cc1c(C(=O)C(C)(C)C)c2cc(OCc3csc(C)n3)ccn2c1C(=O)c1ccc(OC)cc1)C(=O)O] | 2-({1-(2,2-Dimethylpropanoyl)-3-[(4-methoxyphenyl)carbonyl]-7-[(2-methyl-1,3-thiazol-4-yl)methoxy]indolizin-2-yl}methyl)-2-methylbutanoic acid | 575.03 (M − H)− |
| 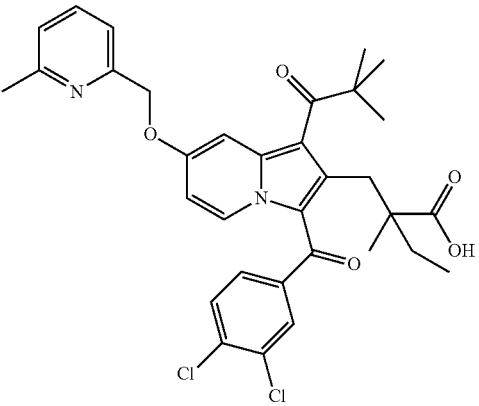 [SMILES: CCC(C)(Cc1c(C(=O)C(C)(C)C)c2cc(OCc3cccc(C)n3)ccn2c1C(=O)c1ccc(Cl)c(Cl)c1)C(=O)O] | 2-({3-[(3,4-Dichlorophenyl)carbonyl]-1-(2,2-dimethylpropanoyl)-7-[(6-methylpyridin-2-yl)methoxy]indolizin-2-yl}methyl)-2-methylbutanoic acid | 609.20 (M)+ |
| 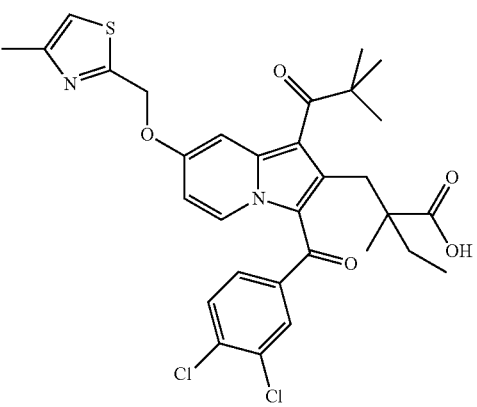 [SMILES: CCC(C)(Cc1c(C(=O)C(C)(C)C)c2cc(OCc3nc(C)cs3)ccn2c1C(=O)c1ccc(Cl)c(Cl)c1)C(=O)O] | 2-({3-[(3,4-Dichlorophenyl)carbonyl]-1-(2,2-dimethylpropanoyl)-7-[(4-methyl-1,3-thiazol-2-yl)methoxy]indolizin-2-yl}methyl)-2-methylbutanoic acid | 615.20 (M)+ |
| 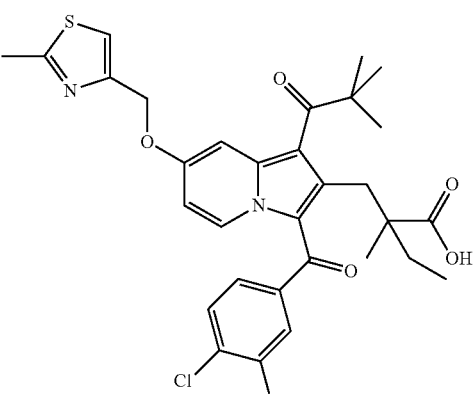 | 2-({3-[(3,4-Dichlorophenyl)carbonyl]-1-(2,2-dimethylpropanoyl)-7-[(2-methyl-1,3-thiazol-4-yl)methoxy]indolizin-2-yl}methyl)-2-methylbutanoic acid | 615.20 (M)+ |

TABLE I-continued

| Structure | Name | Observed m/e |
|---|---|---|
| 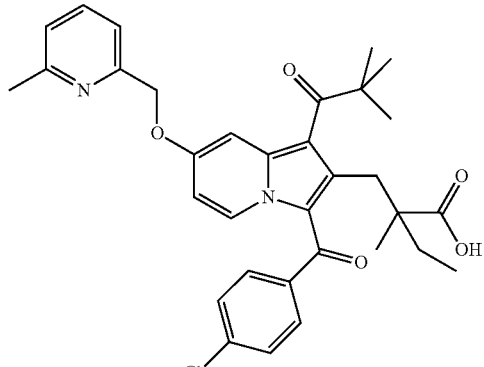 | 2-({3-[(4-Chlorophenyl)carbonyl]-1-(2,2-dimethylpropanoyl)-7-[(6-methylpyridin-2-yl)methoxy]indolizin-2-yl}methyl)-2-methylbutanoic acid | 575.20 (M)+ |
| 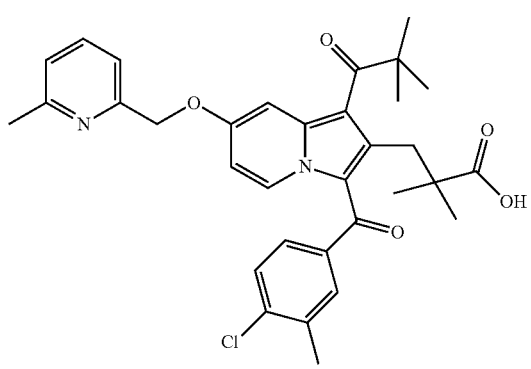 [SMILES: Cc1cccc(COc2ccn3c(C(=O)c4ccc(Cl)c(C)c4)c(CC(C)(C)C(=O)O)c(C(=O)C(C)(C)C)c3c2)n1] | 3-{3-[(4-Chloro-3-methylphenyl)carbonyl]-1-(2,2-dimethylpropanoyl)-7-[(6-methylpyridin-2-yl)methoxy]indolizin-2-yl}-2,2-dimethylpropanoic acid | 575.20 (M)+ |
| 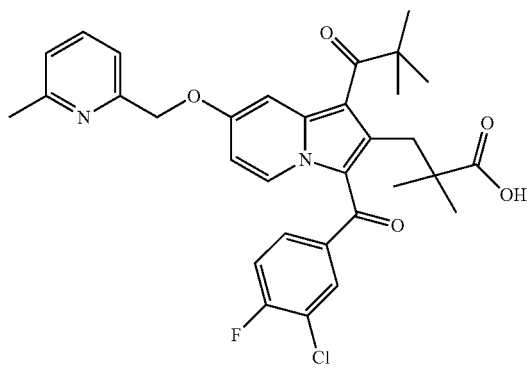 [SMILES: Cc1cccc(COc2ccn3c(C(=O)c4ccc(F)c(Cl)c4)c(CC(C)(C)C(=O)O)c(C(=O)C(C)(C)C)c3c2)n1] | 3-{3-[(3-Chloro-4-fluorophenyl)carbonyl]-1-(2,2-dimethylpropanoyl)-7-[(6-methylpyridin-2-yl)methoxy]indolizin-2-yl}-2,2-dimethylpropanoic acid | 579.20 (M)+ |
| 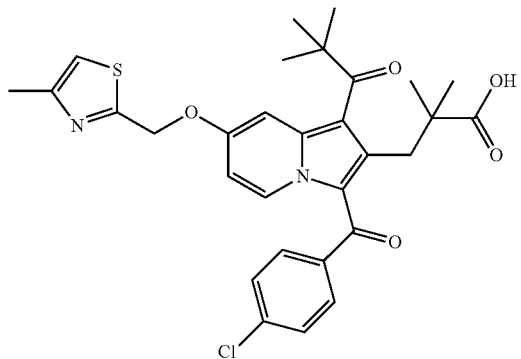 [SMILES: Cc1csc(COc2ccn3c(C(=O)c4ccc(Cl)cc4)c(CC(C)(C)C(=O)O)c(C(=O)C(C)(C)C)c3c2)n1] | 3-{3-[(4-Chlorophenyl)carbonyl]-1-(2,2-dimethylpropanoyl)-7-[(4-methyl-1,3-thiazol-2-yl)methoxy]indolizin-2-yl}-2,2-dimethylpropanoic acid | 567.20 (M)+ |

TABLE I-continued

| Structure | Name | Observed m/e |
|---|---|---|
| 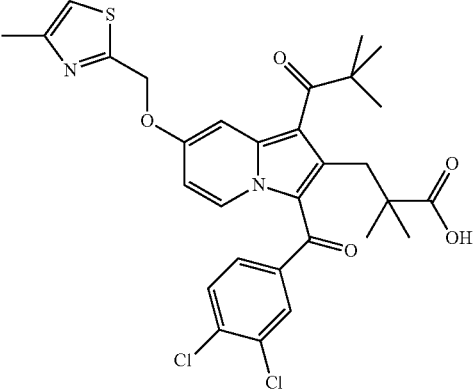 [SMILES: Cc1csc(COc2ccn3c(C(=O)c4ccc(Cl)c(Cl)c4)c(CC(C)(C)C(=O)O)c(C(=O)C(C)(C)C)c3c2)n1] | 3-{3-[(3,4-Dichlorophenyl)carbonyl]-1-(2,2-dimethylpropanoyl)-7-[(4-methyl-1,3-thiazol-2-yl)methoxy]indolizin-2-yl}-2,2-dimethylpropanoic acid | 601.00 (M)+ |
| 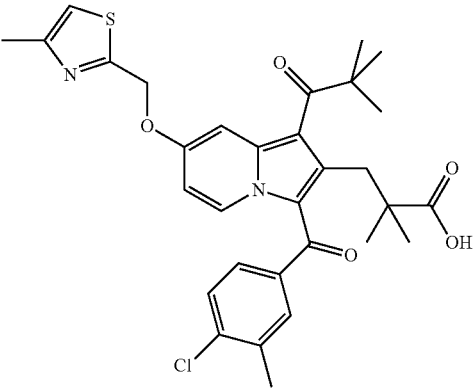 [SMILES: Cc1csc(COc2ccn3c(C(=O)c4ccc(Cl)c(C)c4)c(CC(C)(C)C(=O)O)c(C(=O)C(C)(C)C)c3c2)n1] | 3-{3-[(4-Chloro-3-methylphenyl)carbonyl]-1-(2,2-dimethylpropanoyl)-7-[(4-methyl-1,3-thiazol-2-yl)methoxy]indolizin-2-yl}-2,2-dimethylpropanoic acid | 581.20 (M)+ |
| 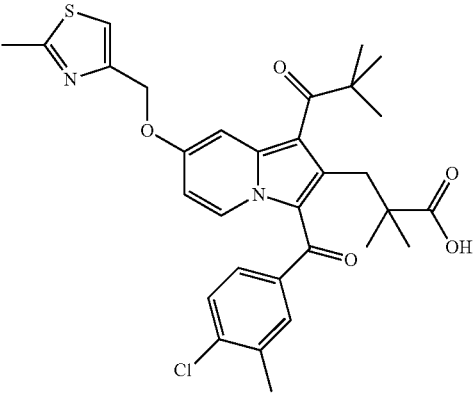 [SMILES: Cc1nc(COc2ccn3c(C(=O)c4ccc(Cl)c(C)c4)c(CC(C)(C)C(=O)O)c(C(=O)C(C)(C)C)c3c2)cs1] | 3-{3-[(4-Chloro-3-methylphenyl)carbonyl]-1-(2,2-dimethylpropanoyl)-7-[(2-methyl-1,3-thiazol-4-yl)methoxy]indolizin-2-yl}-2,2-dimethylpropanoic acid | 581.20 (M)+ |
| 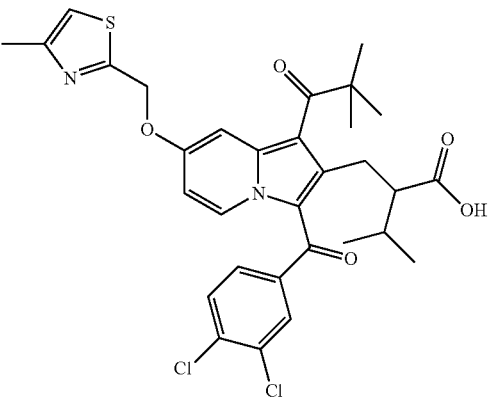 [SMILES: Cc1csc(COc2ccn3c(C(=O)c4ccc(Cl)c(Cl)c4)c(CC(C(=O)O)C(C)C)c(C(=O)C(C)(C)C)c3c2)n1] | 2-({3-[(3,4-Dichlorophenyl)carbonyl]-1-(2,2-dimethylpropanoyl)-7-[(4-methyl-1,3-thiazol-2-yl)methoxy]indolizin-2-yl}methyl)-3-methylbutanoic acid | 615.20 (M)+ |

TABLE I-continued

| Structure | Name | Observed m/e |
|---|---|---|
| 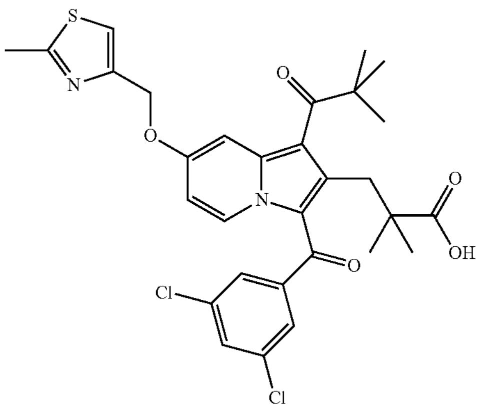 [SMILES: Cc1nc(COc2ccn3c(C(=O)c4cc(Cl)cc(Cl)c4)c(CC(C)(C)C(=O)O)c(C(=O)C(C)(C)C)c3c2)cs1] | 3-{3-[(3,5-Dichlorophenyl)carbonyl]-1-(2,2-dimethylpropanoyl)-7-[(2-methyl-1,3-thiazol-4-yl)methoxy]indolizin-2-yl}-2,2-dimethylpropanoic acid | 601.20 (M)+ |
| 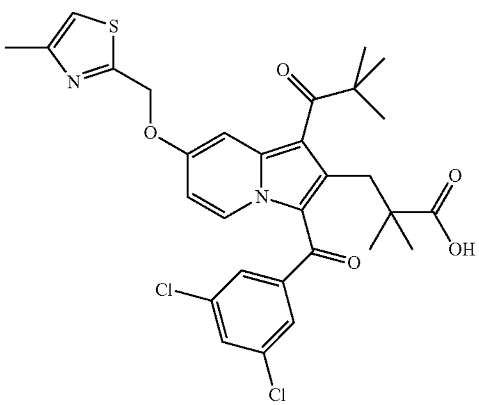 [SMILES: Cc1csc(COc2ccn3c(C(=O)c4cc(Cl)cc(Cl)c4)c(CC(C)(C)C(=O)O)c(C(=O)C(C)(C)C)c3c2)n1] | 3-{3-[(3,5-Dichlorophenyl)carbonyl]-1-(2,2-dimethylpropanoyl)-7-[(4-methyl-1,3-thiazol-2-yl)methoxy]indolizin-2-yl}-2,2-dimethylpropanoic acid | 601.20 (M)+ |
| 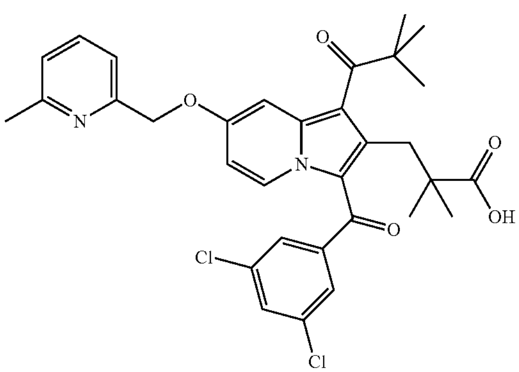 [SMILES: Cc1cccc(COc2ccn3c(C(=O)c4cc(Cl)cc(Cl)c4)c(CC(C)(C)C(=O)O)c(C(=O)C(C)(C)C)c3c2)n1] | 3-{3-[(3,5-Dichlorophenyl)carbonyl]-1-(2,2-dimethylpropanoyl)-7-[(6-methylpyridin-2-yl)methoxy]indolizin-2-yl}-2,2-dimethylpropanoic acid | 595.2 (M)+ |
| 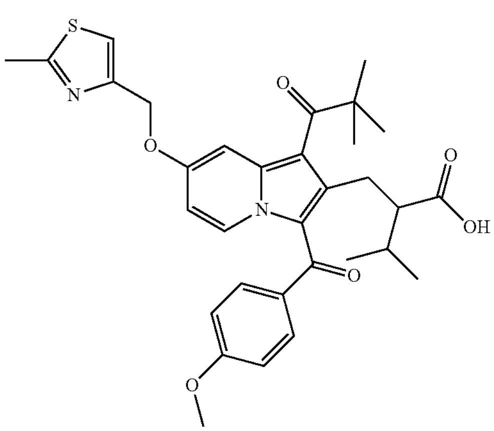 | 2-({1-(2,2-Dimethylpropanoyl)-3-[(4-methoxyphenyl)carbonyl]-7-[(2-methyl-1,3-thiazol-4-yl)methoxy]indolizin-2-yl}methyl)-3-methylbutanoic acid | 577.20 (M)+ |

TABLE I-continued

| Structure | Name | Observed m/e |
|---|---|---|
| 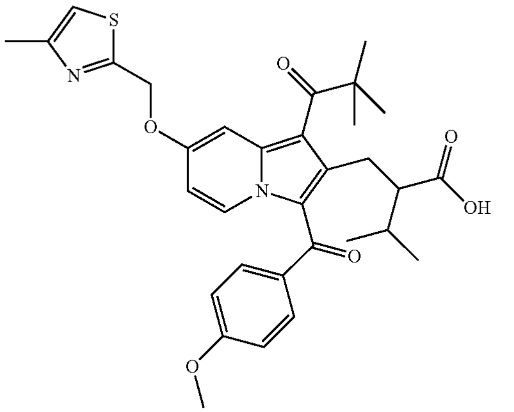 [SMILES: COc1ccc(C(=O)c2c(CC(C(=O)O)C(C)C)c(C(=O)C(C)(C)C)c3cc(OCc4nc(C)cs4)ccn23)cc1] | 2-({1-(2,2-Dimethylpropanoyl)-3-[(4-methoxyphenyl)carbonyl]-7-[(4-methyl-1,3-thiazol-2-yl)methoxy]indolizin-2-yl}methyl)-3-methylbutanoic acid | 577.20 (M)+ |
| 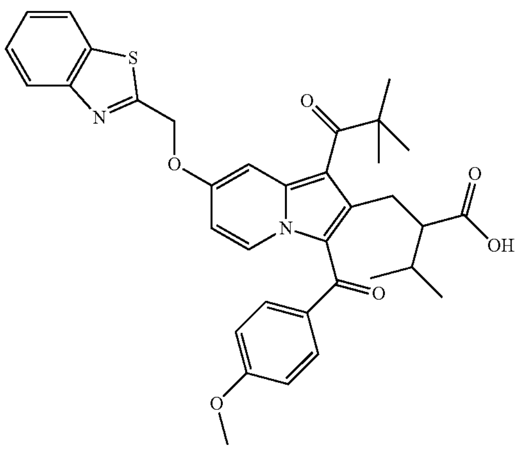 [SMILES: COc1ccc(C(=O)c2c(CC(C(=O)O)C(C)C)c(C(=O)C(C)(C)C)c3cc(OCc4nc5ccccc5s4)ccn23)cc1] | 2-({7-(1,3-Benzothiazol-2-ylmethoxy)-1-(2,2-dimethylpropanoyl)-3-[(4-methoxyphenyl)carbonyl]indolizin-2-yl}methyl)-3-methylbutanoic acid | 613.20 (M)+ |
| 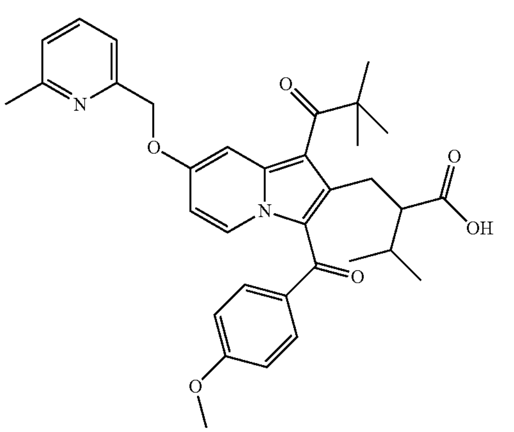 [SMILES: COc1ccc(C(=O)c2c(CC(C(=O)O)C(C)C)c(C(=O)C(C)(C)C)c3cc(OCc4cccc(C)n4)ccn23)cc1] | 2-({1-(2,2-Dimethylpropanoyl)-3-[(4-methoxyphenyl)carbonyl]-7-[(6-methylpyridin-2-yl)methoxy]indolizin-2-yl}methyl)-3-methylbutanoic acid | 571.20 (M)+ |

TABLE I-continued

| Structure | Name | Observed m/e |
|---|---|---|
| 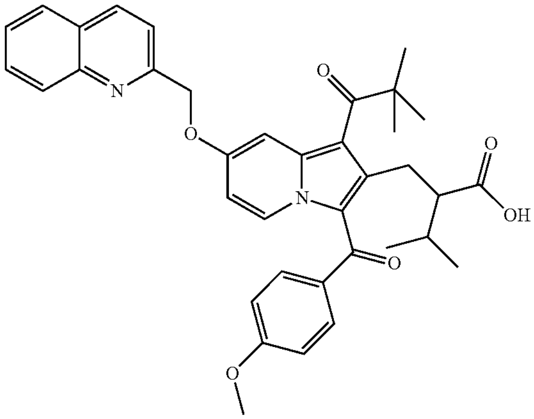 [SMILES: COc1ccc(C(=O)c2c(CC(C(=O)O)C(C)C)c(C(=O)C(C)(C)C)c3cc(OCc4ccc5ccccc5n4)ccn23)cc1] | 2-{[1-(2,2-Dimethylpropanoyl)-3-[(4-methoxyphenyl)carbonyl]-7-(quinolin-2-ylmethoxy)indolizin-2-yl]methyl}-3-methylbutanoic acid | 607.2 (M)+ |
| 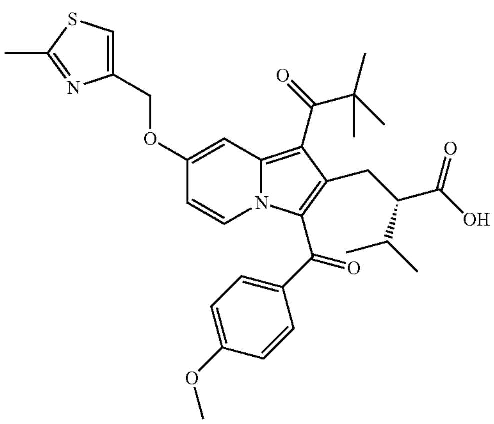 [SMILES: COc1ccc(C(=O)c2c(C[C@H](C(=O)O)C(C)C)c(C(=O)C(C)(C)C)c3cc(OCc4csc(C)n4)ccn23)cc1] | (2S)-2-({1-(2,2-Dimethylpropanoyl)-3-[(4-methoxyphenyl)carbonyl]-7-[(2-methyl-1,3-thiazol-4-yl)methoxy]indolizin-2-yl}methyl)-3-methylbutanoic acid | 577.20 (M)+ |
| 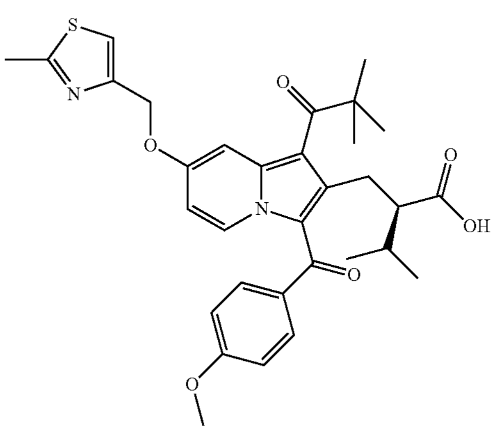 [SMILES: COc1ccc(C(=O)c2c(C[C@@H](C(=O)O)C(C)C)c(C(=O)C(C)(C)C)c3cc(OCc4csc(C)n4)ccn23)cc1] | (2R)-2-({1-(2,2-Dimethylpropanoyl)-3-[(4-methoxyphenyl)carbonyl]-7-[(2-methyl-1,3-thiazol-4-yl)methoxy]indolizin-2-yl}methyl)-3-methylbutanoic acid | 577.20 (M)+ |

TABLE I-continued

| Structure | Name | Observed m/e |
|---|---|---|
| 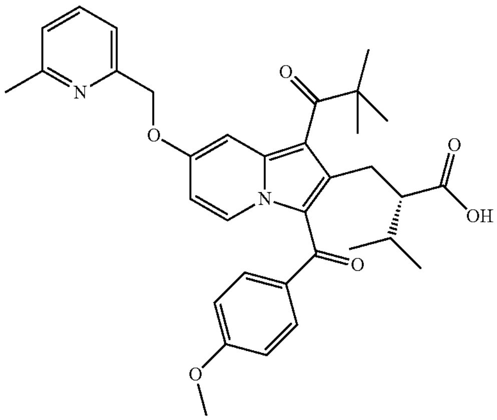 [SMILES: COc1ccc(C(=O)c2c(C[C@H](C(=O)O)C(C)C)c(C(=O)C(C)(C)C)c3cc(OCc4cccc(C)n4)ccn23)cc1] | (2S)-2-({1-(2,2-Dimethylpropanoyl)-3-[(4-methoxyphenyl)carbonyl]-7-[(6-methylpyridin-2-yl)methoxy]indolizin-2-yl}methyl)-3-methylbutanoic acid | 571.20 (M)+ |
| 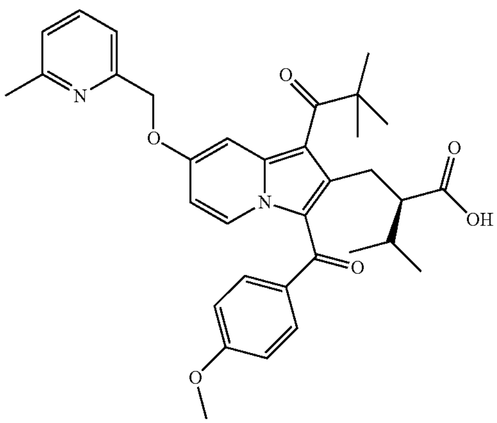 [SMILES: COc1ccc(C(=O)c2c(C[C@@H](C(=O)O)C(C)C)c(C(=O)C(C)(C)C)c3cc(OCc4cccc(C)n4)ccn23)cc1] | (2R)-2-({1-(2,2-Dimethylpropanoyl)-3-[(4-methoxyphenyl)carbonyl]-7-[(6-methylpyridin-2-yl)methoxy]indolizin-2-yl}methyl)-3-methylbutanoic acid | 571.20 (M)+ |
| 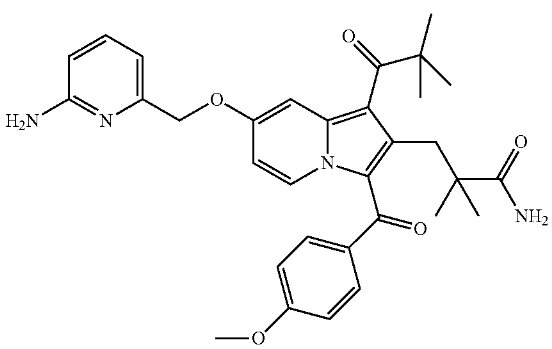 [SMILES: COc1ccc(C(=O)c2c(CC(C)(C)C(N)=O)c(C(=O)C(C)(C)C)c3cc(OCc4cccc(N)n4)ccn23)cc1] | 3-{7-[(6-Aminopyridin-2-yl)methoxy]-1-(2,2-dimethylpropanoyl)-3-(4-methoxybenzoyl)indolizin-2-yl}-2,2-dimethylpropanamide | 557.20 (M + H)+ |
| 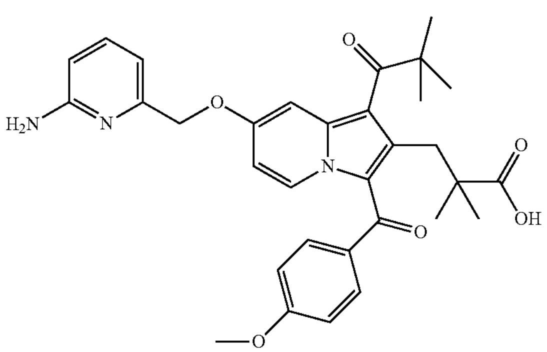 [SMILES: COc1ccc(C(=O)c2c(CC(C)(C)C(=O)O)c(C(=O)C(C)(C)C)c3cc(OCc4cccc(N)n4)ccn23)cc1] | 3-{7-[(6-Aminopyridin-2-yl)methoxy]-1-(2,2-dimethylpropanoyl)-3-(4-methoxybenzoyl)indolizin-2-yl}-2,2-dimethylpropanoic acid | 558.20 (M + H)+ |

In one embodiment, the invention relates to any of the compounds depicted in Table 1 above, and the pharmaceutically acceptable salts thereof.

In another embodiment, the invention relates to compound selected from the group consisting of:

3-[1-(2,2-Dimethylpropanoyl)-3-{[4-(6-methoxypyridin-3-yl)phenyl]carbonyl}-7-(pyridin-2-ylmethoxy)indolizin-2-yl]-2,2-dimethylpropanoic acid;

3-[6-(1,3-Benzothiazol-2-ylmethoxy)-1-[(4-chlorophenyl)carbonyl]-3-(2,2-dimethylpropanoyl)indolizin-2-yl]-2,2-dimethylpropanoic acid;

3-{1-(2,2-Dimethylpropanoyl)-3-[(4-methylphenyl)carbonyl]-7-[(6-methylpyridin-2-yl)methoxy]indolizin-2-yl}-2,2-dimethylpropanoic acid;

3-{1-[(4-Chlorophenyl)carbonyl]-3-(2,2-dimethylpropanoyl)-6-[(2-methyl-1,3-thiazol-4-yl)methoxy]indolizin-2-yl}-2,2-dimethylpropanoic acid;

3-{1-[(4-Chlorophenyl)carbonyl]-3-(2,2-dimethylpropanoyl)-6-[(2-methyl-1,3-thiazol-4-yl)methoxy]indolizin-2-yl}-2,2-dimethyl-N-(methylsulfonyl)propanamide;

3-{1-[(4-Chlorophenyl)carbonyl]-3-(2,2-dimethylpropanoyl)-6-[(6-methylpyridin-2-yl)methoxy]indolizin-2-yl}-2,2-dimethylpropanoic acid;

3-{3-[(4-Chlorophenyl)carbonyl]-1-(2,2-dimethylpropanoyl)-7-(quinolin-2-ylmethoxy)indolizin-2-yl}-2,2-dimethylpropanoic acid;

3-{3-[(4-Chlorophenyl)carbonyl]-1-(2,2-dimethylpropanoyl)-7-[(2-methyl-1,3-thiazol-4-yl)methoxy]indolizin-2-yl}-2,2-dimethylpropanoic acid;

3-{3-[(4-Chlorophenyl)carbonyl]-1-(2,2-dimethylpropanoyl)-7-[(6-methylpyridin-2-yl)methoxy]indolizin-2-yl}-2,2-dimethylpropanoic acid;

3-{1-(2,2-Dimethylpropanoyl)-3-[(4-methoxyphenyl)carbonyl]-7-[(6-methylpyridin-2-yl)methoxy]indolizin-2-yl}-2,2-dimethylpropanoic acid;

3-[1-(2,2-Dimethylpropanoyl)-7-[(6-methylpyridin-2-yl)methoxy]-3-{[4-(morpholin-4-yl)phenyl]carbonyl}indolizin-2-yl]-2,2-dimethylpropanoic acid;

3-[1-(2,2-Dimethylpropanoyl)-7-[(6-methylpyridin-2-yl)methoxy]-3-{[4-(pyrrolidin-1-yl)phenyl]carbonyl}indolizin-2-yl]-2,2-dimethylpropanoic acid;

3-{7-[(2-Aminopyrimidin-4-yl)methoxy]-3-[(4-chlorophenyl)carbonyl]-1-(2,2-dimethylpropanoyl)indolizin-2-yl}-2,2-dimethylpropanoic acid;

3-{3-[(4-Chlorophenyl)carbonyl]-1-(2,2-dimethylpropanoyl)-7-[(4-methyl-1,3-thiazol-2-yl)methoxy]indolizin-2-yl}-2,2-dimethylpropanoic acid;

3-{3-[(4-Chlorophenyl)carbonyl]-1-(2,2-dimethylpropanoyl)-7-[(1-methyl-1H-pyrazol-3-yl)methoxy]indolizin-2-yl}-2,2-dimethylpropanoic acid;

2-({3-[(4-Chlorophenyl)carbonyl]-1-(2,2-dimethylpropanoyl)-7-[(6-methylpyridin-2-yl)methoxy]indolizin-2-yl}methyl)-2-ethylbutanoic acid;

2-({3-[(4-Chlorophenyl)carbonyl]-1-(2,2-dimethylpropanoyl)-7-[(2-methyl-1,3-thiazol-4-yl)methoxy]indolizin-2-yl}methyl)-2-ethylbutanoic acid;

3-{3-[(4-Chlorophenyl)carbonyl]-1-(2,2-dimethylpropanoyl)-7-(1,3-thiazol-4-ylmethoxy)indolizin-2-yl}-2,2-dimethylpropanoic acid;

3-[7-(1,3-Benzothiazol-2-ylmethoxy)-3-[(4-chlorophenyl)carbonyl]-1-(2,2-dimethylpropanoyl)indolizin-2-yl]-2,2-dimethylpropanoic acid;

3-{3-[(4-Chlorophenyl)carbonyl]-1-(2,2-dimethylpropanoyl)-7-(pyridin-2-ylmethoxy)indolizin-2-yl}-2,2-dimethylpropanoic acid;

3-{3-[(4-Chloro-3-methylphenyl)carbonyl]-1-(2,2-dimethylpropanoyl)-7-[(4-methyl-1,3-thiazol-2-yl)methoxy]indolizin-2-yl}-2,2-dimethylpropanoic acid;

3-{3-[(3,4-Dichlorophenyl)carbonyl]-1-(2,2-dimethylpropanoyl)-7-[(4-methyl-1,3-thiazol-2-yl)methoxy]indolizin-2-yl}-2,2-dimethylpropanoic acid;

2-({1-(2,2-Dimethylpropanoyl)-3-[(4-methoxyphenyl)carbonyl]-7-[(4-methyl-1,3-thiazol-2-yl)methoxy]indolizin-2-yl}methyl)-3-methylbutanoic acid;

3-{7-(1,3-Benzothiazol-2-ylmethoxy)-1-(2,2-dimethylpropanoyl)-3-[(4-methoxyphenyl)carbonyl]indolizin-2-yl}-2,2-dimethylpropanoic acid;

2-({7-(1,3-Benzothiazol-2-ylmethoxy)-1-(2,2-dimethylpropanoyl)-3-[(4-methoxyphenyl)carbonyl]indolizin-2-yl}methyl)-3-methylbutanoic acid;

3-{3-[(3,5-Dichlorophenyl)carbonyl]-1-(2,2-dimethylpropanoyl)-7-[(2-methyl-1,3-thiazol-4-yl)methoxy]indolizin-2-yl}-2,2-dimethylpropanoic acid;

2-({1-(2,2-Dimethylpropanoyl)-3-[(4-methoxyphenyl)carbonyl]-7-[(2-methyl-1,3-thiazol-4-yl)methoxy]indolizin-2-yl}methyl)-3-methylbutanoic acid;

(2R)-2-({1-(2,2-Dimethylpropanoyl)-3-[(4-methoxyphenyl)carbonyl]-7-[(2-methyl-1,3-thiazol-4-yl)methoxy]indolizin-2-yl}methyl)-3-methylbutanoic acid;

2-({3-[(3,4-Dichlorophenyl)carbonyl]-1-(2,2-dimethylpropanoyl)-7-[(6-methylpyridin-2-yl)methoxy]indolizin-2-yl}methyl)pentanoic acid;

3-{3-[(4-Chloro-3-methylphenyl)carbonyl]-1-(2,2-dimethylpropanoyl)-7-[(2-methyl-1,3-thiazol-4-yl)methoxy]indolizin-2-yl}-2,2-dimethylpropanoic acid;

2-({1-(2,2-Dimethylpropanoyl)-3-[(4-methoxyphenyl)carbonyl]-7-[(6-methylpyridin-2-yl)methoxy]indolizin-2-yl}methyl)-2-methylbutanoic acid;

3-{1-(2,2-Dimethylpropanoyl)-3-[(4-methoxyphenyl)carbonyl]-7-[(4-methyl-1,3-thiazol-2-yl)methoxy]indolizin-2-yl}-2,2-dimethylpropanoic acid;

3-{3-[(3,4-Dichlorophenyl)carbonyl]-1-(2,2-dimethylpropanoyl)-7-[(6-methylpyridin-2-yl)methoxy]indolizin-2-yl}-2,2-dimethylpropanoic acid;

3-[1-(2,2-Dimethylpropanoyl)-3-[(4-methoxyphenyl)carbonyl]-7-(quinolin-2-ylmethoxy)indolizin-2-yl]-2,2-dimethylpropanoic acid;

2-{[1-(2,2-Dimethylpropanoyl)-3-[(4-methoxyphenyl)carbonyl]-7-(quinolin-2-ylmethoxy)indolizin-2-yl]methyl}-3-methylbutanoic acid;

3-{3-[(3-Chlorophenyl)carbonyl]-1-(2,2-dimethylpropanoyl)-7-[(4-methyl-1,3-thiazol-2-yl)methoxy]indolizin-2-yl}-2,2-dimethylpropanoic acid;

3-{3-[(3,4-Dichlorophenyl)carbonyl]-1-(2,2-dimethylpropanoyl)-7-[(2-methyl-1,3-thiazol-4-yl)methoxy]indolizin-2-yl}-2,2-dimethylpropanoic acid;

2-({3-[(3,4-Dichlorophenyl)carbonyl]-1-(2,2-dimethylpropanoyl)-7-[(4-methyl-1,3-thiazol-2-yl)methoxy]indolizin-2-yl}methyl)pentanoic acid;

2-({1-(2,2-Dimethylpropanoyl)-3-[(4-methoxyphenyl)carbonyl]-7-[(2-methyl-1,3-thiazol-4-yl)methoxy]indolizin-2-yl}methyl)pentanoic acid;

2-({1-(2,2-Dimethylpropanoyl)-3-[(4-methoxyphenyl)carbonyl]-7-[(6-methylpyridin-2-yl)methoxy]indolizin-2-yl}methyl)-3-methylbutanoic acid;

2-({1-(2,2-Dimethylpropanoyl)-3-[(4-methoxyphenyl)carbonyl]-7-[(2-methyl-1,3-thiazol-4-yl)methoxy]indolizin-2-yl}methyl)-2-methylbutanoic acid;

2-({1-(2,2-Dimethylpropanoyl)-3-[(4-methoxyphenyl)carbonyl]-7-[(6-methylpyridin-2-yl)methoxy]indolizin-2-yl}methyl)pentanoic acid;

2-({3-[(4-Chloro-3-methylphenyl)carbonyl]-1-(2,2-dimethylpropanoyl)-7-[(6-methylpyridin-2-yl)methoxy]indolizin-2-yl}methyl)pentanoic acid;

3-{7-[(6-Aminopyridin-2-yl)methoxy]-1-(2,2-dimethylpropanoyl)-3-(4-methoxybenzoyl)indolizin-2-yl}-2,2-dimethylpropanamide;

and pharmaceutically salts thereof.

For all compounds disclosed hereinabove in this application, in the event the nomenclature is in conflict with the structure, it shall be understood that the compound is defined by the structure.

The invention also relates to pharmaceutical preparations, containing as active substance one or more compounds of the invention, or the pharmaceutically acceptable derivatives thereof, optionally combined with conventional excipients and/or carriers.

Compounds of the invention also include their isotopically-labelled forms. An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g. $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. An active agent of a combination of the present invention, a prodrug thereof, or a pharmaceutically acceptable salt of either which contains one or more of the above-mentioned isotopes and/or other isotopes of other atoms is contemplated to be within the scope of the present invention.

The invention includes the use of any compounds of described above containing one or more asymmetric carbon atoms may occur as racemates and racemic mixtures, single enantiomers, diastereomeric mixtures and individual diastereomers. Isomers shall be defined as being enantiomers and diastereomers. All such isomeric forms of these compounds are expressly included in the present invention. Each stereogenic carbon may be in the R or S configuration, or a combination of configurations.

Some of the compounds of the invention can exist in more than one tautomeric form. The invention includes methods using all such tautomers.

All terms as used herein in this specification, unless otherwise stated, shall be understood in their ordinary meaning as known in the art. For example, "$C_{1-6}$ alkoxy" is a $C_{1-6}$ alkyl with a terminal oxygen, such as methoxy, ethoxy, propoxy, butoxy. All alkyl, alkenyl, and alkynyl groups shall be understood as being branched or unbranched where structurally possible and unless otherwise specified. Other more specific definitions are as follows:

The term "alkyl" refers to both branched and unbranched alkyl groups. It should be understood that any combination term using an "alk" or "alkyl" prefix refers to analogs according to the above definition of "alkyl". For example, terms such as "alkoxy", "alkylhio" refer to alkyl groups linked to a second group via an oxygen or sulfur atom. "Alkanoyl" refers to an alkyl group linked to a carbonyl group (C=O).

In all alkyl groups or carbon chains, one or more carbon atoms can be optionally replaced by heteroatoms such as O, S or N. It shall be understood that if N is not substituted then it is NH. It shall also be understood that the heteroatoms may replace either terminal carbon atoms or internal carbon atoms within a branched or unbranched carbon chain.

Such groups can be substituted as herein above described by groups such as oxo to result in definitions such as but not limited to: alkoxycarbonyl, acyl, amido and thioxo. As used herein, "nitrogen" and "sulfur" include any oxidized form of nitrogen and sulfur and the quaternized form of any basic nitrogen. For example, for a —S—$C_{1-6}$ alkyl radical, unless otherwise specified, shall be understood to include —S(O)—$C_{1-6}$ alkyl and —S(O)$_2$—$C_{1-6}$ alkyl.

The term "$C_{3-10}$ carbocycle" refers to a nonaromatic 3 to 10-membered (but preferably, 3 to 6-membered) monocyclic carbocyclic radical or a nonaromatic 6 to 10-membered fused bicyclic, bridged bicyclic, or spirocyclic carbocyclic radical. The $C_{3-10}$ carbocycle may be either saturated or partially unsaturated, and the carbocycle may be attached by any atom of the cycle which results in the creation of a stable structure. Non-limiting examples of 3 to 10-membered monocyclic carbocycles include cyclopropyl, cyclobutyl, cyclopentyl, cyclopentenyl, cyclohexyl, cyclohexenyl, cycloheptanyl, cycloheptenyl, and cyclohexanone. Non-limiting examples of 6 to 10-membered fused bicyclic carbocyclic radicals include bicyclo[3.3.0]octane, bicyclo[4.3.0]nonane, and bicyclo[4.4.0]decanyl (decahydronaphthalenyl). Non-limiting examples of 6 to 10-membered bridged bicyclic carbocyclic radicals include bicyclo[2.2.2]heptanyl, bicyclo[2.2.2]octanyl, and bicyclo[3.2.1]octanyl. Non-limiting examples of 6 to 10-membered spirocyclic carbocyclic radicals include but are not limited to spiro[3,3]heptanyl, spiro[3,4]octanyl and spiro[4,4]heptanyl.

The term "$C_{6-10}$ aryl" refers to aromatic hydrocarbon rings containing from six to ten carbon ring atoms. The term $C_{6-10}$ aryl includes monocyclic rings and bicyclic rings where at least one of the rings is aromatic. Non-limiting examples of $C_{6-10}$ aryls include phenyl, indanyl, indenyl, benzocyclobutanyl, dihydronaphthyl, tetrahydronaphthyl, naphthyl, benzocycloheptanyl and benzocycloheptenyl.

The term "5 to 11-membered heterocycle" refers to a stable nonaromatic 4-8 membered monocyclic heterocyclic radical or a stable nonaromatic 6 to 11-membered fused bicyclic, bridged bicyclic or spirocyclic heterocyclic radical. The 5 to 11-membered heterocycle consists of carbon atoms and one or more, preferably from one to four heteroatoms chosen from nitrogen, oxygen and sulfur. The heterocycle may be either saturated or partially unsaturated. Non-limiting examples of nonaromatic 4-8 membered monocyclic heterocyclic radicals include tetrahydrofuranyl, azetidinyl, pyrrolidinyl, pyranyl, tetrahydropyranyl, dioxanyl, thiomorpholinyl, 1,1-dioxo-1$\lambda^6$-thiomorpholinyl, morpholinyl, piperidinyl, piperazinyl, and azepinyl. Non-limiting examples of nonaromatic 6 to 11-membered fused bicyclic radicals include octahydroindolyl, octahydrobenzofuranyl, and octahydrobenzothiophenyl. Non-limiting examples of nonaromatic 6 to 11-membered bridged bicyclic radicals include 2-azabicyclo[2.2.1]heptanyl, 3-azabicyclo[3.1.0]hexanyl, and 3-azabicyclo[3.2.1]octanyl. Non-limiting examples of nonaromatic 6 to 11-membered spirocyclic heterocyclic radicals include 7-aza-spiro[3,3]heptanyl, 7-spiro[3,4]octanyl, and 7-aza-spiro[3,4]octanyl.

The term "5 to 11-membered heteroaryl" shall be understood to mean an aromatic 5 to 6-membered monocyclic heteroaryl or an aromatic 7 to 11-membered heteroaryl bicyclic ring where at least one of the rings is aromatic, wherein the heteroaryl ring contains 1-4 heteroatoms such as N, O and S, Non-limiting examples of 5 to 6-membered monocyclic heteroaryl rings include furanyl, oxazolyl, isoxazolyl, oxadiazolyl, thiazolyl, pyrazolyl, pyrrolyl, imidazolyl, tetrazolyl, triazolyl, thienyl, thiadiazolyl, pyridinyl, pyrimidinyl, pyridazinyl, pyrazinyl, triazinyl, and purinyl. Non-limiting examples of 7 to 11-membered heteroaryl bicyclic heteroaryl rings include benzimidazolyl, quinolinyl, dihydro-2H-quinolinyl, isoquinolinyl, quinazolinyl, indazolyl, thieno[2,3-d]pyrimidinyl, indolyl, isoindolyl, benzofuranyl, benzopyranyl, benzodioxolyl, benzoxazolyl and benzothiazolyl.

It will be understood that one to three carbon ring moieties in the each of the $C_{3-10}$ carbocyclic rings, the 5 to 11-membered heterocyclic rings, the nonaromatic portion of the bicyclic aryl rings, and the nonaromatic portion of the bicyclic heteroaryl rings can independently be replaced with a carbonyl, thiocarbonyl, or iminyl moiety, i.e., —C(=O)—, —C(=S)— and —C(=NR$^8$)—, respectively, where R$^8$ is as defined above.

The term "heteroatom" as used herein shall be understood to mean atoms other than carbon such as O, N, and S.

The term "halogen" as used in the present specification shall be understood to mean bromine, chlorine, fluorine or iodine. The definitions "halogenated", "partially or fully halogenated"; partially or fully fluorinated; "substituted by one or more halogen atoms", includes for example, mono, di or tri halo derivatives on one or more carbon atoms. For alkyl, a non-limiting example would be —CH$_2$CHF$_2$, —CF$_3$ etc.

Each alkyl, carbocycle, heterocycle or heteroaryl, or the analogs thereof, described herein shall be understood to be optionally partially or fully halogenated.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the invention.

Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal (e.g., magnesium), ammonium and N—(C$_1$-C$_4$ alkyl)$_4^+$ salts.

In addition, within the scope of the invention is use of prodrugs of compounds of the invention. Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

The compounds of formula I may be made using the general synthetic methods described below, which also constitute part of the invention.

General Synthetic Methods

The compounds of the invention may be prepared by the methods described below. In each of the schemes below, the groups R$^1$ to R$^4$, X$^1$ to X$^4$, and D are as defined above for general formula I unless noted otherwise and A=halogen. Optimum reaction conditions and reaction times may vary depending on the particular reactants used. Unless otherwise specified, solvents, temperatures, pressures and other reaction conditions may be readily selected by one of ordinary skill in the art. Specific procedures are provided in the Synthetic Examples section. Typically, reaction progress may be monitored by thin layer chromatography (TLC) or HPLC-MS if desired. Intermediates and products may be purified by chromatography on silica gel, recrystallization and/or reverse phase HPLC. Discrete enantiomers may be obtained by resolution of racemic products using chiral HPLC. Reverse phase HPLC purification methods used anywhere from 0-100% acetonitrile in water containing 0.1% formic acid or 0.1% TFA and used one of the following columns:
a) Waters Sunfire OBD C18 5 μM 30×150 mm column
b) Waters XBridge OBD C18 5 μM 30×150 mm column
c) Waters ODB C8 5 μM 19×150 mm column.
d) Waters Atlantis ODB C18 5 μM 19×50 mm column.
e) Waters Atlantis T3 OBD 5 μM 30×100 mm column
f) Phenomenex Gemini Axia C18 5 μM 30×100 mm column Starting materials and reagents are either commercially available or may be prepared by one skilled in the art using methods described in the chemical literature.

Compounds of formula I may be prepared as shown in Schemes Ia and Ib below.

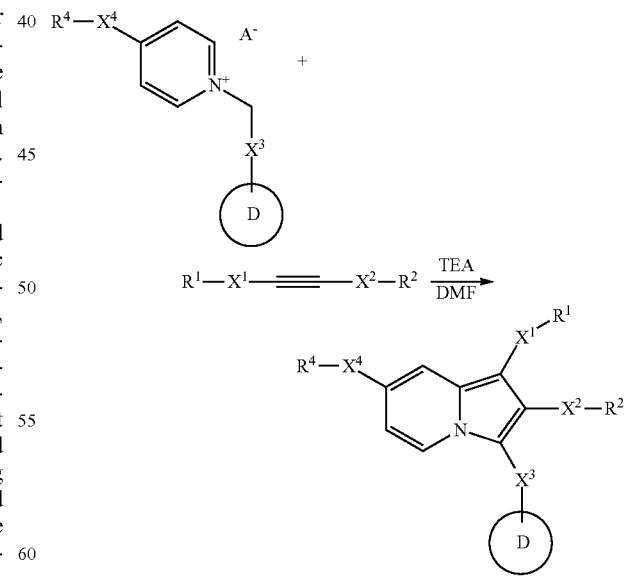

Scheme Ia

In Scheme Ia, a pyridinium salt is treated with TEA, or other suitable base, to generate an ylide to undergo a dipolar cycloaddition with an alkyne in a suitable solvent such as DMF to form the compound of general formula I where A is C and B is N.

Scheme Ib

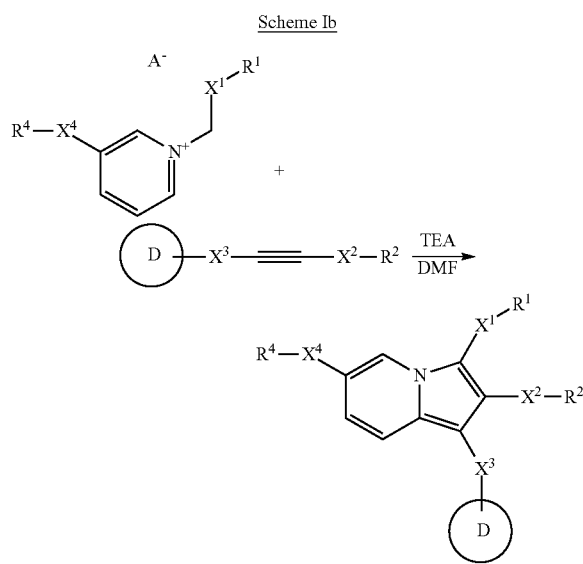

In Scheme Ib, a pyridinium salt is treated with TEA, or other suitable base, to generate an ylide to undergo a dipolar cycloaddition with an alkyne in a suitable solvent such as DMF to form the compound of general formula I where A is N and B is C.

Compounds of formula I prepared by the above methods may be further converted to additional compounds of formula I by methods known in the art and exemplified in the Synthetic Examples section below.

SYNTHETIC EXAMPLES

Synthesis of Intermediates

Example 1

Synthesis of ethyl 2,2-dimethylpent-4-ynoate

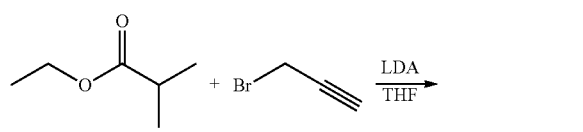

To a cold (−78° C.) solution of THF (100 ml) is added a 1.5M solution of LDA in cyclohexane (260 mL, 390 mmol) via cannulation, followed by the addition of ethyl isobutyrate. The mixture is allowed to stir at −78° C. for 1 hr then propargyl bromide is added dropwise. The reaction mixture is allowed to warm to 23° C. then stirred overnight. The mixture is then treated with saturated aqueous NH₄Cl, extracted with EtOAc, dried over magnesium sulfate, filtered, then concentrated in vacuo to give the title intermediate (54.7 g, 95%).

The following intermediates are also prepared by methods described in Example 1:

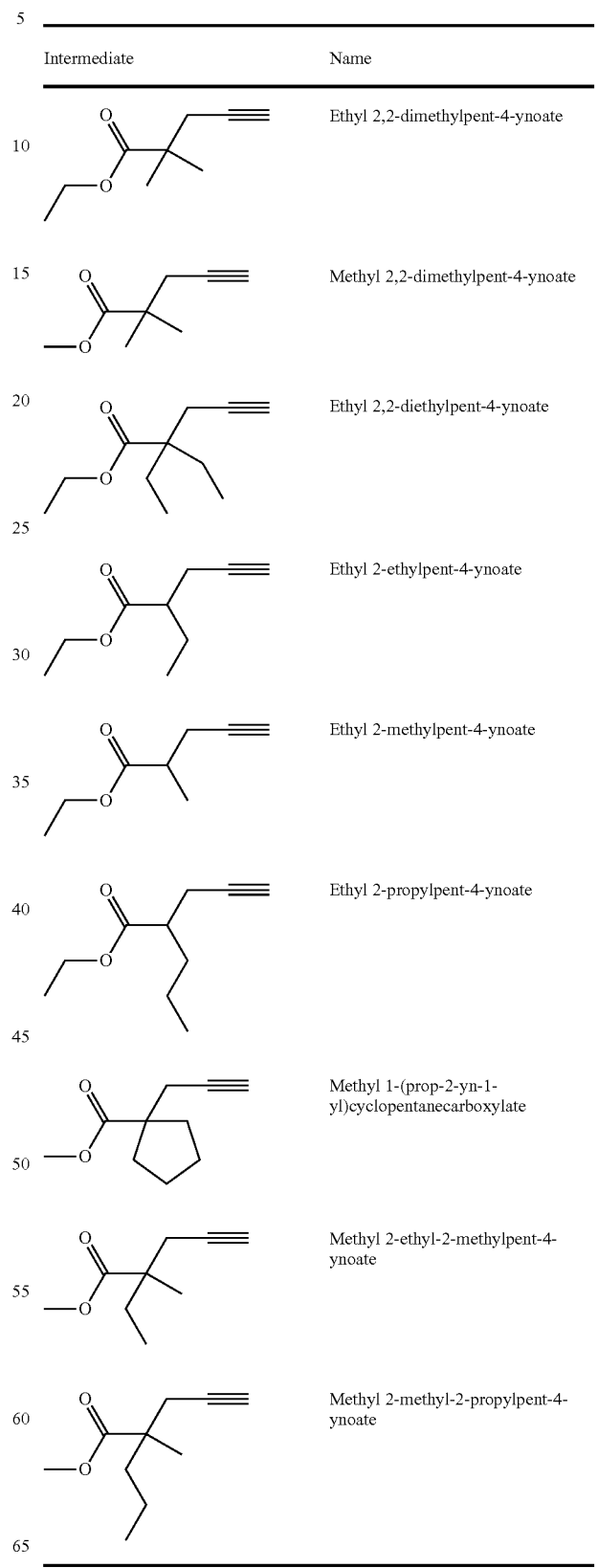

| Intermediate | Name |
| --- | --- |
| | Ethyl 2,2-dimethylpent-4-ynoate |
| | Methyl 2,2-dimethylpent-4-ynoate |
| | Ethyl 2,2-diethylpent-4-ynoate |
| | Ethyl 2-ethylpent-4-ynoate |
| | Ethyl 2-methylpent-4-ynoate |
| | Ethyl 2-propylpent-4-ynoate |
| | Methyl 1-(prop-2-yn-1-yl)cyclopentanecarboxylate |
| | Methyl 2-ethyl-2-methylpent-4-ynoate |
| | Methyl 2-methyl-2-propylpent-4-ynoate |

Example 2

Synthesis of ethyl 2,2,7,7-tetramethyl-6-oxooct-4-ynoate

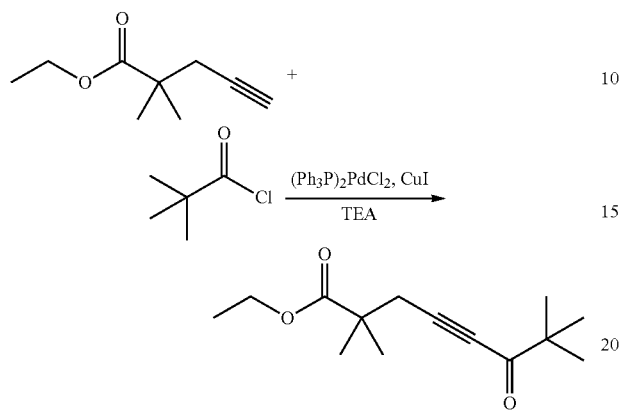

To a solution of ethyl 2,2-dimethylpent-4-ynoate (1.00 g, 6.5 mmol), 2,2-dimethyl-propionyl chloride (0.8 mL, 6.5 mmol), and dichlorobis(triphenylphosphine) palladium(II) (460 mg, 0.65 mmol) in triethylamine (TEA) (12 mL) is added CuI (62 mg, 0.32 mmol). The mixture is stirred at 23° C. for 3 h then partitioned between $Et_2O$ and saturated aqueous $NH_4Cl$. The organics are washed with water, dried with $MgSO_4$, filtered, and concentrated in vacuo. The residue is purified by flash chromatography ($SiO_2$, hexanes to 10% EtOAc in hexanes) to give the title intermediate (828 mg, 54%).

The following intermediates are also prepared by methods described in Example 2: (Please include the structures in excel file under sheet named Example 2)

| Intermediate | Name |
|---|---|
|  | Ethyl 6-cyclopropyl-2,2-dimethyl-6-oxohex-4-ynoate |
|  | Ethyl 6-cyclobutyl-2,2-dimethyl-6-oxohex-4-ynoate |
|  | Ethyl 2,2,8,8-tetramethyl-6-oxonon-4-ynoate |
|  | Ethyl 2,2-dimethyl-6-oxo-6-(2,2,3,3-tetramethylcyclopropyl)hex-4-ynoate |
|  | Ethyl 6-cyclopentyl-2,2-dimethyl-6-oxohex-4-ynoate |

-continued

| Intermediate | Name |
|---|---|
| (structure) | Ethyl 6-cyclohexyl-2,2-dimethyl-6-oxohex-4-ynoate |
| (structure) | Ethyl 2,2-dimethyl-6-oxo-6-phenylhex-4-ynoate |
| (structure) | Ethyl 6-(4-chlorophenyl)-2,2-dimethyl-6-oxohex-4-ynoate |
| (structure) | Ethyl 7-(acetyloxy)-2,2,7-trimethyl-6-oxooct-4-ynoate |
| (structure) | Methyl 2,2,7,7-tetramethyl-6-oxooct-4-ynoate |
| (structure) | Methyl 6-(4-chlorophenyl)-2,2-dimethyl-6-oxohex-4-ynoate |

Example 3

Synthesis of 4-(benzyloxy)pyridine

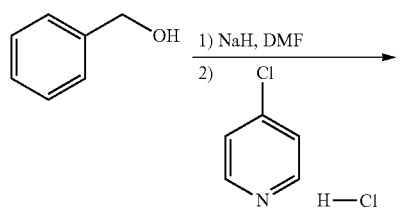

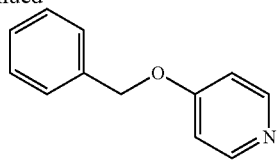

A flask is charged with NaH (60% dispersion in mineral oil, 0.72 g, 18.0 mmol) then suspended in DMF (30 mL) and cooled to 5° C. To this mixture is added benzyl alcohol (1.04 mL, 10.0 mmol) drop-wise. The mixture is stirred for 15 minutes then 4-chloropyridine-HCl (1.00 g, 6.67 mmol) is added in three portions over 5 min. The resulting mixture is stirred at 5° C. for 10 min then warmed to 60° C. and stirred for 1.5 h. The mixture is then cooled to 23° C., treated with water, and extracted with EtOAc. The combined organics are dried with MgSO$_4$, filtered, and concentrated in vacuo. Purification of the crude by flash chromatography (SiO$_2$, 5% EtOAc in hexanes to 50% EtOAc in hexanes) gives the title intermediate (1.10 g, 89%).

The following intermediates are also prepared by the methods described in Example 3:

| Structure | Name |
|---|---|
| 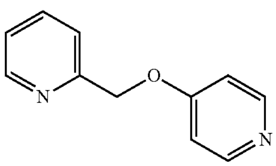 [SMILES: c1ccc(COc2ccncc2)nc1] | 2-[(Pyridin-4-yloxy)methyl]pyridine |
| 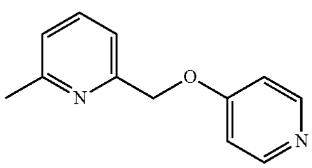 | 2-Methyl-6-[(pyridin-4-yloxy)methyl]pyridine |

Example 4

Synthesis of 1-[2-(4-chlorophenyl)-2-oxoethyl]-4-(propan-2-yl)pyridinium Bromide

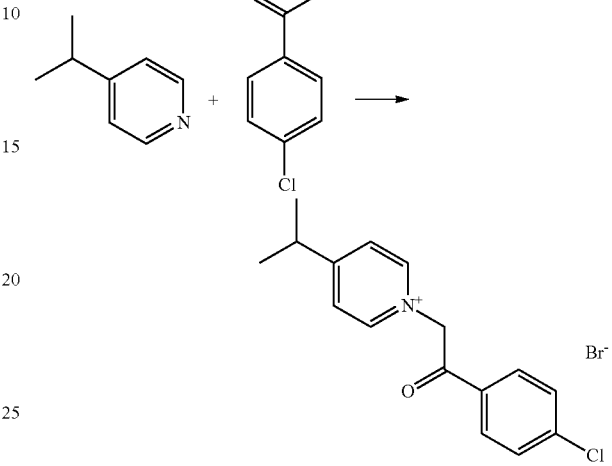

To a solution of 4-isopropylpyridine (3.12 g, 25.7 mmol) in acetonitrile (25 mL) is added 2-bromo-4'-chloro-acetophenone (6.01 g, 25.7 mmol). The mixture is stirred at 23° C. overnight then the resulting precipitate is filtered, collected, and dried to afford the title intermediate (7.10 g, 78%).

The following intermediates are also obtained by the methods described in Example 4:

| Structure | Name |
|---|---|
| 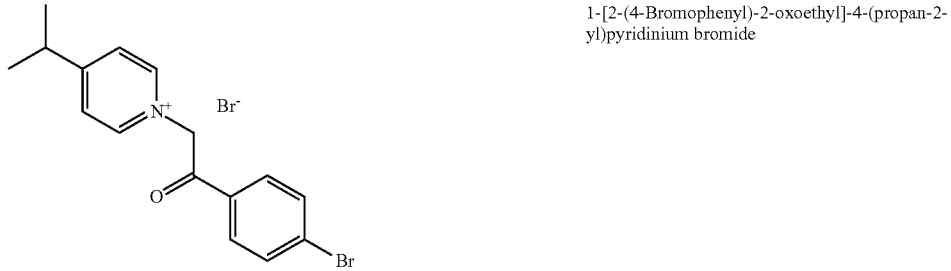 | 1-[2-(4-Bromophenyl)-2-oxoethyl]-4-(propan-2-yl)pyridinium bromide |
| 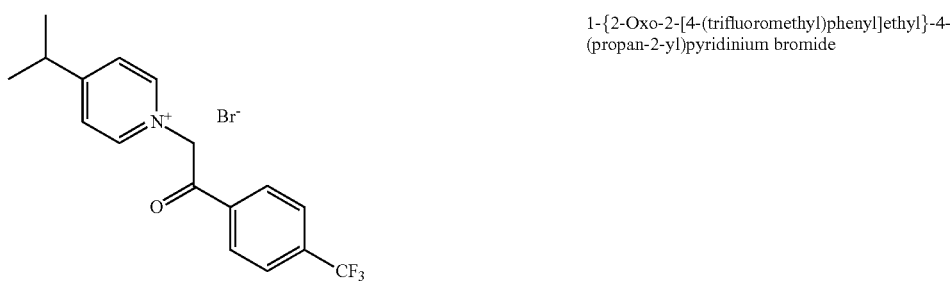 | 1-{2-Oxo-2-[4-(trifluoromethyl)phenyl]ethyl}-4-(propan-2-yl)pyridinium bromide |

-continued

| Structure | Name |
|---|---|
| 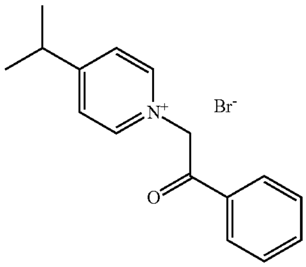 [SMILES: CC(C)c1cc[n+](CC(=O)c2ccccc2)cc1 ; [Br-]] | 1-(2-Oxo-2-phenylethyl)-4-(propan-2-yl)pyridinium bromide |
| 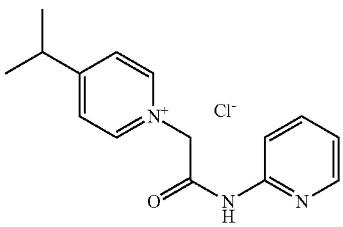 [SMILES: CC(C)c1cc[n+](CC(=O)Nc2ccccn2)cc1 ; [Cl-]] | 1-[2-Oxo-2-(pyridin-2-ylamino)ethyl]-4-(propan-2-yl)pyridinium chloride |
| 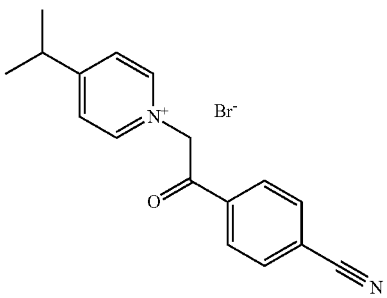 [SMILES: CC(C)c1cc[n+](CC(=O)c2ccc(C#N)cc2)cc1 ; [Br-]] | 1-[2-(4-Cyanophenyl)-2-oxoethyl]-4-(propan-2-yl)pyridinium bromide |
| 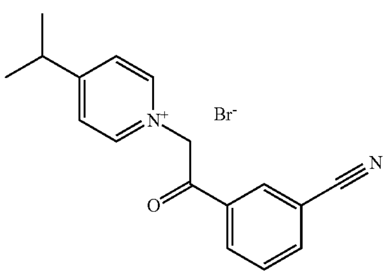 [SMILES: CC(C)c1cc[n+](CC(=O)c2cccc(C#N)c2)cc1 ; [Br-]] | 1-[2-(3-Cyanophenyl)-2-oxoethyl]-4-(propan-2-yl)pyridinium bromide |
| 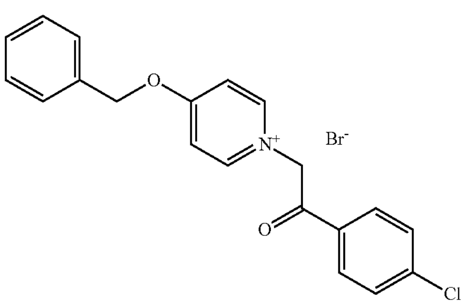 [SMILES: O=C(C[n+]1ccc(OCc2ccccc2)cc1)c1ccc(Cl)cc1 ; [Br-]] | 4-(Benzyloxy)-1-[2-(4-chlorophenyl)-2-oxoethyl]pyridinium bromide |
| 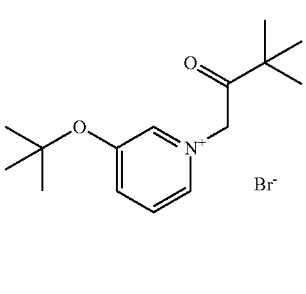 [SMILES: CC(C)(C)Oc1ccc[n+](CC(=O)C(C)(C)C)c1 ; [Br-]] | 3-tert-Butoxy-1-(3,3-dimethyl-2-oxobutyl)pyridinium bromide |

-continued

| Structure | Name |
|---|---|
| 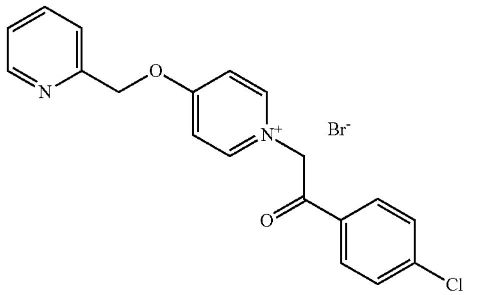 [SMILES: O=C(C[n+]1ccc(OCc2ccccn2)cc1)c1ccc(Cl)cc1 ; [Br-]] | 1-[2-(4-Chlorophenyl)-2-oxoethyl]-4-(pyridin-2-ylmethoxy)pyridinium bromide |
| 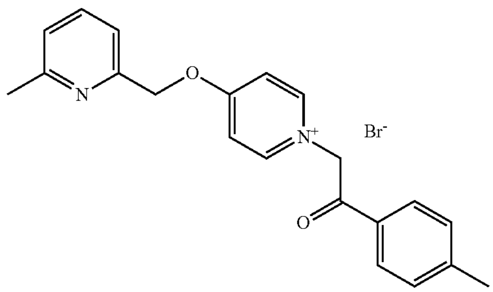 | 1-[2-(4-Methylphenyl)-2-oxoethyl]-4-[(6-methylpyridin-2-yl)methoxy]pyridinium bromide |
| 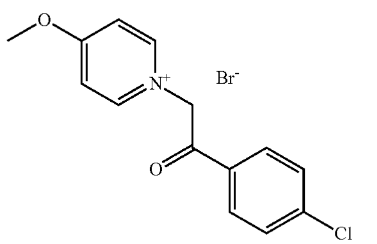 [SMILES: COc1cc[n+](CC(=O)c2ccc(Cl)cc2)cc1 ; [Br-]] | 1-[2-(4-Chlorophenyl)-2-oxoethyl]-4-methoxypyridinium bromide |
| 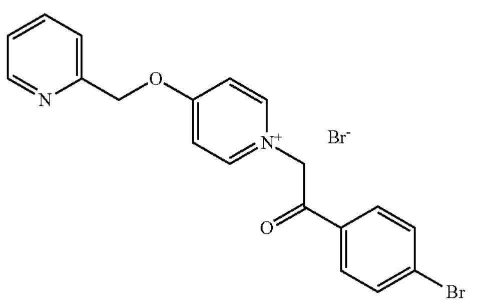 [SMILES: O=C(C[n+]1ccc(OCc2ccccn2)cc1)c1ccc(Br)cc1 ; [Br-]] | 1-[2-(4-Bromophenyl)-2-oxoethyl]-4-(pyridin-2-ylmethoxy)pyridinium bromide |
| 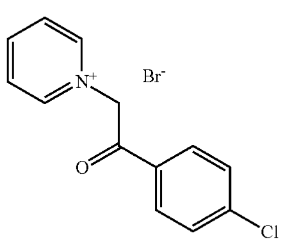 [SMILES: O=C(C[n+]1ccccc1)c1ccc(Cl)cc1 ; [Br-]] | 1-[2-(4-Chlorophenyl)-2-oxoethyl]pyridinium bromide |
| 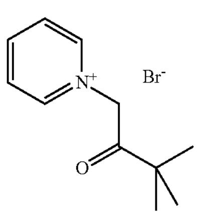 | 1-(3,3-Dimethyl-2-oxobutyl)pyridinium bromide |

| Structure | Name |
|---|---|
| 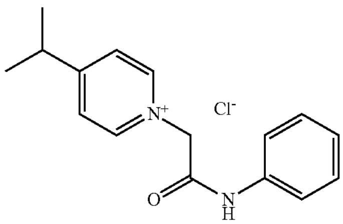 [SMILES: CC(C)c1cc[n+](CC(=O)Nc2ccccc2)cc1 ; [Cl-]] | 1-[2-Oxo-2-(phenylamino)ethyl]-4-(propan-2-yl)pyridinium chloride |
| 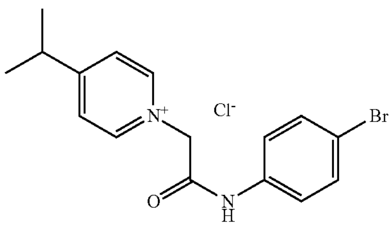 [SMILES: CC(C)c1cc[n+](CC(=O)Nc2ccc(Br)cc2)cc1 ; [Cl-]] | 1-{2-[(4-Bromophenyl)amino]-2-oxoethyl}-4-(propan-2-yl)pyridinium chloride |
| 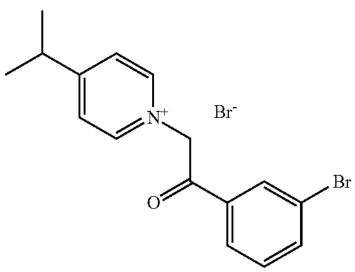 [SMILES: CC(C)c1cc[n+](CC(=O)c2cccc(Br)c2)cc1 ; [Br-]] | 1-[2-(3-Bromophenyl)-2-oxoethyl]-4-(propan-2-yl)pyridinium bromide |
| 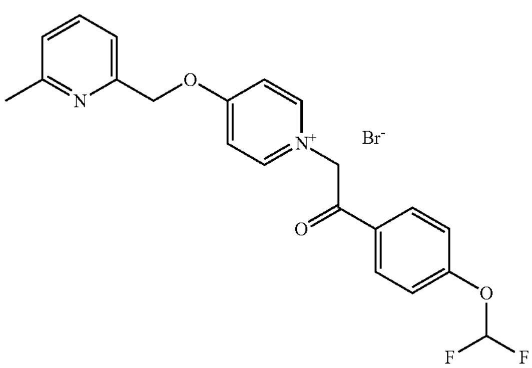 [SMILES: Cc1cccc(COc2cc[n+](CC(=O)c3ccc(OC(F)F)cc3)cc2)n1 ; [Br-]] | 1-{2-[4-(Difluoromethoxy)phenyl]-2-oxoethyl}-4-[(6-methylpyridin-2-yl)methoxy]pyridinium bromide |
| 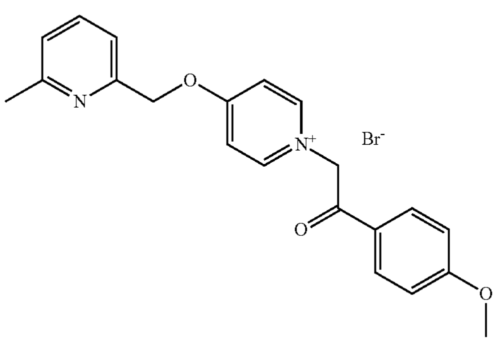 | 1-[2-(4-Methoxyphenyl)-2-oxoethyl]-4-[(6-methylpyridin-2-yl)methoxy]pyridinium bromide |

-continued
| Structure | Name |
|---|---|
| 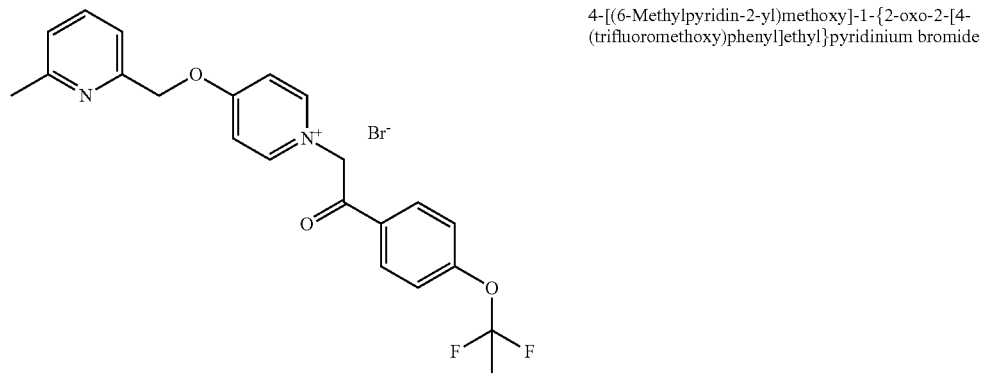 | 4-[(6-Methylpyridin-2-yl)methoxy]-1-{2-oxo-2-[4-(trifluoromethoxy)phenyl]ethyl}pyridinium bromide |
| 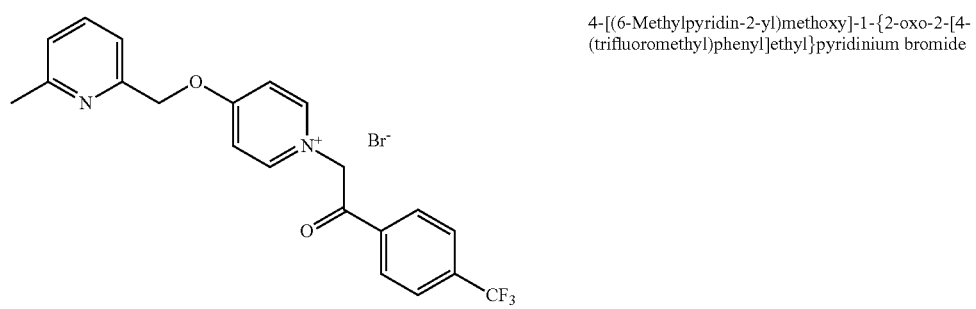 | 4-[(6-Methylpyridin-2-yl)methoxy]-1-{2-oxo-2-[4-(trifluoromethyl)phenyl]ethyl}pyridinium bromide |
| 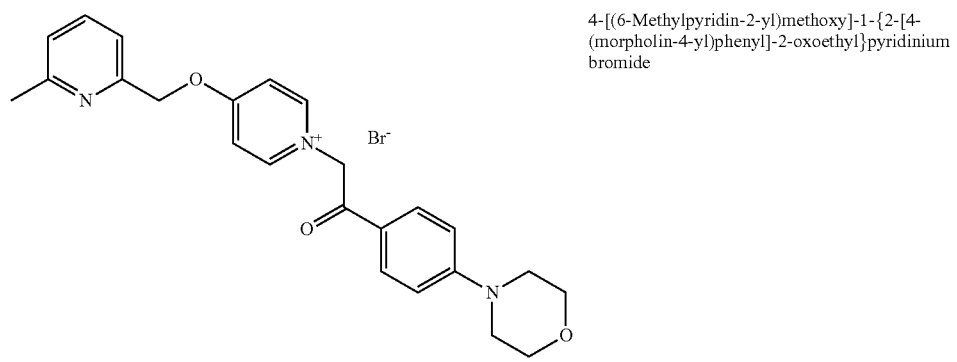 | 4-[(6-Methylpyridin-2-yl)methoxy]-1-{2-[4-(morpholin-4-yl)phenyl]-2-oxoethyl}pyridinium bromide |
| 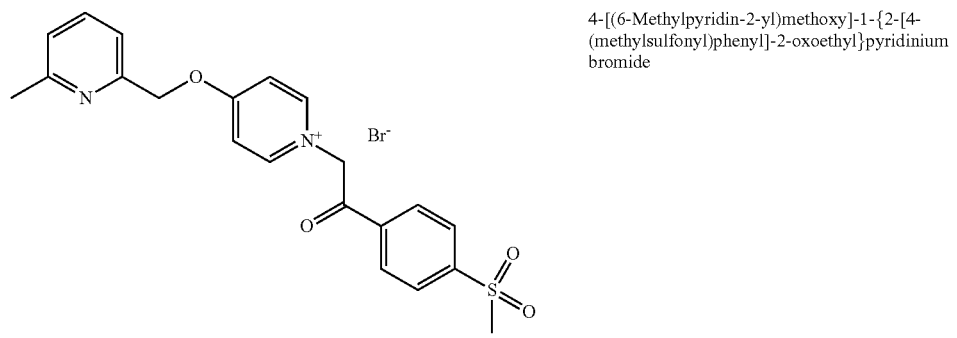 | 4-[(6-Methylpyridin-2-yl)methoxy]-1-{2-[4-(methylsulfonyl)phenyl]-2-oxoethyl}pyridinium bromide |

| Structure | Name |
|---|---|
| 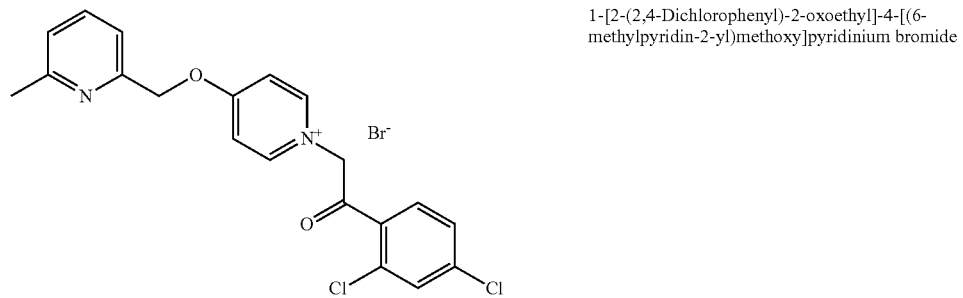 | 1-[2-(2,4-Dichlorophenyl)-2-oxoethyl]-4-[(6-methylpyridin-2-yl)methoxy]pyridinium bromide |
| 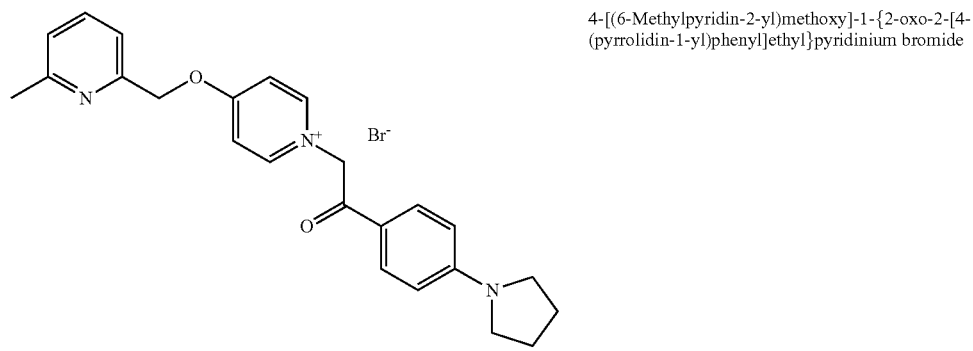 | 4-[(6-Methylpyridin-2-yl)methoxy]-1-{2-oxo-2-[4-(pyrrolidin-1-yl)phenyl]ethyl}pyridinium bromide |
| 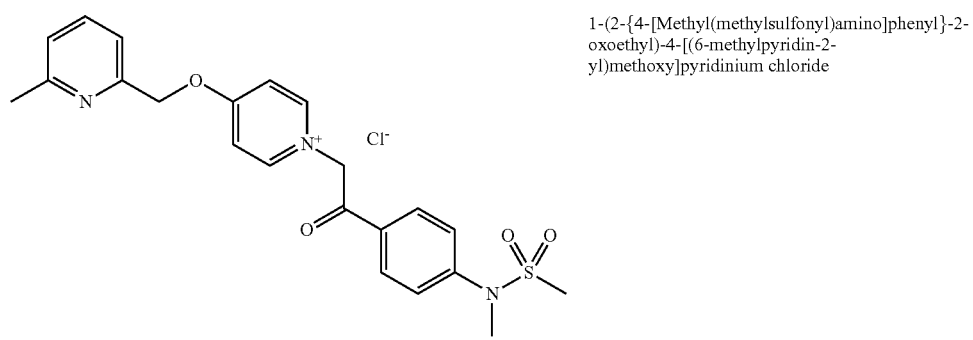 | 1-(2-{4-[Methyl(methylsulfonyl)amino]phenyl}-2-oxoethyl)-4-[(6-methylpyridin-2-yl)methoxy]pyridinium chloride |
| 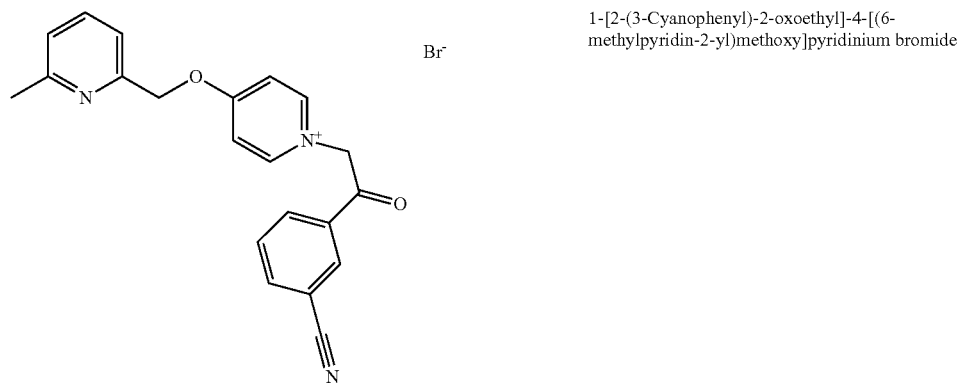 | 1-[2-(3-Cyanophenyl)-2-oxoethyl]-4-[(6-methylpyridin-2-yl)methoxy]pyridinium bromide |

| Structure | Name |
|---|---|
| 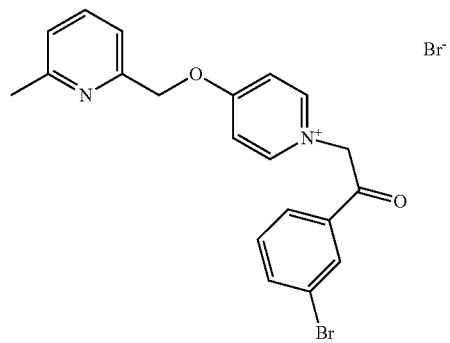 [SMILES: Cc1cccc(COc2cc[n+](CC(=O)c3cccc(Br)c3)cc2)n1 ; [Br-]] | 1-[2-(3-Bromophenyl)-2-oxoethyl]-4-[(6-methylpyridin-2-yl)methoxy]pyridinium bromide |
| 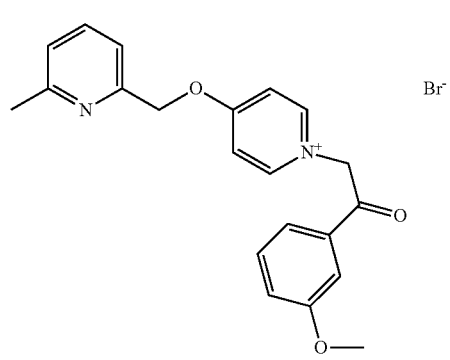 [SMILES: COc1cccc(C(=O)C[n+]2ccc(OCc3cccc(C)n3)cc2)c1 ; [Br-]] | 1-[2-(3-Methoxyphenyl)-2-oxoethyl]-4-[(6-methylpyridin-2-yl)methoxy]pyridinium bromide |
| 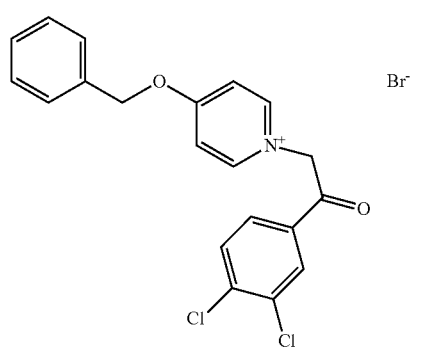 [SMILES: O=C(C[n+]1ccc(OCc2ccccc2)cc1)c1ccc(Cl)c(Cl)c1 ; [Br-]] | 4-(Benzyloxy)-1-[2-(3,4-dichlorophenyl)-2-oxoethyl]pyridinium bromide |
| 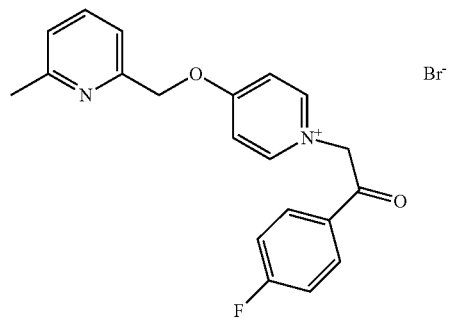 [SMILES: Cc1cccc(COc2cc[n+](CC(=O)c3ccc(F)cc3)cc2)n1 ; [Br-]] | 1-[2-(4-Fluorophenyl)-2-oxoethyl]-4-[(6-methylpyridin-2-yl)methoxy]pyridinium bromide |

-continued
| Structure | Name |
|---|---|
| 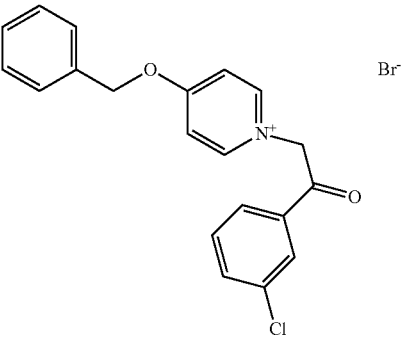 [SMILES: O=C(C[n+]1ccc(OCc2ccccc2)cc1)c1cccc(Cl)c1 ; [Br-]] Br⁻ | 4-(Benzyloxy)-1-[2-(3-chlorophenyl)-2-oxoethyl]pyridinium bromide |
| 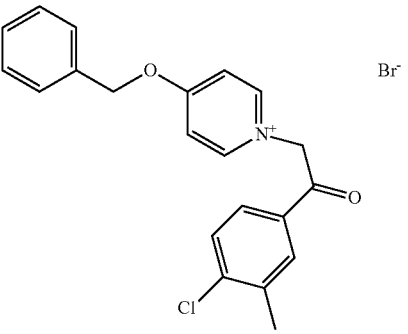 [SMILES: Cc1cc(C(=O)C[n+]2ccc(OCc3ccccc3)cc2)ccc1Cl ; [Br-]] Br⁻ | 4-(Benzyloxy)-1-[2-(4-chloro-3-methylphenyl)-2-oxoethyl]pyridinium bromide |
| 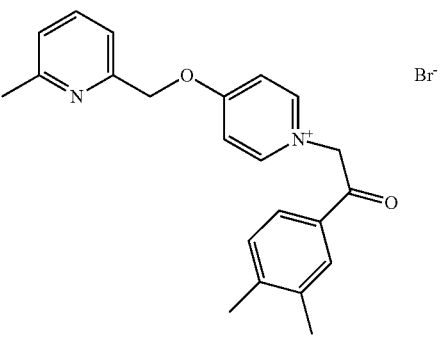 [SMILES: Cc1cccc(COc2cc[n+](CC(=O)c3ccc(C)c(C)c3)cc2)n1 ; [Br-]] Br⁻ | 1-[2-(3,4-Dimethylphenyl)-2-oxoethyl]-4-[(6-methylpyridin-2-yl)methoxy]pyridinium bromide |
| 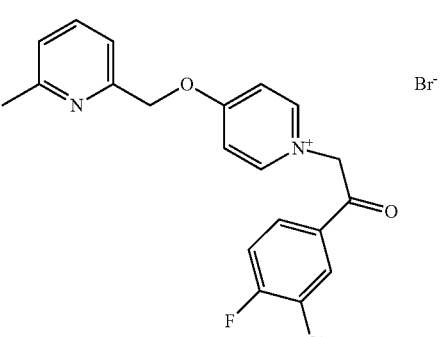 Br⁻ | 1-[2-(3-Chloro-4-fluorophenyl)-2-oxoethyl]-4-[(6-methylpyridin-2-yl)methoxy]pyridinium bromide |

-continued

| Structure | Name |
|---|---|
| 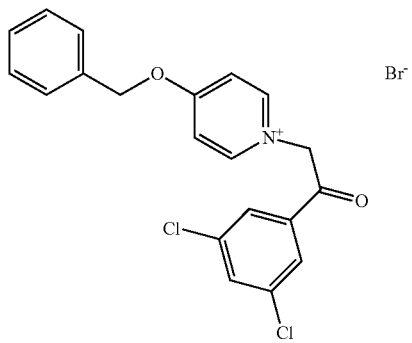 [SMILES: O=C(C[n+]1ccc(OCc2ccccc2)cc1)c1cc(Cl)cc(Cl)c1 ; [Br-]] | 4-(Benzyloxy)-1-[2-(3,5-dichlorophenyl)-2-oxoethyl]pyridinium bromide |

Example 5

Synthesis of methyl 3-[7-(benzyloxy)-3-[(4-chlorophenyl)carbonyl]-1-(2,2-dimethylpropanoyl)indolizin-2-yl]-2,2-dimethylpropanoate

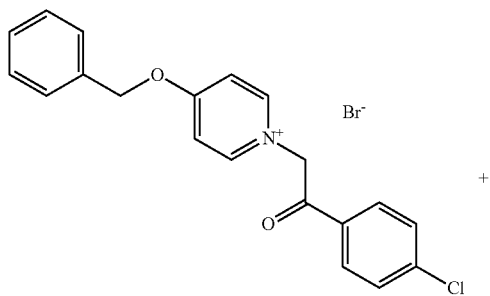

+

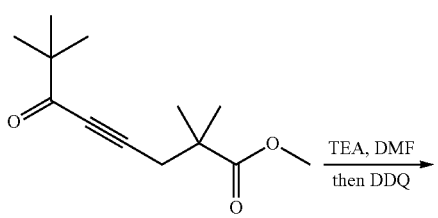

TEA, DMF
then DDQ
→

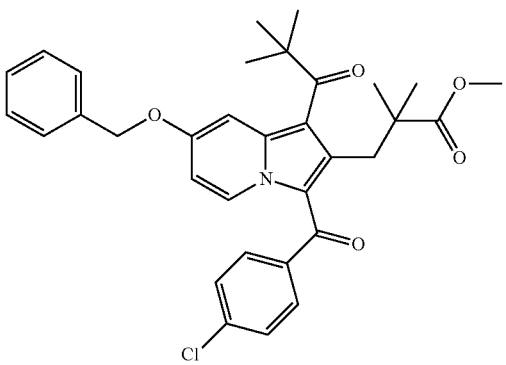

Method A: To a suspension of 4-(benzyloxy)-1-[2-(4-chlorophenyl)-2-oxoethyl]pyridinium bromide (470 mg, 1.12 mmol) and methyl 2,2,7,7-tetramethyl-6-oxooct-4-ynoate (252 mg, 1.12 mmol) in DMF (3.0 mL) is added TEA (0.22 mL, 1.58 mmol). The mixture is stirred at 70° C. for 18 h then treated with DDQ (255 mg, 1.12 mmol) and stirred for an additional 1 h. The mixture is then cooled to 23° C. and partitioned between water and EtOAc. The organics are collected, dried with MgSO$_4$, filtered, and concentrated in vacuo. Purification of the crude by flash chromatography (SiO$_2$, hexanes to 10% EtOAc in hexanes) gives the title intermediate (98 mg, 15%).

Method B: To a suspension of 4-(benzyloxy)-1-[2-(4-chlorophenyl)-2-oxoethyl]pyridinium bromide (33.60 g, 80.25 mmol) and methyl 2,2,7,7-tetramethyl-6-oxooct-4-ynoate (15.00 g, 66.88 mmol) in DMSO (300 mL) is added K$_2$CO$_3$ (18.49 g, 133.8 mmol). The mixture is stirred at 23° C. for 20 h then partitioned between water and EtOAc. The organics are collected, dried with MgSO$_4$, filtered, and concentrated in vacuo. Purification of the crude by flash chromatography (SiO$_2$, hexanes to 10% EtOAc in hexanes) gives the title intermediate (17.50 g, 47%).

The following intermediates are also obtained by the methods described in Example 5:

| Structure | Name |
|---|---|
| 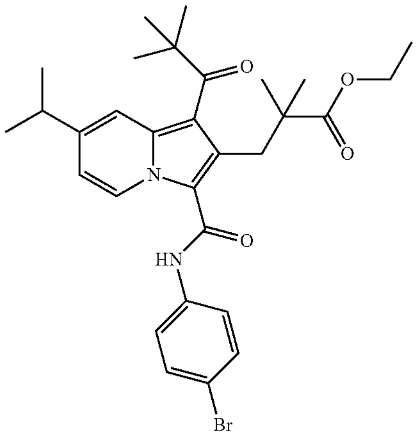 [SMILES: CCOC(=O)C(C)(C)Cc1c(C(=O)C(C)(C)C)c2cc(C(C)C)ccn2c1C(=O)Nc1ccc(Br)cc1] | Ethyl 3-{3-[(4-bromophenyl)carbamoyl]-1-(2,2-dimethylpropanoyl)-7-(propan-2-yl)indolizin-2-yl}-2,2-dimethylpropanoate |
| 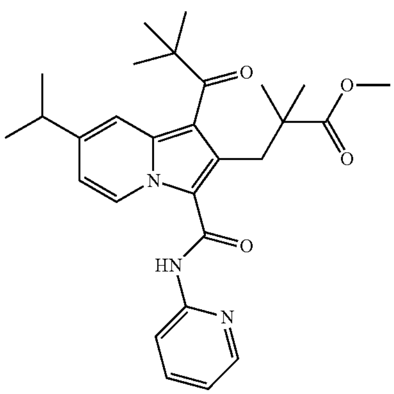 [SMILES: COC(=O)C(C)(C)Cc1c(C(=O)C(C)(C)C)c2cc(C(C)C)ccn2c1C(=O)Nc1ccccn1] | Methyl 3-[1-(2,2-dimethylpropanoyl)-7-(propan-2-yl)-3-(pyridin-2-ylcarbamoyl)indolizin-2-yl]-2,2-dimethylpropanoate |
| 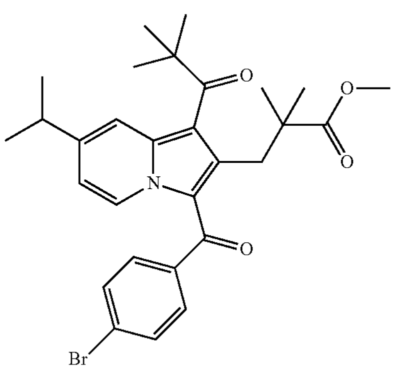 [SMILES: COC(=O)C(C)(C)Cc1c(C(=O)C(C)(C)C)c2cc(C(C)C)ccn2c1C(=O)c1ccc(Br)cc1] | Methyl 3-{3-[(4-bromophenyl)carbonyl]-1-(2,2-dimethylpropanoyl)-7-(propan-2-yl)indolizin-2-yl}-2,2-dimethylpropanoate |
| 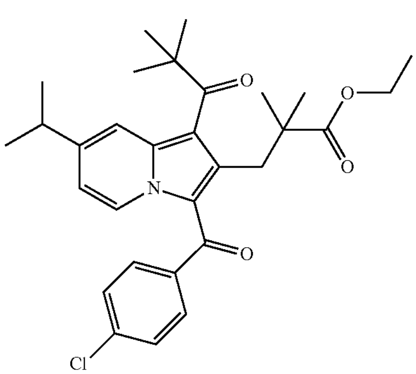 [SMILES: CCOC(=O)C(C)(C)Cc1c(C(=O)C(C)(C)C)c2cc(C(C)C)ccn2c1C(=O)c1ccc(Cl)cc1] | Ethyl 3-{3-[(4-chlorophenyl)carbonyl]-1-(2,2-dimethylpropanoyl)-7-(propan-2-yl)indolizin-2-yl}-2,2-dimethylpropanoate |

-continued

| Structure | Name |
|---|---|
| 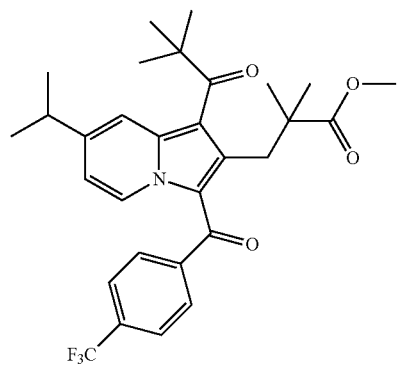 [SMILES: COC(=O)C(C)(C)Cc1c(C(=O)C(C)(C)C)c2cc(C(C)C)ccn2c1C(=O)c1ccc(C(F)(F)F)cc1] | Methyl 3-[1-(2,2-dimethylpropanoyl)-7-(propan-2-yl)-3-{[4-(trifluoromethyl)phenyl]-carbonyl}indolizin-2-yl]-2,2-dimethylpropanoate |
| 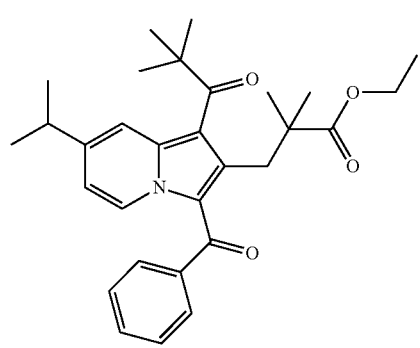 [SMILES: CCOC(=O)C(C)(C)Cc1c(C(=O)C(C)(C)C)c2cc(C(C)C)ccn2c1C(=O)c1ccccc1] | Ethyl 3-[1-(2,2-dimethylpropanoyl)-3-(phenylcarbonyl)-7-(propan-2-yl)indolizin-2-yl]-2,2-dimethylpropanoate |
| 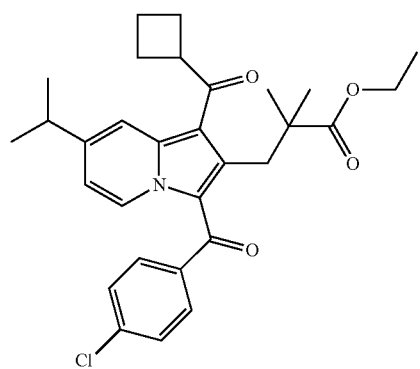 [SMILES: CCOC(=O)C(C)(C)Cc1c(C(=O)C2CCC2)c2cc(C(C)C)ccn2c1C(=O)c1ccc(Cl)cc1] | Ethyl 3-{3-[(4-chlorophenyl)carbonyl]-1-(cyclobutylcarbonyl)-7-(propan-2-yl)indolizin-2-yl}-2,2-dimethylpropanoate |
| 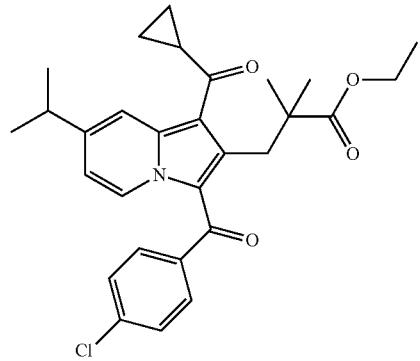 [SMILES: CCOC(=O)C(C)(C)Cc1c(C(=O)C2CC2)c2cc(C(C)C)ccn2c1C(=O)c1ccc(Cl)cc1] | Ethyl 3-{3-[(4-chlorophenyl)carbonyl]-1-(cyclopropylcarbonyl)-7-(propan-2-yl)indolizin-2-yl}-2,2-dimethylpropanoate |

| Structure | Name |
|---|---|
| 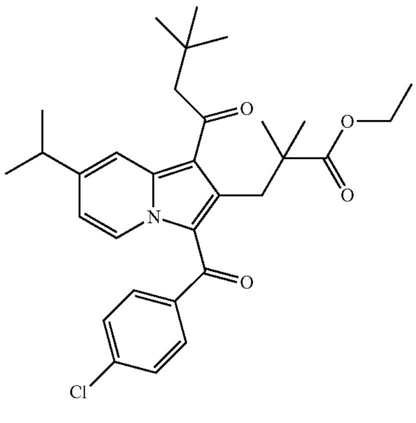 [SMILES: CCOC(=O)C(C)(C)Cc1c(C(=O)CC(C)(C)C)c2cc(C(C)C)ccn2c1C(=O)c1ccc(Cl)cc1] | Ethyl 3-{3-[(4-chlorophenyl)carbonyl]-1-(3,3-dimethylbutanoyl)-7-(propan-2-yl)indolizin-2-yl}-2,2-dimethylpropanoate |
| 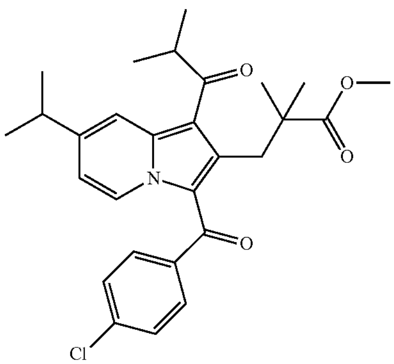 [SMILES: COC(=O)C(C)(C)Cc1c(C(=O)C(C)C)c2cc(C(C)C)ccn2c1C(=O)c1ccc(Cl)cc1] | Methyl 3-{3-[(4-chlorophenyl)carbonyl]-1-(2-methylpropanoyl)-7-(propan-2-yl)indolizin-2-yl}-2,2-dimethylpropanoate |
| 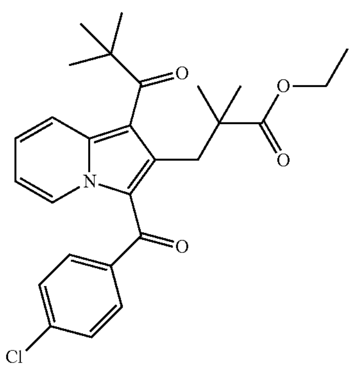 [SMILES: CCOC(=O)C(C)(C)Cc1c(C(=O)C(C)(C)C)c2ccccn2c1C(=O)c1ccc(Cl)cc1] | Ethyl 3-{3-[(4-chlorophenyl)carbonyl]-1-(2,2-dimethylpropanoyl)indolizin-2-yl}-2,2-dimethylpropanoate |
| 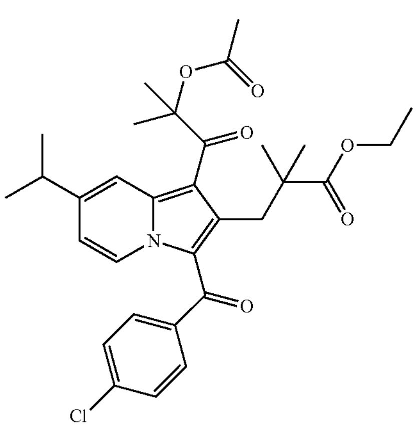 [SMILES: CCOC(=O)C(C)(C)Cc1c(C(=O)C(C)(C)OC(C)=O)c2cc(C(C)C)ccn2c1C(=O)c1ccc(Cl)cc1] | Ethyl 3-{1-[2-(acetyloxy)-2-methylpropanoyl]-3-[(4-chlorophenyl)carbonyl]-7-(propan-2-yl)indolizin-2-yl}-2,2-dimethylpropanoate |

-continued

| Structure | Name |
|---|---|
| 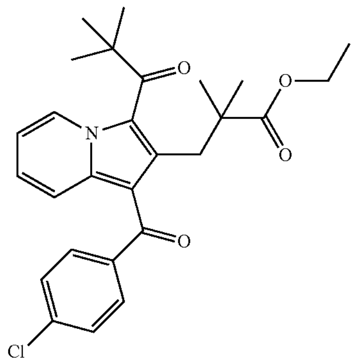 [SMILES: CCOC(=O)C(C)(C)Cc1c(C(=O)c2ccc(Cl)cc2)c2ccccn2c1C(=O)C(C)(C)C] | Ethyl 3-{1-[(4-chlorophenyl)carbonyl]-3-(2,2-dimethylpropanoyl)indolizin-2-yl}-2,2-dimethylpropanoate |
| 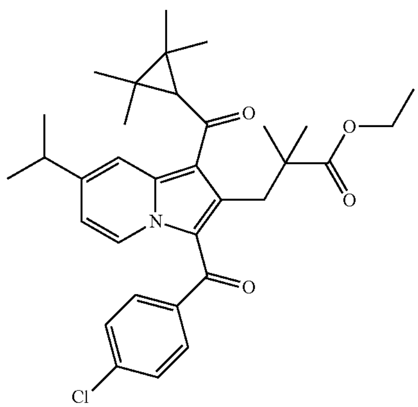 [SMILES: CCOC(=O)C(C)(C)Cc1c(C(=O)C2C(C)(C)C2(C)C)c2cc(C(C)C)ccn2c1C(=O)c1ccc(Cl)cc1] | Ethyl 3-{3-[(4-chlorophenyl)carbonyl]-7-(propan-2-yl)-1-[(2,2,3,3-tetramethylcyclopropyl)carbonyl]indolizin-2-yl}-2,2-dimethylpropanoate |
| 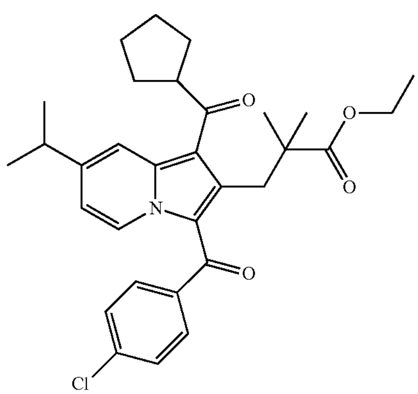 [SMILES: CCOC(=O)C(C)(C)Cc1c(C(=O)C2CCCC2)c2cc(C(C)C)ccn2c1C(=O)c1ccc(Cl)cc1] | Ethyl 3-{3-[(4-chlorophenyl)carbonyl]-1-(cyclopentylcarbonyl)-7-(propan-2-yl)indolizin-2-yl}-2,2-dimethylpropanoate |
| 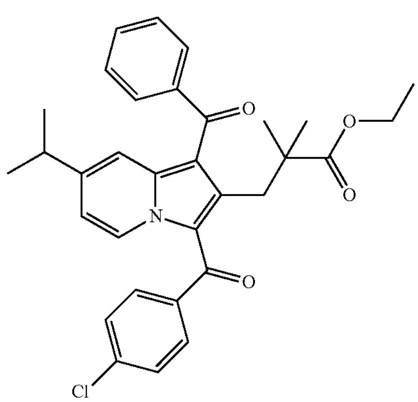 [SMILES: CCOC(=O)C(C)(C)Cc1c(C(=O)c2ccccc2)c2cc(C(C)C)ccn2c1C(=O)c1ccc(Cl)cc1] | Ethyl 3-{3-[(4-chlorophenyl)carbonyl]-1-(phenylcarbonyl)-7-(propan-2-yl)indolizin-2-yl}-2,2-dimethylpropanoate |

| Structure | Name |
|---|---|
| 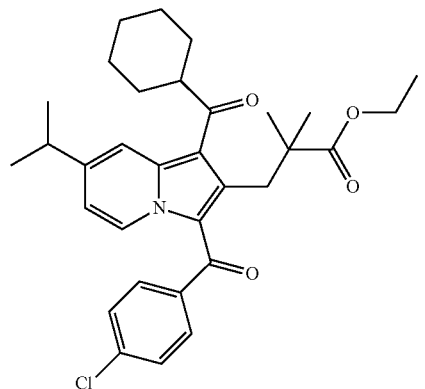 [SMILES: CCOC(=O)C(C)(C)Cc1c(C(=O)C2CCCCC2)c2cc(C(C)C)ccn2c1C(=O)c1ccc(Cl)cc1] | Ethyl 3-{3-[(4-chlorophenyl)carbonyl]-1-(cyclohexylcarbonyl)-7-(propan-2-yl)indolizin-2-yl}-2,2-dimethylpropanoate |
| 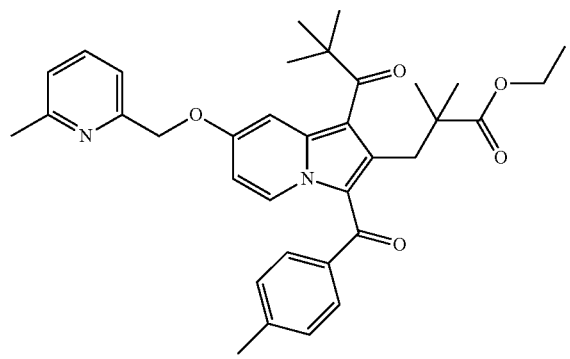 [SMILES: CCOC(=O)C(C)(C)Cc1c(C(=O)C(C)(C)C)c2cc(OCc3cccc(C)n3)ccn2c1C(=O)c1ccc(C)cc1] | Ethyl 3-{1-(2,2-dimethylpropanoyl)-3-[(4-methylphenyl)carbonyl]-7-[(6-methylpyridin-2-yl)methoxy]indolizin-2-yl}-2,2-dimethylpropanoate |
| 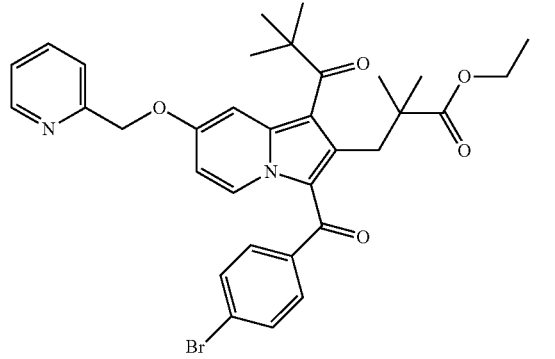 [SMILES: CCOC(=O)C(C)(C)Cc1c(C(=O)C(C)(C)C)c2cc(OCc3ccccn3)ccn2c1C(=O)c1ccc(Cl)cc1] | Ethyl 3-{3-[(4-bromophenyl)carbonyl]-1-(2,2-dimethylpropanoyl)-7-(pyridin-2-ylmethoxy)indolizin-2-yl}-2,2-dimethylpropanoate |
| 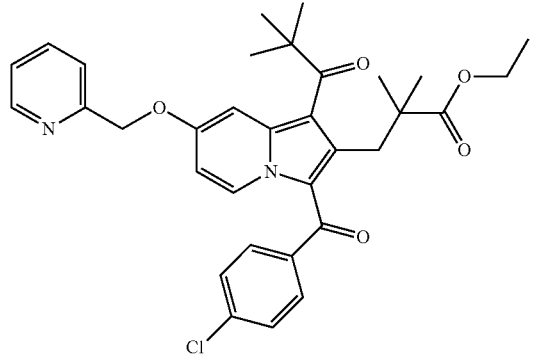 | Ethyl 3-{3-[(4-chlorophenyl)carbonyl]-1-(2,2-dimethylpropanoyl)-7-(pyridin-2-ylmethoxy)indolizin-2-yl}-2,2-dimethylpropanoate |

| Structure | Name |
|---|---|
| 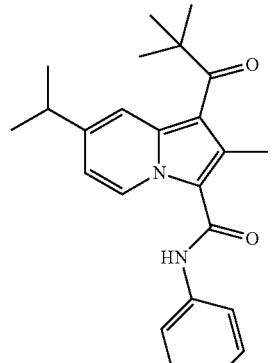 | 1-(2,2-Dimethylpropanoyl)-2-methyl-N-phenyl-7-(propan-2-yl)indolizine-3-carboxamide |
| 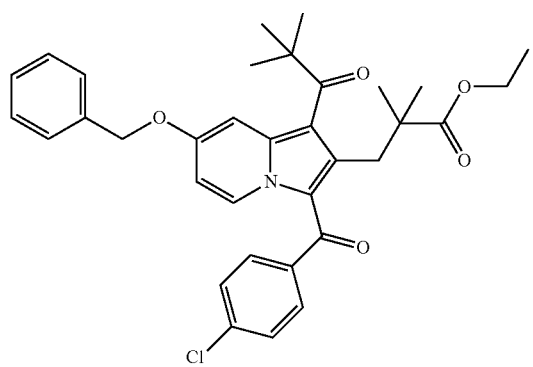 [SMILES: CCOC(=O)C(C)(C)Cc1c(C(=O)C(C)(C)C)c2cc(OCc3ccccc3)ccn2c1C(=O)c1ccc(Cl)cc1] | Ethyl 3-[7-(benzyloxy)-3-[(4-chlorophenyl)carbonyl]-1-(2,2-dimethylpropanoyl)indolizin-2-yl]-2,2-dimethylpropanoate |
| 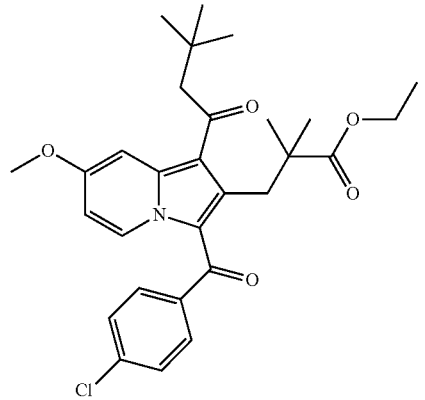 [SMILES: CCOC(=O)C(C)(C)Cc1c(C(=O)CC(C)(C)C)c2cc(OC)ccn2c1C(=O)c1ccc(Cl)cc1] | Ethyl 3-{3-[(4-chlorophenyl)carbonyl]-1-(3,3-dimethylbutanoyl)-7-methoxyindolizin-2-yl}-2,2-dimethylpropanoate |
| 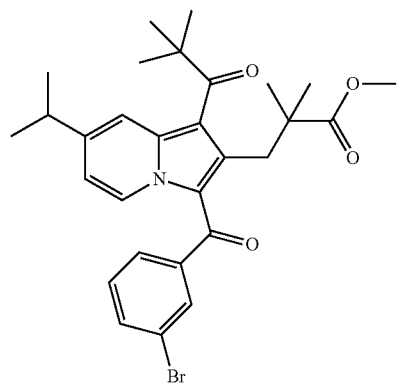 [SMILES: COC(=O)C(C)(C)Cc1c(C(=O)C(C)(C)C)c2cc(C(C)C)ccn2c1C(=O)c1cccc(Br)c1] | Methyl 3-{3-[(3-bromophenyl)carbonyl]-1-(2,2-dimethylpropanoyl)-7-(propan-2-yl)indolizin-2-yl}-2,2-dimethylpropanoate |

| Structure | Name |
|---|---|
| 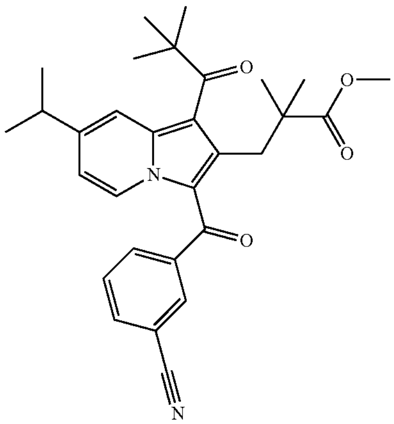 [SMILES: COC(=O)C(C)(C)Cc1c(C(=O)C(C)(C)C)c2cc(C(C)C)ccn2c1C(=O)c1cccc(C#N)c1] | Methyl 3-{3-[(3-cyanophenyl)carbonyl]-1-(2,2-dimethylpropanoyl)-7-(propan-2-yl)indolizin-2-yl}-2,2-dimethylpropanoate |
| 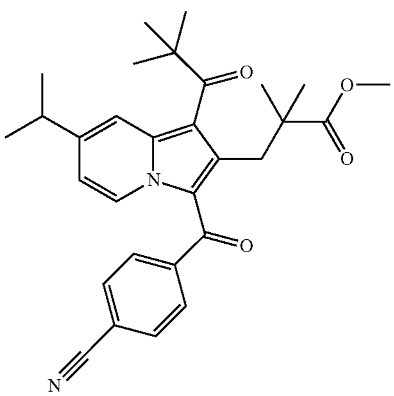 [SMILES: COC(=O)C(C)(C)Cc1c(C(=O)C(C)(C)C)c2cc(C(C)C)ccn2c1C(=O)c1ccc(C#N)cc1] | Methyl 3-{3-[(4-cyanophenyl)carbonyl]-1-(2,2-dimethylpropanoyl)-7-(propan-2-yl)indolizin-2-yl}-2,2-dimethylpropanoate |
| 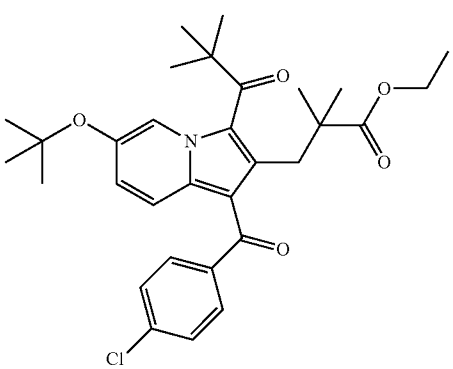 [SMILES: CCOC(=O)C(C)(C)Cc1c(C(=O)c2ccc(Cl)cc2)c2ccc(OC(C)(C)C)cn2c1C(=O)C(C)(C)C] | Ethyl 3-{6-tert-butoxy-1-[(4-chlorophenyl)carbonyl]-3-(2,2-dimethylpropanoyl)indolizin-2-yl}-2,2-dimethylpropanoate |
| 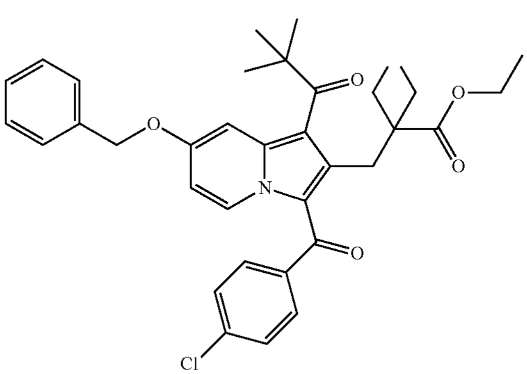 [SMILES: CCOC(=O)C(CC)(CC)Cc1c(C(=O)C(C)(C)C)c2cc(OCc3ccccc3)ccn2c1C(=O)c1ccc(Cl)cc1] | Ethyl 3-[7-(benzyloxy)-3-[(4-chlorophenyl)carbonyl]-1-(2,2-dimethylpropanoyl)indolizin-2-yl]-2,2-diethylpropanoate |

| Structure | Name |
|---|---|
| 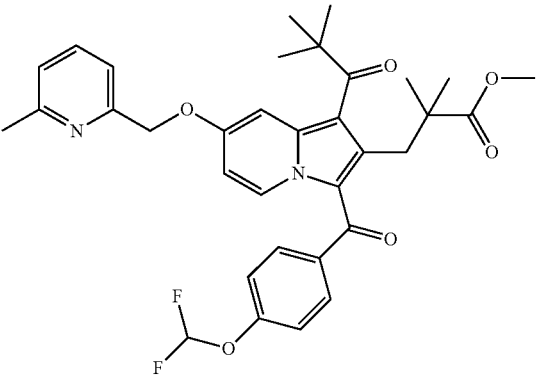 | Methyl 3-(3-{[4-(difluoromethoxy)phenyl]carbonyl}-1-(2,2-dimethylpropanoyl)-7-[(6-methylpyridin-2-yl)methoxy]indolizin-2-yl)-2,2-dimethylpropanoate |
| 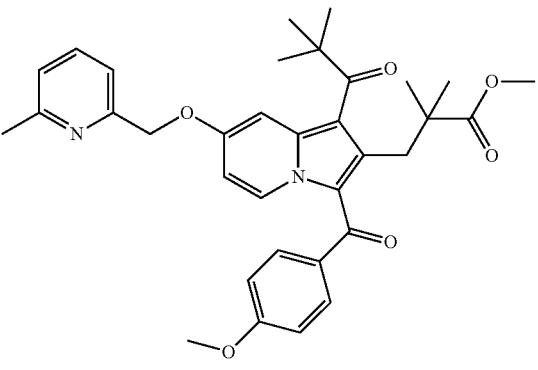 | Methyl 3-{1-(2,2-dimethylpropanoyl)-3-[(4-methoxyphenyl)carbonyl]-7-[(6-methylpyridin-2-yl)methoxy]indolizin-2-yl}-2,2-dimethylpropanoate |
| 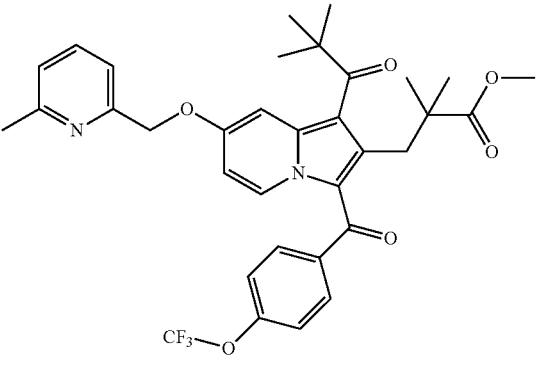 | Methyl 3-[1-(2,2-dimethylpropanoyl)-7-[(6-methylpyridin-2-yl)methoxy]-3-{[4-(trifluoromethoxy)phenyl]carbonyl}indolizin-2-yl]-2,2-dimethylpropanoate |
| 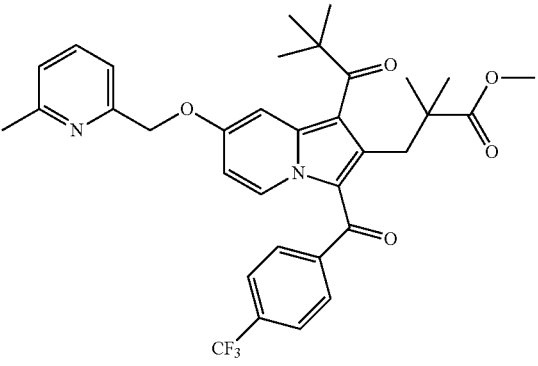 | Methyl 3-[1-(2,2-dimethylpropanoyl)-7-[(6-methylpyridin-2-yl)methoxy]-3-{[4-(trifluoromethyl)phenyl]carbonyl}indolizin-2-yl]-2,2-dimethylpropanoate |

| Structure | Name |
|---|---|
| 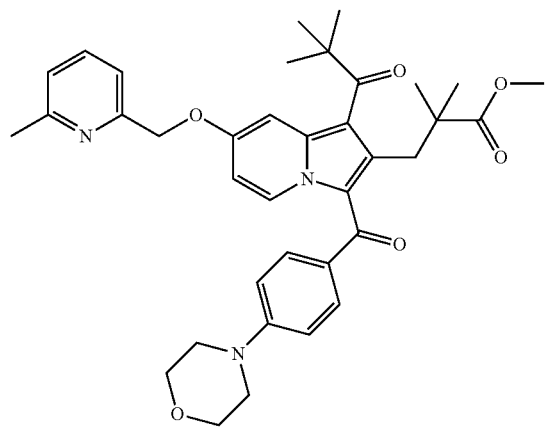 | Methyl 3-[1-(2,2-dimethylpropanoyl)-7-[(6-methylpyridin-2-yl)methoxy]-3-{[4-(morpholin-4-yl)phenyl]carbonyl}indolizin-2-yl]-2,2-dimethylpropanoate |
| 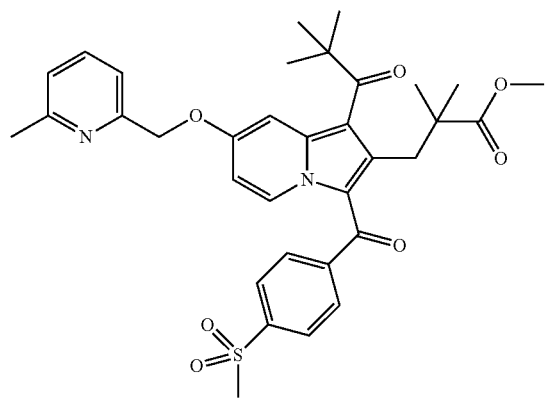 | Methyl 3-[1-(2,2-dimethylpropanoyl)-7-[(6-methylpyridin-2-yl)methoxy]-3-{[4-(methylsulfonyl)phenyl]carbonyl}indolizin-2-yl]-2,2-dimethylpropanoate |
| 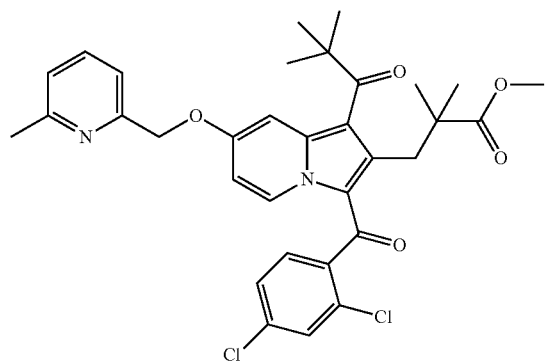 | Methyl 3-{3-[(2,4-dichlorophenyl)carbonyl]-1-(2,2-dimethylpropanoyl)-7-[(6-methylpyridin-2-yl)methoxy]indolizin-2-yl}-2,2-dimethylpropanoate |

| Structure | Name |
|---|---|
| 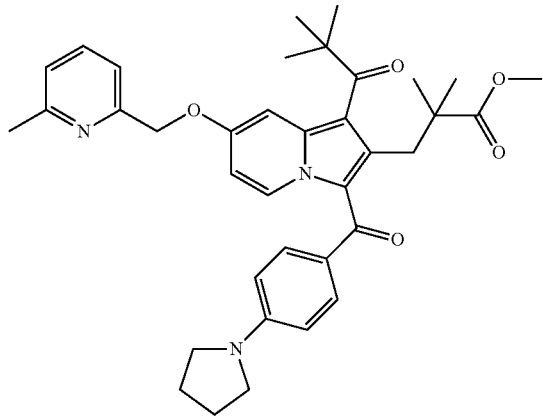 | Methyl 3-[1-(2,2-dimethylpropanoyl)-7-[(6-methylpyridin-2-yl)methoxy]-3-{[4-(pyrrolidin-1-yl)phenyl]carbonyl}indolizin-2-yl]-2,2-dimethylpropanoate |
| 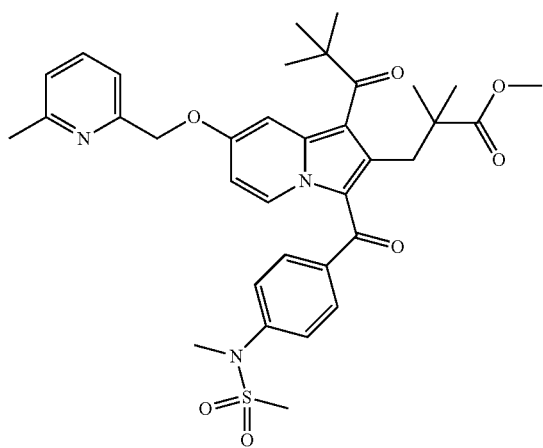 | Methyl 3-{1-(2,2-dimethylpropanoyl)-3-({4-[methyl(methylsulfonyl)amino]phenyl}carbonyl)-7-[(6-methylpyridin-2-yl)methoxy]indolizin-2-yl}-2,2-dimethylpropanoate |

The following intermediates are also obtained by the methods described in Example 5:

Ethyl 2-{[7-(benzyloxy)-3-[(4-chlorophenyl)carbonyl]-1-(2,2-dimethylpropanoyl)indolizin-2-yl]methyl}butanoate;

Ethyl 3-[7-(benzyloxy)-3-[(4-chlorophenyl)carbonyl]-1-(2,2-dimethylpropanoyl)indolizin-2-yl]-2-methylpropanoate;

Methyl 3-[7-(benzyloxy)-3-[(3,4-dichlorophenyl)carbonyl]-1-(2,2-dimethylpropanoyl)indolizin-2-yl]-2,2-dimethylpropanoate;

Methyl 1-{[7-(benzyloxy)-3-[(4-chlorophenyl)carbonyl]-1-(2,2-dimethylpropanoyl)indolizin-2-yl]methyl}cyclopentanecarboxylate;

Ethyl 2-{[7-(benzyloxy)-3-[(4-chlorophenyl)carbonyl]-1-(2,2-dimethylpropanoyl)indolizin-2-yl]methyl}pentanoate;

Methyl 3-[7-(benzyloxy)-3-[(3-chlorophenyl)carbonyl]-1-(2,2-dimethylpropanoyl)indolizin-2-yl]-2,2-dimethylpropanoate;

Ethyl 2-{[7-(benzyloxy)-3-[(3,4-dichlorophenyl)carbonyl]-1-(2,2-dimethylpropanoyl)indolizin-2-yl]methyl}pentanoate;

Ethyl 2-({7-(benzyloxy)-1-(2,2-dimethylpropanoyl)-3-[(4-methoxyphenyl)carbonyl]indolizin-2-yl}methyl)pentanoate;

Ethyl 2-{[7-(benzyloxy)-3-[(4-chloro-3-methylphenyl)carbonyl]-1-(2,2-dimethylpropanoyl)indolizin-2-yl]methyl}pentanoate;

Methyl 2-({7-(benzyloxy)-1-(2,2-dimethylpropanoyl)-3-[(4-methoxyphenyl)carbonyl]indolizin-2-yl}methyl)-2-methylpentanoate;

Methyl 2-({7-(benzyloxy)-1-(2,2-dimethylpropanoyl)-3-[(4-methoxyphenyl)carbonyl]indolizin-2-yl}methyl)-2-methylbutanoate;

Methyl 2-{[7-(benzyloxy)-3-[(3,4-dichlorophenyl)carbonyl]-1-(2,2-dimethylpropanoyl)indolizin-2-yl]methyl}-2-methylbutanoate;

Methyl 2-{[7-(benzyloxy)-3-[(4-chlorophenyl)carbonyl]-1-(2,2-dimethylpropanoyl)indolizin-2-yl]methyl}-2-methylbutanoate;

Methyl 3-[7-(benzyloxy)-3-[(4-chloro-3-methylphenyl)carbonyl]-1-(2,2-dimethylpropanoyl)indolizin-2-yl]-2,2-dimethylpropanoate;

Methyl 2-{[7-(benzyloxy)-3-[(3,4-dichlorophenyl)carbonyl]-1-(2,2-dimethylpropanoyl)indolizin-2-yl]methyl}-3-methylbutanoate;

Methyl 3-[7-(benzyloxy)-3-[(3,5-dichlorophenyl)carbonyl]-1-(2,2-dimethylpropanoyl)indolizin-2-yl]-2,2-dimethylpropanoate;

Methyl 2-({7-(benzyloxy)-1-(2,2-dimethylpropanoyl)-3-[(4-methoxyphenyl)carbonyl]indolizin-2-yl}methyl)-3-methylbutanoate;

Methyl 3-{3-[(3-cyanophenyl)carbonyl]-1-(2,2-dimethylpropanoyl)-7-[(6-methylpyridin-2-yl)methoxy]indolizin-2-yl}-2,2-dimethylpropanoate;

Methyl 3-{3-[(3-bromophenyl)carbonyl]-1-(2,2-dimethylpropanoyl)-7-[(6-methylpyridin-2-yl)methoxy]indolizin-2-yl}-2,2-dimethylpropanoate;
Methyl 3-{1-(2,2-dimethylpropanoyl)-3-[(3-methoxyphenyl)carbonyl]-7-[(6-methylpyridin-2-yl)methoxy]indolizin-2-yl}-2,2-dimethylpropanoate;
Methyl 3-{1-(2,2-dimethylpropanoyl)-3-[(4-fluorophenyl)carbonyl]-7-[(6-methylpyridin-2-yl)methoxy]indolizin-2-yl}-2,2-dimethylpropanoate;
Methyl 3-{3-[(3,4-dimethylphenyl)carbonyl]-1-(2,2-dimethylpropanoyl)-7-[(6-methylpyridin-2-yl)methoxy]indolizin-2-yl}-2,2-dimethylpropanoate; and
Methyl 3-{3-[(3-chloro-4-fluorophenyl)carbonyl]-1-(2,2-dimethylpropanoyl)-7-[(6-methylpyridin-2-yl)methoxy]indolizin-2-yl}-2,2-dimethylpropanoate.

Synthesis of Final Compounds

Example 6

Synthesis of 3-{3-[(4-chlorophenyl)carbonyl]-1-(2,2-dimethylpropanoyl)-7-(pyridin-2-ylmethoxy)indolizin-2-yl}-2,2-dimethylpropanoic Acid

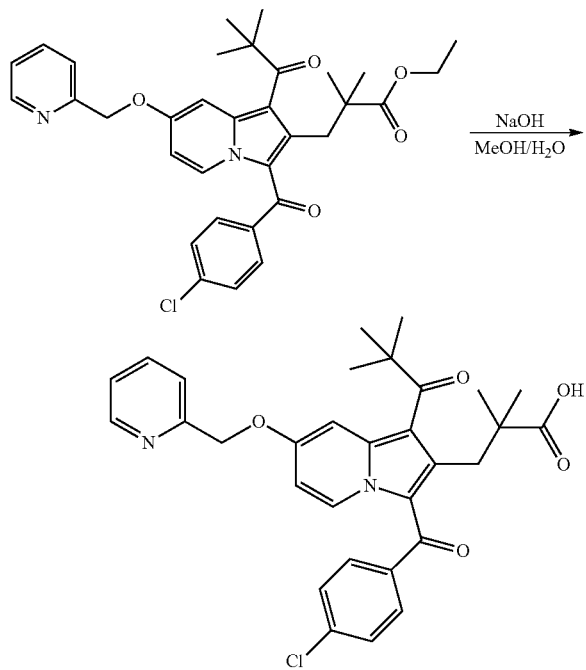

A solution of ethyl 3-{3-[(4-chlorophenyl)carbonyl]-1-(2,2-dimethylpropanoyl)-7-(pyridin-2-ylmethoxy)indolizin-2-yl}-2,2-dimethylpropanoate (98 mg, 0.17 mmol) in THF (1 mL), MeOH (1 mL), and 6M aqueous NaOH (0.75 mL) is heated at 50° C. for 3 h then cooled to 23° C. and acidified to pH=1 with concentrated aqueous HCl. The mixture is partitioned between $CH_2Cl_2$ and brine then the organics are collected and dried with $MgSO_4$, filtered, and concentrated in vacuo to afford the title compound (80 mg, 86%).

The following compounds are also obtained by the methods described in Example 6:
3-(3-{[4-(Difluoromethoxy)phenyl]carbonyl}-1-(2,2-dimethylpropanoyl)-7-[(6-methylpyridin-2-yl)methoxy]indolizin-2-yl)-2,2-dimethylpropanoic acid;
3-{1-(2,2-Dimethylpropanoyl)-3-[(4-methoxyphenyl)carbonyl]-7-[(6-methylpyridin-2-yl)methoxy]indolizin-2-yl}-2,2-dimethylpropanoic acid;
3-[1-(2,2-Dimethylpropanoyl)-7-[(6-methylpyridin-2-yl)methoxy]-3-{[4-(trifluoromethoxy)phenyl]carbonyl}indolizin-2-yl]-2,2-dimethylpropanoic acid;
3-[1-(2,2-Dimethylpropanoyl)-7-[(6-methylpyridin-2-yl)methoxy]-3-{[4-(trifluoromethyl)phenyl]carbonyl}indolizin-2-yl]-2,2-dimethylpropanoic acid;
3-[1-(2,2-Dimethylpropanoyl)-7-[(6-methylpyridin-2-yl)methoxy]-3-{[4-(morpholin-4-yl)phenyl]carbonyl}indolizin-2-yl]-2,2-dimethylpropanoic acid;
3-[1-(2,2-Dimethylpropanoyl)-7-[(6-methylpyridin-2-yl)methoxy]-3-{[4-(methylsulfonyl)phenyl]carbonyl}indolizin-2-yl]-2,2-dimethylpropanoic acid;
3-{3-[(2,4-Dichlorophenyl)carbonyl]-1-(2,2-dimethylpropanoyl)-7-[(6-methylpyridin-2-yl)methoxy]indolizin-2-yl}-2,2-dimethylpropanoic acid;
3-[1-(2,2-Dimethylpropanoyl)-7-[(6-methylpyridin-2-yl)methoxy]-3-{[4-(pyrrolidin-1-yl)phenyl]carbonyl}indolizin-2-yl]-2,2-dimethylpropanoic acid;
3-{1-(2,2-Dimethylpropanoyl)-3-({4-[methyl(methylsulfonyl)amino]phenyl}carbonyl)-7-[(6-methylpyridin-2-yl)methoxy]indolizin-2-yl}-2,2-dimethylpropanoic acid;
3-{3-[(4-Bromophenyl)carbamoyl]-1-(2,2-dimethylpropanoyl)-7-(propan-2-yl)indolizin-2-yl}-2,2-dimethylpropanoic acid;
3-[1-(2,2-Dimethylpropanoyl)-7-(propan-2-yl)-3-(pyridin-2-ylcarbamoyl)indolizin-2-yl]-2,2-dimethylpropanoic acid;
3-{3-[(4-Bromophenyl)carbonyl]-1-(2,2-dimethylpropanoyl)-7-(propan-2-yl)indolizin-2-yl}-2,2-dimethylpropanoic acid;
3-{3-[(4-Chlorophenyl)carbonyl]-1-(2,2-dimethylpropanoyl)-7-(propan-2-yl)indolizin-2-yl}-2,2-dimethylpropanoic acid;
3-[1-(2,2-Dimethylpropanoyl)-7-(propan-2-yl)-3-{[4-(trifluoromethyl)phenyl]carbonyl}indolizin-2-yl]-2,2-dimethylpropanoic acid;
3-[1-(2,2-Dimethylpropanoyl)-3-(phenylcarbonyl)-7-(propan-2-yl)indolizin-2-yl]-2,2-dimethylpropanoic acid;
3-{3-[(4-Chlorophenyl)carbonyl]-1-(cyclobutylcarbonyl)-7-(propan-2-yl)indolizin-2-yl}-2,2-dimethylpropanoic acid;
3-{3-[(4-Chlorophenyl)carbonyl]-1-(cyclopropylcarbonyl)-7-(propan-2-yl)indolizin-2-yl}-2,2-dimethylpropanoic acid;
3-{3-[(4-Chlorophenyl)carbonyl]-1-(3,3-dimethylbutanoyl)-7-(propan-2-yl)indolizin-2-yl}-2,2-dimethylpropanoic acid;
3-{3-[(4-Chlorophenyl)carbonyl]-1-(2-methylpropanoyl)-7-(propan-2-yl)indolizin-2-yl}-2,2-dimethylpropanoic acid;
3-{3-[(4-Chlorophenyl)carbonyl]-1-(2-hydroxy-2-methylpropanoyl)-7-(propan-2-yl)indolizin-2-yl}-2,2-dimethylpropanoic acid;
3-{3-[(4-Chlorophenyl)carbonyl]-1-(2,2-dimethylpropanoyl)indolizin-2-yl}-2,2-dimethylpropanoic acid;
3-{1-[(4-Chlorophenyl)carbonyl]-3-(2,2-dimethylpropanoyl)indolizin-2-yl}-2,2-dimethylpropanoic acid;
3-{3-[(4-Chlorophenyl)carbonyl]-7-(propan-2-yl)-1-[(2,2,3,3-tetramethylcyclopropyl)carbonyl]indolizin-2-yl}-2,2-dimethylpropanoic acid;
3-{3-[(4-Chlorophenyl)carbonyl]-1-(cyclopentylcarbonyl)-7-(propan-2-yl)indolizin-2-yl}-2,2-dimethylpropanoic acid;
3-{3-[(4-Chlorophenyl)carbonyl]-1-(phenylcarbonyl)-7-(propan-2-yl)indolizin-2-yl}-2,2-dimethylpropanoic acid;

3-{3-[(4-Chlorophenyl)carbonyl]-1-(cyclohexylcarbonyl)-7-(propan-2-yl)indolizin-2-yl}-2,2-dimethylpropanoic acid;

3-{1-(2,2-Dimethylpropanoyl)-3-[(4-methylphenyl)carbonyl]-7-[(6-methylpyridin-2-yl)methoxy]indolizin-2-yl}-2,2-dimethylpropanoic acid;

3-{3-[(4-Bromophenyl)carbonyl]-1-(2,2-dimethylpropanoyl)-7-(pyridin-2-ylmethoxy)indolizin-2-yl}-2,2-dimethylpropanoic acid;

3-[7-(Benzyloxy)-3-[(4-chlorophenyl)carbonyl]-1-(2,2-dimethylpropanoyl)indolizin-2-yl]-2,2-dimethylpropanoic acid;

3-{3-[(3-Cyanophenyl)carbonyl]-1-(2,2-dimethylpropanoyl)-7-[(6-methylpyridin-2-yl)methoxy]indolizin-2-yl}-2,2-dimethylpropanoic acid;

3-{3-[(3-Bromophenyl)carbonyl]-1-(2,2-dimethylpropanoyl)-7-[(6-methylpyridin-2-yl)methoxy]indolizin-2-yl}-2,2-dimethylpropanoic acid;

3-{1-(2,2-Dimethylpropanoyl)-3-[(3-methoxyphenyl)carbonyl]-7-[(6-methylpyridin-2-yl)methoxy]indolizin-2-yl}-2,2-dimethylpropanoic acid;

3-{1-(2,2-Dimethylpropanoyl)-3-[(4-fluorophenyl)carbonyl]-7-[(6-methylpyridin-2-yl)methoxy]indolizin-2-yl}-2,2-dimethylpropanoic acid;

3-{3-[(3,4-Dimethylphenyl)carbonyl]-1-(2,2-dimethylpropanoyl)-7-[(6-methylpyridin-2-yl)methoxy]indolizin-2-yl}-2,2-dimethylpropanoic acid; and 3-{3-[(3-Chloro-4-fluorophenyl)carbonyl]-1-(2,2-dimethylpropanoyl)-7-[(6-methylpyridin-2-yl)methoxy]indolizin-2-yl}-2,2-dimethylpropanoic acid.

Example 7

Synthesis of 3-{3-[(4-chlorophenyl)carbonyl]-1-(2,2-dimethylpropanoyl)-7-(quinolin-2-ylmethoxy)indolizin-2-yl}-2,2-dimethylpropanoic Acid

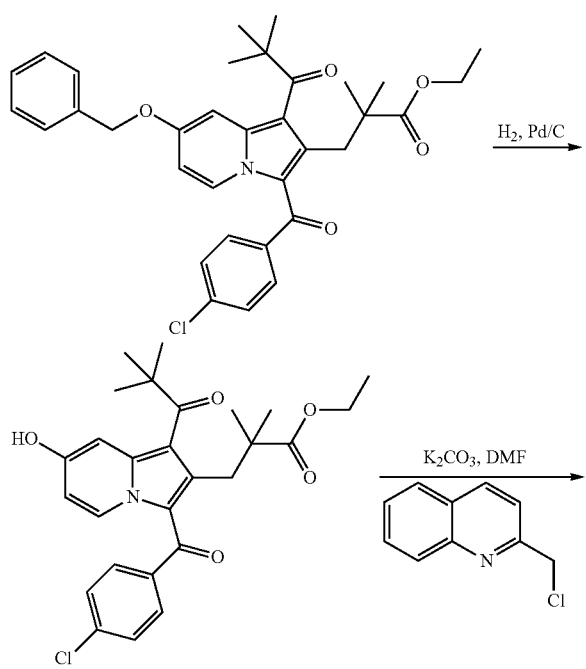

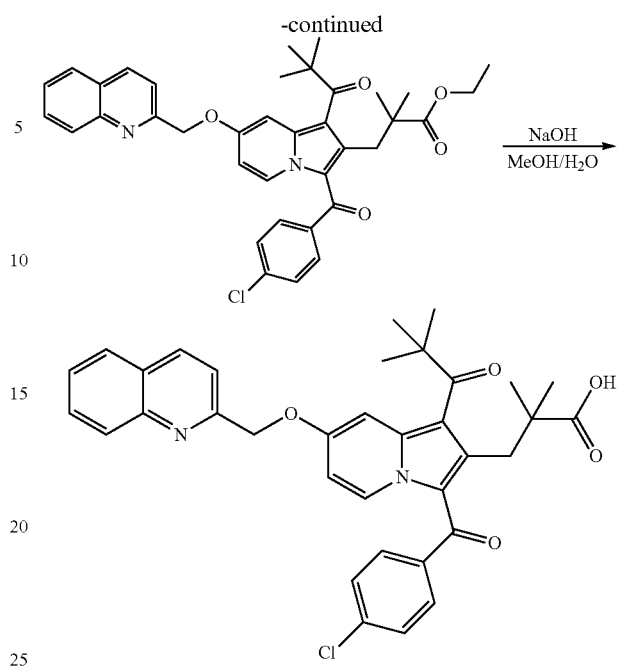

To a stirred solution of ethyl 3-[7-(benzyloxy)-3-[(4-chlorophenyl)carbonyl]-1-(2,2-dimethylpropanoyl)indolizin-2-yl]-2,2-dimethylpropanoate (3.50 g, 6.10 mmol) in EtOH (50 mL) is added 10% Pd/C (480 mg). The suspension is stirred under an atmosphere of hydrogen for 1.5 h then filtered through a pad of diatomaceous earth and washed with EtOH. The filtrate is concentrated in vacuo to give ethyl 3-{3-[(4-chlorophenyl)carbonyl]-1-(2,2-dimethylpropanoyl)-7-hydroxyindolizin-2-yl}-2,2-dimethylpropanoate (2.50 g, 85%). Also obtained is ethyl 3-[1-(2,2-dimethylpropanoyl)-7-hydroxy-3-(phenylcarbonyl)indolizin-2-yl]-2,2-dimethylpropanoate (0.28 g, 10%). A suspension of ethyl 3-{3-[(4-chlorophenyl)carbonyl]-1-(2,2-dimethylpropanoyl)-7-hydroxyindolizin-2-yl}-2,2-dimethylpropanoate (100 mg, 0.207 mmol), 2-(chloromethyl)quinoline-HCl (66.0 mg, 0.310 mmol), and potassium carbonate (114 mg, 0.826 mmol) in DMF (3 mL) is stirred for 24 h at 23° C. The mixture is filtered and concentrated in vacuo to give ethyl 3-{3-[(4-chlorophenyl)carbonyl]-1-(2,2-dimethylpropanoyl)-7-(quinolin-2-ylmethoxy)indolizin-2-yl}-2,2-dimethylpropanoate that is dissolved in THF (2 mL), MeOH (3 mL), and 6M aqueous NaOH (2 mL) and heated at 70° C. for 1 h then cooled to 23° C. and acidified to pH=1 with concentrated aqueous HCl. The mixture is partitioned between $CH_2Cl_2$ and brine then organics are dried with $MgSO_4$, filtered, and concentrated in vacuo. Purification of the crude by HPLC (25 to 75% $CH_3CN$/0.1% TFA in water) gives the title compound (60 mg, 49%).

The following compounds are also obtained by methods described in Example 7:

3-[7-(1,3-Benzothiazol-2-ylmethoxy)-3-[(4-chlorophenyl)carbonyl]-1-(2,2-dimethylpropanoyl)indolizin-2-yl]-2,2-dimethylpropanoic acid;

3-{3-[(4-Chlorophenyl)carbonyl]-1-(2,2-dimethylpropanoyl)-7-[(6-methylpyridin-2-yl)methoxy]indolizin-2-yl}-2,2-dimethylpropanoic acid;

3-{7-[(2-Aminopyrimidin-4-yl)methoxy]-3-[(4-chlorophenyl)carbonyl]-1-(2,2-dimethylpropanoyl)indolizin-2-yl}-2,2-dimethylpropanoic acid;

3-{3-[(4-Chlorophenyl)carbonyl]-1-(2,2-dimethylpropanoyl)-7-[(2-methyl-1,3-thiazol-4-yl)methoxy]indolizin-2-yl}-2,2-dimethylpropanoic acid;

3-{3-[(4-Chlorophenyl)carbonyl]-1-(2,2-dimethylpropanoyl)-7-[(2-methoxy-1,3-thiazol-4-yl)methoxy]indolizin-2-yl}-2,2-dimethylpropanoic acid;

3-{7-[(2-Bromo-1,3-thiazol-4-yl)methoxy]-3-[(4-chlorophenyl)carbonyl]-1-(2,2-dimethylpropanoyl)indolizin-2-yl}-2,2-dimethylpropanoic acid;

3-{3-[(4-Chlorophenyl)carbonyl]-1-(2,2-dimethylpropanoyl)-7-[(1-methyl-1H-pyrazol-3-yl)methoxy]indolizin-2-yl}-2,2-dimethylpropanoic acid;

3-{3-[(4-Chlorophenyl)carbonyl]-1-(2,2-dimethylpropanoyl)-7-[(1,5-dimethyl-1H-pyrazol-3-yl)methoxy]indolizin-2-yl}-2,2-dimethylpropanoic acid;

3-{7-[(4-Bromo-1,3-thiazol-2-yl)methoxy]-3-[(4-chlorophenyl)carbonyl]-1-(2,2-dimethylpropanoyl)indolizin-2-yl}-2,2-dimethylpropanoic acid;

3-{3-[(4-Chlorophenyl)carbonyl]-1-(2,2-dimethylpropanoyl)-7-(1,3-thiazol-4-ylmethoxy)indolizin-2-yl}-2,2-dimethylpropanoic acid;

3-{3-[(4-Chlorophenyl)carbonyl]-1-(2,2-dimethylpropanoyl)-7-(1,3-thiazol-2-ylmethoxy)indolizin-2-yl}-2,2-dimethylpropanoic acid;

3-{3-[(4-Chlorophenyl)carbonyl]-7-[(5-chloropyridin-2-yl)methoxy]-1-(2,2-dimethylpropanoyl)indolizin-2-yl}-2,2-dimethylpropanoic acid;

3-{3-[(4-Chlorophenyl)carbonyl]-1-(2,2-dimethylpropanoyl)-7-[(5-methyl-1,2,4-oxadiazol-3-yl)methoxy]indolizin-2-yl}-2,2-dimethylpropanoic acid;

2-({3-[(4-Chlorophenyl)carbonyl]-1-(2,2-dimethylpropanoyl)-7-[(6-methylpyridin-2-yl)methoxy]indolizin-2-yl}methyl)-2-ethylbutanoic acid;

3-{3-[(4-Chlorophenyl)carbonyl]-1-(2,2-dimethylpropanoyl)-7-[(4-methoxypyridin-2-yl)methoxy]indolizin-2-yl}-2,2-dimethylpropanoic acid;

Methyl 3-{3-[(4-chlorophenyl)carbonyl]-1-(2,2-dimethylpropanoyl)-7-[(4-methoxypyridin-2-yl)methoxy]indolizin-2-yl}-2,2-dimethylpropanoate;

3-{3-[(4-Chlorophenyl)carbonyl]-1-(2,2-dimethylpropanoyl)-7-[(4-methyl-1,3-thiazol-2-yl)methoxy]indolizin-2-yl}-2,2-dimethylpropanoic acid;

3-{3-[(4-Chlorophenyl)carbonyl]-1-(2,2-dimethylpropanoyl)-7-(pyrimidin-2-ylmethoxy)indolizin-2-yl}-2,2-dimethylpropanoic acid;

2-({3-[(4-Chlorophenyl)carbonyl]-1-(2,2-dimethylpropanoyl)-7-(pyridin-2-ylmethoxy)indolizin-2-yl}methyl)-2-ethylbutanoic acid;

3-{3-[(4-Chlorophenyl)carbonyl]-1-(2,2-dimethylpropanoyl)-7-[(4-methoxy-3,5-dimethylpyridin-2-yl)methoxy]indolizin-2-yl}-2,2-dimethylpropanoic acid;

3-{3-[(4-Chlorophenyl)carbonyl]-7-[(3,4-dimethoxypyridin-2-yl)methoxy]-1-(2,2-dimethylpropanoyl)indolizin-2-yl}-2,2-dimethylpropanoic acid;

2-({3-[(4-Chlorophenyl)carbonyl]-1-(2,2-dimethylpropanoyl)-7-[(2-methyl-1,3-thiazol-4-yl)methoxy]indolizin-2-yl}methyl)-2-ethylbutanoic acid;

3-(3-[(4-Chlorophenyl)carbonyl]-1-(2,2-dimethylpropanoyl)-7-{[3-methyl-4-(2,2,2-trifluoroethoxy)pyridin-2-yl]methoxy}indolizin-2-yl)-2,2-dimethylpropanoic acid;

3-{3-[(4-Chlorophenyl)carbonyl]-1-(2,2-dimethylpropanoyl)-7-[(5-methoxypyridin-2-yl)methoxy]indolizin-2-yl}-2,2-dimethylpropanoic acid;

3-{3-[(4-Chlorophenyl)carbonyl]-1-(2,2-dimethylpropanoyl)-7-[(6-fluoropyridin-2-yl)methoxy]indolizin-2-yl}-2,2-dimethylpropanoic acid;

3-{3-[(4-Chlorophenyl)carbonyl]-1-(2,2-dimethylpropanoyl)-7-[(4-methylpyridin-2-yl)methoxy]indolizin-2-yl}-2,2-dimethylpropanoic acid;

Ethyl 3-{3-[(4-chlorophenyl)carbonyl]-1-(2,2-dimethylpropanoyl)-7-[(4-methoxy-3,5-dimethylpyridin-2-yl)methoxy]indolizin-2-yl}-2,2-dimethylpropanoate;

3-{3-[(4-Chlorophenyl)carbonyl]-1-(2,2-dimethylpropanoyl)-7-[(5-methylpyridin-2-yl)methoxy]indolizin-2-yl}-2,2-dimethylpropanoic acid;

3-{1-(2,2-Dimethylpropanoyl)-3-[(4-methoxyphenyl)carbonyl]-7-[(4-methyl-1,3-thiazol-2-yl)methoxy]indolizin-2-yl}-2,2-dimethylpropanoic acid;

3-{1-(2,2-Dimethylpropanoyl)-3-[(4-methoxyphenyl)carbonyl]-7-[(2-methyl-1,3-thiazol-4-yl)methoxy]indolizin-2-yl}-2,2-dimethylpropanoic acid;

2-({3-[(4-Chlorophenyl)carbonyl]-1-(2,2-dimethylpropanoyl)-7-[(6-methylpyridin-2-yl)methoxy]indolizin-2-yl}methyl)butanoic acid;

3-{3-[(4-Chlorophenyl)carbonyl]-1-(2,2-dimethylpropanoyl)-7-[(6-methylpyridin-2-yl)methoxy]indolizin-2-yl}-2-methylpropanoic acid;

3-{3-[(3,4-Dichlorophenyl)carbonyl]-1-(2,2-dimethylpropanoyl)-7-[(6-methylpyridin-2-yl)methoxy]indolizin-2-yl}-2,2-dimethylpropanoic acid;

1-{[7-(1,3-Benzothiazol-2-ylmethoxy)-3-[(4-chlorophenyl)carbonyl]-1-(2,2-dimethylpropanoyl)indolizin-2-yl]methyl}cyclopentanecarboxylic acid;

1-({3-[(4-Chlorophenyl)carbonyl]-1-(2,2-dimethylpropanoyl)-7-[(6-methylpyridin-2-yl)methoxy]indolizin-2-yl}methyl)cyclopentanecarboxylic acid;

2-({3-[(4-Chlorophenyl)carbonyl]-1-(2,2-dimethylpropanoyl)-7-[(6-methylpyridin-2-yl)methoxy]indolizin-2-yl}methyl)pentanoic acid;

3-{3-[(3-Chlorophenyl)carbonyl]-1-(2,2-dimethylpropanoyl)-7-[(2-methyl-1,3-thiazol-4-yl)methoxy]indolizin-2-yl}-2,2-dimethylpropanoic acid;

3-{3-[(3-Chlorophenyl)carbonyl]-1-(2,2-dimethylpropanoyl)-7-[(4-methyl-1,3-thiazol-2-yl)methoxy]indolizin-2-yl}-2,2-dimethylpropanoic acid 2-({3-[(3,4-Dichlorophenyl)carbonyl]-1-(2,2-dimethylpropanoyl)-7-[(4-methyl-1,3-thiazol-2-yl)methoxy]indolizin-2-yl}methyl)pentanoic acid;

2-({3-[(3,4-Dichlorophenyl)carbonyl]-1-(2,2-dimethylpropanoyl)-7-[(6-methylpyridin-2-yl)methoxy]indolizin-2-yl}methyl)pentanoic acid;

2-({1-(2,2-Dimethylpropanoyl)-3-[(4-methoxyphenyl)carbonyl]-7-[(2-methyl-1,3-thiazol-4-yl)methoxy]indolizin-2-yl}methyl)pentanoic acid;

2-({1-(2,2-Dimethylpropanoyl)-3-[(4-methoxyphenyl)carbonyl]-7-[(4-methyl-1,3-thiazol-2-yl)methoxy]indolizin-2-yl}methyl)pentanoic acid;

2-({1-(2,2-Dimethylpropanoyl)-3-[(4-methoxyphenyl)carbonyl]-7-[(6-methylpyridin-2-yl)methoxy]indolizin-2-yl}methyl)pentanoic acid;

3-{7-(1,3-Benzothiazol-2-ylmethoxy)-1-(2,2-dimethylpropanoyl)-3-[(4-methoxyphenyl)carbonyl]indolizin-2-yl}-2,2-dimethylpropanoic acid;

3-[1-(2,2-Dimethylpropanoyl)-3-[(4-methoxyphenyl)carbonyl]-7-(quinolin-2-ylmethoxy)indolizin-2-yl]-2,2-dimethylpropanoic acid;

2-({3-[(4-Chloro-3-methylphenyl)carbonyl]-1-(2,2-dimethylpropanoyl)-7-[(6-methylpyridin-2-yl)methoxy]indolizin-2-yl}methyl)pentanoic acid;

2-({3-[(4-Chloro-3-methylphenyl)carbonyl]-1-(2,2-dimethylpropanoyl)-7-[(2-methyl-1,3-thiazol-4-yl)methoxy]indolizin-2-yl}methyl)pentanoic acid;

2-({1-(2,2-Dimethylpropanoyl)-3-[(4-methoxyphenyl)carbonyl]-7-[(6-methylpyridin-2-yl)methoxy]indolizin-2-yl}methyl)-2-methylpentanoic acid;
2-({1-(2,2-Dimethylpropanoyl)-3-[(4-methoxyphenyl)carbonyl]-7-[(2-methyl-1,3-thiazol-4-yl)methoxy]indolizin-2-yl}methyl)-2-methylpentanoic acid;
2-{[1-(2,2-Dimethylpropanoyl)-3-[(4-methoxyphenyl)carbonyl]-7-(quinolin-2-ylmethoxy)indolizin-2-yl]methyl}-2-methylpentanoic acid;
2-({1-(2,2-Dimethylpropanoyl)-3-[(4-methoxyphenyl)carbonyl]-7-[(6-methylpyridin-2-yl)methoxy]indolizin-2-yl}methyl)-2-methylbutanoic acid;
2-({1-(2,2-Dimethylpropanoyl)-3-[(4-methoxyphenyl)carbonyl]-7-[(4-methyl-1,3-thiazol-2-yl)methoxy]indolizin-2-yl}methyl)-2-methylbutanoic acid;
2-({1-(2,2-Dimethylpropanoyl)-3-[(4-methoxyphenyl)carbonyl]-7-[(2-methyl-1,3-thiazol-4-yl)methoxy]indolizin-2-yl}methyl)-2-methylbutanoic acid;
2-({3-[(3,4-Dichlorophenyl)carbonyl]-1-(2,2-dimethylpropanoyl)-7-[(6-methylpyridin-2-yl)methoxy]indolizin-2-yl}methyl)-2-methylbutanoic acid;
2-({3-[(3,4-Dichlorophenyl)carbonyl]-1-(2,2-dimethylpropanoyl)-7-[(4-methyl-1,3-thiazol-2-yl)methoxy]indolizin-2-yl}methyl)-2-methylbutanoic acid;
2-({3-[(3,4-Dichlorophenyl)carbonyl]-1-(2,2-dimethylpropanoyl)-7-[(2-methyl-1,3-thiazol-4-yl)methoxy]indolizin-2-yl}methyl)-2-methylbutanoic acid;
2-({3-[(4-Chlorophenyl)carbonyl]-1-(2,2-dimethylpropanoyl)-7-[(6-methylpyridin-2-yl)methoxy]indolizin-2-yl}methyl)-2-methylbutanoic acid;
3-{3-[(4-Chloro-3-methylphenyl)carbonyl]-1-(2,2-dimethylpropanoyl)-7-[(6-methylpyridin-2-yl)methoxy]indolizin-2-yl}-2,2-dimethylpropanoic acid;
3-{3-[(4-Chlorophenyl)carbonyl]-1-(2,2-dimethylpropanoyl)-7-[(4-methyl-1,3-thiazol-2-yl)methoxy]indolizin-2-yl}-2,2-dimethylpropanoic acid;
3-{3-[(3,4-Dichlorophenyl)carbonyl]-1-(2,2-dimethylpropanoyl)-7-[(4-methyl-1,3-thiazol-2-yl)methoxy]indolizin-2-yl}-2,2-dimethylpropanoic acid;
3-{3-[(4-Chloro-3-methylphenyl)carbonyl]-1-(2,2-dimethylpropanoyl)-7-[(4-methyl-1,3-thiazol-2-yl)methoxy]indolizin-2-yl}-2,2-dimethylpropanoic acid;
3-{3-[(4-Chloro-3-methylphenyl)carbonyl]-1-(2,2-dimethylpropanoyl)-7-[(2-methyl-1,3-thiazol-4-yl)methoxy]indolizin-2-yl}-2,2-dimethylpropanoic acid;
2-({3-[(3,4-Dichlorophenyl)carbonyl]-1-(2,2-dimethylpropanoyl)-7-[(4-methyl-1,3-thiazol-2-yl)methoxy]indolizin-2-yl}methyl)-3-methylbutanoic acid;
3-{3-[(3,5-Dichlorophenyl)carbonyl]-1-(2,2-dimethylpropanoyl)-7-[(2-methyl-1,3-thiazol-4-yl)methoxy]indolizin-2-yl}-2,2-dimethylpropanoic acid;
3-{3-[(3,5-Dichlorophenyl)carbonyl]-1-(2,2-dimethylpropanoyl)-7-[(4-methyl-1,3-thiazol-2-yl)methoxy]indolizin-2-yl}-2,2-dimethylpropanoic acid;
3-{3-[(3,5-Dichlorophenyl)carbonyl]-1-(2,2-dimethylpropanoyl)-7-[(6-methylpyridin-2-yl)methoxy]indolizin-2-yl}-2,2-dimethylpropanoic acid;
2-({1-(2,2-Dimethylpropanoyl)-3-[(4-methoxyphenyl)carbonyl]-7-[(2-methyl-1,3-thiazol-4-yl)methoxy]indolizin-2-yl}methyl)-3-methylbutanoic acid;
2-({1-(2,2-Dimethylpropanoyl)-3-[(4-methoxyphenyl)carbonyl]-7-[(4-methyl-1,3-thiazol-2-yl)methoxy]indolizin-2-yl}methyl)-3-methylbutanoic acid;
2-({7-(1,3-Benzothiazol-2-ylmethoxy)-1-(2,2-dimethylpropanoyl)-3-[(4-methoxyphenyl)carbonyl]indolizin-2-yl}methyl)-3-methylbutanoic acid;
2-({1-(2,2-Dimethylpropanoyl)-3-[(4-methoxyphenyl)carbonyl]-7-[(6-methylpyridin-2-yl)methoxy]indolizin-2-yl}methyl)-3-methylbutanoic acid; and
2-{[1-(2,2-Dimethylpropanoyl)-3-[(4-methoxyphenyl)carbonyl]-7-(quinolin-2-ylmethoxy)indolizin-2-yl]methyl}-3-methylbutanoic acid.

Example 8

Synthesis of 3-{3-[(4-chlorophenyl)carbonyl]-1-(2,2-dimethylpropanoyl)-7-[(6-methoxypyridin-2-yl)methoxy]indolizin-2-yl}-2,2-dimethylpropanoic Acid

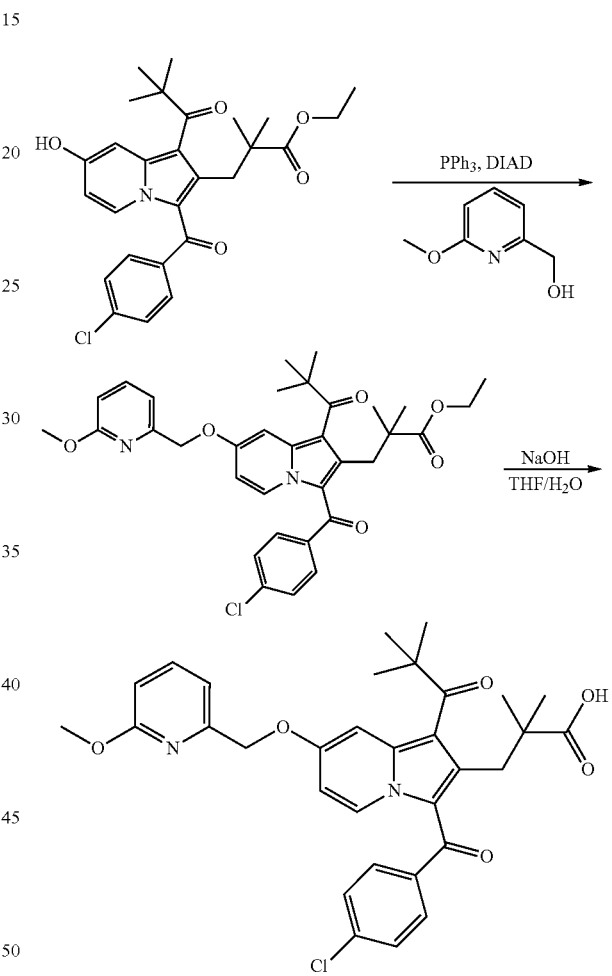

To a cold (0° C.) solution of ethyl 3-{3-[(4-chlorophenyl)carbonyl]-1-(2,2-dimethylpropanoyl)-7-hydroxyindolizin-2-yl}-2,2-dimethylpropanoate (100 mg, 0.21 mmol), (6-methoxy-pyridin-2-yl)-methanol (35 mg, 0.25 mmol), and triphenylphosphine (65 mg, 0.25 mmol) in THF (5 mL) is added DIAD (48 μL, 0.25 mmol). The reaction is allowed to gradually warm to 23° C. and then stirred overnight. Silica gel is added and the mixture is concentrated in vacuo then purified by flash chromatography (SiO₂, hexanes to 15% EtOAc in hexanes) to give ethyl 3-{3-[(4-chlorophenyl)carbonyl]-1-(2,2-dimethylpropanoyl)-7-[(6-methoxypyridin-2-yl)methoxy]indolizin-2-yl}-2,2-dimethylpropanoate (20 mg, 16%).

A solution of ethyl 3-{3-[(4-chlorophenyl)carbonyl]-1-(2,2-dimethylpropanoyl)-7-[(6-methoxypyridin-2-yl)methoxy]indolizin-2-yl}-2,2-dimethylpropanoate (20 mg, 0.033 mmol) in THF (2.0 mL) and 10M aqueous NaOH (1.5 mL) is heated at 45° C. for 1.5 h. The mixture is then acidified with HOAc, concentrated in vacuo, and partitioned between EtOAc and water. The organics are collected, dried with MgSO$_4$, filtered, and concentrated in vacuo to give the title compound (19 mg, quant).

The following compounds are also obtained by methods described in Example 8:

3-{3-[(4-Chlorophenyl)carbonyl]-1-(2,2-dimethylpropanoyl)-7-[(1R)-1-(pyridin-2-yl)ethoxy]indolizin-2-yl}-2,2-dimethylpropanoic acid; and 3-{3-[(4-Chlorophenyl)carbonyl]-1-(2,2-dimethylpropanoyl)-7-[(1S)-1-(pyridin-2-yl)ethoxy]indolizin-2-yl}-2,2-dimethylpropanoic acid.

Example 9

Synthesis of 3-{3-[(4-chlorophenyl)carbonyl]-1-(3,3-dimethylbutanoyl)-7-(quinolin-2-ylmethoxy)indolizin-2-yl}-2,2-dimethylpropanoic Acid

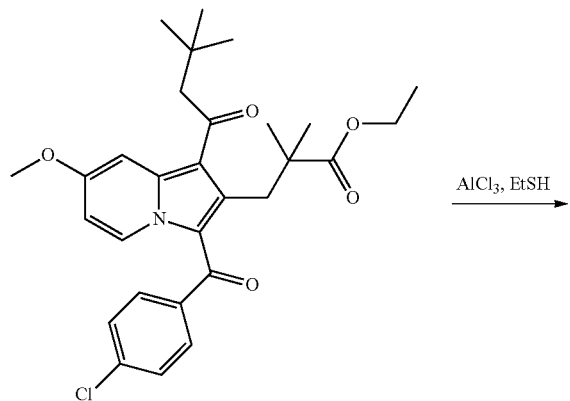

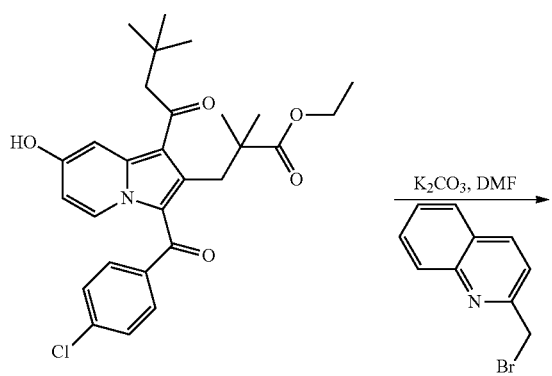

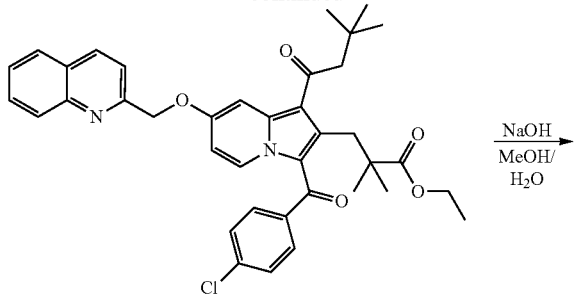

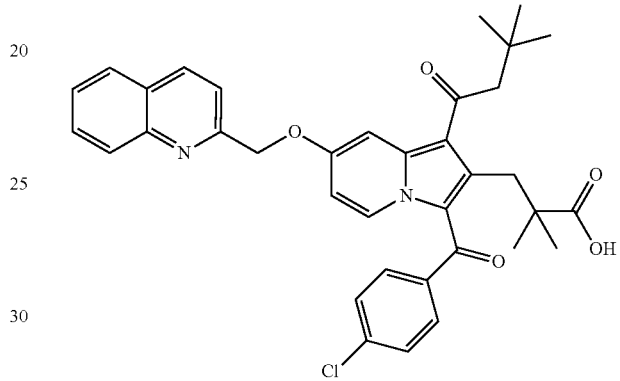

To a solution of ethyl 3-{3-[(4-chlorophenyl)carbonyl]-1-(3,3-dimethylbutanoyl)-7-methoxyindolizin-2-yl}-2,2-dimethylpropanoate (310 mg, 0.605 mmol) in CH$_2$Cl$_2$ (5.0 mL) is added aluminum chloride (363 mg, 2.72 mmol). The solution is stirred for 3 h at 23° C. then treated with ethanethiol (0.112 mL, 1.51 mmol) and allowed to stir for 18 h. The mixture is poured into cold 1M aqueous Rochelle's salt solution, extracted with CH$_2$Cl$_2$, washed with brine, dried with MgSO$_4$, filtered, and concentrated in vacuo. Purification of the crude by flash chromatography (SiO$_2$, hexanes to 1:1 hexanes:EtOAc) gives ethyl 3-{3-[(4-chlorophenyl)carbonyl]-1-(3,3-dimethylbutanoyl)-7-hydroxyindolizin-2-yl}-2,2-dimethylpropanoate (32 mg, 10%).

A suspension of ethyl 3-{3-[(4-chlorophenyl)carbonyl]-1-(3,3-dimethylbutanoyl)-7-hydroxyindolizin-2-yl}-2,2-dimethylpropanoate (30 mg, 0.06 mmol), 2-(bromomethyl)quinoline (20 mg, 0.09 mmol), and potassium carbonate (17 mg, 0.12 mmol) in DMF (1.0 mL) is stirred for 96 h at 50° C. The mixture is cooled to 23° C. then filtered and concentrated in vacuo. Purification of the crude by flash chromatography (SiO$_2$, hexanes to 1:1 hexanes:EtOAc) gives ethyl 3-{3-[(4-chlorophenyl)carbonyl]-1-(3,3-dimethylbutanoyl)-7-(quinolin-2-ylmethoxy)indolizin-2-yl}-2,2-dimethylpropanoate (39 mg, quant).

A solution of ethyl 3-{3-[(4-chlorophenyl)carbonyl]-1-(3,3-dimethylbutanoyl)-7-(quinolin-2-ylmethoxy)indolizin-2-yl}-2,2-dimethylpropanoate (39 mg, 0.06 mmol) in THF (1 mL), MeOH (1 mL), and 6M aqueous NaOH (1 mL) is heated at 70° C. for 2.5 h then cooled to 23° C. and acidified to pH=1 with 6 M aqueous HCl. The mixture is partitioned between CH$_2$Cl$_2$ and brine then the organics are collected and dried with MgSO$_4$, filtered, and concentrated in vacuo. The crude is purified by flash chromatography (SiO$_2$, CH$_2$Cl$_2$ to 10% MeOH in CH$_2$Cl$_2$) to give the title compound (8 mg, 22%).

Example 10

Synthesis of 3-[6-(1,3-benzothiazol-2-ylmethoxy)-1-[(4-chlorophenyl)carbonyl]-3-(2,2-dimethylpropanoyl)indolizin-2-yl]-2,2-dimethylpropanoic Acid

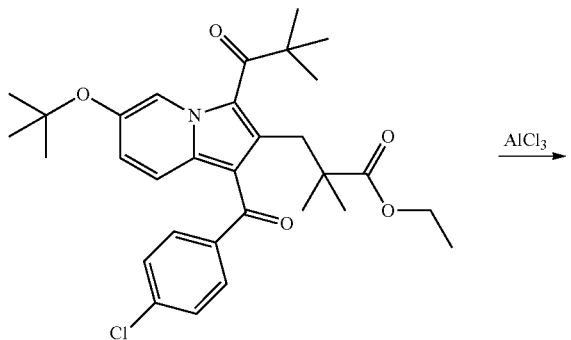

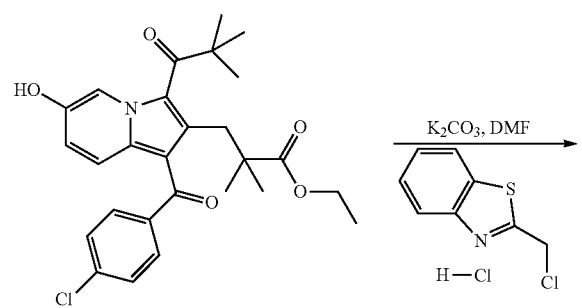

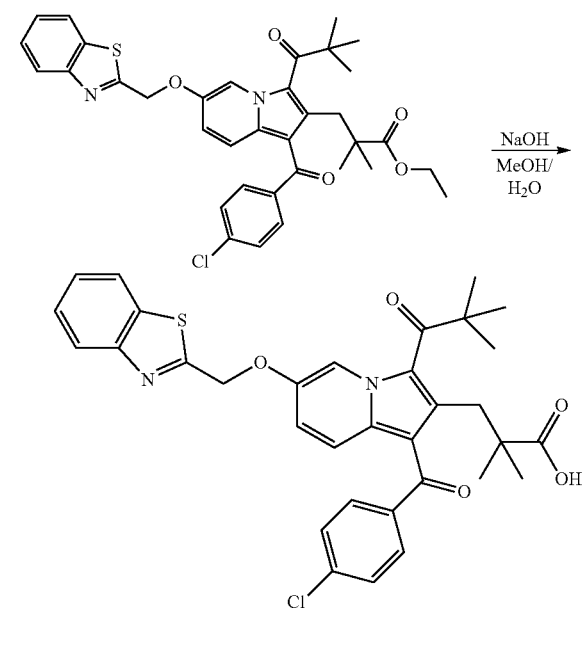

To a solution of the ethyl 3-{6-tert-butoxy-1-[(4-chlorophenyl)carbonyl]-3-(2,2-dimethylpropanoyl)indolizin-2-yl}-2,2-dimethylpropanoate (1.23 g, 2.27 mmol) in CH$_2$Cl$_2$ (10 mL) is added aluminum chloride (454 mg, 3.41 mmol). The reaction is stirred for 30 min at 23° C. then treated with a saturated aqueous solution of Rochelle's salt. The mixture is partitioned between CH$_2$Cl$_2$ and brine, then organics are collected, dried with MgSO$_4$, filtered, and concentrated in vacuo. Purification of the crude by flash chromatography (SiO$_2$, hexanes to 25% EtOAc in hexanes) affords ethyl 3-{1-[(4-chlorophenyl)carbonyl]-3-(2,2-dimethylpropanoyl)-6-hydroxyindolizin-2-yl}-2,2-dimethylpropanoate (605 mg, 22%).

A suspension of ethyl 3-{1-[(4-chlorophenyl)carbonyl]-3-(2,2-dimethylpropanoyl)-6-hydroxyindolizin-2-yl}-2,2-dimethylpropanoate (85.0 mg, 0.176 mmol), 2-(chloromethyl)-1,3-benzothiazole-HCl (60.1 mg, 0.263 mmol), and potassium carbonate (97.1, 0.703 mmol) in DMF (3.0 mL) is stirred at 50° C. for 1 h. The mixture is cooled to 23° C. then filtered, concentrated in vacuo, and purified by flash chromatography (SiO$_2$, hexanes to 1:1 hexanes:EtOAc) to yield ethyl 3-[6-(1,3-benzothiazol-2-ylmethoxy)-1-[(4-chlorophenyl)carbonyl]-3-(2,2-dimethylpropanoyl)indolizin-2-yl]-2,2-dimethylpropanoate (74 mg, 67%).

A solution of ethyl 3-[6-(1,3-benzothiazol-2-ylmethoxy)-1-[(4-chlorophenyl)carbonyl]-3-(2,2-dimethylpropanoyl)indolizin-2-yl]-2,2-dimethylpropanoate (74 mg, 0.12 mmol) in THF (0.5 mL), MeOH (1.0 mL), and 6M aqueous NaOH (1.0 mL) is heated at 70° C. for 1 h then cooled to 23° C. and acidified to pH=1 with concentrated aqueous HCl. The mixture is partitioned between CH$_2$Cl$_2$ and brine and organics are collected, dried with MgSO$_4$, filtered, and concentrated in vacuo. Purification of the crude by flash chromatography (SiO$_2$, CH$_2$Cl$_2$ to 10% MeOH in CH$_2$Cl$_2$) gives the title compound (59 mg, 83%).

The following compounds are also obtained by methods described in Example 10:

3-{1-[(4-Chlorophenyl)carbonyl]-3-(2,2-dimethylpropanoyl)-6-[(6-methylpyridin-2-yl)methoxy]indolizin-2-yl}-2,2-dimethylpropanoic acid;

3-{1-[(4-Chlorophenyl)carbonyl]-3-(2,2-dimethylpropanoyl)-6-(quinolin-2-ylmethoxy)indolizin-2-yl}-2,2-dimethylpropanoic acid;

3-{1-[(4-Chlorophenyl)carbonyl]-3-(2,2-dimethylpropanoyl)-6-[(2-methyl-1,3-thiazol-4-yl)methoxy]indolizin-2-yl}-2,2-dimethylpropanoic acid;

3-{1-[(4-Chlorophenyl)carbonyl]-3-(2,2-dimethylpropanoyl)-6-(pyridin-2-ylmethoxy)indolizin-2-yl}-2,2-dimethylpropanoic acid;

3-{1-[(4-Chlorophenyl)carbonyl]-3-(2,2-dimethylpropanoyl)-6-(1,3-thiazol-2-ylmethoxy)indolizin-2-yl}-2,2-dimethylpropanoic acid;

3-{1-[(4-Chlorophenyl)carbonyl]-3-(2,2-dimethylpropanoyl)-6-(1,3-thiazol-4-ylmethoxy)indolizin-2-yl}-2,2-dimethylpropanoic acid;

3-{1-[(4-Chlorophenyl)carbonyl]-3-(2,2-dimethylpropanoyl)-6-(pyrazin-2-ylmethoxy)indolizin-2-yl}-2,2-dimethylpropanoic acid; and Methyl 3-{1-[(4-chlorophenyl)carbonyl]-3-(2,2-dimethylpropanoyl)-6-[(2-methyl-1,3-thiazol-4-yl)methoxy]indolizin-2-yl}-2,2-dimethylpropanoate.

Example 11

Synthesis of 3-[1-(2,2-dimethylpropanoyl)-3-(phenylcarbonyl)-7-(pyrimidin-2-ylmethoxy)indolizin-2-yl]-2,2-dimethylpropanoic Acid

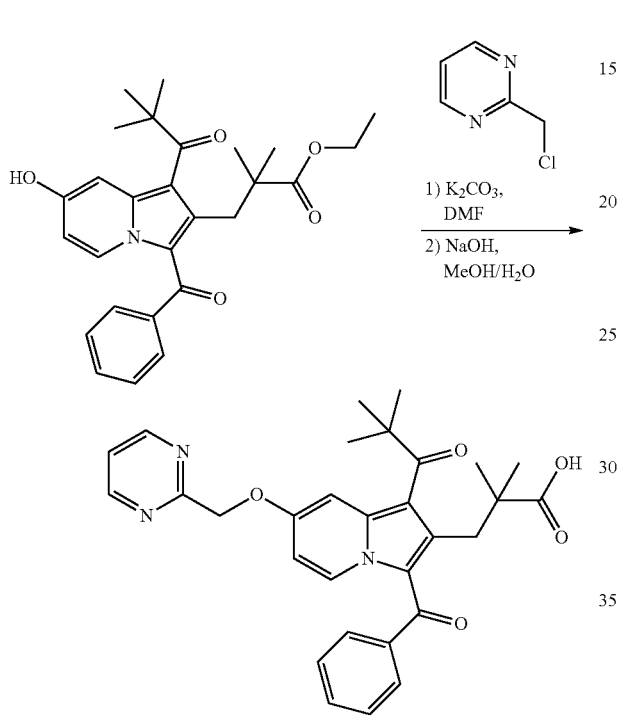

A suspension of ethyl 3-[1-(2,2-dimethylpropanoyl)-7-hydroxy-3-(phenylcarbonyl)indolizin-2-yl]-2,2-dimethylpropanoate (See Example 9) (93.0 mg, 0.207 mmol), 2-(chloromethyl)pyrimidine-HCl (51.1 mg, 0.310 mmol), and potassium carbonate (114 mg, 0.826 mmol) in DMF (3 mL) is stirred for 24 h at 23° C. The mixture is filtered and concentrated in vacuo to give ester that is dissolved in THF (2 mL) MeOH (3 mL) and 6M aqueous NaOH (2 mL) and heated at 70° C. for 1 h then cooled to 23° C. and acidified to pH=1 with concentrated aqueous HCl. The mixture is partitioned between $CH_2Cl_2$ and brine then organics are dried with $MgSO_4$, filtered, and concentrated in vacuo. Purification of the crude by HPLC (25 to 75% $CH_3CN$/0.1% TFA in water) gives the title compound (57 mg, 54%).

The following compounds are also obtained by methods described in Example 11:

3-[1-(2,2-Dimethylpropanoyl)-3-(phenylcarbonyl)-7-(pyridin-2-ylmethoxy)indolizin-2-yl]-2,2-dimethylpropanoic acid;

3-[1-(2,2-Dimethylpropanoyl)-7-[(2-methyl-1,3-thiazol-4-yl)methoxy]-3-(phenylcarbonyl)indolizin-2-yl]-2,2-dimethylpropanoic acid;

3-[1-(2,2-Dimethylpropanoyl)-7-[(2-methoxy-1,3-thiazol-4-yl)methoxy]-3-(phenylcarbonyl)indolizin-2-yl]-2,2-dimethylpropanoic acid; and 3-[1-(2,2-Dimethylpropanoyl)-3-(phenylcarbonyl)-7-(quinolin-2-ylmethoxy)indolizin-2-yl]-2,2-dimethylpropanoic acid.

Example 12

Synthesis of 3-{3-[(4-bromophenyl)(methyl)carbamoyl]-1-(2,2-dimethylpropanoyl)-7-(propan-2-yl)indolizin-2-yl}-2,2-dimethylpropanoic Acid

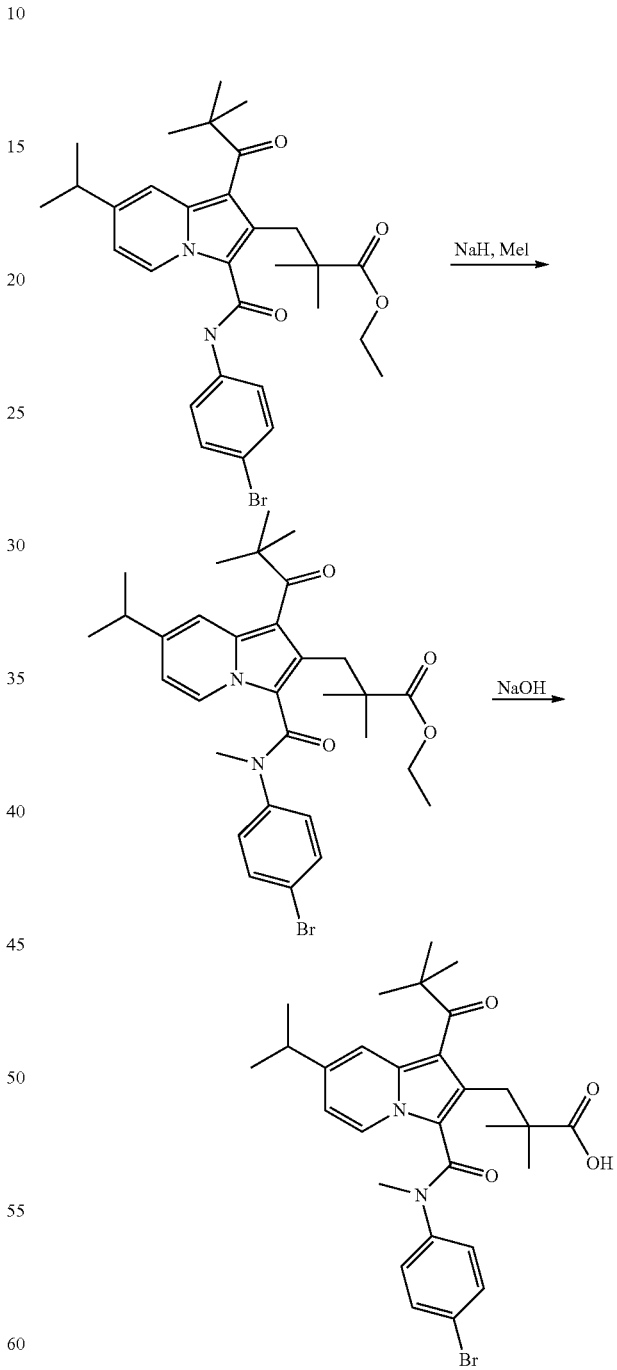

To a stirred solution of ethyl 3-{3-[(4-bromophenyl)carbamoyl]-1-(2,2-dimethylpropanoyl)-7-(propan-2-yl)indolizin-2-yl}-2,2-dimethylpropanoate (100 mg, 0.18 mmol) in DMF (2 mL) is added NaH (60% dispersion in mineral oil, 7.7 mg, 0.19 mmol) at 0° C. The suspension is stirred for 10 minutes then iodomethane (12.0 μl 0.19 mmol) is introduced and the reaction mixture is stirred overnight. The mixture is quenched with water, extracted with EtOAc, dried with MgSO₄, filtered, and concentrated in vacuo. Purification of the crude by flash chromatography (SiO₂, hexanes to 40% EtOAc in hexanes) gives ethyl 3-{3-[(4-bromophenyl)(methyl)carbamoyl]-1-(2,2-dimethylpropanoyl)-7-(propan-2-yl)indolizin-2-yl}-2,2-dimethylpropanoate (75 mg, 73%) that is dissolved in THF (8 mL), MeOH (1 mL), and water (1 mL) and treated with 10M aqueous NaOH (0.1 mL). The mixture is stirred for 16 h then concentrated and acidified with HOAc. The resulting solid is filtered, washed with water, collected, and dried to give the title compound (50 mg, 70%).

The following compound is also obtained by the methods described in Example 12:

3-[1-(2,2-Dimethylpropanoyl)-3-[methyl(pyridin-2-yl)carbamoyl]-7-(propan-2-yl)indolizin-2-yl]-2,2-dimethylpropanoic acid.

Example 13

Synthesis of N-{[1-(2,2-dimethylpropanoyl)-2-methyl-7-(propan-2-yl)indolizin-3-yl]carbonyl}-N-phenyl-beta-alanine

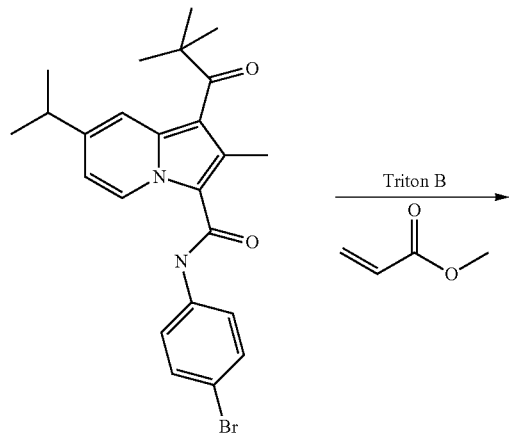

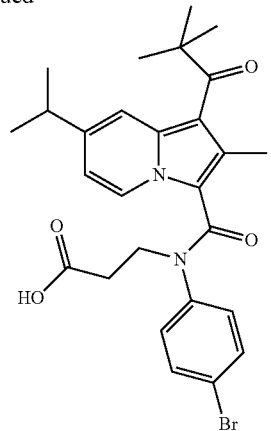

To a stirred solution of 1-(2,2-dimethylpropanoyl)-2-methyl-N-phenyl-7-(propan-2-yl)indolizine-3-carboxamide (70 mg, 0.19 mmol) in DMF (2.0 mL) is added Triton B (8 μl, 0.02 mmol) followed by methyl acrylate (18 μl, 0.20 mmol). The reaction is stirred for 3 days at 23° C. after which time DBU (0.20 mL, 1.31 mmol) and additional methyl acrylate (0.10 mL, 1.11 mmol) are introduced. The reaction is heated at 50° C. for 18 h and then cooled to 23° C., poured into water, extracted with EtOAc, dried with MgSO₄, filtered, and concentrated in vacuo. Purification of the crude by flash chromatography (SiO₂, hexanes to 30% EtOAc in hexanes) gives methyl N-{[1-(2,2-dimethylpropanoyl)-2-methyl-7-(propan-2-yl)indolizin-3-yl]carbonyl}-N-phenyl-beta-alaninate (60 mg, 70%).

To a stirred solution of methyl N-{[1-(2,2-dimethylpropanoyl)-2-methyl-7-(propan-2-yl)indolizin-3-yl]carbonyl}-N-phenyl-beta-alaninate (60 mg, 0.13 mmol) in 1,4-dioxane (5 mL) and water (1 mL) is added 10M aqueous NaOH (50 μL). The mixture is stirred at 23° C. for 2 h then acidified with HOAc, diluted water (5 mL), extracted with CH₂Cl₂, dried with MgSO₄, filtered, and concentrated in vacuo to afford the title compound (42 mg, 72%).

Example 14

Synthesis of 3-{3-[(4-chlorophenyl)carbonyl]-1-(2,2-dimethylpropanoyl)-7-(propan-2-yl)indolizin-2-yl}-N,N,2,2-tetramethylpropanamide

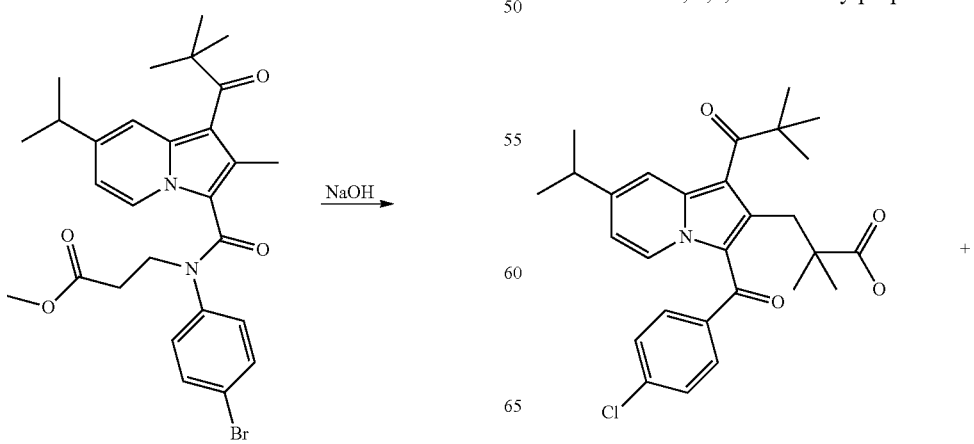

163

-continued

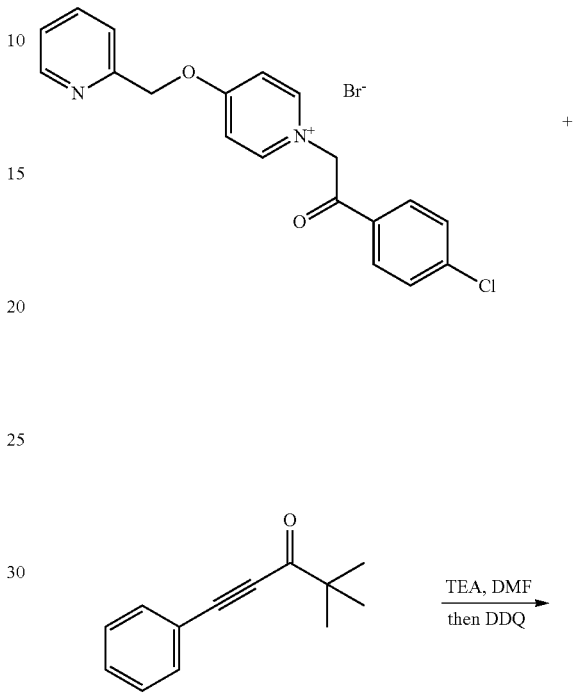

To a solution of 3-{3-[(4-chlorophenyl)carbonyl]-1-(2,2-dimethylpropanoyl)-7-(propan-2-yl)indolizin-2-yl}-2,2-dimethylpropanoic acid (100 mg, 0.207 mmol), O-(7-azabenzotriazol-1-yl)-N,N,N',N'-tetramethyluronium hexafluorophosphate (157.7 mg, 0.415 mmol), and dimethylamine-HCl (18.6 mg, 0.228 mmol) is added TEA (0.173 mL, 1.245 mmol). The reaction is stirred for 16 h then purified by HPLC to give the title compound (36 mg, 34%).

The following compounds are also obtained by the methods described in Example 14:

3-{3-[(4-Chlorophenyl)carbonyl]-1-(2,2-dimethylpropanoyl)-7-(propan-2-yl)indolizin-2-yl}-2,2-dimethyl-N-(methylsulfonyl)propanamide;

3-{3-[(4-Chlorophenyl)carbonyl]-1-(2,2-dimethylpropanoyl)-7-(propan-2-yl)indolizin-2-yl}-2,2-dimethylpropanamide;

3-{3-[(4-Chlorophenyl)carbonyl]-1-(2,2-dimethylpropanoyl)-7-(propan-2-yl)indolizin-2-yl}-2,2-dimethyl-N-(pyridin-2-yl)propanamide;

3-{3-[(4-Chlorophenyl)carbonyl]-1-(2,2-dimethylpropanoyl)-7-(propan-2-yl)indolizin-2-yl}-2,2-dimethyl-N-(pyridin-3-yl)propanamide;

3-{3-[(4-Chlorophenyl)carbonyl]-1-(2,2-dimethylpropanoyl)-7-(propan-2-yl)indolizin-2-yl}-2,2-dimethyl-N-(pyridin-4-yl)propanamide;

3-{1-[(4-Chlorophenyl)carbonyl]-3-(2,2-dimethylpropanoyl)-6-[(2-methyl-1,3-thiazol-4-yl)methoxy]indolizin-2-yl}-2,2-dimethylpropanamide; and 3-{1-[(4-Chlorophenyl)carbonyl]-3-(2,2-dimethylpropanoyl)-6-[(2-methyl-1,3-thiazol-4-yl)methoxy]indolizin-2-yl}-2,2-dimethyl-N-(methylsulfonyl)propanamide.

164

Example 15

Synthesis of 1-{3-[(4-chlorophenyl)carbonyl]-2-phenyl-7-(pyridin-2-ylmethoxy)indolizin-1-yl}-2,2-dimethylpropan-1-one

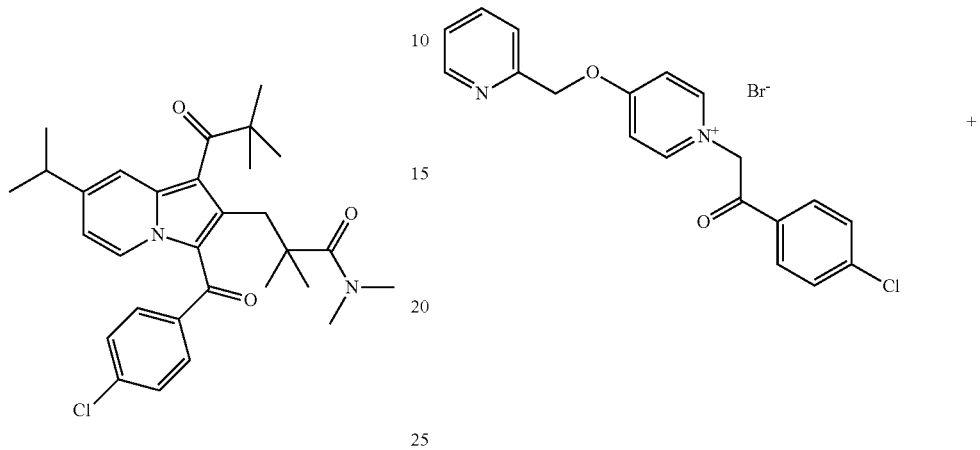

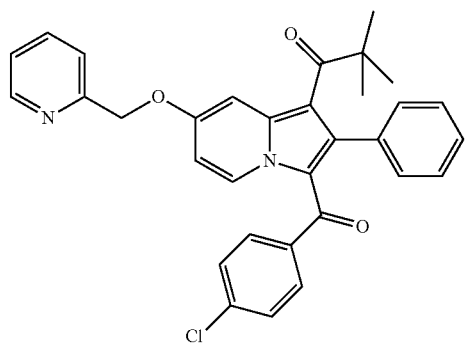

To a suspension of 1-[2-(4-chlorophenyl)-2-oxoethyl]-4-(pyridin-2-ylmethoxy)pyridinium bromide (750 mg, 1.79 mmol) and 4,4-dimethyl-1-phenylpent-1-yn-3-one (333 mg, 1.79 mmol) in DMF (10.0 mL) is added TEA (0.37 mL, 2.68 mmol). The mixture is stirred at 70° C. for 18 h then treated with DDQ (406 mg, 1.79 mmol) and stirred for an additional 1 h. The mixture is then cooled to 23° C. and partitioned between water and EtOAc. The organics are collected, dried with MgSO$_4$, filtered, and concentrated in vacuo. Purification of the crude by flash chromatography (SiO$_2$, hexanes to 50% EtOAc in hexanes) gives the title compound (121 mg, 13%).

Example 16

Synthesis of 3-[1-(2,2-dimethylpropanoyl)-7-(pyridin-2-ylmethoxy)-3-{[4-(pyridin-3-yl)phenyl]carbonyl}indolizin-2-yl]-2,2-dimethylpropanoic Acid

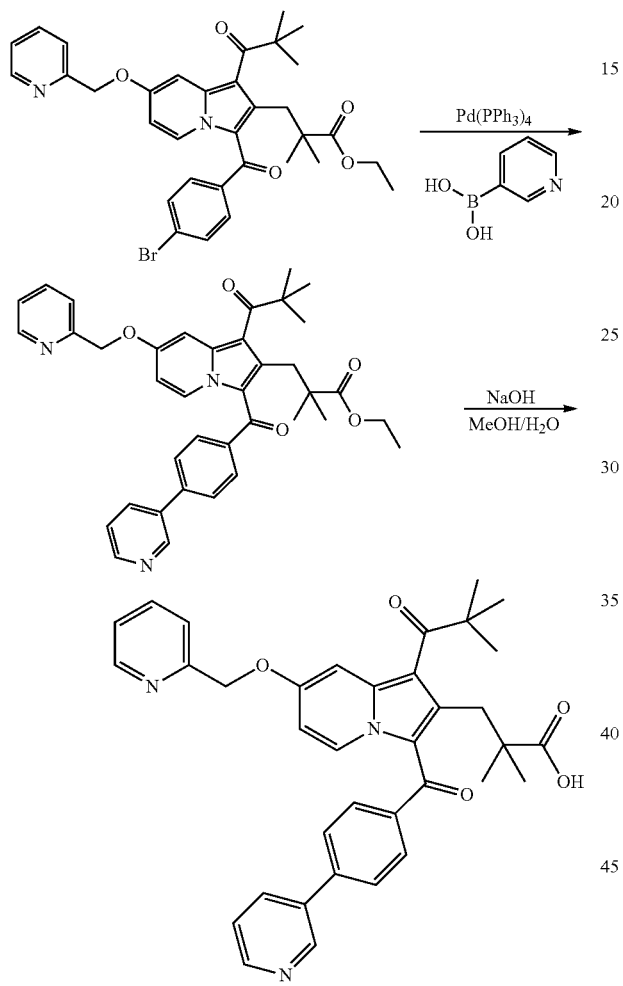

A solution of ethyl 3-{3-[(4-bromophenyl)carbonyl]-1-(2,2-dimethylpropanoyl)-7-(pyridin-2-ylmethoxy)indolizin-2-yl}-2,2-dimethylpropanoate (225 mg, 0.363 mmol), 3-pyridyl boronic acid (89.3, 0.726 mmol), tetrakis(triphenylphosphine)palladium(0) (42.0 mg, 0.036 mmol) in THF (4.0 mL) and aqueous 20% Na$_2$CO$_3$ (2.0 mL) is heated at 70° C. for 24 h then cooled to 23° C. The mixture is partitioned between Et$_2$O and water then the organics are collected, dried with MgSO$_4$, filtered, and concentrated in vacuo. Purification of the crude by flash chromatography (SiO$_2$, hexanes to EtOAc) gives ethyl 3-[1-(2,2-dimethylpropanoyl)-7-(pyridin-2-ylmethoxy)-3-{[4-(pyridin-3-yl)phenyl]carbonyl}indolizin-2-yl]-2,2-dimethylpropanoate (147 mg, 65%) which is dissolved in THF (1.0 mL), MeOH (1.0 mL), and 6M aqueous NaOH (0.8 mL) and heated at 50° C. for 3 h then cooled to 23° C. and acidified to pH=1 with concentrated aqueous HCl. The mixture is concentrated in vacuo, diluted with DMSO, filtered, and filtrate is purified by HPLC (25% CH$_3$CN to 85% CH$_3$CN in 0.1% TFA in water) to give the title compound (62 mg, 44%).

The following compounds are also obtained by methods described in Example 16:

3-[1-(2,2-Dimethylpropanoyl)-3-{[4-(5-methoxypyridin-3-yl)phenyl]carbonyl}-7-(pyridin-2-ylmethoxy)indolizin-2-yl]-2,2-dimethylpropanoic acid;

3-[1-(2,2-Dimethylpropanoyl)-3-{[4-(4-methoxypyridin-3-yl)phenyl]carbonyl}-7-(pyridin-2-ylmethoxy)indolizin-2-yl]-2,2-dimethylpropanoic acid; and 3-[1-(2,2-Dimethylpropanoyl)-3-{[4-(6-methoxypyridin-3-yl)phenyl]carbonyl}-7-(pyridin-2-ylmethoxy)indolizin-2-yl]-2,2-dimethylpropanoic acid.

Example 17

Synthesis of 3-[1-(2,2-dimethylpropanoyl)-3-{[4-(6-methoxypyridin-3-yl)phenyl]carbonyl}-7-(propan-2-yl)indolizin-2-yl]-2,2-dimethylpropanoic Acid

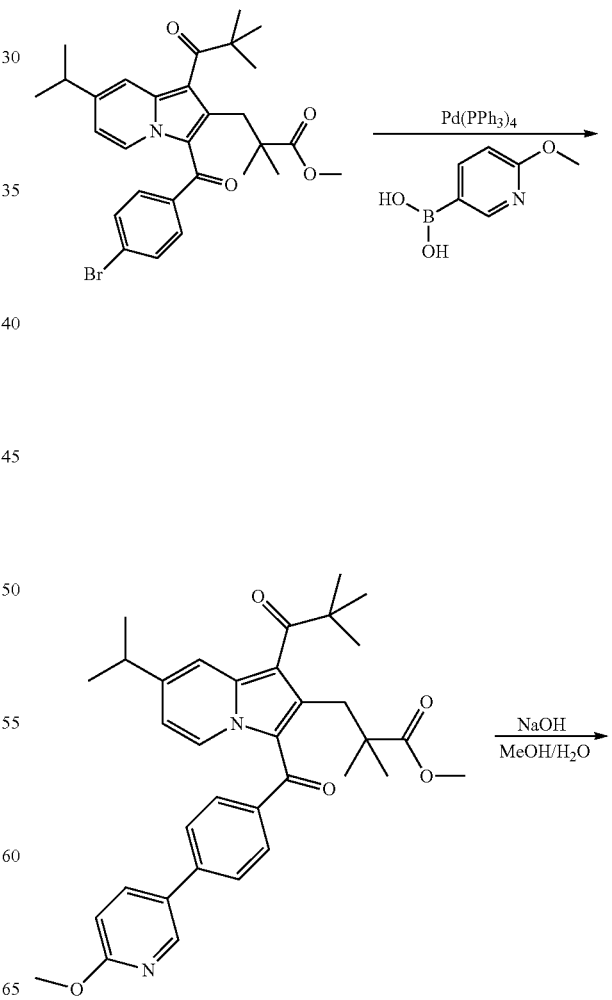

-continued

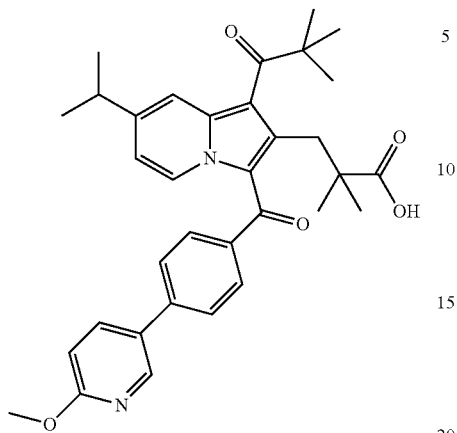

A solution of methyl 3-{3-[(4-bromophenyl)carbonyl]-1-(2,2-dimethylpropanoyl)-7-(propan-2-yl)indolizin-2-yl}-2,2-dimethylpropanoate (100 mg, 0.185 mmol), 2-(methoxy)pyridine-5-boronic acid (42.5 mg, 0.278 mmol), tetrakis(triphenylphosphine)palladium(0) (21.4 mg, 0.019 mmol) in THF (2.0 mL) and aqueous 20% Na$_2$CO$_3$ (1.0 mL) is heated at 70° C. for 1 h. The mixture is cooled to 23° C. and partitioned between Et$_2$O and water. The organics are collected, dried with MgSO$_4$, filtered, and concentrated in vacuo. Purification of the crude by flash chromatography (SiO$_2$, hexanes to 30% EtOAc in hexanes) gives methyl 3-[1-(2,2-dimethylpropanoyl)-3-{[3-(6-methoxypyridin-3-yl)phenyl]carbonyl}-7-(propan-2-yl)indolizin-2-yl]-2,2-dimethylpropanoate (93 mg, 88%) which is dissolved in MeOH (1.5 mL), and 6M aqueous NaOH (1.5 mL) and heated at 70° C. for 1 h. The mixture is then cooled to 23° C., acidified to pH=1 with concentrated aqueous HCl, and partitioned between CH$_2$Cl$_2$ and brine. The organics are collected, dried with MgSO$_4$, filtered, and concentrated in vacuo to give the title compound (68 mg, 75%).

The following compounds are also obtained by methods described in Example 17:

3-[1-(2,2-Dimethylpropanoyl)-7-(propan-2-yl)-3-{[4-(pyridin-3-yl)phenyl]carbonyl}indolizin-2-yl]-2,2-dimethylpropanoic acid;

3-[1-(2,2-Dimethylpropanoyl)-7-(propan-2-yl)-3-{[4-(pyrimidin-5-yl)phenyl]carbonyl}indolizin-2-yl]-2,2-dimethylpropanoic acid; and 3-[1-(2,2-Dimethylpropanoyl)-3-{[4-(2-methoxypyrimidin-5-yl)phenyl]carbonyl}-7-(propan-2-yl)indolizin-2-yl]-2,2-dimethylpropanoic acid.

Example 18

Synthesis of 3-[1-(2,2-dimethylpropanoyl)-3-{[3-(6-methoxypyridin-3-yl)phenyl]carbonyl}-7-(propan-2-yl)indolizin-2-yl]-2,2-dimethylpropanoic Acid

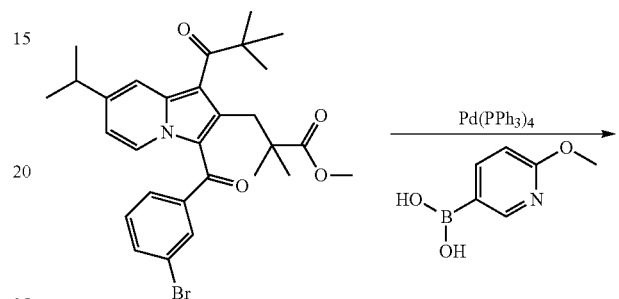

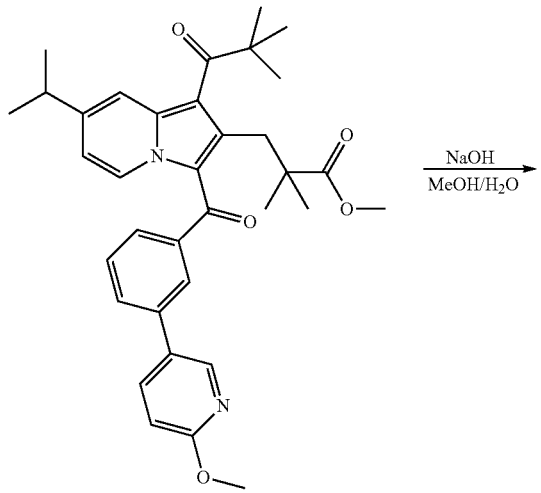

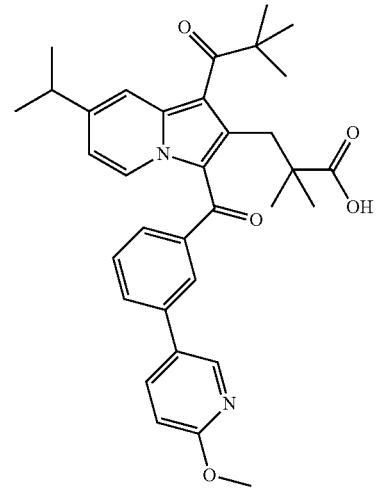

A solution of methyl 3-{3-[(3-bromophenyl)carbonyl]-1-(2,2-dimethylpropanoyl)-7-(propan-2-yl)indolizin-2-yl}-2,2-dimethylpropanoate (100 mg, 0.185 mmol), 2-(methoxy)pyridine-5-boronic acid (42.5 mg, 0.278 mmol), tetrakis(triphenylphosphine)palladium(0) (21.4 mg, 0.019 mmol) in THF (2.0 mL) and aqueous 20% $Na_2CO_3$ (1.0 mL) is heated at 70° C. for 1 h. The mixture is cooled to 23° C. and partitioned between $Et_2O$ and water. The organics are collected, dried with $MgSO_4$, filtered, and concentrated in vacuo. Purification of the crude by flash chromatography ($SiO_2$, hexanes to 30% EtOAc in hexanes) gives methyl 3-[1-(2,2-dimethylpropanoyl)-3-{[3-(6-methoxypyridin-3-yl)phenyl]carbonyl}-7-(propan-2-yl)indolizin-2-yl]-2,2-dimethylpropanoate (26 mg, 25%) which is dissolved in MeOH (1.5 mL), and 6M aqueous NaOH (1.5 mL) and heated at 70° C. for 1 h. The mixture is then cooled to 23° C., acidified to pH=1 with concentrated aqueous HCl, and partitioned between $CH_2Cl_2$ and brine. The organics are collected, dried with $MgSO_4$, filtered, and concentrated in vacuo to give the title compound (20 mg, 79%).

The following compounds are also obtained by methods described in experimental 18:

3-[1-(2,2-Dimethylpropanoyl)-7-(propan-2-yl)-3-{[3-(pyridin-3-yl)phenyl]carbonyl}indolizin-2-yl]-2,2-dimethylpropanoic acid; and 3-[1-(2,2-Dimethylpropanoyl)-7-(propan-2-yl)-3-{[3-(pyrimidin-5-yl)phenyl]carbonyl}indolizin-2-yl]-2,2-dimethylpropanoic acid.

Example 19

Synthesis of 3-{3-[(3-carbamoylphenyl)carbonyl]-1-(2,2-dimethylpropanoyl)-7-(propan-2-yl)indolizin-2-yl}-2,2-dimethylpropanoic Acid

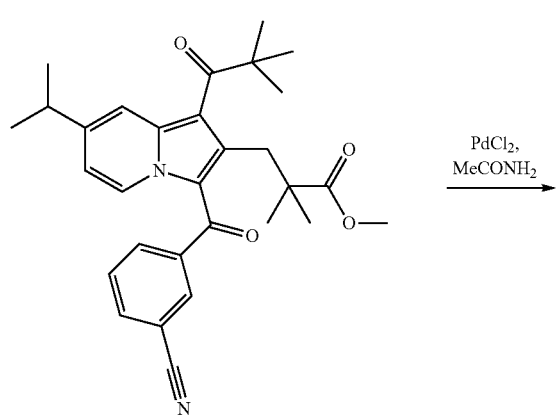

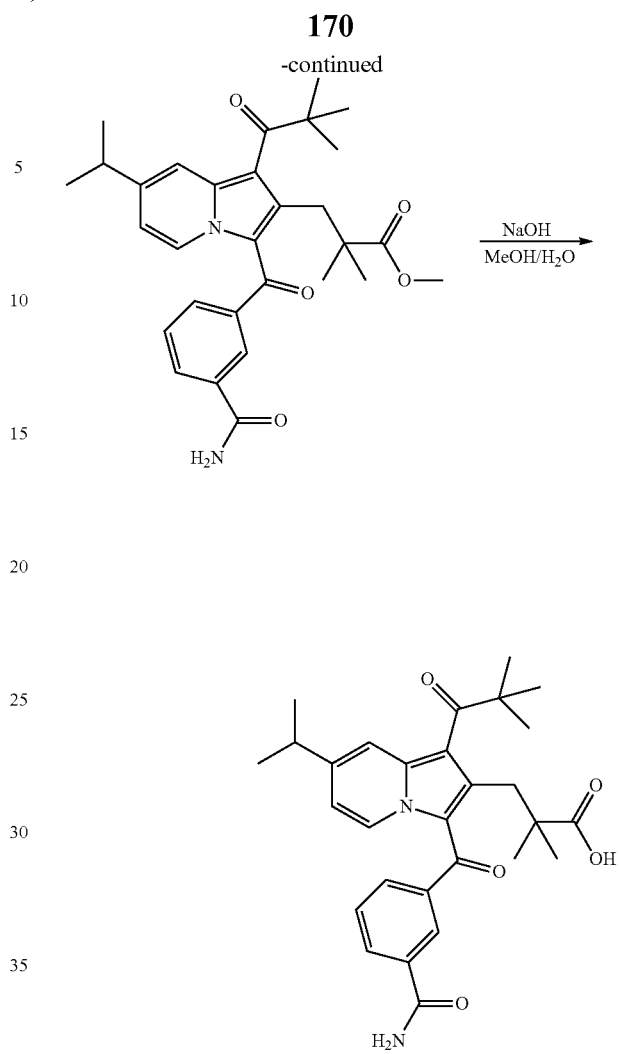

A solution of methyl 3-{3-[(3-cyanophenyl)carbonyl]-1-(2,2-dimethylpropanoyl)-7-(propan-2-yl)indolizin-2-yl}-2,2-dimethylpropanoate (125 mg, 0.257 mmol), palladium(II) chloride (9.1 mg, 0.051 mmol), and acetamide (152 mg, 2.57 mmol) in THF (1.5 mL) and water (0.5 mL) is heated at 50° C. for 3 h then cooled to 23° C. and partitioned between water and $Et_2O$. The organics are washed with water, dried with $MgSO_4$, filtered, and concentrated in vacuo. Purification of the crude by flash chromatography ($SiO_2$, hexanes to 75% EtOAc in hexanes) gives methyl 3-{3-[(3-carbamoylphenyl)carbonyl]-1-(2,2-dimethylpropanoyl)-7-(propan-2-yl)indolizin-2-yl}-2,2-dimethylpropanoate (114 mg, 88%).

A solution of methyl 3-{3-[(3-carbamoylphenyl)carbonyl]-1-(2,2-dimethylpropanoyl)-7-(propan-2-yl)indolizin-2-yl}-2,2-dimethylpropanoate (111 mg, 0.220 mmol) in MeOH (2 mL) and 6M aqueous NaOH (2 mL) is heated at 70° C. for 1 h then cooled to 23° C., acidified to pH=1 with concentrated aqueous HCl, then partitioned between $CH_2Cl_2$ and brine. The organics are dried with $MgSO_4$, filtered, and concentrated in vacuo. Purification of the crude by reverse phase HPLC (35% $CH_3CN$ to 95% $CH_3CN$ in 0.1% TFA in water) gives the title compound (20 mg, 19%).

The following compounds were also obtained by methods described in Example 19:

3-{[2-(2-Carboxy-2-methylpropyl)-1-(2,2-dimethylpropanoyl)-7-(propan-2-yl)indolizin-3-yl]carbonyl}benzoic acid; and 3-{3-[(4-Carbamoylphenyl)carbonyl]-1-(2,2-dimethylpropanoyl)-7-(propan-2-yl)indolizin-2-yl}-2,2-dimethylpropanoic acid.

Example 20

Synthesis of 3-[3-(4-chlorobenzyl)-1-(2,2-dimethylpropanoyl)-7-(propan-2-yl)indolizin-2-yl]-2,2-dimethylpropanoic Acid

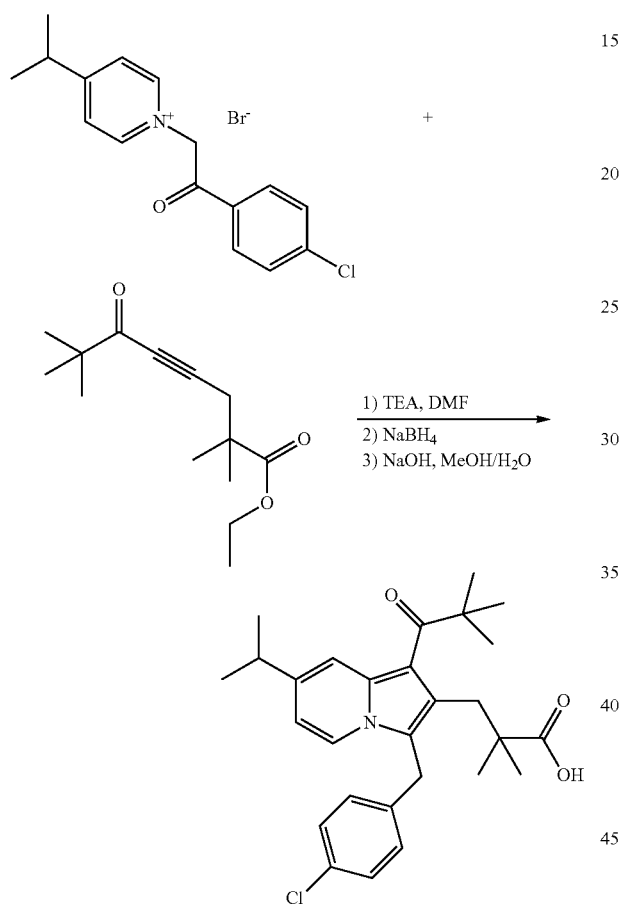

To a solution of 1-[2-(4-chlorophenyl)-2-oxoethyl]-4-(propan-2-yl)pyridinium bromide (1.55 g, 4.37 mmol) and ethyl 2,2,7,7-tetramethyl-6-oxooct-4-ynoate (1.04 g, 4.37 mmol) in DMF (8.0 mL) is added TEA (0.9 mL, 6.56 mmol). The mixture is heated at 70° C. for 24 h then cooled to 23° C. and partitioned between Et₂O and water. The organics are washed with water, dried with MgSO₄, filtered, and concentrated in vacuo. Purification of the crude by flash chromatography (SiO₂, hexanes to 10% EtOAc in hexanes) gives dihydroindolizine (340 mg, 15%) that is dissolved in MeOH (10 mL) and treated with sodium borohydride (25 mg, 0.664 mmol). The mixture is stirred for 10 min then treated with water, extracted with EtOAc, dried with MgSO₄, filtered, and concentrated in vacuo. The residue is dissolved in MeOH (4 mL) and 6M aqueous NaOH (4 mL) and heated at 70° C. for 1 h then cooled to 23° C. The mixture is acidified to pH=1 with concentrated aqueous HCl, then partitioned between CH₂Cl₂ and brine. The organics are dried with MgSO₄, filtered, and concentrated in vacuo. Purification of the crude by reverse phase HPLC gives the title compound (44 mg, 14%).

Example 21

Synthesis of 3-[1-(2,2-dimethylpropanoyl)-3-{[4-(6-methoxypyridin-3-yl)phenyl]carbamoyl}-7-(propan-2-yl)indolizin-2-yl]-2,2-dimethylpropanoic Acid

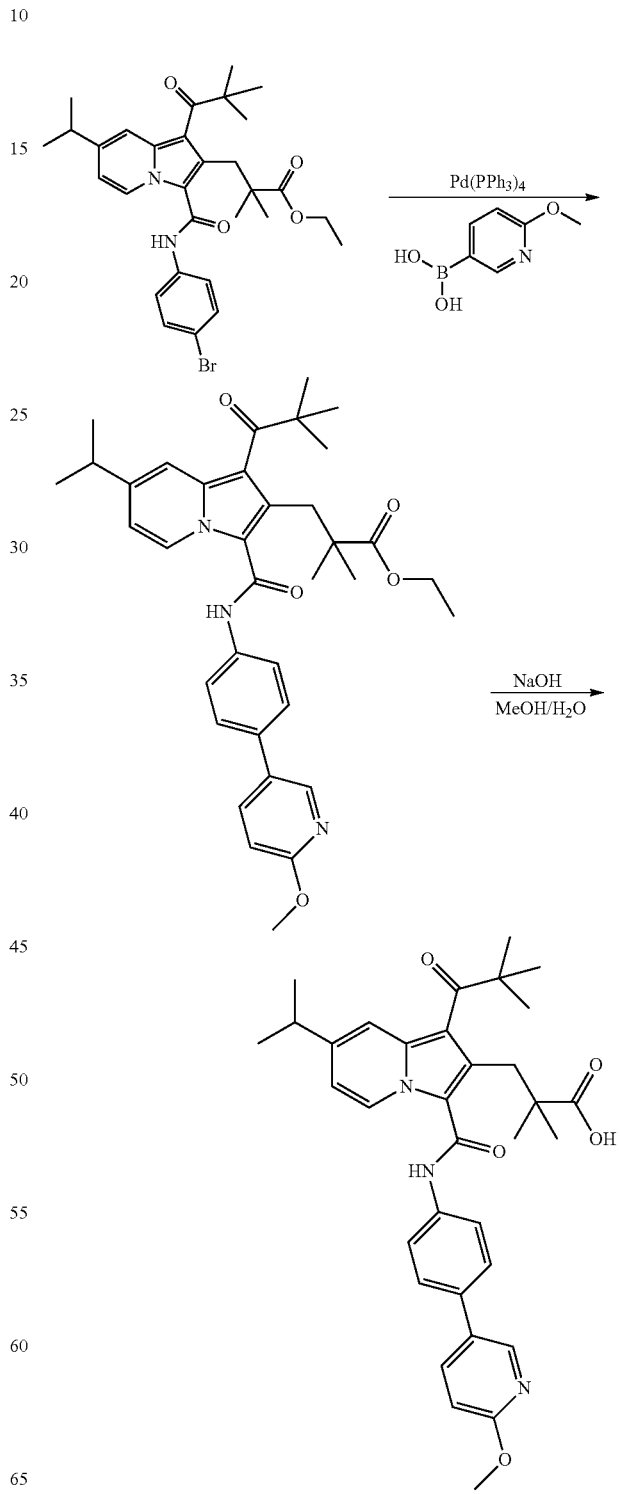

A solution of ethyl 3-{3-[(4-bromophenyl)carbamoyl]-1-(2,2-dimethylpropanoyl)-7-(propan-2-yl)indolizin-2-yl}-2,2-dimethylpropanoate (55 mg, 0.097 mmol), 2-(methoxy)pyridine-5-boronic acid (15 mg, 0.097 mmol) and tetrakis(triphenylphosphine)palladium (0) (5 mg, 0.007 mmol) in 1,4-dioxane (4 mL) is heated in the microwave at 120° C. for 20 minutes then 100° C. for 16 h. The mixture is cooled to 23° C., poured into water and extracted with EtOAc. The combined organics are dried with $MgSO_4$, filtered, and concentrated in vacuo. Purification of the crude by flash chromatography ($SiO_2$, hexanes to 50% EtOAc in hexanes) gives ethyl 3-[1-(2,2-dimethylpropanoyl)-3-{[4-(6-methoxypyridin-3-yl)phenyl]carbamoyl}-7-(propan-2-yl)indolizin-2-yl]-2,2-dimethylpropanoate (22 mg, 38%) that is dissolved in 1,4-dioxane (3 mL) and water (0.5 mL). To this mixture is added 10M aqueous NaOH (5 drops) and solution is stirred at 23° C. until reaction is complete. The mixture is acidified with HOAc and resulting solid is filtered, washed with water, collected, and dried to give the title compound (14 mg, 67%).

Example 22

Synthesis of 3-{7-[(6-aminopyridin-2-yl)methoxy]-1-(2,2-dimethylpropanoyl)-3-(4-methoxybenzoyl)indolizin-2-yl}-2,2-dimethylpropanamide

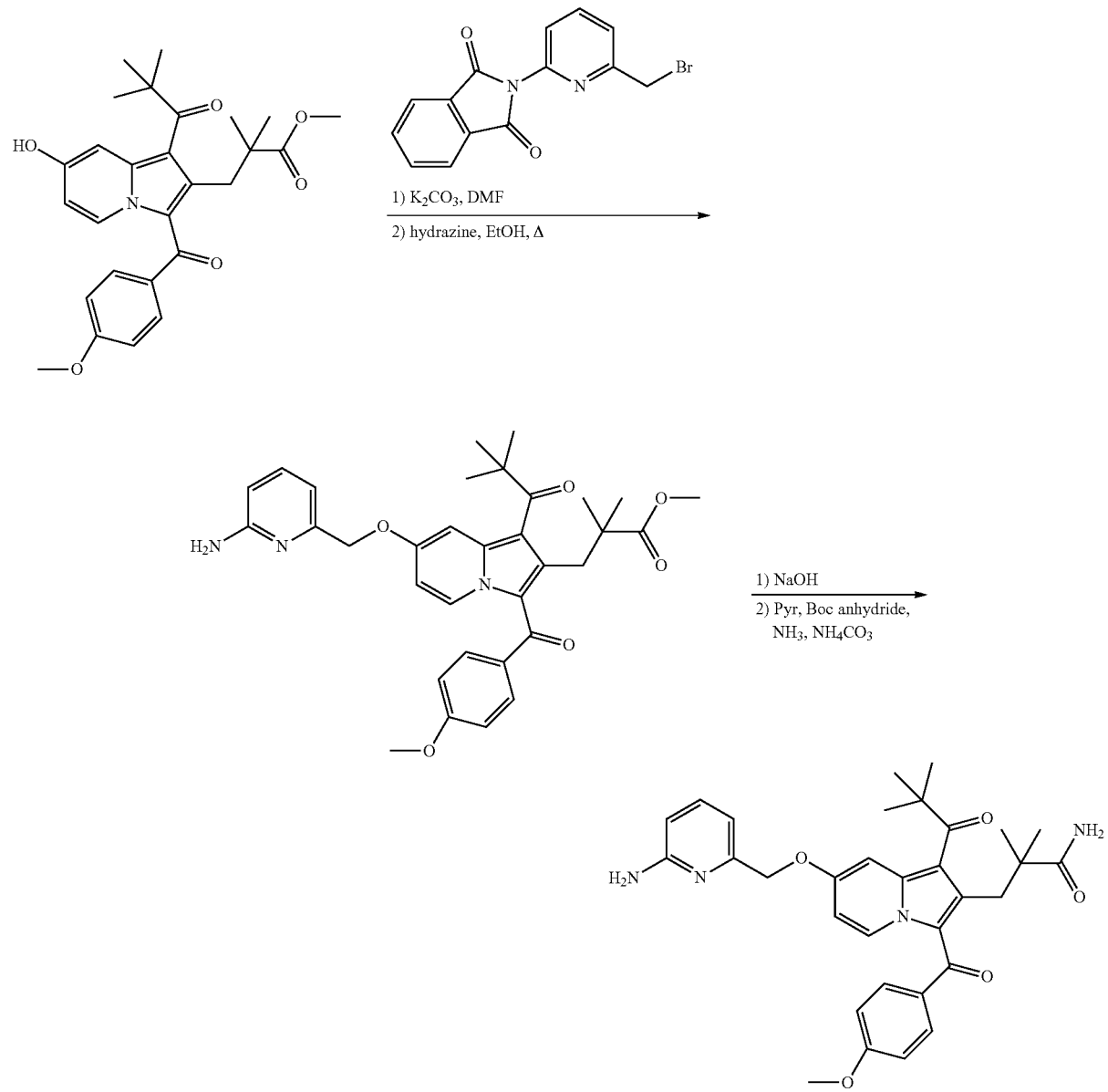

A suspension of methyl 3-[1-(2,2-dimethylpropanoyl)-7-hydroxy-3-(4-methoxybenzoyl)indolizin-2-yl]-2,2-dimethylpropanoate (350 mg, 0.75 mmol), 2-(6-bromomethyl-pyridin-2-yl)-isoindole-1,3-dione (286 mg, 0.90 mmol), and potassium carbonate (416 mg, 3.0 mmol) in DMF (4 mL) is stirred for 6 h at 70° C. The mixture is partitioned between $CH_2Cl_2$ and brine. The organics are collected, dried with $MgSO_4$, filtered, and concentrated in vacuo. Purification of the crude by flash chromatography ($SiO_2$, heptane to 50%

EtOAc in heptane) gives methyl 3-[1-(2,2-dimethylpropanoyl)-7-{[6-(1,3-dioxo-1,3-dihydro-2H-isoindol-2-yl)pyridin-2-yl]methoxy}-3-(4-methoxybenzoyl)indolizin-2-yl]-2,2-dimethylpropanoate that is dissolved in EtOH (5 mL) and treated with a 50% aqueous hydrazine (wt/wt) solution (0.75 mL). The mixture is heated at 70° C. for 2 h then cooled to 23° C. and filtered. The volatile components from the filtrate are removed in vacuo. The residue is purified by flash chromatography ($SiO_2$, heptane to 50% EtOAc in heptane) giving methyl 3-{7-[(6-aminopyridin-2-yl)methoxy]-1-(2,2-dimethylpropanoyl)-3-(4-methoxybenzoyl)indolizin-2-yl}-2,2-dimethylpropanoate (342 mg, 78%) that is dissolved in MeOH (2 mL), THF (2 mL), and aqueous 5M sodium hydroxide (1 mL). The solution is heated at 70° C. for 3 h then cooled and acidified with AcOH. The mixture is partitioned between $CH_2Cl_2$ and brine then organics are collected, dried with $MgSO_4$, filtered, and concentrated in vacuo to give 3-{7-[(6-aminopyridin-2-yl)methoxy]-1-(2,2-dimethylpropanoyl)-3-(4-methoxybenzoyl)indolizin-2-yl}-2,2-dimethylpropanoic acid (310 mg, 98%) that is dissolved in DMF (3 mL). This solution is treated with ammonium carbonate (57 mg, 0.73 mmol), Boc-anhydride (136 mg, 0.62 mmol), and pyridine (0.1 mL, 1.5 mmol) and stirred for 30 min. The mixture is directly purified by reverse phase HPLC to give the title compound (115 mg, 40%).

Assessment of Biological Properties

Compounds are assessed for the ability to bind to FLAP in a binding assay that measures compound-specific displacement of an iodinated ($^{125}$I) FLAP inhibitor via a Scintillation Proximity Assay format (adapted from S. Charleson et al., Mol. Pharmacol., 1992, 41, 873-879).

Cell pellets produced from sf9 insect cells expressing recombinant human FLAP protein are resuspended in buffer A [15 mM Tris-HCl (pH 7.5), 2 mM $MgCl_2$, 0.3 mM EDTA, 1 mM PMSF]. The cells are lysed with a Dounce homogenizer and the material is centrifuged at 10,000×g for 10 minutes. The supernatant is then collected and centrifuged at 100,000×g for 60 minutes. To prepare membrane protein for an assay, an aliquot of the 100,000×g pellet is resuspended in 1 ml of buffer A, Dounce homogenized, and finally subjected to polytron mixing (30 seconds). Membrane protein (25 µl, 5 µg) is mixed with WGA SPA beads (Amersham) and stirred for 1 h. To an assay plate (Perkin Elmer FlexiPlate) is added 25 µl of test compound prepared in Binding buffer [100 mM Tris (pH 7.5), 140 mM NaCl, 5% glycerol, 2 mM EDTA, 0.5 mM TCEP, 0.05% Tween 20], 25 µl of [$^{125}$I]L-691,831 (an iodinated analog of MK-591, Charleson et al. Mol. Pharmacol., 41, 873-879, 1992) and finally 50 µl of the bead/protein mixture. (final concentrations: beads, 200 µg/well; protein, 5 µg/well; [$^{125}$I] probe, 0 08 nM/well (17 nCi/well). The plates are shaken for 2 h before reading on a Microbeta plate reader. Non-specific binding is determined by the addition of 10 µM cold L-691,831 compound.

In general, the preferred potency range ($IC_{50}$) of compounds in the above assay is between 0.1 nM to 10 µM, the more preferred potency range is 0.1 nM to 1 µM, and the most preferred potency range is 0.1 nM to 100 nM.

Representative compounds of the invention have been tested in the above assay and have shown activity as FLAP inhibitors as shown in Table II.

TABLE II

| Name | hFLAP binding $IC_{50}$ (nM) |
|---|---|
| 3-[1-(2,2-dimethylpropanoyl)-3-{[4-(4-methoxypyridin-3-yl)phenyl]carbonyl}-7-(pyridin-2-ylmethoxy)indolizin-2-yl]-2,2-dimethylpropanoic acid | 67 |
| 3-{3-[(4-chlorophenyl)carbonyl]-1-(2,2-dimethylpropanoyl)-7-(pyridin-2-ylmethoxy)indolizin-2-yl}-2,2-dimethylpropanoic acid | 44 |
| 3-{1-[(4-chlorophenyl)carbonyl]-3-(2,2-dimethylpropanoyl])-6-(quinolin-2-ylmethoxy)indolizin-2-yl}-2,2-dimethylpropanoic acid | 14 |
| 3-{3-[(4-chlorophenyl)carbonyl]-1-(2,2--dimethylpropanoyl)-7-[(5methyl-1,2,4-oxadiazol-3-yl)methoxy]indolizin-2-yl}-2,2-dimethylpropanoic acid | 90 |
| 3-{3-[(4-chlorophenyl)carbonyl]-1-(2,2-dimethylpropanoyl)-7-[(4-methoxy-3,5-dimethylpyridin-2-yl)methoxy]indolizin-2-yl}-2,2-dimethylpropanoic acid | 58 |
| 3-{1-[(4-chlorophenyl)carbonyl]-3-(2,2-dimethylpropanoyl)-6-[(2-methyl-1,3-thiazol-4-yl)methoxy]indolizin-2-yl}-2,2-dimethyl-N-(methylsulfonyl)propanamide | 4 |
| 3-[1-(2,2-dimethylpropanoyl)-3-{[4-6-methoxypryidin-3-yl)phenyl]carbonyl}-7-(propan-2-yl)indolizin-2-yl]-2,2-dimethylpropanoic acid | 232 |
| 3-{3-[(4-chlorophenyl)carbonyl]-1-(2,2-dimethylpropanoyl)-7-[(2-methoxy-1,3-thiazol-4-yl)methoxy]indolizin-2-yl}-2,2-dimethylpropanoic acid | 69 |
| 3-{1-[(4-chlorophenyl)carbonyl]-3-(2,2-dimethylpropanoyl)-6-[(2-methyl-1,3-thiazol-4-yl)methoxy]indolizin-2-yl}-2,2-dimethylpropanoic acid | 38 |
| 3-{3-[(4-chlorophenyl)carbonyl]-1-(2,2-dimethylpropanoyl)-7-[(4-methoxypyridin-2-yl)methoxy]indolizin-2-yl}-2,2-dimethylpropanoic acid | 8 |
| 3-{3-[(4-chlorophenyl)carbonyl]-1-(2,2-dimethylpropanoyl)-7-(1,3-thiazol-4-ylmethoxy)indolizin-2-yl}-2,2-dimethylpropanoic acid | 118 |
| 3-{3-[(4-chlorophenyl)carbonyl]-1-(2,2-dimethylpropanoyl)-7-[(6-methylpyridin-2-yl)methoxy]indolizin-2-yl}-2,2-dimethylpropanoic acid | 17 |
| 3-[7-(1,3-benzothiazol-2-ylmethoxy)-3-{(4-chlorophenyl)carbonyl]-1-(2,2-dimethylpropanoyl)indolizin-2-yl]-2,2-dimethylpropanoic acid | 4 |
| 3-[1-(2,2-dimethylpropanoyl)-7-(propan-2-yl)-3-{[4-(trifluoromethyl)phenyl]carbonyl}indolizin-2-yl]-2,2-dimethylpropanoic acid | 316 |
| 3-{3-[(4-chlorophenyl)carbonyl]-1-(3,3-dimethylbutanoyl)-7-(quinolin-2-ylmethoxy)indolizin-2-yl}-2,2-dimethylpropanoic acid | 85 |
| 3-[1-(2,2-dimethylpropanoyl)-3-{[4-(5-methoxypyridin-3-yl)phenyl]carbonyl}-7-(pyridin-2-ylmethoxy)indolizin-2-yl]-2,2-dimethylpropanoic acid | 22 |
| 3-{1-(2,2-dimethylpropanoyl)-3-[(4-methylphenyl)carbonyl]-7-[(6-methylpyridin-2-yl)methoxy]indolizin-2-yl}-2,2-dimethylpropanoic acid | 3 |
| 3-{3-[(4-bromophenyl)(methyl)carbamoyl]-1-(2,2-dimethylpropanoyl)-7-(propan-2-yl)indolizin-2-yl}-2,2-dimethylpropanoic acid | 156 |
| 3-{1-[(4-chlorophenyl)carbonyl]-3-(2,2-dimethylpropanoyl)-6-(pyridin-2-ylmethoxy)indolizin-2-yl}-2,2-dimethylpropanoic acid | 79 |

TABLE II-continued

| Name | hFLAP binding IC$_{50}$ (nM) |
|---|---|
| 3-{3-[(4-chlorophenyl)carbonyl]-1-(2,2-dimethylpropanoyl)-7-(pyrimidin-2-ylmethoxy)indolizin-2-yl}-2,2-dimethylpropanoic acid | 64 |
| 3-{3-[(4-chlorophenyl)carbonyl]-1-(2,2-dimethylpropanoyl)-7-(quinolin-2-ylmethoxy)indolizin-2-yl}-2,2-dimethylpropanoic acid | 8 |
| 3-{3-[(4-chlorophenyl)carbonyl]-1-(2,2-dimethylpropanoyl)-7-[(6-methoxypyridin-2-yl)methoxy]indolizin-2-yl}-2,2-dimethylpropanoic acid | 8 |
| 3-[1-(2,2-dimethylpropanoyl)-7-(propan-2-yl)-3-{[4-(pyridin-3-yl)phenyl]carbonyl}indolizin-2-yl]-2,2-dimethylpropanoic acid | 165 |
| 3-[1-(2,2-dimethylpropanoyl)-7-[(2-methyl-1,3-thiazol-4-yl)methoxy]-3-(phenylcarbonyl)indolizin-2-yl]-2,2-dimethylpropanoic acid | 101 |
| 3-{3-[(4-chlorophenyl)carbonyl]-1-(2,2-dimethylpropanoyl)-7-(1,3-thiazol-2-ylmethoxy)indolizin-2-yl}-2,2-dimethylpropanoic acid | 25 |
| 3-{1-[(4-chlorophenyl)carbonyl]-3-(2,2-dimethylpropanoyl)-6-[(6-methylpyridin-2-yl)methoxy]indolizin-2-yl}-2,2-dimethylpropanoic acid | 8 |
| 3-{3-[(4-chlorophenyl)carbonyl]-1-(2,2-dimethylpropanoyl)-7-[(2-methyl-1,3-thiazol-4-yl)methoxy]indolizin-2-yl}-2,2-dimethylpropanoic acid | 18 |
| 3-{3-[(4-bromophenyl)carbonyl]-1-(2,2-dimethylpropanoyl)-7-(pyridin-2-ylmethoxy)indolizin-2-yl}-2,2-dimethylpropanoic acid | 99 |
| 3-[6-(1,3-benzothiazol-2-ylmethoxy)-1-[(4-chlorophenyl)carbonyl]-3-(2,2-dimethylpropanoyl)indolizin-2-yl]-2,2-dimethylpropanoic acid | 9 |
| 3-{1-[(4-chlorophenyl)carbonyl]-3-(2,2-dimethylpropanoyl)-6-[(2-methyl-1,3-thiazol-4-yl)methoxy]indolizin-2-yl}-2,2-dimethylpropanoic acid | 38 |
| 3-{3-[(4-chloro-3-methylphenyl)carbonyl]-1-(2,2-dimethylpropanoyl)-7-[(4-methyl-1,3-thiazol-2-yl)methoxy]indolizin-2-yl}-2,2-dimethylpropanoic acid | 1 |
| 3-{3-[(3,4-dichlorophenyl)carbonyl]-1-(2,2-dimethylpropanoyl)-7-[(4-methyl-1,3-thiazol-2-yl)methoxy]indolizin-2-yl}-2,2-dimethylpropanoic acid | 1 |
| 2-({1-(2,2-dimethylpropanoyl)-3-[(4-methoxyphenyl)carbonyl]-7-[(4-methyl-1,3-thiazol-2-yl)methoxy]indolizin-2-yl}methyl)-3-methylbutanoic acid | 4 |
| 3-{7-(1,3-benzothiazol-2-ylmethoxy)-1-(2,2-dimethylpropanoyl)-3-[(4-methoxyphenyl)carbonyl]indolizin-2-yl}-2,2-dimethylpropanoic acid | 1 |
| 2-({7-(1,3-benzothiazol-2-ylmethoxy)-1-(2,2-dimethylpropanoyl)-3-[(4-methoxyphenyl)carbonyl]indolizin-2-yl}methyl)-3-methylbutanoic acid | 1 |
| 3-{3-[(3,5-dichlorophenyl)carbonyl]-1-(2,2-dimethylpropanoyl)-7-[(2-methyl-1,3-thiazol-4-yl)methoxy]indolizin-2-yl}-2,2-dimethylpropanoic acid | 1 |
| 2-({1-(2,2-dimethylpropanoyl)-3-[(4-methoxyphenyl)carbonyl]-7-[(2-methyl-1,3-thiazol-4-yl)methoxy]indolizin-2-yl}methyl)-3-methylbutanoic acid | 13 |
| (2R)-2-({1-(2,2-dimethylpropanoyl)-3-[(4-methoxyphenyl)carbonyl]-7-[(2-methyl-1,3-thiazol-4-yl)methoxy]indolizin-2-yl}methyl)-3-methylbutanoic acid | 7 |
| 2-({3-[(3,4-dichlorophenyl)carbonyl]-1-(2,2-dimethylpropanoyl)-7-[(6-methylpyridin-2-yl)methoxy]indolizin-2-yl}methyl)pentanoic acid | 2 |
| 3-{3-[(4-chloro-3-methylphenyl)carbonyl]-1-(2,2-dimethylpropanoyl)-7-[(2-methyl-1,3-thiazol-4-yl)methoxy]indolizin-2-yl}-2,2-dimethylpropanoic acid | 2 |
| 2-({1-(2,2-dimethylpropanoyl)-3-[(4-methoxyphenyl)carbonyl]-7-[(6-methylpyridin-2-yl)methoxy]indolizin-2-yl}methyl)-2-methylbutanoic acid | 2 |
| 3-{1-(2,2-dimethylpropanoyl)-3-[(4-methoxyphenyl)carbonyl]-7-[(4-methyl-1,3-thiazol-2-yl)methoxy]indolizin-2-yl}-2,2-dimethylpropanoic acid | 3 |
| 3-{3-[(3,4-dichlorophenyl)carbonyl]-1-(2,2-dimethylpropanoyl)-7-[(6-methylpyridin-2-yl)methoxy]indolizin-2-yl}-2,2-dimethylpropanoic acid | 1 |
| 3-[1-(2,2-dimethylpropanoyl)-3-[(4-methoxyphenyl)carbonyl]-7-(quinolin-2-ylmethoxy)indolizin-2-yl]-2,2-dimethylpropanoic acid | 1 |
| 2-{[1-(2,2-dimethylpropanoyl)-3-[(4-methoxyphenyl)carbonyl]-7-(quinolin-2-ylmethoxy)indolizin-2-yl]methyl}-3-methylbutanoic acid | 1 |
| 3-{3-[(3-chlorophenyl)carbonyl]-1-(2,2-dimethylpropanoyl)-7-[(4-methyl-1,3-thiazol-2-yl)methoxy]indolizin-2-yl}-2,2-dimethylpropanoic acid | 1 |
| 3-{3-[(3,4-dichlorophenyl)carbonyl]-1-(2,2-dimethylpropanoyl)-7-[(2-methyl-1,3-thiazol-4-yl)methoxy]indolizin-2-yl}-2,2-dimethylpropanoic acid | 111 |
| 2-({3-[(3,4-dichlorophenyl)carbonyl]-1-(2,2-dimethylpropanoyl)-7-[(4-methyl-1,3-thiazol-2-yl)methoxy]indolizin-2-yl}methyl)pentanoic acid | 15 |
| 2-({1-(2,2-dimethylpropanoyl)-3-[(4-methoxyphenyl)carbonyl]-7-[(2-methyl-1,3-thiazol-4-yl)methoxy]indolizin-2-yl}methyl)pentanoic acid | 7 |
| 2-({1-(2,2-dimethylpropanoyl)-3-[(4-methoxyphenyl)carbonyl]-7-[(6-methylpyridin-2-yl)methoxy]indolizin-2-yl}methyl)-3-methylbutanoic acid | 3 |
| 2-({1-(2,2-dimethylpropanoyl)-3-[(4-methoxyphenyl)carbonyl]-7-[(2-methyl-1,3-thiazol-4-yl)methoxy]indolizin-2-yl}methyl)-2-methylbutanoic acid | 2 |
| 2-({1-(2,2-dimethylpropanoyl)-3-[(4-methoxyphenyl)carbonyl]-7-[(6-methylpyridin-2-yl)methoxy]indolizin-2-yl}methyl)pentanoic acid | 3 |
| 2-({3-[(4-chloro-3-methylphenyl)carbonyl]-1-(2,2-dimethylpropanoyl)-7-[(6-methylpyridin-2-yl)methoxy]indolizin-2-yl}methyl)pentanoic acid | 3 |
| 3-{7-[(6-aminopyridin-2-yl)methoxy]-1-(2,2-dimethylpropanoyl)-3-(4-methoxybenzoyl)indolizin-2-yl}-2,2-dimethylpropanamide | 2 |

Method of Use

The compounds of the invention are effective inhibitors of 5-lipoxygenase activating protein (FLAP) and thus inhibit leukotriene production. Therefore, in one embodiment of the invention, there is provided methods of treating leukotriene-mediated disorders using compounds of the invention. In another embodiment, there is provided methods of treating cardiovascular, inflammatory, allergic, pulmonary and fibrotic diseases, renal diseases and cancer using compounds of the invention.

Without wishing to be bound by theory, by inhibiting the activity of FLAP, the compounds of the invention block the production of LTs resulting from the oxidation of arachidonic acid by 5-LO and subsequent metabolism. Thus, the inhibition of FLAP activity is an attractive means for preventing and treating a variety of diseases mediated by LTs. These include:

Cardiovascular diseases including atherosclerosis, myocardial infarction, stroke, aortic aneurysm, sickle cell crisis, ischemia-reperfusion injury, pulmonary arterial hypertension and sepsis;

Allergic diseases including asthma, allergic rhinitis, rhinosinusitis, atopic dermatitis and urticaria;

Fibrotic diseases including airway remodeling in asthma, idiopathic pulmonary fibrosis, scleroderma, asbestosis;

Pulmonary syndromes including adult respiratory distress syndrome, viral bronchiolitis, obstructive sleep apnea, chronic obstructive pulmonary disease, cystic fibrosis, and bronchopulmonary dysplasia;

Inflammatory diseases including rheumatoid arthritis, osteoarthritis, gout, glomerulonephritis, interstitial cystitis, psoriasis, inflammatory bowel disease systemic lupus erythematosus, transplant rejection; and Cancer including solid tumors, leukemias and lymphomas.
Renal diseases such as glomerulonephritis.

For treatment of the above-described diseases and conditions, a therapeutically effective dose will generally be in the range from about 0.01 mg to about 100 mg/kg of body weight per dosage of a compound of the invention; preferably, from about 0.1 mg to about 20 mg/kg of body weight per dosage. For example, for administration to a 70 kg person, the dosage range would be from about 0.7 mg to about 7000 mg per dosage of a compound of the invention, preferably from about 7.0 mg to about 1400 mg per dosage. Some degree of routine dose optimization may be required to determine an optimal dosing level and pattern. The active ingredient may be administered from 1 to 6 times a day.

General Administration and Pharmaceutical Compositions

When used as pharmaceuticals, the compounds of the invention are typically administered in the form of a pharmaceutical composition. Such compositions can be prepared using procedures well known in the pharmaceutical art and comprise at least one compound of the invention. The compounds of the invention may also be administered alone or in combination with adjuvants that enhance stability of the compounds of the invention, facilitate administration of pharmaceutical compositions containing them in certain embodiments, provide increased dissolution or dispersion, increased antagonist activity, provide adjunct therapy, and the like. The compounds according to the invention may be used on their own or in conjunction with other active substances according to the invention, optionally also in conjunction with other pharmacologically active substances. In general, the compounds of this invention are administered in a therapeutically or pharmaceutically effective amount, but may be administered in lower amounts for diagnostic or other purposes.

Administration of the compounds of the invention, in pure form or in an appropriate pharmaceutical composition, can be carried out using any of the accepted modes of administration of pharmaceutical compositions. Thus, administration can be, for example, orally, buccally (e.g., sublingually), nasally, parenterally, topically, transdermally, vaginally, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, preferably in unit dosage forms suitable for simple administration of precise dosages. The pharmaceutical compositions will generally include a conventional pharmaceutical carrier or excipient and a compound of the invention as the/an active agent, and, in addition, may include other medicinal agents, pharmaceutical agents, carriers, adjuvants, diluents, vehicles, or combinations thereof. Such pharmaceutically acceptable excipients, carriers, or additives as well as methods of making pharmaceutical compositions for various modes or administration are well-known to those of skill in the art. The state of the art is evidenced, e.g., by *Remington: The Science and Practice of Pharmacy,* 20th Edition, A. Gennaro (ed.), Lippincott Williams & Wilkins, 2000; *Handbook of Pharmaceutical Additives,* Michael & Irene Ash (eds.), Gower, 1995; *Handbook of Pharmaceutical Excipients,* A. H. Kibbe (ed.), American Pharmaceutical Ass'n, 2000; H. C. Ansel and N. G. Popovish, *Pharmaceutical Dosage Forms and Drug Delivery Systems,* 5th ed., Lea and Febiger, 1990; each of which is incorporated herein by reference in their entireties to better describe the state of the art.

As one of skill in the art would expect, the forms of the compounds of the invention utilized in a particular pharmaceutical formulation will be selected (e.g., salts) that possess suitable physical characteristics (e.g., water solubility) that are required for the formulation to be efficacious.

What is claimed is:
1. A compound of formula (I):

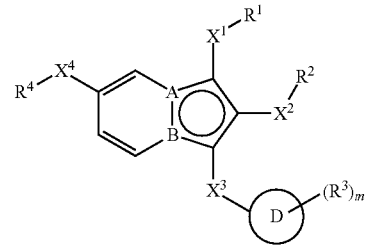

or pharmaceutically acceptable salts thereof, wherein:
A is N and B is C, or A is C and B is N;
ring D is $C_{6-10}$ aryl;
$X^1$ is —C(O)—;
$X^2$ is —CH$_2$C(C$_{1-2}$alkyl)$_2$— or

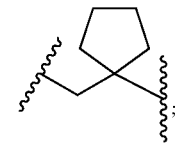 [SMILES: *CC1(*)CCCC1]

$X^3$ is —C(O)—, or —C(O)—N(R$^{10}$)—;
$X^4$ is —(CH$_2$)$_p$ or —(CH$_2$)$_p$—O—(CH$_2$)$_q$—, wherein one or more hydrogen atoms of said —(CH$_2$)$_p$—O—(CH$_2$)$_q$— can be replaced by $C_{1-6}$ alkyl;
$R^1$ is $C_{1-6}$ alkyl, $C_{1-6}$ alkoxy, $C_{1-6}$ alkoxy $C_{1-6}$ alkyl, $C_{2-6}$ alkenyl, $C_{2-6}$ alkynyl, $C_{3-6}$ cycloalkyl, 4 to 8-membered heterocyclyl, phenyl, 5 to 6-membered heteroaryl, or N(R$^8$)$_2$—, wherein each $C_{1-6}$ alkyl, $C_{1-6}$ alkoxy, $C_{1-6}$ alkoxy $C_{1-6}$ alkyl, $C_{2-6}$ alkenyl, $C_{2-6}$ alkynyl, $C_{3-6}$ cycloalkyl, 4 to 8-membered heterocyclyl, phenyl, and 5 to 6-membered heteroaryl of said $R^1$ substituent where possible is optionally substituted with one to four hydroxyl, halogen, or $C_{1-6}$ alkyl;
$R^2$ is R$_9$OC(O)—, NH(R$^8$)—C(O)— or R$^9$—S(O)$_2$—NH—C(O)—;
each $R^3$ when present is independently hydroxyl, halogen, cyano, $C_{1-6}$ alkyl, $C_{1-6}$ alkoxy, $C_{1-6}$ alkoxy $C_{1-6}$ alkyl, $C_{3-10}$ cycloalkyl, 5 to 11-membered heterocyclyl, $C_{6-10}$ aryl, 5 to 11-membered heteroaryl, $R^9$—C(O)—, $R^9$—O—C(O)—, $N(R^8)_2$—, $N(R^8)_2$—C(O)—, $R^9$—C(O)—N($R^8$)—, $(N(R^8)_2)(R^8N=)$C—N($R^8$)—C(O)—, $R^9$—S(O)$_j$—, $N(R^8)_2$—S(O)$_j$—, $R^9$—S(O)$_j$—N($R^8$)—, $R^9$—S(O)$_j$—N($R^8$)—C(O)—, $N(R^8)_2$—S(O)$_j$—N($R^8$)—C(O)—, or $N(R^8)_2$—C(O)—N($R^8$)—S(O)$_j$—, wherein each $C_{1-6}$ alkyl, $C_{1-6}$ alkoxy, $C_{1-6}$ alkoxy $C_{1-6}$ alkyl, $C_{3-10}$ cycloalkyl, 5 to 11-membered heterocyclyl, $C_{6-10}$ aryl, and 5 to 11-membered heteroaryl of said $R^3$ substituent where possible is optionally substituted with one to four $R^6$ groups;

$R^4$ is hydrogen, $C_{1-6}$ alkyl, $C_{3-10}$ cycloalkyl, 5 to 11-membered heterocyclyl, $C_{6-10}$ aryl, or 5 to 11-membered heteroaryl, wherein each $C_{1-6}$ alkyl, $C_{3-10}$ cycloalkyl, 5 to 11-membered heterocyclyl, $C_{6-10}$ aryl, and 5 to 11-membered heteroaryl of said $R^4$ where possible is optionally substituted with one to four $R^7$ groups;

$R^6$, and $R^7$ are each independently halogen hydroxyl, carboxy, $C_{1-6}$ alkyl, $C_{1-6}$ alkoxy, $C_{1-6}$ alkoxy $C_{1-6}$ alkyl, $R^9$—C(O)—, $R^9$—O—C(O)—, $N(R^8)_2$—, $N(R^8)_2$—C(O)—, $R^9$—C(O)—N($R^8$)—, $R^9$—S(O)$_j$—, $R^9$—S(O)$_j$—N($R^8$)—, or $N(R^8)_2$—S(O)$_j$—;

each $R^8$ is independently hydrogen, $C_{1-6}$ alkyl, $C_{3-10}$ cycloalkyl, 5 to 11-membered heterocyclyl, $C_{6-10}$ aryl, or 5 to 11-membered heteroaryl, wherein two $R^8$ groups when attached to the same nitrogen atom can join to form a 4 to 8-membered heterocyclyl;

each $R^9$ is independently hydrogen, $C_{1-6}$ alkyl, $C_{3-10}$ cycloalkyl, 5 to 11-membered heterocyclyl, $C_{6-10}$ aryl, or 5 to 11-membered heteroaryl;

$R^{10}$ is hydrogen, $C_{1-6}$ alkyl, carboxy $C_{1-6}$ alkyl, or $C_{1-6}$ alkoxy $C_{1-6}$ alkyl;

j is 0, 1 or 2;

m is 0, 1, 2 or 3;

n is an integer from 1 to 6; and p and q are each independently 0, 1 or 2.

2. The compound of claim 1, or a pharmaceutically acceptable salt thereof, wherein A is N and B is C.

3. The compound of claim 1, or a pharmaceutically acceptable salt thereof, wherein A is C and B is N.

4. The compound of claim 1, or a pharmaceutically acceptable salt thereof, wherein:

$X^1$ is —C(O)—;

$X^2$ is —CH$_2$C(C$_{1-2}$alkyl)$_2$— or

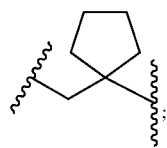 [SMILES: *CC1(*)CCCC1]

$X^3$ is —C(O)—; and $X^4$ is —CH$_2$—O—, wherein one or more hydrogen atoms of said —CH$_2$—O— can be replaced by $C_{1-6}$ alkyl.

5. The compound of claim 1, or a pharmaceutically acceptable salt thereof, wherein:

A is C and B is N, or A is N and B is C;

ring D is phenyl;

$X^1$ is —C(O)—;

$X^2$ is —CH$_2$C(C$_{1-2}$alkyl)$_2$— or

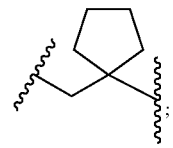 [SMILES: *CC1(*)CCCC1]

$X^3$ is —C(O)— or —C(O)N(R$_{10}$)—;

$X^4$ is —CH$_2$O—;

$R^1$ is $C_{1-6}$ alkyl or $C_{3-6}$cycloalkyl;

$R^2$ is $R_9$OC(O)—, NH($R^8$)—C(O)— or $R^9$—S(O)$_2$—NH—C(O)—;

each $R^3$ when present is independently hydroxyl, halogen, cyano, $C_{1-6}$ alkyl, $C_{1-6}$ alkoxy, $C_{3-6}$cycloalkyl, phenyl, heteroaryl selected from pyridine, pyrimidine and pyrazine, heterocyclyl selected from morpholine, thiomorpholine, pyrrolidine and piperidine, $R^9$—C(O)—, $R^9$—O—C(O)—, $N(R^8)_2$—, $N(R^8)_2$—C(O)—, $R^9$—C(O)—N($R^8$)—, $R^9$—S(O)$_j$—, $N(R^8)_2$—S(O)$_2$—, $R^9$—S(O)$_2$—N($R^8$)—, $R^9$—S(O)$_2$—N($R^8$)—C(O)—, $N(R^8)_2$—S(O)$_2$—N($R^8$)—C(O)—, or $N(R^8)_2$—C(O)—N($R^8$)—S(O)$_2$—, wherein each $C_{1-6}$ alkyl, $C_{1-6}$ alkoxy, $C_{3-6}$ cycloalkyl, phenyl heteroaryl and heterocyclyl of said $R^3$ substituent where possible is optionally substituted with one to four $R^6$ groups;

$R^4$ is phenyl or heteroaryl, selected from pyridine, pyrimidine, pyrazine, quinoline, isoquinoline, benzothiazole, benzoxazole, thiazole, oxazole and 1,2,4-oxadiazole wherein each phenyl or heteroaryl of said $R^4$ where possible is optionally substituted with one to four $R^7$ groups;

$R^5$, $R^6$, and $R^7$ are each independently halogen hydroxyl, carboxy, $C_{1-6}$ alkyl, $C_{1-6}$ alkoxy, $C_{1-6}$ alkoxy $C_{1-6}$ alkyl, $R^9$—C(O)—, $R^9$—O—C(O)—, $N(R^8)_2$—, $N(R^8)_2$—C(O)—, $R^9$—C(O)—N($R^8$)—, $R^9$—S(O)$_j$—, $R^9$—S(O)$_2$—N($R^8$)—, or $N(R^8)_2$—S(O)$_2$—;

each $R^8$ is independently hydrogen, $C_{1-6}$ alkyl, $C_{3-10}$ cycloalkyl or pyridyl;

each $R^9$ is independently hydrogen, $C_{1-6}$ alkyl, $C_{3-6}$ cycloalkyl;

$R^{10}$ is hydrogen, $C_{1-6}$ alkyl or carboxy $C_{1-6}$ alkyl; and j is 0, 1 or 2.

6. The compound of claim 5, or a pharmaceutically acceptable salt thereof, wherein A is C and B is N.

7. The compound of claim 1, or a pharmaceutically acceptable salt thereof, wherein:

A is C and B is N;

ring D is phenyl;

$X^1$ is —C(O)—;

$X^2$ is —CH$_2$C(C$_{1-2}$ alkyl)$_2$—;

$X^3$ is —C(O)—;

$X^4$ is —CH$_2$O—;

$R^1$ is —C(CH$_3$)$_3$;

$R^2$ is CO$_2$H;

each $R^3$ when present is independently hydroxyl, halogen, cyano, $C_{1-6}$ alkyl, $C_{1-6}$ alkoxy, $C_{3-6}$ cycloalkyl, phenyl, heteroaryl selected from pyridine, pyrimidine and pyrazine, heterocyclyl selected from morpholine, thiomorpholine, pyrrolidine and piperidine, $R^9$—C(O)—, $R^9$—O—C(O)—, $N(R^8)_2$—, $N(R^8)_2$—C(O)—, $R^9$—C(O)—N($R^8$)—, $R^9$—S(O)$_2$—, $N(R^8)_2$—S(O)$_2$—, or $R^9$—S(O)$_2$—N($R^8$)—, wherein each $C_{1-6}$ alkyl, $C_{1-6}$ alkoxy, $C_{3-6}$ cycloalkyl, phenyl heteroaryl and heterocyclyl of said $R^3$ substituent where possible is optionally substituted with one to four $R^6$ groups;

R[4] is phenyl or heteroaryl, selected from pyridine, pyrimidine, pyrazine, quinoline, isoquinoline, benzothiazole, benzoxazole, thiazole, oxazole and 1,2,4-oxadiazole, wherein each phenyl or heteroaryl of said R[4] where possible is optionally substituted with one to four R[7] groups;

R[5], R[6], and R[7] are each independently halogen hydroxyl, carboxy, $C_{1-6}$ alkyl, $C_{1-6}$ alkoxy, $C_{1-6}$ alkoxy $C_{1-6}$ alkyl, R[9]—C(O)—, R[9]—O—C(O)—, N(R[8])$_2$—, N(R[8])$_2$—C(O)—, R[9]—C(O)—N(R[8])—, R[9]—S(O)$_j$—, R[9]—S(O)$_2$—N(R[8])—, or N(R[8])$_2$—S(O)$_2$—;

each R[8] is independently hydrogen, $C_{1-6}$ alkyl, $C_{3-10}$ cycloalkyl or pyridyl;

each R[9] is independently hydrogen, $C_{1-6}$ alkyl, $C_{3-6}$ cycloalkyl; and

R[10] is hydrogen, $C_{1-6}$ alkyl or carboxy $C_{1-6}$ alkyl.

8. The compound of claim 1, or a pharmaceutically acceptable salt thereof, wherein X[2] and R[2] together represents:
(b) a moiety selected from:

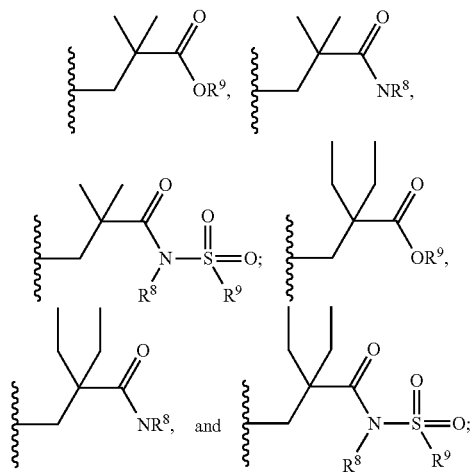

wherein R[8] is hydrogen, methyl, or pyridyl; and
R[9] is hydrogen or methyl.

9. The compound of claim 1, or a pharmaceutically acceptable salt thereof, wherein X[3], ring D, and R[3] taken together represent a moiety selected from:

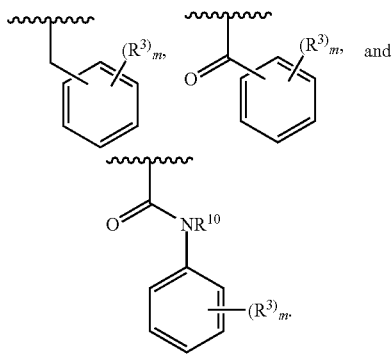

10. The compound of claim 1, or a pharmaceutically acceptable salt thereof, wherein R[4] is hydrogen, $C_{1-6}$ alkyl, $C_{6-10}$ aryl, or 5 to 11-membered heteroaryl, wherein each $C_{1-6}$ alkyl, $C_{6-10}$ aryl, and 5 to 11-membered heteroaryl of said R[4] where possible is optionally substituted with one to four R[7] groups.

11. The compound of claim 10, or a pharmaceutically acceptable salt thereof, wherein
X[4] and R[4] together represent:
(a) hydrogen or 2-propyl, or
(b) a moiety selected from:

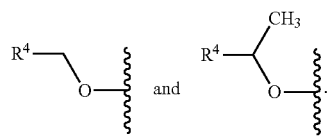

12. The compound of claim 1, selected from the group consisting of:
3-[1-(2,2-Dimethylpropanoyl)-3-{[4-(6-methoxypyridin-3-yl)phenyl]carbonyl}-7-(pyridin-2-ylmethoxy)indolizin-2-yl]-2,2-dimethylpropanoic acid;
3-[6-(1,3-Benzothiazol-2-ylmethoxy)-1-[(4-chlorophenyl)carbonyl]-3-(2,2-dimethylpropanoyl)indolizin-2-yl]-2,2-dimethylpropanoic acid;
3-{1-(2,2-Dimethylpropanoyl)-3-[(4-methylphenyl)carbonyl]-7-[(6-methylpyridin-2-yl)methoxy]indolizin-2-yl}-2,2-dimethylpropanoic acid;
3-{1-[(4-Chlorophenyl)carbonyl]-3-(2,2-dimethylpropanoyl)-6-[(2-methyl-1,3-thiazol-4-yl)methoxy]indolizin-2-yl}-2,2-dimethylpropanoic acid;
3-{1-[(4-Chlorophenyl)carbonyl]-3-(2,2-dimethylpropanoyl)-6-[(2-methyl-1,3-thiazol-4-yl)methoxy]indolizin-2-yl}-2,2-dimethyl-N-(methylsulfonyl)propanamide;
3-{1-[(4-Chlorophenyl)carbonyl]-3-(2,2-dimethylpropanoyl)-6-[(6-methylpyridin-2-yl)methoxy]indolizin-2-yl}-2,2-dimethylpropanoic acid;
3-{3-[(4-Chlorophenyl)carbonyl]-1-(2,2-dimethylpropanoyl)-7-(quinolin-2-ylmethoxy)indolizin-2-yl}-2,2-dimethylpropanoic acid;
3-{3-[(4-Chlorophenyl)carbonyl]-1-(2,2-dimethylpropanoyl)-7-[(2-methyl-1,3-thiazol-4-yl)methoxy]indolizin-2-yl}-2,2-dimethylpropanoic acid;
3-{3-[(4-Chlorophenyl)carbonyl]-1-(2,2-dimethylpropanoyl)-7-[(6-methylpyridin-2-yl)methoxy]indolizin-2-yl}-2,2-dimethylpropanoic acid;
3-{1-(2,2-Dimethylpropanoyl)-3-[(4-methoxyphenyl)carbonyl]-7-[(6-methylpyridin-2-yl)methoxy]indolizin-2-yl}-2,2-dimethylpropanoic acid;
3-[1-(2,2-Dimethylpropanoyl)-7-[(6-methylpyridin-2-yl)methoxy]-3-{[4-(morpholin-4-yl)phenyl]carbonyl}indolizin-2-yl]-2,2-dimethylpropanoic acid;
3-[1-(2,2-Dimethylpropanoyl)-7-[(6-methylpyridin-2-yl)methoxy]-3-{[4-(pyrrolidin-1-yl)phenyl]carbonyl}indolizin-2-yl]-2,2-dimethylpropanoic acid;
3-{7-[(2-Aminopyrimidin-4-yl)methoxy]-3-[(4-chlorophenyl)carbonyl]-1-(2,2-dimethylpropanoyl)indolizin-2-yl}-2,2-dimethylpropanoic acid;
3-{3-[(4-Chlorophenyl)carbonyl]-1-(2,2-dimethylpropanoyl)-7-[(4-methyl-1,3-thiazol-2-yl)methoxy]indolizin-2-yl}-2,2-dimethylpropanoic acid;
3-{3-[(4-Chlorophenyl)carbonyl]-1-(2,2-dimethylpropanoyl)-7-[(1-methyl-1H-pyrazol-3-yl)methoxy]indolizin-2-yl}-2,2-dimethylpropanoic acid;
2-({3-[(4-Chlorophenyl)carbonyl]-1-(2,2-dimethylpropanoyl)-7-[(6-methylpyridin-2-yl)methoxy]indolizin-2-yl}methyl)-2-ethylbutanoic acid;

2-({3-[(4-Chlorophenyl)carbonyl]-1-(2,2-dimethylpropanoyl)-7-[(2-methyl-1,3-thiazol-4-yl)methoxy]indolizin-2-yl}methyl)-2-ethylbutanoic acid;

3-{3-[(4-Chlorophenyl)carbonyl]-1-(2,2-dimethylpropanoyl)-7-(1,3-thiazol-4-ylmethoxy)indolizin-2-yl}-2,2-dimethylpropanoic acid;

3-[7-(1,3-Benzothiazol-2-ylmethoxy)-3-[(4-chlorophenyl)carbonyl]-1-(2,2-dimethylpropanoyl)indolizin-2-yl]-2,2-dimethylpropanoic acid;

3-{3-[(4-Chlorophenyl)carbonyl]-1-(2,2-dimethylpropanoyl)-7-(pyridin-2-ylmethoxy)indolizin-2-yl}-2,2-dimethylpropanoic acid;

3-{3-[(4-Chloro-3-methylphenyl)carbonyl]-1-(2,2-dimethylpropanoyl)-7-[(4-methyl-1,3-thiazol-2-yl)methoxy]indolizin-2-yl}-2,2-dimethylpropanoic acid;

and pharmaceutically salts thereof.

13. A pharmaceutical composition comprising the compound of claim 1, or a pharmaceutically acceptable salt thereof, and a pharmaceutically acceptable excipient and/or carrier.

* * * * *

UNITED STATES PATENT AND TRADEMARK OFFICE
CERTIFICATE OF CORRECTION

| | | |
|---|---|---|
| PATENT NO. | : 8,618,300 B2 | Page 1 of 1 |
| APPLICATION NO. | : 13/061996 | |
| DATED | : December 31, 2013 | |
| INVENTOR(S) | : Bosanac et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 126 days.

Signed and Sealed this
Twelfth Day of May, 2015

Michelle K. Lee
*Director of the United States Patent and Trademark Office*